US012661322B2

(12) United States Patent
Graham et al.

(10) Patent No.: US 12,661,322 B2
(45) Date of Patent: Jun. 23, 2026

(54) MULTIVALENT NANOPARTICLE-BASED VACCINES

(71) Applicant: The USA, as represented by the Secretary, Department of Health and Human Services, Bethesda, MD (US)

(72) Inventors: Barney S. Graham, Smyrna, GA (US); Masaru Kanekiyo, Chevy Chase, MD (US); Hadi M. Yassine, Boyds, MD (US)

(73) Assignee: The United States of America, as represented by the Secretary, Department of Health and Human Services, Bethesda, MD (US)

( * ) Notice: Subject to any disclaimer, the term of this patent is extended or adjusted under 35 U.S.C. 154(b) by 0 days.

(21) Appl. No.: 18/615,895

(22) Filed: Mar. 25, 2024

(65) Prior Publication Data

US 2024/0226012 A1      Jul. 11, 2024

Related U.S. Application Data

(62) Division of application No. 17/519,142, filed on Nov. 4, 2021, now Pat. No. 11,938,221, which is a division of application No. 15/540,898, filed as application No. PCT/US2015/068272 on Dec. 31, 2015, now Pat. No. 11,191,727.

(60) Provisional application No. 62/098,755, filed on Dec. 31, 2014.

(51) Int. Cl.
| | |
|---|---|
| *A61K 39/12* | (2006.01) |
| *A61K 9/16* | (2006.01) |
| *A61K 39/145* | (2006.01) |
| *C12N 7/00* | (2006.01) |
| *A61K 39/00* | (2006.01) |

(52) U.S. Cl.
CPC .............. *A61K 9/167* (2013.01); *A61K 39/12* (2013.01); *A61K 39/145* (2013.01); *C12N 7/00* (2013.01); *A61K 2039/575* (2013.01); *A61K 2039/6031* (2013.01); *A61K 2039/6068* (2013.01); *A61K 2039/6075* (2013.01); *A61K 2039/70* (2013.01); *C12N 2760/16134* (2013.01); *C12N 2760/16171* (2013.01); *Y02A 50/30* (2018.01)

(58) Field of Classification Search
None
See application file for complete search history.

(56) References Cited

U.S. PATENT DOCUMENTS

| | | | |
|---|---|---|---|
| 7,094,598 B2 | 8/2006 | Nabel et al. | |
| 7,097,841 B2 | 8/2006 | Carter et al. | |
| 7,608,268 B2 | 10/2009 | Carter et al. | |
| 9,441,019 B2 | 9/2016 | Nabel et al. | |
| 2002/0054882 A1 | 5/2002 | Okuno et al. | |
| 2003/0211996 A1 | 11/2003 | Gowans et al. | |
| 2005/0042229 A1 | 2/2005 | Yang et al. | |
| 2005/0108791 A1 | 5/2005 | Edgerton | |
| 2006/0251679 A1 | 11/2006 | Carter et al. | |
| 2007/0082054 A1 | 4/2007 | Mooter et al. | |
| 2007/0224205 A1 | 9/2007 | Powell et al. | |
| 2008/0299151 A1 | 12/2008 | Fomsgaard | |
| 2009/0233377 A1 | 9/2009 | Iwahori et al. | |
| 2010/0137412 A1 | 6/2010 | Zhou et al. | |
| 2010/0285982 A1 | 11/2010 | Golding et al. | |
| 2010/0297174 A1 | 11/2010 | Garcia-Sastre et al. | |
| 2011/0038025 A1 | 2/2011 | Naitou et al. | |
| 2011/0177122 A1 | 7/2011 | Nabel et al. | |
| 2011/0212128 A1 | 9/2011 | Galarza et al. | |
| 2016/0303224 A1 | 10/2016 | Kanekiyo et al. | |
| 2017/0189518 A1 | 7/2017 | Nabel et al. | |

FOREIGN PATENT DOCUMENTS

| | | |
|---|---|---|
| EP | 1504037 | 12/2009 |
| WO | WO 2003/094849 | 11/2003 |
| WO | WO 2009/109428 | 9/2009 |
| WO | WO 2010/036948 | 4/2010 |
| WO | WO 2010/117786 A1 | 10/2010 |
| WO | WO 2011/035422 | 3/2011 |

(Continued)

OTHER PUBLICATIONS

A3KF33, UniProtKB A3KF33_157A5, Sep. 21, 2011 [online]. [Retrieved on Feb. 26, 2013]. Retrieved from the internet <URL: http://www.uniprot.org/uniprot/A3KF33.txt?version=36>.

(Continued)

*Primary Examiner* — Benjamin P Blumel

(74) *Attorney, Agent, or Firm* — Klarquist Sparkman, LLP

(57) ABSTRACT

Novel, nanoparticle-based vaccines are provided that elicit an immune response to a broad range of infectious agents, such as influenza viruses. The nanoparticles comprise a heterogeneous population of fusion proteins, each comprising a monomeric subunit of a self-assembly protein, such as ferritin, joined to one or more immunogenic portions of a protein from an infectious agent, such as influenza virus. The fusion proteins self-assemble to form nanoparticles that display a heterogeneous population of immunogenic portions on their surface. When administered to an individual, such nanoparticles elicit an immune response to different strains, types, subtypes and species within the same taxonomic family. Thus, such nanoparticles can be used to vaccinate an individual against infection by different Types, subtypes and/or strains of infectious agents. Also provided are specific fusion proteins, nucleic acid molecules encoding such fusion proteins and methods of using nanoparticles of the invention to vaccinate individuals.

10 Claims, 13 Drawing Sheets

Specification includes a Sequence Listing.

(56) References Cited

FOREIGN PATENT DOCUMENTS

| WO | WO 2011/044152 | | 4/2011 |
|---|---|---|---|
| WO | WO 2012/162428 | | 11/2012 |
| WO | WO 2013/044203 | A2 | 3/2013 |
| WO | WO 2015/054639 | | 4/2015 |
| WO | WO 2015/183969 | | 12/2015 |
| WO | WO 2016/021209 | | 2/2016 |

OTHER PUBLICATIONS

C0LT38, UniProtKB C0LT38_9INFB, Sep. 21, 2011 [online]. [Retrieved on Feb. 26, 2013]. Retrieved from the internet <URL: http://www.uniprot.org/uniprot/C0LT38.txt?version=18>.

GenBank Accession No. 3EGM_A submitted Sep. 11, 2008, 2 pages.

GenBank Accession No. AAP34324, submitted May 1, 2003, 2 pages.

Bachmann et al., "Neutralizing antiviral B cell responses," *Annu Rev Immunol.* 15: 235-270, 1997.

Bernacchioni et al. "Loop Electrostatics Modulates the Intersubunit Interactions in Ferritin," *ACS Chemical Biology* 9: 2517-2525, 2014.

Caton et al., "The antigenic structure of the influenza virus A/PR/8/34 hemagglutinin (H1 subtype)," *Cell* 31: 417-427, 1982.

Cohen et al., "Ferritin as an Endogenous MRI Reporter for Non-invasive Imaging Neoplasia of Gene Expression in C6 Glioma Tumors," *Neoplasia* 7.2: 109-117, Feb. 2005.

Corti et al., "Heterosubtypic neutralizing antibodies are produced by individuals immunized with a seasonal influenza vaccine," *J Clin Invest* 120: 1663-1673, 2010.

Corti et al., "A neutralizing antibody selected from plasma cells that binds to group 1 and group 2 influenza A hemagglutinins," *Science* 333: 850-856, 2011.

Dintzis et al., "Molecular determinants of immunogenicity: the immunon model of immune response," *Proc Natl Acad Sci USA* 73: 3671-3675, 1976.

Ekiert et al., "A highly conserved neutralizing epitope on group 2 influenza A viruses," *Science* 333: 843-850, 2011.

Ekiert et al., "Antibody recognition of a highly conserved influenza virus epitope," *Science* 324: 246-251, 2009.

Greenstone et al., "Chimeric papillomavirus virus-like particles elicit antitumor immunity against the E7 oncoprotein in an HPV16 tumor model," *Proc. Natl. Acad. Sci. USA* 95: 1800-1805, Feb. 1998.

Harrison, "The Structure and Function of Ferritin," *Biochemical Education* 14.4: 154-162, 1986.

Haynes, "Influenza virus-like particle vaccines," *Expert Rev Vaccines* 8: 435-445, 2009.

He et al., "Presenting native-like trimeric HIV-1 antigens with self-assembling nanoparticles," *Nature Communications* 7: 12041, Jun. 2016 (15 pages).

International Preliminary Report on Patentability for International Application No. PCT/US2015/068272, dated Jul. 13, 2017, 10 pages.

International Search Report and Written Opinion prepared by the European Patent Office on Mar. 23, 2016, for International Application No. PCT/US2015/068272, 17 pages.

Joyce et al., "Vaccine-Induced Antibodies that Neutralize Group 1 and Group 2 Influenza A Viruses," *Cell* 166.3: 609-623, Jul. 2016.

Kanekiyo et al., "Rational Design of an Epstein-Barr Virus Vaccine Targeting the Receptor-Binding Site," *Cell* 162.5: 1090-1100, Aug. 2015.

Kanekiyo et al., "Self-assembling influenza nanoparticle vaccines elicit broadly neutralizing H1N1 antibodies," *Nature* 499.7456: 102-106, Jul. 4, 2013.

Kang et al., "Influenza vaccines based on virus-like particles," *Virus Research* 143.2: 140-146, Aug. 1, 2009.

Kashyap et al., "Combinatorial antibody libraries from survivors of the Turkish H5N1 avian influenza outbreak reveal virus neutralization strategies," *Proc Natl Acad Sci USA* 105: 5986-5991, 2008.

Kong et al., "Protective immunity to lethal challenge of the 1918 pandemic influenza virus by vaccination," *Proc Natl Acad Sci USA* 103: 15987-15991, 2006.

Kossovsky et al., "Nanocrystalline Epstein-Barr virus decoys," *Journal of Applied Biomaterials* 2.4: 251-259, Jan. 1991.

Krause et al., "A broadly neutralizing human monoclonal antibody that recognizes a conserved, novel epitope on the globular head of the influenza H1N1 virus hemagglutinin," *J Virol* 85: 10905-10908, 2011.

Lambert et al., "Influenza vaccines for the future," *N Engl J Med* 363: 2036-2044, 2010.

Lee et al., "Adaptations of nanoscale viruses and other protein cages for medical applications", *Nanomedicine* 2.3: 137-149, Sep. 1, 2006.

Lee et al. "Viruses and Virus-Like Protein Assemblies—Chemically Programmable Nanoscale Building Blocks," *Nano Res* 2: 349-364, 2009.

Li et al., "Ferritin nanoparticle technology: A new platform for antigen presentation and vaccine development," *Industrial Biotechnol* 2: 143-147, 2006.

Lopez-Sagaseta et al., "Self-assembling protein nanoparticles in the design of vaccines," *Computational and Structural Biotechnology Journal* 14: 58-68, 2016.

Meldrum et al., "Magnetoferritin: in vitro synthesis of a novel magnetic protein," *Science* 257: 522-523, 1992.

Nabel et al., "Induction of unnatural immunity: prospects for a broadly protective universal influenza vaccine," *Nat Med* 16: 1389-1391, 2010.

Ni et al., "Structural Insights into the Membrane Fusion Mechanism Mediated by Influenza Virus Hemagglutinin," *Biochemistry* 53: 846-854, 2014.

Official Action for Australia Patent Application No. 2015373928, dated Oct. 5, 2018, 29 pages.

Official Action for Canada Patent Application No. 2,974,346, dated May 30, 2019, 4 pages.

English Translation of Official Action for China Patent Application No. 201580076324.6, dated Mar. 26, 2020, 8 pages.

Official Action for European Patent Application No. 15825772.5, dated Jul. 2, 2018, 3 pages.

Official Action for European Patent Application No. 15825772.5, dated Apr. 9, 2019, 4 pages.

Official Action with English Translation for Japan Patent Application No. 2017-534796, dated Jul. 10, 2018, 9 pages.

Official Action with English Translation for Japan Patent Application No. 2017/534796, dated May 21, 2019, 5 pages.

Okuno et al., "A common neutralizing epitope conserved between the hemagglutinins of influenza A virus H1 and H2 strains," *J Virol* 67: 2552-2558, 1993.

Pulford et al., "Expression of the Epstein-Barr Virus Envelope Fusion Glycoprotein GB85 Gene by a Recombinant Baculovirus," *Journal of General Virology* 75.11: 3241-3248, Nov. 1994.

Roldao et al., "Virus-like particles in vaccine development," *Expert Rev Vaccines* 9: 1149-1176, 2010.

Ruiss et al., "A Virus-Like Particle-Based Epstein-Barr Virus Vaccine," *J Virol* 85.24: 13105-13113, Dec. 2011.

Scorza et al., "Universal influenza vaccines: Shifting to better vaccines," *Vaccine* 34.26: 2926-2933, Mar. 2016.

Sheridan, "Flu vaccine makers upgrade technology—and pray for time," *Nat Biotechnol*, 27: 489-491, 2009.

Steel et al., "Influenza Virus Vaccine Based on the Conserved Hemagglutinin Stalk Domain," *mBio* 1.1: e00018-10, May 18, 2010 (9 pages).

Sui et al., "Structural and functional bases for broad-spectrum neutralization of avian and human influenza A viruses," *Nat Struct Mol Biol* 16: 265-273, 2009.

Treanor et al., "Safety and immunogenicity of a recombinant hemagglutinin vaccine for H5 influenza in humans," *Vaccine* 19: 1732-1737, 2001.

(56) References Cited

OTHER PUBLICATIONS

Treanor, "Safety and immunogenicity of a baculovirus-expressed hemagglutinin influenza vaccine: a randomized controlled trial," *JAMA* 297: 1577-1582, 2007.

Vallhov et al., "Exosomes Containing Glycoprotein 350 Released by EBV-Transformed B Cells Selectively Target B Cells through CD21 and Block EBV Infection in Vitro," *J Immunol.* 186.1: 73-82, Jan. 2011.

Wang et al., "Broadly protective monoclonal antibodies against H3 influenza viruses following sequential immunization with different hemagglutinins," *PLoS Pathog* 6.2: e1000796, 2010 (9 pages).

Wei et al., "Cross-neutralization of 1918 and 2009 influenza viruses: role of glycans in viral evolution and vaccine design," *Sci Transl Med* 2: 24ra21, 2010 (17 pages).

Wei et al., "Induction of broadly neutralizing H1N1 influenza antibodies by vaccination," *Science* 329: 1060-1064, 2010.

Wei et al., "Comparative efficacy of neutralizing antibodies elicited by recombinant hemagglutinin proteins from avian H5N1 influenza virus," *J Virol* 82: 6200-6208, 2008.

Whittle et al., "Broadly neutralizing human antibody that recognizes the receptor-binding pocket of influenza virus hemagglutinin," *Proc Natl Acad Sci USA* 108: 14216-14221, 2011.

WHO Reference on Animal Influenza Diagnosis and Surveillance, 2002, Department of Communicable Disease Surveillance and Response, World Health Organization).

Wu et al., "Mammalian expression of virus-like particles for advanced mimicry of authentic influenza virus," *PLoS One* 5: e9784, 2010 (17 pages).

Xiong et al., "PCR-based accurate synthesis of long DNA sequences," *Nat Protoc* 1.2: 791-797, 2006.

Yamashita et al., "Ferritin in the field of nanodevices," *Biochim Biophys Acta* 1800: 846-857, 2010.

Yang et al., "Immunization by avian H5 influenza hemagglutinin mutants with altered receptor binding specificity," *Science* 317: 825-828, 2007.

Yassine et al., "Hemagglutinin-stem nanoparticles generate heterosubtypic influenza protection," *Nat Med.* 21.9: 1065-1070, Sep. 2015.

Zhang et al., "Self-Assembly in the Ferritin Nano-Cage Protein Super Family," *Int. J. Mol. Sci.* 12: 5406-5421, 2011.

Zhang et al. "Universal Influenza Vaccines, a Dream to Be Realized Soon," *Viruses* 6: 1974-1991, 2014.

FIG. 1

Top

270°

180°

90°

0°

200 Å

Top view

Side view

```
                        SEQUENCE LISTING

Sequence total quantity: 192
SEQ ID NO: 1              moltype = AA  length = 517
FEATURE                   Location/Qualifiers
source                    1..517
                          mol_type = protein
                          organism = Influenza virus
SEQUENCE: 1
MKAKLLVLLC TFTATYADTI CIGYHANNST DTVDTVLEKN VTVTHSVNLL EDSHNGKLCL  60
LKGIAPLQLG NCSVAGWILG NPECELLISK ESWSYIVETP NPENGTCYPG YFADYEELRE  120
QLSSVSSFER FEIFPKESSW PNHTVTGVSA SCSHNGKSSF YRNLLWLTGK NGLYPNLSKS  180
YVNNKEKEVL VLWGVHHPPN IGNQRALYHT ENAYVSVVSS HYSRRFTPEI AKRPKVRDQE  240
GRINYYWTLL EPGDTIIFEA NGNLIAPWYA FALSRGFGSG IITSNAPMDE CDAKCQTPQG  300
AINSSLPFQN VHPVTIGECP KYVRSAKLRM VTGLRNIPSI QSRGLFGAIA GFIEGGWTGM  360
VDGWYGYHHQ NEQGSGYAAD QKSTQNAING ITNKVNSVIE KMNTQFTAVG KEFNKLERRM  420
ENLNKKVDDG FLDIWTYNAE LLVLLENERT LDFHDSNVKN LYEKVKSQLK NNAKEIGNGC  480
FEFYHKCNNE CMESVKNGTY DYPKYSEESK LNREKID                           517

SEQ ID NO: 2              moltype = AA  length = 518
FEATURE                   Location/Qualifiers
source                    1..518
                          mol_type = protein
                          organism = Influenza virus
SEQUENCE: 2
MKAILVVLLY TFATANADTL CIGYHANNST DTVDTVLEKN VTVTHSVNLL EDKHNGKLCK  60
LRGVAPLHLG KCNIAGWILG NPECESLSTA SSWSYIVETP SSDNGTCYPG DFIDYEELRE  120
QLSSVSSFER FEIFPKTSSW PNHDSNKGVT AACPHAGAKS FYKNLIWLVK KGNSYPKLSK  180
SYINDKGKEV LVLWGIHHPS TSADQQSLYQ NADTYVFVGS SRYSKKFKPE IAIRPKVRDQ  240
EGRMNYYWTL VEPGDKITFE ATGNLVVPRY AFAMERNAGS GIIISDTPVH DCNTTCQTPK  300
GAINTSLPFQ NIHPITIGKC PKYVKSTKLR LATGLRNIPS IQSRGLFGAI AGFIEGGWTG  360
MVDGWYGYHH QNEQGSGYAA DLKSTQNAID EITNKVNSVI EKMNTQFTAV GKEFNHLEKR  420
IENLNKKVDD GFLDIWTYNA ELLVLLENER TLDYHDSNVK NLYEKVRSQL KNNAKEIGNG  480
CFEFYHKCDN TCMESVKNGT YDYPKYSEEA KLNREEID                          518

SEQ ID NO: 3              moltype = AA  length = 514
FEATURE                   Location/Qualifiers
source                    1..514
                          mol_type = protein
                          organism = Influenza virus
SEQUENCE: 3
MAIIYLILLF TAVRGDQICI GYHANNSTEK VDTILERNVT VTHAKDILEK THNGKLCKLN  60
GIPPLELGDC SIAGWLLGNP ECDRLLSVPE WSYIMEKENP RDGLCYPGSF NDYEELKHLL  120
SSVKHFEKVK ILPKDRWTQH TTTGGSRACA VSGNPSFFRN MVWLTKKGSN YPVAKGSYNN  180
TSGEQMLIIW GVHHPNDETE QRTLYQNVGT YVSVGTSTLN KRSTPDIATR PKVNQGGRM   240
EFSWTLLDMW DTINFESTGN LIAPEYGFKI SKRGSSGIMK TEGTLENCET KCQTPLGAIN  300
TTLPFHNVHP LTIGECPKYV KSEKLVLATG LRNVPQIESR GLFGAIAGFI EGGWQGMVDG  360
WYGYHHSNDQ GSGYAADKES TQKAFDGITN KVNSVIEKMN TQFEAVGKEF SNLERRLENL  420
NKKMEDGFLD VWTYNAELLV LMENERTLDF HDSNVKNLYD KVRMQLRDNV KELGNGCFEF  480
YHKCDDECMN SVKNGTYDYP KYEEESKLNR NEIK                              514

SEQ ID NO: 4              moltype = AA  length = 519
FEATURE                   Location/Qualifiers
source                    1..519
                          mol_type = protein
                          organism = Influenza virus
SEQUENCE: 4
MKTIIALSYI FCLALGQDLP GNDNSTATLC LGHHAVPNGT LVKTITDDQI EVTNATELVQ  60
SSSTGKICNN PHRILDGIDC TLIDALLGDP HCDVFQNETW DLFVERSKAF SNCYPYDVPD  120
YASLRSLVAS SGTLEFITEG FTWTGVTQNG GSNACKRGPG SGFFSRLNWL TKSGSTYPVL  180
```

```
NVTMPNNDNF DKLYIWGVHH PSTNQEQTSL YVQASGRVTV STRRSQQTII PNIESRPWVR   240
GLSSRISIYW TIVKPGDVLV INSNGNLIAP RGYFKMRTGK SSIMRSDAPI DTCISECITP   300
NGSIPNDKPF QNVNKITYGA CPKYVKQNTL KLATGMRNVP EKQTRGLFGA IAGFIENGWE   360
GMIDGWYGFR HQNSEGTGQA ADLKSTQAAI DQINGKLNRV IEKTNEKFHQ IEKEFSEVEG   420
RIQDLEKYVE DTKIDLWSYN AELLVALENQ HTIDLTDSEM NKLFEKTRRQ LRENAEDMGN   480
GCFKIYHKCD NACIESIRNG TYDHDVYRDE ALNNRFQIK                          519

SEQ ID NO: 5             moltype = AA  length = 519
FEATURE                  Location/Qualifiers
source                   1..519
                         mol_type = protein
                         organism = Influenza virus
SEQUENCE: 5
MKTIIALSYI LCLVFTQKLP GNDNSTATLC LGHHAVPNGT IVKTITNDQI EVTNATELVQ   60
SSSTGEICDS PHQILDGENC TLIDALLGDP QCDGFQNKKW DLFVERSKAY SNCYPYDVPD   120
YASLRSLVAS SGTLEFNNES FNWTGVTQNG TSSACIRRSN NSFFSRLNWL THLKFKYPAL   180
NVTMPNNEKF DKLYIWGVHH PGTDNDQIFP YAQASGRITV STKRSQQTVI PNIGSRPRVR   240
NIPSRISIYW TIVKPGDILL INSTGNLIAP RGYFKIRSGK SSIMRSDAPI GKCNSECITP   300
NGSIPNDKPF QNVNRITYGA CPRYVKQNTL KLATGMRNVP EKQTRGIFGA IAGFIENGWE   360
GMVDGWYGFR HQNSEGIGQA ADLKSTQAAI DQINGKLNRL IGKTNEKFHQ IEKEFSEVEG   420
RIQDLEKYVE DTKIDLWSYN AELLVALENQ HTIDLTDSEM NKLFEKTKKQ LRENAEDMGN   480
GCFKIYHKCD NACIGSIRNG TYDHDVYRDE ALNNRFQIK                          519

SEQ ID NO: 6             moltype = AA  length = 520
FEATURE                  Location/Qualifiers
source                   1..520
                         mol_type = protein
                         organism = Influenza virus
SEQUENCE: 6
MEKIVLLLAI VSLVKSDQIC IGYHANNSTE QVDTIMEKNV TVTHAQDILE KTHNGKLCDL   60
DGVKPLILRD CSVAGWLLGN PMCDEFINVP EWSYIVEKAN PTNDLCYPGS FNDYEELKHL   120
LSRINHFEKI QIIPKSSWSD HEASSGVSSA CPYLGSPSFF RNVVWLIKKN STYPTIKKSY   180
NNTNQEDLLV LWGIHHPNDA AEQTRLYQNP TTYISIGTST LNQRLVPKIA TRSKVNGQSG   240
RMEFFWTILK PNDAINFESN GNFIAPEYAY KIVKKGDSAI MKSELEYGNC NTKCQTPMGA   300
INSSMPFHNI HPLTIGECPK YVKSNRLVLA TGLRNSPQRE SRRKKRGLFG AIAGFIEGGW   360
QGMVDGWYGY HHSNEQGSGY AADKESTQKA IDGVTNKVNS IIDKMNTQFE AVGREFNNLE   420
RRIENLNKKM EDGFLDVWTY NAELLVLMEN ERTLDFHDSN VKNLYDKVRL QLRDNAKELG   480
NGCFEFYHKC DNECMESIRN GTYNYPQYSE EARLKREEIS                         520

SEQ ID NO: 7             moltype = AA  length = 534
FEATURE                  Location/Qualifiers
source                   1..534
                         mol_type = protein
                         organism = Influenza virus
SEQUENCE: 7
MKAIIVLLMV VTSNADRICT GITSSNSPHV VKTATQGEVN VTGVIPLTTT PTKSYFANLK   60
GTRTRGKLCP DCLNCTDLDV ALGRPMCVGT TPSAKASILH EVKPVTSGCF PIMHDRTKIR   120
QLPNLLRGYE NIRLSTQNVI DAEKAPGGPY RLGTSGSCPN ATSKSGFFAT MAWAVPKDNN   180
KNATNPLTVE VPYICTEGED QITVWGFHSD DKTQMKNLYG DSNPQKFTSS ANGVTTHYVS   240
QIGSFPDQTE DGGLPQSGRI VVDYMMQKPG KTGTIVYQRG VLLPQKVWCA SGRSKVIKGS   300
LPLIGEADCL HEKYGGLNKS KPYYTGEHAK AIGNCPIWVK TPLKLANGTK YRPPAKLLKE   360
RGFFGAIAGF LEGGWEGMIA GWHGYTSHGA HGVAVAADLK STQEAINKIT KNLNSLSELE   420
VKNLQRLSGA MDELHNEILE LDEKVDDLRA DTISSQIELA VLLSNEGIIN SEDEHLLALE   480
RKLKKMLGPS AVEIGNGCFE TKHKCNQTCL DRIAAGTFNA GEFSLPTFDS LNIT          534

SEQ ID NO: 8             moltype = AA  length = 519
FEATURE                  Location/Qualifiers
source                   1..519
                         mol_type = protein
                         organism = Influenza virus
SEQUENCE: 8
MKTIIALSYI LCLVFAQKLP GNDNSTATLC LGHHAVPNGT IVKTITNDQI EVTNATELVQ   60
SSSTGEICDS PHQILDGKNC TLIDALLGDP QCDGFQNKKW DLFVERSKAY SNCYPYDVPD   120
YASLRSLVAS SGTLEFNNES FNWTGVTQNG TSSACIRRSK NSFFSRLNWL THLNFKYPAL   180
NVTMPNNEQF DKLYIWGVHH PGTDKDQIFL YAQASGRITV STKRSQQTVS PNIGSRPRVR   240
NIPSRISIYW TIVKPGDILL INSTGNLIAP RGYFKIRSGK SSIMRSDAPI GKCNSECITP   300
NGSIPNDKPF QNVNRITYGA CPRYVKQNTL KLATGMRNVP EKQTRGIFGA IAGFIENGWE   360
GMVDGWYGFR HQNSEGRGQA ADLKSTQAAI DQINGKLNRL IGKTNEKFHQ IEKEFSEVEG   420
RIQDLEKYVE DTKIDLWSYN AELLVALENQ HTIDLTDSEM NKLFEKTKKQ LRENAEDMGN   480
GCFKIYHKCD NACIGSIRNG TYDHDVYRDE ALNNRFQIK                          519

SEQ ID NO: 9             moltype = AA  length = 517
FEATURE                  Location/Qualifiers
source                   1..517
                         mol_type = protein
                         organism = Influenza virus
SEQUENCE: 9
MKVKLLVLLC TFTATYADTI CIGYHANNST DTVDTVLEKN VTVTHSVNLL ENSHNGKLCL   60
LKGIAPLQLG NCSVAGWILG NPECELLISK ESWSYIVEKP NPENGTCYPG HFADYEELRE   120
```

```
QLSSVSSFER FEIFPKESSW PNHTVTGVSA SCSHNGESSF YRNLLWLTGK NGLYPNLSKS  180
YANNKEKEVL VLWGVHHPPN IGIQKALYHT ENAYVSVVSS HYSRKFTPEI AKRPKVRDQE  240
GRINYYWTLL EPGDTIIFEA NGNLIAPRYA FALSRGFGSG IINSNAPMDK CDAKCQTPQG  300
AINSSLPFQN VHPVTIGECP KYVRSAKLRM VTGLRNIPSI QSRGLFGAIA GFIEGGWTGM  360
VDGWYGYHHQ NEQGSGYAAD QKSTQNAING ITNKVNSVIE KMNTQFTAVG KEFNKLERRM  420
ENLNKKVDDG FIDIWTYNAE LLVLLENERT LDFHDSNVKN LYEKVKSQLK NNAKEIGNGC  480
FEFYHKCNDE CMESVKNGTY DYPKYSEESK LNREKID                           517

SEQ ID NO: 10           moltype = AA  length = 535
FEATURE                 Location/Qualifiers
source                  1..535
                        mol_type = protein
                        organism = Influenza virus
SEQUENCE: 10
MKAIIVLLMV VTSNADRICT GITSSNSPHV VKTATQGEVN VTGVIPLTTT PTKSHFANLK  60
GTETRGKLCP KCLNCTDLDV ALGRPKCTGK IPSARVSILH EVRPVTSGCF PIMHDRTKIR  120
QLPNLLRGYE HIRLSTHNVI NAENAPGGPY KIGTSGSCPN ITNGNGFFAT MAWAVPKNDK  180
NKTATNPLTI EVPYICTEGE DQITVWGFHS DNETQMAKLY GDSKPQKFTS SANGVTTHYV  240
SQIGGFPNQT EDGGLPQSGR IVVDYMVQKS GKTGTITYQR GILLPQKVWC ASGRSKVIKG  300
SLPLIGEADC LHEKYGGLNK SKPYYTGEHA KAIGNCPIWV KTPLKLANGT KYRPPAKLLK  360
ERGFFGAIAG FLEGGWEGMI AGWHGYTSHG AHGVAVAADL KSTQEAINKI TKNLNSLSEL  420
EVKNLQRLSG AMDELHNEIL ELDEKVDDLR ADTISSQIEL AVLLSNEGII NSEDEHLLAL  480
ERKLKKMLGP SAVEIGNGCF ETKHKCNQTC LDRIAAGTFD AGEFSLPTFD SLNIT        535

SEQ ID NO: 11           moltype = AA  length = 501
FEATURE                 Location/Qualifiers
source                  1..501
                        mol_type = protein
                        organism = Influenza virus
SEQUENCE: 11
DTICIGYHAN NSTDTVDTLL EKNVTVTHSV NLLEDSHNGK LCKLKGIAPL QLGKCNIAGW  60
LLGNPECDSL LPAKSWSYIV ETPNSENGAC YPGDFIDYEE LKEQLSSVSS LERFEIFPKE  120
SSWPNHNTLK GVTAACSHRG KSSFYRNLLW LTKTGDSYPK LNNSYVNNKG KEVLVLWGVH  180
HPSSSNEQQS LYHNVNAYVS VVSSNYNRRF TPEIAARPKV RDQPGRMNYY WTLLEPGDTI  240
IFEATGNLIA PWYAFALSRG FGSGIITSNA SMHECNTKSQ TPQGAINSSL PFQNIHPVPI  300
GECPKYVRST KLRMVTGLRN IPSIQSRGLF GAIAGFIEGG WTGMIDGWYG YHHQNEQGSG  360
YAADQKSTQN AINGITNKVN SIIEKMNTQF TAVSKEFNNL EKRMENLNKK VDDGFLDIWT  420
YNAELLVLLE NERTLDFHDS NVKNLYEKVK SQLKNNAKEI GNGCFEFYHK CDNECMESVR  480
NGTYDYPKYS EESKLNREKI D                                            501

SEQ ID NO: 12           moltype = AA  length = 501
FEATURE                 Location/Qualifiers
source                  1..501
                        mol_type = protein
                        organism = Influenza virus
SEQUENCE: 12
DTICIGYHAN NSTDTVDTVL EKNVTVTHSV NLLEDSHNGK LCRLKGIAPL QLGKCSIAGW  60
ILGNPECESL FSKKSWSYIA ETPNSENGTC YPGYFADYEE LREQLSSVSS FERFEIFPKE  120
RSWPKHNVTR GVTASCSHKG KSSFYRNLLW LTEKNGSYPN LSKSYVNNKE KEVLVLWGVH  180
HPSNIEDQKT IYRKENAYVS VVSSNYNRRF TPEIAERPKV RGQAGRINYY WTLLEPGDTI  240
IFEANGNLIA PWHAFALSRG FGSGIITSNA SMDECDTKCQ TPQGAINSSL PFQNIHPVTI  300
GECPKYVRST KLRMVTGLRN IPSIQSRGLF GAIAGFIEGG WTGMIDGWYG YHHQNEQGSG  360
YAADQKSTQN AINGITNKVN SVIEKMNTQF TAVGKEFNKL EKRMENLNKK VDDGFLDIWT  420
YNAELLVLLE NERTLDFHDS NVKNLYEKVK SQLKNNAKEI GNGCFEFYHK CNNECMESVK  480
NGTYDYPKYS EESKLNREKI D                                            501

SEQ ID NO: 13           moltype = AA  length = 501
FEATURE                 Location/Qualifiers
source                  1..501
                        mol_type = protein
                        organism = Influenza virus
SEQUENCE: 13
DTICIGYHAN NSTDTVDTVL EKNVTVTHSV NLLEDSHNGK LCRLKGIAPL QLGNCSVAGW  60
ILGNPKCESL FSKESWSYIA ETPNPENGTC YPGYFADYEE LREQLSSVSS FERFEIFPKE  120
SSWPNHTVTK GVTTSCSHNG KSSFYRNLLW LTEKNGLYPN LSKSYVNNKE KEVLVLWGVH  180
HPSNIRDQRA IYHTENAYVS VVSSHYSRRF TPEIAKRPKV RGQEGRINYY WTLLEPGDTI  240
IFEANGNLIA PWYAFALSRG FGSGIITSNA SMDECDAKCQ TPQGAINSSL PFQNVHPVTI  300
GECPKYVRST KLRMVTGLRN IPSIQSRGLF GAIAGFIEGG WTGMIDGWYG YHHQNEQGSG  360
YAADQKSTQN AINGITNKVN SVIEKMNTQF TAVGKEFNKL ERRMENLNKK VDDGFLDIWT  420
YNAELLVLLE NGRTLDFHDS NVKNLYEKVK SQLKNNAKEI GNGCFEFYHK CNNECMESVK  480
NGTYDYPKYS EESKLNRGKI D                                            501

SEQ ID NO: 14           moltype = AA  length = 501
FEATURE                 Location/Qualifiers
source                  1..501
                        mol_type = protein
                        organism = Influenza virus
SEQUENCE: 14
DTICIGYHAN NSTDTVDTVL EKNVTVTHSV NLLEDSHNGK LCRLKGIAPL QLGNCSIAGW  60
```

-continued

```
ILGNPECESL FSKKSWSYIA ETPNSENGTC YPGYFADYEE LREQLSSVSS FERFEIFPKE  120
SSWPNHTVTK GVTASCSHKG RSSFYRNLLW LTKKNGSYPN LSKSYVNNKE KEVLVLWGVH  180
HPSNIGDQRA IYHTENAYVS VVSSHYNRRF TPEIAKRPKV RDQEGRINYY WTLLEPGDTI  240
IFEANGNLIA PWYAFALSRG FGSGIITSNA SMDECDAKCQ TPQGAINSSL PFQNVHPVTI  300
GECPKYVRST KLRMVTGLRN IPSIQSRGLF GAIAGFIEGG WTGMIDGWYG YHHQNEQGSG  360
YAADQKSTQN AINGITNKVN SVIEKMNTQF TAVGKEFNKL ERRMENLNKK VDDGFLDIWT  420
YNAELLVLLE NERTLDFHDS NVKNLYEKVK SQLKNNAKEI GNGCFEFYHK CNNECMESVK  480
NGTYDYPKYS EESKLNREKI D                                           501

SEQ ID NO: 15             moltype = AA   length = 501
FEATURE                   Location/Qualifiers
source                    1..501
                          mol_type = protein
                          organism = Influenza virus
SEQUENCE: 15
DTICIGYHAN NSTDTVDTVL EKNVTVTHSV NLLEDNHNGK LCKLKGIAPL QLGKCSIAGW  60
ILGNPECESL FSKKSWSYIA ETPNSENGTC YPGYFADYEE LREQLSSVSS FERFEIFPKE  120
SSWPKHNVTK GVTASCSHKG KSSFYRNLLW LTEKNGSYPN LSKSYVNNKE KEVLVLWGVH  180
HPSNIEDQKT IYRKENAYVS VVSSHYNRRF TPEIAKRPKV RNQEGRINYY WTLLEPGDTI  240
IFEANGNLIA PWYAFALSRG FGSGIITSNA SMDECDAKCQ TPQGAINSSL PFQNVHPVTI  300
GECPKYVRST KLRMVTGLRN IPSIQSRGLF GAIAGFIEGG WTGMIDGWYG YHHQNEQGSG  360
YAADQKSTQN AINGITNKVN SIIEKMNTQF TAVGKEFNKL EKRMENLNKK VDDGFLDIWT  420
YNAELLVLLE NERTLDFHDS NVKNLYEKVK SQLKNNAKEI GNGCFEFYHK CNNECMESVK  480
NGTYDYPKYS EESKLNREKI D                                           501

SEQ ID NO: 16             moltype = AA   length = 501
FEATURE                   Location/Qualifiers
source                    1..501
                          mol_type = protein
                          organism = Influenza virus
SEQUENCE: 16
DTICIGYHAN NSTDTVDTVL EKNVTVTHSV NLLEDSHNGK LCRLKGIAPL QLGKCNIAGW  60
ILGNPECESL LSNRSWSYIA ETPNSENGIC YPGDFADYEE LREQLSSVSS FERFEIFPKE  120
SSWPKHNITR GVTVACSHAK KSSFYKNLLW LTEANGLYPS LSKSYVNDRE KEVLVLWGVH  180
HPSNIEDQRT LYRKENAYVS VVSSNYNRRF TPEIAERPKV RGQPGRMNYY WTLLEPGDKI  240
IFEANGNLIA PWYAFALSRG PGSGIITSNA SMDECDTKCQ TPQGAINSSL PFQNIHPVTI  300
GECPKYVRST KLRMVTGLRN IPSIQSRGLF GAIAGFIEGG WTGMVDGWYG YHHQNEQGSG  360
YAADQKSTQN AINGITNKVN SVIEKMNTQF TAVGKEFNKL EKRMENLNKK VDDGFLDIWT  420
YNAELLVLLE NERTLDFHDS NVKNLYEKVK NQLRNNAKEI GNGCFEFYHK CDNECMESVK  480
NGTYDYPKYS EESKLNRAKI D                                           501

SEQ ID NO: 17             moltype = AA   length = 500
FEATURE                   Location/Qualifiers
source                    1..500
                          mol_type = protein
                          organism = Influenza virus
SEQUENCE: 17
DTICIGYHAN NSTDTVDTVL EKNVTVTHSV NLLEDSHNGK LCRLKGIAPL QLGKCNIAGW  60
ILGNPECESL LSERSWSYIV ETPNSENGTC YPGDFIDYEE LREQLSSVSS FERFEIFSKE  120
SSWPKHTTGG VTAACSHAGK SSFYRNLLWL TEKDGSYPNL NNSYVNKKGK EVLVLWGVHH  180
PSNIKDQQTL YQKENAYVSV VSSNYNRRFT PEIAERPKVR GQAGRINYYW TLLKPGDTIM  240
FEANGNLIAP WYAFALSRGF GSGIITSNAS MHECDTKCQT PQGAINSSLP FQNIHPVTIG  300
ECPKYVRSTK LRMVTGLRNI PSIQSRGLFG AIAGFIEGGW TGMIDGWYGY HHQNEQGSGY  360
AADQKSTQNA INGITNKVNS VIEKMNTQFT AVGKEFNNLE KRMENLNKKV DDGFLDIWTY  420
NAELLVLLEN ERTLDFHDSN VKNLYEKVKN QLRNNAKEIG NGCFEFYHKC NNECMESVKN  480
GTYDYPKYSE ESKLNREKID                                             500

SEQ ID NO: 18             moltype = AA   length = 501
FEATURE                   Location/Qualifiers
source                    1..501
                          mol_type = protein
                          organism = Influenza virus
SEQUENCE: 18
DTICIGYHAN NSTDTVDTVL EKNVTVTHSV NLLEDSHNGK LCRLKGIAPL QLGKCSIAGW  60
ILGNPECESL FSKKSWSYIA ETPNSENGTC YPGYFADYEE LREQLSSVSS FERFEIFPKE  120
RSWPKHNVTR GVTASCSHKG KSSFYRNLLW LTEKNGSYPN LSKSYVNNKE KEVLVLWGVH  180
HPSNIEDQKT IYRKENAYVS VVSSNYNRRF TPEIAERPKV RGQAGRINYY WTLLEPGDTI  240
IFEANGNLIA PWYAFALSRG FGSGIITSNA SMDECDTKCQ TPQGAINSSL PFQNVHPVTI  300
GECPKYVRST KLRMVTGLRN IPSIQSRGLF GAIAGFIEGG WTGMIDGWYG YHHQNEQGSG  360
YAADQKSTQN AINGITNKVN SVIEKMNTQF TAVGKEFNKL EKRMENLNKK VDDGFLDIWT  420
YNAELLVLLE NERTLDFHDS NVKNLYEKVK SQLKNNAKEI GNGCFEFYHK CNNECMESVK  480
NGTYDYPKYS EESKLNREKI D                                           501

SEQ ID NO: 19             moltype = AA   length = 501
FEATURE                   Location/Qualifiers
source                    1..501
                          mol_type = protein
                          organism = Influenza virus
SEQUENCE: 19
```

```
DTICIGYHAN NSTDTVDTVL EKNVTVTHSV NLLEDSHNGK LCRLKGIAPL QLGKCNIAGW    60
ILGNPECESL LSKRSWSYIA ETPNSENGAC YPGDFADYEE LREQLSSVSS FERFEIFPKE   120
RSWPKHNITR GVTAACSHAG KSSFYKNLLW LTETDGSYPK LSKSYVNNKE KEVLVLWGVH   180
HPSNIEDQKT LYRKENAYVS VVSSNYNRRF TPEIAERPKV RGQAGRINYY WTLLEPGDTI   240
IFEANGNLIA PWYAFALSRD FGSGIITSNA SMDECDTKCQ TPQGAINSSL PFQNIHPVTI   300
GECPKYVKST KLRMVTGLRN IPSIQSRGLF GAIAGFIEGG WTGMIDGWYG YHHQNEQGSG   360
YAADQKSTQN AINWITNKVN SVIEKMNTQF TAVGKEFNKL EKRMENLNKK VDDGFLDIWT   420
YNAELLVLLE NERTLDFHDS NVKNLYEKVK NQLRNNAKEI GNGCFEFYHK CNNECMESVK   480
NGTYDYPKYS EESKLNREKI D                                             501
```

SEQ ID NO: 20        moltype = AA  length = 500
FEATURE              Location/Qualifiers
source               1..500
                     mol_type = protein
                     organism = Influenza virus SEQUENCE: 20
```
DTICIGYHAN NSTDTVDTVL EKNVTVTHSV NLLENSHNGK LCLLKGIAPL QLGNCSVAGW    60
ILGNPECELL ISKESWSYIV EKPNPENGTC YPGHFADYEE LREQLSSVSS FERFEIFPKE   120
SSWPNHTVTG VSASCSHNGE SSFYRNLLWL TGKNGLYPNL SKSYANNKEK EVLVLWGVHH   180
PPNIGNQKAL YHTENAYVSV VSSHYSRKFT PEIAKRPKVR DQEGRINYYW TLLEPGDTII   240
FEANGNLIAP RYAFALSRGF GSGIINSNAP MDKCDAKCQT PQGAINSSLP FQNVHPVTIG   300
ECPKYVRSAK LRMVTGLRNI PSIQSRGLFG AIAGFIEGGW TGMVDGWYGY HHQNEQGSGY   360
AADQKSTQNA INGITNKVNS VIEKMNTQFT AVGKEFNKLE RRMENLNKKV DDGFIDIWTY   420
NAELLVLLEN ERTLDFHDSN VKNLYEKVKS QLKNNAKEIG NGCFEFYHKC NDECMESVKN   480
GTYDYPKYSE ESKLNREKID                                               500
```

SEQ ID NO: 21        moltype = AA  length = 501
FEATURE              Location/Qualifiers
source               1..501
                     mol_type = protein
                     organism = Influenza virus SEQUENCE: 21
```
DTICIGYHAN NSTDTVDTVL EKNVTVTHSV NLLEDSHNGK LCRLKGIAPL QLGKCSIAGW    60
ILGNPECESL FSKKSWSYIA ETPNSENGTC YPGYFADYEE LREQLSSVSS FERFEIFPKE   120
SSWPKHNVTR GVTASCSHKG KCSFYRNLLW LTEKNGSYPN LSKSYVNNKE KEVLVLWGVH   180
HPSNIEDQKT IYRKENAYVS VVSSHYNRRF TPEIAKRPKV RDQEGRINYY WTLLEPGDTI   240
IFEANGNLIA PWYAFALSRG FGSGIITSNA SMDECDAKCQ TPQGAINSSL PFQNVHPVTI   300
GECPKYVRST KLRMVTGLRN IPSIQSRGLF GAIAGFIEGG WTGMIDGWYG YHHQNEQGSG   360
YAADQKSTQN AINGITNKVN SVIEKMNTQF TAVGKEFNKL EKRMENLNKK VDDGFLDIWT   420
YNAELLVLLE NERTLDFHDS NVKNLYEKVK SQLKNNAKEI GNGCFEFYHK CNNECMESVK   480
NGTYDYPKYS EESKLNREKI D                                             501
```

SEQ ID NO: 22        moltype = AA  length = 501
FEATURE              Location/Qualifiers
source               1..501
                     mol_type = protein
                     organism = Influenza virus SEQUENCE: 22
```
DTICIGYHAN NSTDTVDTVL EKNVTVTHSV NLLEDSHNGK LCRLKGIAPL QLGKCNIAGW    60
ILGNPECESL FSKKSWSYIA ETPNSENGTC YPGYFADYEE LREQLSSVSS FERFEIFPKE   120
RSWPKHNITR GVTAACSHKG KSSFYRNLLW LTEKNGSYPN LSKSYVNNKE KEVLVLWGVH   180
HPSNIEDQKT LYRKENAYVS VVSSNYNRRF TPEIAERPKV RGQAGRINYY WTLLEPGDTI   240
IFEANGNLIA PWHAFALSRG FGSGIITSNA SMDECDTKCQ TPQGAINSSL PFQNIHPVTI   300
GECPKYVRST KLRMVTGLRN IPSIQSRGLF GAIAGFIEGG WTGMIDGWYG YHHQNEQGSG   360
YAADQKSTQN AINGITNKVN SVIEKMNTQF TAVGKEFNKL EKRMENLNKK VDDGFLDIWT   420
YNAELLVLLE NERTLDFHDS NVKNLYEKVK SQLKNNAKEI GNGCFEFYHK CNNECMESVK   480
NGTYDYPKYS EESKLNREKI D                                             501
```

SEQ ID NO: 23        moltype = AA  length = 504
FEATURE              Location/Qualifiers
source               1..504
                     mol_type = protein
                     organism = Influenza virus SEQUENCE: 23
```
DQICIGYHAN NSTEQVDTIM EKNVTVTHAQ DILERTHNGK LCDLNGVKPL ILRDCSVAGW    60
LLGNPMCDEF INVPEWSYIV EKASPANDLC YPGNFNDYEE LKHLLSRINH FEKIQIIPKS   120
SWSNHDASSG VSSACPYLGR SSFFRNVVWL IKKNSAYPTI KRSYNNTNQE DLLVLWGVHH   180
PNDAAEQTKL YQNPTTYISV GTSTLNQRLV PEIATRPKVN GQSGRMEFFW TILKPNDAIN   240
FESNGNFIAP EYAYKIVKKG DSTIMKSELE YGNCNTKCQT PMGAINSSMP FHNIHPLTIG   300
ECPKYVKSNR LVLATGLRNT PQRERRRKKR GLFGAIAGFI EGGWQGMVDG WYGYHHSNEQ   360
GSCYSADKES TQKAIDGVTN KVNSIINKMN TQFEAVGREF NNLERRIENL NKKMEDGFLD   420
VWTYNAELLV LMENERTLDF HDSNVKNLYD KVRLQLRDNA KELGNGCFEF YHKCDNECME   480
SVKNGTYDYP QYSEEARLNR EEIS                                          504
```

SEQ ID NO: 24        moltype = AA  length = 503
FEATURE              Location/Qualifiers
source               1..503
                     mol_type = protein
                     organism = Influenza virus

```
SEQUENCE: 24
DHICIGYHAN NSTEQVDTIM EKNVTVTHAQ DILEKTHNGK LCDLNGVKPL ILKDCSVAGW   60
LLGNPMCDEF INVPEWSYIV EKANPANDLC YPGNFNDYEE LKHLLSRINH FEKIQIIPKD   120
SWSDHEASLG VSSACPYQGN SSFFRNVVWL IKKGNAYPTI KKSYNNTNQE DLLVLWGIHH   180
PNDEAEQTRL YQNPTTYISI GTSTLNQRLV PKIATRSKVN GQSGRIDFFW TILKPNDAIN   240
FESNGNFIAP EYAYKIVKKG DSTIMKSEVE YGNCNTRCQT PMGAINSSMP FHNIHPLTIG   300
ECPKYVKSNK LVLATGLRNS PQRERRRKRG LFGAIAGFIE GGWQGMVDGW YGYHHSNEQG   360
SGYAADKEST QKAIDGVTNK VNSIIDKMNT QFEAVGREFN NLERRIENLN KKMEDGFLDV   420
WTYNAELLVL MENERTLDFH DSNVKNLYDK VRLQLRDNAK ELGNGCFEFY HKCDNECMES   480
VRNGTYDYPQ YSEEARLKRE EIS                                          503

SEQ ID NO: 25              moltype = AA   length = 503
FEATURE                    Location/Qualifiers
source                     1..503
                           mol_type = protein
                           organism = Influenza virus
SEQUENCE: 25
DQICVGYHAN NSTEQVDTIM EKNVTVTHAQ DILEKTHNGK LCNLDGVKPL ILKDCSVAGW   60
LLGNPMCDEF LNVSEWSYIV EKASPANGLC YPGDFNDYEE LKHLLSRINH FEKIKIIPKS   120
SWSNHEASGV SSACSYLGKP SFFRNLVWLI KKNNTYPPIK VNYTNTNQED LLVLWGIHHP   180
NDETEQVKIY QNPTTYISVG TSTLNQRLVP KIATRSKVNG QSGRMEFFWT ILKPNDAINF   240
DSNGNFIAPE YAYKIVKKGD SAIMKSELEY GNCNTKCQTP MGAINSSMPF HNIHPLTIGE   300
CPKYVKSNRL VLATGLRNAP QREGGRRKRG LFGAIAGFIE GGWQGMVDGW YGYHHSNEQG   360
SGYAADKEST QKAIDGITNK VNSIIDKMNT QFEAVGREFN NLERRIENLN KKMEDGFLDV   420
WTYNAELLVL MENERTLDFH DSNVKNLYEK VRLQLRDNAK ELGNGCFEFY HKCDNECMES   480
VKNGTYDYPQ YSEEARLNRE EIS                                          503

SEQ ID NO: 26              moltype = AA   length = 504
FEATURE                    Location/Qualifiers
source                     1..504
                           mol_type = protein
                           organism = Influenza virus
SEQUENCE: 26
DQICIGYHAN NSTEQVDTIM EKNVTVTHAQ DILEKTHNGK LCDLDGVKPL ILRDCSVAGW   60
LLGNPMCDEF INVPEWSYIV EKASPANDLC YPGDFNDYEE LKHLLSRINH FEKIQIIPKS   120
SWSNHEASSG VSSACPYLGK SSFFRNVVWL IKKNSTYPTI KRSYNNTNQE DLLVLWGIHH   180
PNDAAEQTKL YQNPTTYISV GTSTLNQRLV PKIATRSKVN GQSGRMEFFW TILKPNDAIN   240
FESNGNFIAP EYAYKIVKKG DSAIMKSELE YGNCNTKCQT PMGAINSSMP FHNIHPLTIG   300
ECPKYVKSNR LVLATGLRNT PQRERRRKKR GLFGAIAGFI EGGWQGMVDG WYGYHHSNEQ   360
GSGYAADKES TQKAIDGVTN KVNSIIDKMN TQFEAVGREF NNLERRIENL NKKMEDGFLD   420
VWTYNAELLV LMENERTLDF HDSNVKNLYD KVRLQLRDNA KELGNGCFEF YHKCDNECME   480
SVKNGTYDYP QYSEEARLNR EEIS                                         504

SEQ ID NO: 27              moltype = AA   length = 504
FEATURE                    Location/Qualifiers
source                     1..504
                           mol_type = protein
                           organism = Influenza virus
SEQUENCE: 27
DQICIGYHAN NSTEQVDTIM EKNVAVTHAQ DILEKTHNGK LCDLDGVKPL ILRDCSVAGW   60
LLGNPMCDEF INVPEWSYIV EKASPANGLC YPGDFNDYEE LKHLLSRINH FEKIQIIPKS   120
SWSNHEASSG VSSACPYQGK SSFFRNVVWL IKKNSTYPTI KRSYNNTNQE DLLVLWGIHH   180
PNDAAEQTRL YQNPTTYISV GTSTLNQRLV PKIATRSKVN GQSGRMEFFW TILKPNDAIN   240
FESNGNFIAP EYAYKIVKKG DSAIMKSELE YGNCNTKCQT PMGAINSSMP FHNIHPLTIG   300
ECPKYVKSNR LVLATGLRNS PQRERRRKKR GLFGAIAGFI EGGWQGMVDG WYGYHHSNEQ   360
GSGYAADKES TQKAIDGVTN KVNSIIDKMN TQFEAVGREF NNLERRIENL NKKMEDGFLD   420
VWTYNAELLV LMENERTLDF HDSNVKNLYD KVRLQLRDNA KELGNGCFEF YHKCDNECME   480
SVRNGTYDYP QYSEEARLKR EEIS                                         504

SEQ ID NO: 28              moltype = AA   length = 503
FEATURE                    Location/Qualifiers
source                     1..503
                           mol_type = protein
                           organism = Influenza virus
SEQUENCE: 28
QKLPGNDNST ATLCLGHHAV PNGTIVKTIT NDQIEVTNAT ELVQNSSIGE ICDSPHQILD   60
GENCTLIDAL LGDPQCDGFQ NKKWDLFVER SKAYSNCYPY DVPDYASLRS LVASSGTLEF   120
NNESFNWTGV TQNGTSSACI RRSNNSFFSR LNWLTGLNFK YPALNVTMPN NEQFDKLYIW   180
GVHHPVTDKD QIFLYAQSSG RITVSTKRSQ QAVIPNIGYR PRIRNIPSRI SIYWTIVKPG   240
DILLINSTGN LIAPRGYFKI RSGKSSIMRS DAPIGKCNSE CITPNGSIPN DKPFQNVNRI   300
TYGACPRYVK QSTLKLATGM RNVPEKQTRG IFGAIAGFIE NGWEGMVDGW YGFRHQNSEG   360
RGQAADLKST QAAIDQINGK LNRLIGKTNE KFHQIEKEFS EVEGRIQDLE KYVEDTKIDL   420
WSYNAELLVA LENQHTIDLT DSEMNKLFEK TKKQLRENAE DMGNGCFKIY HKCDNACIGS   480
IRNGTYDHDV YRDEALNNRF QIK                                          503

SEQ ID NO: 29              moltype = AA   length = 532
FEATURE                    Location/Qualifiers
source                     1..532
                           mol_type = protein
```

-continued

```
                        organism = Influenza virus
SEQUENCE: 29
DRICTGITSS NSPHVVKTAT QGEVNVTGVI PLTTTPTKSY FANLKGTKTR GKLCPDCLNC   60
TDLDVALGRP MCVGTTPSAK ASILHEVRPV TSGCFPIMHD RTKIRQLANL LRGYENIRLS  120
TQNVIDAEKA PGGPYRLGTS GSCPNATSKS GFFATMAWAV PKDNNKNATN PLTVEVPYIC  180
AEGEDQITVW GFHSDDKTQM KNLYGDSNPQ KFTSSANGVT THYVSQIGGF PDQTEDGGLP  240
QSGRIVVDYM MQKPGKTGTI VYQRGVLLPQ KVWCASGRSK VIKGSLPLIG EADCLHEKYG  300
GLNKSKPYYT GEHAKAIGNC PIWVKTPLKL ANGTKYRPPA KLLKERGFFG AIAGFLEGGW  360
EGMIAGWHGY TSHGAHGVAV AADLKSTQEA INKITKNLNS LSELEVKNLQ RLSGAMDELH  420
NEILELDEKV DDLRADTISS QIELAVLLSN EGIINSEDEH LLALERKLKK MLGPSAVDIG  480
NGCFETKHKC NQTCLDRIAA GTFNAGEFSL PTFDSLNITA ASLNDDGLDN HT          532

SEQ ID NO: 30            moltype = AA  length = 533
FEATURE                  Location/Qualifiers
source                   1..533
                         mol_type = protein
                         organism = Influenza virus
SEQUENCE: 30
DRICTGITSS NSPHVVKTAT QGEVNVTGVI PLTTTPTKSH FANLKGTETR GKLCPKCLNC   60
TDLDVALGRP KCTGKIPSAR VSILHEVRPV TSGCFPIMHD RTKIRQLPNL LRGYEHIRLS  120
THNVINAENA PGGPYKIGTS GSCPNITNGN GFFATMAWAV PKNDKNKTAT NPLTIEVPYI  180
CTEGEDQITV WGFHSDNETQ MAKLYGDSKP QKFTSSANGV TTHYVSQIDG KFPNQTEDGG  240
PQSGRIVVDY MVQKSGKTGT ITYQRGILLP QKVWCASGRS KVIKGSLPLI GEADCLHEKY  300
GGLNKSKPYY TGEHAKAIGN CPIWVKTPLK LANGTKYRPP AKLLKERGFF GAIAGFLEGG  360
WEGMIAGWHG YTSHGAHGVA VAADLKSTQE AINKITKNLN SLSELEVKNL QRLSGAMDEL  420
HNEILELDEK VDDLRADTIS SQIELAVLLS NEGIINSEDE HLLALERKLK KMLGPSAVEI  480
GNGCFETKHK CNQTCLDRIA AGTFDAGEFS LPTFDSLNIT AASLNDDGLD NHT         533

SEQ ID NO: 31            moltype = AA  length = 503
FEATURE                  Location/Qualifiers
source                   1..503
                         mol_type = protein
                         organism = Influenza virus
SEQUENCE: 31
QKLPGNDNST ATLCLGHHAV PNGTIVKTIT NDRIEVTNAT ELVQNSSIGE ICDSPHQILD   60
GENCTLIDAL LGDPQCDGFQ NKKWDLFVER SKAYSNCYPY DVPDYASLRS LVASSGTLEF  120
NNESFNWNGV TQNGTSSACI RRSNNSFFSR LNWLTHLNFK YPALNVTMPN NEQFDKLYIW  180
GVHHPVTDKD QIFLYAQPSG RITVSTKRSQ QAVIPNIGFR PRIRNIPSRI SIYWTIVKPG  240
DILLINSTGN LIAPRGYFKI RSGKSSIMRS DAPIGKCKSE CITPNGSIPN DKPFQNVNRI  300
TYGACPRYVK QSTLKLATGM RNVPEKQTRG IFGAIAGFIE NGWEGMVDGW YGFRHQNSEG  360
RGQAADLKST QAAIDQINGK LNRLIGKTNE KFHQIEKEFS EVEGRIQDLE KYVEDTKIDL  420
WSYNAELLVA LENQHTIDLT DSEMNKLFEK TKKQLRENAE DMGNGCFKIY HKCDNACIGS  480
IRNGTYDHDV YRDEALNNRF QIK                                          503

SEQ ID NO: 32            moltype = AA  length = 213
FEATURE                  Location/Qualifiers
source                   1..213
                         mol_type = protein
                         organism = Influenza virus
SEQUENCE: 32
IAPLQLGNCS VAGWILGNPE CELLISKESW SYIVETPNPE NGTCYPGYFA DYEELREQLS   60
SVSSFERFEI FPKESSWPNH TVTGVSASCS HNGKSSFYRN LLWLTGKNGL YPNLSKSYVN  120
NKEKEVLVLW GVHHPPNIGN QRALYHTENA YVSVVSSHYS RRFTPEIAKR PKVRDQEGRI  180
NYYWTLLEPG DTIIFEANGN LIAPWYAFAL SRG                               213

SEQ ID NO: 33            moltype = AA  length = 213
FEATURE                  Location/Qualifiers
source                   1..213
                         mol_type = protein
                         organism = Influenza virus
SEQUENCE: 33
IAPLQLGNCS VAGWILGNPE CELLISKESW SYIVETPNPE NGTCFPGYFA DYEELREQLS   60
SVSSFERFEI FPKESSWPNH TVTGVSASCS HNGKSSFYRN LLWLTGKNGL YPNLSKSYVN  120
NKEKEVLVLW GVHHPPNIGN QRALYHTENA YVSVVSSHYS RRFTPEIAKR PKVRDQEGRI  180
NYYWTLLEPG DTIIFEANGN LIAPWYAFAL SRG                               213

SEQ ID NO: 34            moltype = AA  length = 214
FEATURE                  Location/Qualifiers
source                   1..214
                         mol_type = protein
                         organism = Influenza virus
SEQUENCE: 34
VAPLHLGKCN IAGWILGNPE CESLSTASSW SYIVETPSSD NGTCYPGDFI DYEELREQLS   60
SVSSFERFEI FPKTSSWPNH DSNKGVTAAC PHAGAKSFYK NLIWLVKKGN SYPKLSKSYI  120
NDKGKEVLVL WGIHHPSTSA DQQSLYQNAD TYVFVGSSRY SKKFKPEIAI RPKVRDQEGR  180
MNYYWTLVEP GDKITFEATG NLVVPRYAFA MERN                              214

SEQ ID NO: 35            moltype = AA  length = 214
FEATURE                  Location/Qualifiers
```

```
source                   1..214
                         mol_type = protein
                         organism = Influenza virus
SEQUENCE: 35
VAPLHLGKCN IAGWILGNPE CESLSTASSW SYIVETPSSD NGTCFPGDFI DYEELREQLS    60
SVSSFERFEI FPKTSSWPNH DSNKGVTAAC PHAGAKSFYK NLIWLVKKGN SYPKLSKSYI   120
NDKGKEVLVL WGIHHPSTSA DQQSLYQNAD TYVFVGSSRY SKKFKPEIAI RPKVRDQEGR   180
MNYYWTLVEP GDKITFEATG NLVVPRYAFA MERN                               214

SEQ ID NO: 36           moltype = AA  length = 213
FEATURE                 Location/Qualifiers
source                  1..213
                        mol_type = protein
                        organism = Influenza virus
SEQUENCE: 36
IPPLELGDCS IAGWLLGNPE CDRLLSVPEW SYIMEKENPR DGLCYPGSFN DYEELKHLLS    60
SVKHFEKVKI LPKDRWTQHT TTGGSRACAV SGNPSFFRNM VWLTKKGSNY PVAKGSYNNT   120
SGEQMLIIWG VHHPNDETEQ RTLYQNVGTY VSVGTSTLNK RSTPDIATRP KVNGQGGRME   180
FSWTLLDMWD TINFESTGNL IAPEYGFKIS KRG                                213

SEQ ID NO: 37           moltype = AA  length = 209
FEATURE                 Location/Qualifiers
source                  1..209
                        mol_type = protein
                        organism = Influenza virus
SEQUENCE: 37
HRILDGIDCT LIDALLGDPH CDVFQNETWD LFVERSKAFS NCYPYDVPDY ASLRSLVASS    60
GTLEFITEGF TWTGVTQNGG SNACKRGPGS GFFSRLNWLT KSGSTYPVLN VTMPNNDNFD   120
KLYIWGVHHP STNQEQTSLY VQASGRVTVS TRRSQQTIIP NIESRPWVRG LSSRISIYWT   180
IVKPGDVLVI NSNGNLIAPR GYFKMRTGK                                     209

SEQ ID NO: 38           moltype = AA  length = 209
FEATURE                 Location/Qualifiers
source                  1..209
                        mol_type = protein
                        organism = Influenza virus
SEQUENCE: 38
HQILDGENCT LIDALLGDPQ CDGFQNKKWD LFVERSKAYS NCYPYDVPDY ASLRSLVASS    60
GTLEFNNESF NWTGVTQNGT SSACIRRSNN SFFSRLNWLT HLKFKYPALN VTMPNNEKFD   120
KLYIWGVHHP GTDNDQIFPY AQASGRITVS TKRSQQTVIP NIGSRPRVRN IPSRISIYWT   180
IVKPGDILLI NSTGNLIAPR GYFKIRSGK                                     209

SEQ ID NO: 39           moltype = AA  length = 232
FEATURE                 Location/Qualifiers
source                  1..232
                        mol_type = protein
                        organism = Influenza virus
SEQUENCE: 39
RTRGKLCPDC LNCTDLDVAL GRPMCVGTTP SAKASILHEV KPVTSGCFPI MHDRTKIRQL    60
PNLLRGYENI RLSTQNVIDA EKAPGGPYRL GTSGSCPNAT SKSGFFATMA WAVPKDNNKN   120
ATNPLTVEVP YICTEGEDQI TVWGFHSDDK TQMKNLYGDS NPQKFTSSAN GVTTHYVSQI   180
GSFPDQTEDG GLPQSGRIVV DYMMQKPGKT GTIVYQRGVL LPQKVWCASG RS           232

SEQ ID NO: 40           moltype = AA  length = 209
FEATURE                 Location/Qualifiers
source                  1..209
                        mol_type = protein
                        organism = Influenza virus
SEQUENCE: 40
HQILDGKNCT LIDALLGDPQ CDGFQNKKWD LFVERSKAYS NCYPYDVPDY ASLRSLVASS    60
GTLEFNNESF NWTGVTQNGT SSACIRRSKN SFFSRLNWLT HLNFKYPALN VTMPNNEQFD   120
KLYIWGVHHP GTDKDQIFLY AQASGRITVS TKRSQQTVSP NIGSRPRVRN IPSRISIYWT   180
IVKPGDILLI NSTGNLIAPR GYFKIRSGK                                     209

SEQ ID NO: 41           moltype = AA  length = 214
FEATURE                 Location/Qualifiers
source                  1..214
                        mol_type = protein
                        organism = Influenza virus
SEQUENCE: 41
IAPLQLGKCN IAGWLLGNPE CDSLLPAKSW SYIVETPNSE NGACFPGDFI DYEELKEQLS    60
SVSSLERFEI FPKESSWPNH NTLKGVTAAC SHRGKSSFYR NLLWLTKTGD SYPKLNNSYV   120
NNKGKEVLVL WGVHHPSSSN EQQSLYHNVN AYVSVVSSNY NRRFTPEIAA RPKVRDQPGR   180
MNYYWTLLEP GDTIIFEATG NLIAPWYAFA LSRG                               214

SEQ ID NO: 42           moltype = AA  length = 214
FEATURE                 Location/Qualifiers
source                  1..214
                        mol_type = protein
```

```
                           organism = Influenza virus
SEQUENCE: 42
IAPLQLGKCS IAGWILGNPE CESLFSKKSW SYIAETPNSE NGTCFPGYFA DYEELREQLS    60
SVSSFERFEI FPKERSWPKH NVTRGVTASC SHKGKSSFYR NLLWLTEKNG SYPNLSKSYV   120
NNKEKEVLVL WGVHHPSNIE DQKTIYRKEN AYVSVVSSNY NRRFTPEIAE RPKVRGQAGR   180
INYYWTLLEP GDTIIFEANG NLIAPWHAFA LSRG                               214

SEQ ID NO: 43            moltype = AA  length = 214
FEATURE                  Location/Qualifiers
source                   1..214
                         mol_type = protein
                         organism = Influenza virus
SEQUENCE: 43
IAPLQLGNCS VAGWILGNPK CESLFSKESW SYIAETPNPE NGTCFPGYFA DYEELREQLS    60
SVSSFERFEI FPKESSWPNH TVTKGVTTSC SHNGKSSFYR NLLWLTEKNG LYPNLSKSYV   120
NNKEKEVLVL WGVHHPSNIR DQRAIYHTEN AYVSVVSSHY SRRFTPEIAK RPKVRGQEGR   180
INYYWTLLEP GDTIIFEANG NLIAPWYAFA LSRG                               214

SEQ ID NO: 44            moltype = AA  length = 214
FEATURE                  Location/Qualifiers
source                   1..214
                         mol_type = protein
                         organism = Influenza virus
SEQUENCE: 44
IAPLQLGNCS IAGWILGNPE CESLFSKKSW SYIAETPNSE NGTCFPGYFA DYEELREQLS    60
SVSSFERFEI FPKESSWPNH TVTKGVTASC SHKGRSSFYR NLLWLTKKNG SYPNLSKSYV   120
NNKEKEVLVL WGVHHPSNIG DQRAIYHTEN AYVSVVSSHY NRRFTPEIAK RPKVRDQEGR   180
INYYWTLLEP GDTIIFEANG NLIAPWYAFA LSRG                               214

SEQ ID NO: 45            moltype = AA  length = 214
FEATURE                  Location/Qualifiers
source                   1..214
                         mol_type = protein
                         organism = Influenza virus
SEQUENCE: 45
IAPLQLGKCS IAGWILGNPE CESLFSKKSW SYIAETPNSE NGTCFPGYFA DYEELREQLS    60
SVSSFERFEI FPKESSWPKH NVTKGVTASC SHKGKSSFYR NLLWLTEKNG SYPNLSKSYV   120
NNKEKEVLVL WGVHHPSNIE DQKTIYRKEN AYVSVVSSHY NRRFTPEIAK RPKVRNQEGR   180
INYYWTLLEP GDTIIFEANG NLIAPWYAFA LSRG                               214

SEQ ID NO: 46            moltype = AA  length = 214
FEATURE                  Location/Qualifiers
source                   1..214
                         mol_type = protein
                         organism = Influenza virus
SEQUENCE: 46
IAPLQLGKCN IAGWILGNPE CESLLSNRSW SYIAETPNSE NGICFPGDFA DYEELREQLS    60
SVSSFERFEI FPKESSWPKH NITRGVTVAC SHAKKSSFYK NLLWLTEANG LYPSLSKSYV   120
NDREKEVLVL WGVHHPSNIE DQRTLYRKEN AYVSVVSSNY NRRFTPEIAE RPKVRGQPGR   180
MNYYWTLLEP GDKIIFEANG NLIAPWYAFA LSRG                               214

SEQ ID NO: 47            moltype = AA  length = 213
FEATURE                  Location/Qualifiers
source                   1..213
                         mol_type = protein
                         organism = Influenza virus
SEQUENCE: 47
IAPLQLGKCN IAGWILGNPE CESLLSERSW SYIVETPNSE NGTCFPGDFI DYEELREQLS    60
SVSSFERFEI FSKESSWPKH TTGGVTAACS HAGKSSFYRN LLWLTEKDGS YPNLNNSYVK   120
KKGKEVLVLW GVHHPSNIKD QQTLYQKENA YVSVVSSNYN RRFTPEIAER PKVRGQAGRI   180
NYYWTLLKPG DTIMFEANGN LIAPWYAFAL SRG                                213

SEQ ID NO: 48            moltype = AA  length = 214
FEATURE                  Location/Qualifiers
source                   1..214
                         mol_type = protein
                         organism = Influenza virus
SEQUENCE: 48
IAPLQLGKCS IAGWILGNPE CESLFSKKSW SYIAETPNSE NGTCFPGYFA DYEELREQLS    60
SVSSFERFEI FPKERSWPKH NVTRGVTASC SHKGKSSFYR NLLWLTEKNG SYPNLSKSYV   120
NNKEKEVLVL WGVHHPSNIE DQKTIYRKEN AYVSVVSSNY NRRFTPEIAE RPKVRGQAGR   180
INYYWTLLEP GDTIIFEANG NLIAPWYAFA LSRG                               214

SEQ ID NO: 49            moltype = AA  length = 214
FEATURE                  Location/Qualifiers
source                   1..214
                         mol_type = protein
                         organism = Influenza virus
SEQUENCE: 49
```

-continued

```
IAPLQLGKCN IAGWILGNPE CESLLSKRSW SYIAETPNSE NGACFPGDFA DYEELREQLS    60
SVSSFERFEI FPKERSWPKH NITRGVTAAC SHAGKSSFYK NLLWLTETDG SYPKLSKSYV    120
NNKEKEVLVL WGVHHPSNIE DQKTLYRKEN AYVSVVSSNY NRRFTPEIAE RPKVRGQAGR    180
INYYWTLLEP GDTIIFEANG NLIAPWYAFA LSRD                                214

SEQ ID NO: 50            moltype = AA   length = 213
FEATURE                  Location/Qualifiers
source                   1..213
                         mol_type = protein
                         organism = Influenza virus
SEQUENCE: 50
IAPLQLGNCS VAGWILGNPE CELLISKESW SYIVEKPNPE NGTCFPGHFA DYEELREQLS    60
SVSSFERFEI FPKESSWPNH TVTGVSASCS HNGESSFYRN LLWLTGKNGL YPNLSKSYAN    120
NKEKEVLVLW GVHHPPNIGI QKALYHTENA YVSVVSSHYS RKFTPEIAKR PKVRDQEGRI    180
NYYWTLLEPG DTIIFEANGN LIAPRYAFAL SRG                                 213

SEQ ID NO: 51            moltype = AA   length = 214
FEATURE                  Location/Qualifiers
source                   1..214
                         mol_type = protein
                         organism = Influenza virus
SEQUENCE: 51
IAPLQLGKCS IAGWILGNPE CESLFSKKSW SYIAETPNSE NGTCFPGYFA DYEELREQLS    60
SVSSFERFEI FPKESSWPKH NVTRGVTASC SHKGKCSFYR NLLWLTEKNG SYPNLSKSYV    120
NNKEKEVLVL WGVHHPSNIE DQKTIYRKEN AYVSVVSSHY NRRFTPEIAK RPKVRDQEGR    180
INYYWTLLEP GDTIIFEANG NLIAPWYAFA LSRG                                214

SEQ ID NO: 52            moltype = AA   length = 214
FEATURE                  Location/Qualifiers
source                   1..214
                         mol_type = protein
                         organism = Influenza virus
SEQUENCE: 52
IAPLQLGKCN IAGWILGNPE CESLFSKKSW SYIAETPNSE NGTCFPGYFA DYEELREQLS    60
SVSSFERFEI FPKERSWPKH NITRGVTAAC SHKGKSSFYR NLLWLTEKNG SYPNLNKSYV    120
NNKEKEVLVL WGVHHPSNIE DQKTLYRKEN AYVSVVSSNY NRRFTPEIAE RPKVRGQAGR    180
INYYWTLLEP GDTIIFEANG NLIAPWHAFA LSRG                                214

SEQ ID NO: 53            moltype = AA   length = 213
FEATURE                  Location/Qualifiers
source                   1..213
                         mol_type = protein
                         organism = Influenza virus
SEQUENCE: 53
VKPLILRDCS VAGWLLGNPM CDEFINVPEW SYIVEKANPT NDLCFPGSFN DYEELKHLLS    60
RINHFEKIQI IPKSSWSDHE ASSGVSSACP YLGSPSFFRN VVWLIKKNST YPTIKKSYNN    120
TNQEDLLVLW GIHHPNDAAE QTRLYQNPTT YISIGTSTLN QRLVPKIATR SKVNGQSGRM    180
EFFWTILKPN DAINFESNGN FIAPEYAYKI VKK                                 213

SEQ ID NO: 54            moltype = AA   length = 213
FEATURE                  Location/Qualifiers
source                   1..213
                         mol_type = protein
                         organism = Influenza virus
SEQUENCE: 54
VKPLILRDCS VAGWLLGNPM CDEFINVPEW SYIVEKASPA NDLCFPGNFN DYEELKHLLS    60
RINHFEKIQI IPKSSWSNHD ASSGVSSACP YLGRSSFFRN VVWLIKKNSA YPTIKRSYNN    120
TNQEDLLVLW GVHHPNDAAE QTKLYQNPTT YISVGTSTLN QRLVPEIATR PKVNGQSGRM    180
EFFWTILKPN DAINFESNGN FIAPEYAYKI VKK                                 213

SEQ ID NO: 55            moltype = AA   length = 213
FEATURE                  Location/Qualifiers
source                   1..213
                         mol_type = protein
                         organism = Influenza virus
SEQUENCE: 55
VKPLILKDCS VAGWLLGNPM CDEFINVPEW SYIVEKANPA NDLCFPGNFN DYEELKHLLS    60
RINHFEKIQI IPKDSWSDHE ASLGVSSACP YQGNSSFFRN VVWLIKKGNA YPTIKKSYNN    120
TNQEDLLVLW GIHHPNDEAE QTRLYQNPTT YISIGTSTLN QRLVPKIATR SKVNGQSGRI    180
DFFWTILKPN DAINFESNGN FIAPEYAYKI VKK                                 213

SEQ ID NO: 56            moltype = AA   length = 212
FEATURE                  Location/Qualifiers
source                   1..212
                         mol_type = protein
                         organism = Influenza virus
SEQUENCE: 56
VKPLILKDCS VAGWLLGNPM CDEFLNVSEW SYIVEKASPA NGLCFPGDFN DYEELKHLLS    60
RINHFEKIKI IPKSSWSNHE ASGVSSACSY LGKPSFFRNL VWLIKKNNTY PPIKVNYTNT    120
```

```
NQEDLLVLWG IHHPNDETEQ VKIYQNPTTY ISVGTSTLNQ RLVPKIATRS KVNGQSGRME   180
FFWTILKPND AINFDSNGNF IAPEYAYKIV KK                                  212

SEQ ID NO: 57              moltype = AA  length = 213
FEATURE                    Location/Qualifiers
source                     1..213
                           mol_type = protein
                           organism = Influenza virus
SEQUENCE: 57
VKPLILRDCS VAGWLLGNPM CDEFINVPEW SYIVEKASPA NDLCFPGDFN DYEELKHLLS   60
RINHFEKIQI IPKSSWSNHE ASSGVSSACP YLGKSSFFRN VVWLIKKNST YPTIKRSYNN   120
TNQEDLLVLW GIHHPNDAAE QTKLYQNPTT YISVGTSTLN QRLVPKIATR SKVNGQSGRM   180
EFFWTILKPN DAINFESNGN FIAPEYAYKI VKK                                213

SEQ ID NO: 58              moltype = AA  length = 213
FEATURE                    Location/Qualifiers
source                     1..213
                           mol_type = protein
                           organism = Influenza virus
SEQUENCE: 58
VKPLILRDCS VAGWLLGNPM CDEFINVPEW SYIVEKASPA NGLCFPGDFN DYEELKHLLS   60
RINHFEKIQI IPKSSWSNHE ASSGVSSACP YQGKSSFFRN VVWLIKKNST YPTIKRSYNN   120
TNQEDLLVLW GIHHPNDAAE QTRLYQNPTT YISVGTSTLN QRLVPKIATR SKVNGQSGRM   180
EFFWTILKPN DAINFESNGN FIAPEYAYKI VKK                                213

SEQ ID NO: 59              moltype = AA  length = 208
FEATURE                    Location/Qualifiers
source                     1..208
                           mol_type = protein
                           organism = Influenza virus
SEQUENCE: 59
HQILDGENCT LIDALLGDPQ CDGFQNKKWD LFVERSKAYS NCFPYDVPDY ASLRSLVASS   60
GTLEFNNESF NWTGVTQNGT SSACIRRSNN SFFSRLNWLT QLNFKYPALN VTMPNNEQFD   120
KLYIWGVHHP VTDKDQIFLY AQSSGRITVS TKRSQQAVIP NIGYRPRIRN IPSRISIYWT   180
IVKPGDILLI NSTGNLIAPR GYFKIRSG                                      208

SEQ ID NO: 60              moltype = AA  length = 231
FEATURE                    Location/Qualifiers
source                     1..231
                           mol_type = protein
                           organism = Influenza virus
SEQUENCE: 60
KTRGKLCPDC LNCTDLDVAL GRPMCVGTTP SAKASILHEV RPVTSGCFPI MHDRTKIRQL   60
ANLLRGYENI RLSTQNVIDA EKAPGGPYRL GTSGSCPNAT SKSGFFATMA WAVPKDNNKN   120
ATNPLTVEVP YICAEGEDQI TVWGFHSDDK TQMKNLYGDS NPQKFTSSAN GVTTHYVSQI   180
GGFPDQTEDG GLPQSGRIVV DYMMQKPGKT GTIVYQRGVL LPQKVWCASG R            231

SEQ ID NO: 61              moltype = AA  length = 232
FEATURE                    Location/Qualifiers
source                     1..232
                           mol_type = protein
                           organism = Influenza virus
SEQUENCE: 61
ETRGKLCPKC LNCTDLDVAL GRPKCTGKIP SARVSILHEV RPVTSGCFPI MHDRTKIRQL   60
PNLLRGYEHI RLSTHNVINA ENAPGGPYKI GTSGSCPNIT GTGSFFATMA WAVPKNDKNK   120
TATNPLTIEV PYICTEGEDQ ITVWGFHSDN ETQMAKLYGD SKPQKFTSSA NGVTTHYVSQ   180
IGGFPNQTED GGLPQSGRIV VDYMVQKSGK TGTITYQRGI LLPQKVWCAS GR           232

SEQ ID NO: 62              moltype = AA  length = 208
FEATURE                    Location/Qualifiers
source                     1..208
                           mol_type = protein
                           organism = Influenza virus
SEQUENCE: 62
QILDGENCTL IDALLGDPQC DGFQNKKWDL FVERSKAYSN CYPYDVPDYA SLRSLVASSG   60
TLEFNNESFN WNGVTQNGTS SACIRRSNNS FFSRLNWLTH LNFKYPALNV TMPNNEQFDK   120
LYIWGVHHPV TDKDQIFLYA QPSGRITVST KRSQQAVIPN IGFRPRIRNI PSRISIYWTI   180
VKPGDILLIN STGNLIAPRG YFKIRSGK                                      208

SEQ ID NO: 63              moltype = DNA  length = 504
FEATURE                    Location/Qualifiers
source                     1..504
                           mol_type = genomic DNA
                           organism = Helicobacter pylori
SEQUENCE: 63
atgttatcaa aagacatcat taagttgcta aacgaacaag tgaataagga aatgaactct   60
tccaacttgt atatgagcat gagttcatgg tgctataccc atagcttaga tggcgcgggg   120
cttttcttgt ttgaccatgc ggctgaagaa tacgagcatg ctaaaaagct tattatcttc   180
ttgaatgaaa acaatgtgcc tgtgcaattg accagcatca gcgcgcctga gcataagttt   240
```

```
gaaggtttga ctcaaatttt ccaaaaagcc tatgaacatg agcaacacat cagcgagtct    300
attaacaata tcgtagatca cgccataaaa agcaaagatc atgcgacttt caatttcttg    360
caatggtatg tggctgaaca gcatgaagaa gaagtgcttt tcaaggatat tttggataaa    420
attgagttga ttggtaatga aaaccatggc ttgtatttag ccgatcagta tgtcaaaggg    480
atcgctaaaa gcaggaaatc ttaa                                           504

SEQ ID NO: 64              moltype = AA   length = 167
FEATURE                    Location/Qualifiers
source                     1..167
                           mol_type = protein
                           organism = Helicobacter pylori
SEQUENCE: 64
MLSKDIIKLL NEQVNKEMNS SNLYMSMSSW CYTHSLDGAG LFLFDHAAEE YEHAKKLIIF    60
LNENNVPVQL TSISAPEHKF EGLTQIFQKA YEHEQHISES INNIVDHAIK SKDHATFNFL    120
QWYVAEQHEE EVLFKDILDK VELIGNENHG LYLADQYVKG IAKSRKS                   167

SEQ ID NO: 65              moltype = DNA   length = 504
FEATURE                    Location/Qualifiers
source                     1..504
                           mol_type = genomic DNA
                           organism = Helicobacter pylori
SEQUENCE: 65
ttaagatttc ctgcttttag cgatcccttt gacatactga tcggctaaat acaagccatg    60
gttttcatta ccaatcaact caattttatc caaaatatcc ttgaaaagca cttcttcttc    120
atgctgttca gccacatacc attgcaagaa attgaaagtc gcatgatctt tgcttttat    180
ggcgtgatct acgatattgt taatagactc gctgatggt tgctcatgtt cataggcttt    240
ttggaaaatt tgagtcaaac cttcaaactt atgctcaggc gcgctgatgc tggtcaattg    300
cacaggcaca ttgttttcat tcaagaagat aataagcttt ttagcatgct cgtattcttc    360
agccgcatgg tcaaacaaga aaagccccgc gccatctaag ctatgggtat agcaccatga    420
actcatgctc atatacaagt tggaagagtt catttcctta ttcacttgtt cgtttagcaa    480
cttaatgatg tcttttgata acat                                           504

SEQ ID NO: 66              moltype =    length =
SEQUENCE: 66
000

SEQ ID NO: 67              moltype = AA   length = 165
FEATURE                    Location/Qualifiers
source                     1..165
                           mol_type = protein
                           organism = Escherichia coli
SEQUENCE: 67
MLKPEMIEKL NEQMNLELYS SLLYQQMSAW CSYHTFEGAA AFLRRHAQEE MTHMQRLFDY    60
LTDTGNLPRI NTVESPFAEY SSLDELFQET YKHEQLITQK INELAHAAMT NQDYPTFNFL    120
QWYVSEQHEE EKLFKSIIDK LSLAGKSGEG LYFIDKELST LDAQN                     165

SEQ ID NO: 68              moltype =    length =
SEQUENCE: 68
000

SEQ ID NO: 69              moltype =    length =
SEQUENCE: 69
000

SEQ ID NO: 70              moltype = AA   length = 173
FEATURE                    Location/Qualifiers
source                     1..173
                           mol_type = protein
                           organism = Rana catesbeiana
SEQUENCE: 70
MESQVRQNFH QDCEAGLNRT VNLKFHSSYV YLSMASYFNR DDVALSNFAK FFRERSEEEK    60
EHAEKLIEYQ NQRGGRVFLQ SVEKPERDDW ANGLEALQTA LKLQKSVNQA LLDLHAVAAD    120
KSDPHMTDFL ESPYLSESVE TIKKLGDHIT SLKKLWSSHP GMAEYLFNKH TLG            173

SEQ ID NO: 71              moltype =    length =
SEQUENCE: 71
000

SEQ ID NO: 72              moltype = DNA   length = 531
FEATURE                    Location/Qualifiers
misc_feature               1..531
                           note = Synthetic
source                     1..531
                           mol_type = other DNA
                           organism = synthetic construct
SEQUENCE: 72
tccggagaga gccaggtgag gcagcagttc agcaaggaca tcgagaagct gctgaacgag    60
caggtgaaca aggagatgca gagcagcaac ctgtacatga gcatgagcag ctggtgctac    120
acccacagcc tggacggcgc cggcctgttc ctgttcgacc acgccgccga ggagtacgag    180
```

```
cacgccaaga agctgatcat cttcctgaac gagaacaacg tgcccgtgca gctgaccagc  240
atcagcgccc ccgagcacaa gttcgagggc ctgacccaga tcttccagaa ggcctacgag  300
cacgagcagc acatcagcga gagcatcaac aacatcgtgg accacgccat caagagcaag  360
gaccacgcca ccttcaactt cctgcagtgg tacgtggccg agcagcacga ggaggaggtg  420
ctgttcaagg acatcctgga caagatcgag ctgatcggca cgagaacca cggcctgtac  480
ctggccgacc agtacgtgaa gggcatcgcc aagagcagga gagcggatc c  531
```

```
SEQ ID NO: 73          moltype = AA  length = 177
FEATURE                Location/Qualifiers
REGION                 1..177
                       note = Synthetic
source                 1..177
                       mol_type = protein
                       organism = synthetic construct
SEQUENCE: 73
SGESQVRQQF SKDIEKLLNE QVNKEMQSSN LYMSMSSWCY THSLDGAGLF LFDHAAEEYE  60
HAKKLIIFLN ENNVPVQLTS ISAPEHKFEG LTQIFQKAYE HEQHISESIN NIVDHAIKSK  120
DHATFNFLQW YVAEQHEEEV LFKDILDKIE LIGNENHGLY LADQYVKGIA KSRKSGS  177
```

```
SEQ ID NO: 74          moltype = DNA  length = 531
FEATURE                Location/Qualifiers
misc_feature           1..531
                       note = Synthetic
source                 1..531
                       mol_type = other DNA
                       organism = synthetic construct
SEQUENCE: 74
ggatccgctc ttcctgctct tggcgatgcc cttcacgtac tggtcggcca ggtacaggcc  60
gtggttctcg ttgccgatca gctcgatctt gtccaggatg tccttgaaca gcacctcctc  120
ctcgtgctgc tcggccacgt accactgcag gaagttgaag gtggcgtggt ccttgctctt  180
gatggcgtgg tccacgatgt tgttgatgct ctcgctgatg tgctgctcgt gctcgtaggc  240
cttctggaag atctgggtca ggccctcgaa cttgtgctcg ggggcgctga tgctggtcag  300
ctgcacgggc acgttgttct cgttcaggaa gatgatcagc ttcttggcgt gctcgtactc  360
ctcggcggcg tggtcgaaca ggaacaggcc ggcgccgtcc aggctgtggg tgtagcacca  420
gctgctcatg ctcatgtaca ggttgctgct ctgcatctcc ttgttcacct gctcgttcag  480
cagcttctcg atgtccttgc tgaactgctg cctcacctgg ctctctccgg a  531
```

```
SEQ ID NO: 75          moltype = DNA  length = 516
FEATURE                Location/Qualifiers
misc_feature           1..516
                       note = Synthetic
source                 1..516
                       mol_type = other DNA
                       organism = synthetic construct
SEQUENCE: 75
tccggagaga gccaggtgag gcagaacttc aagcccgaga tggaggagaa gctgaacgag  60
cagatgaacc tggagctgta cagcagcctg ctgtaccagc agatgagcgc ctggtgcagc  120
taccacacct tcgagggcgc cgccgccttc ctgaggaggc acgcccagga ggagatgacc  180
cacatgcaga ggctgttcga ctacctgacc gacaccggca acctgcccag gatcaacacc  240
gtggagagcc ccttcgccga gtacagcagc ctggacgagc tgttccagga gacctacaag  300
cacgagcagc tgatcaccca gaagatcaac gagctggccc acgccgccat gaccaaccag  360
gactacccca ccttcaactt cctgcagtgg tacgtgagcg agcagcacga ggaggagaag  420
ctgttcaaga gcatcatcga caagctgagc ctggccggca gagcggcga gggcctgtac  480
ttcatcgaca aggagctgag caccctggac ggatcc  516
```

```
SEQ ID NO: 76          moltype = AA  length = 172
FEATURE                Location/Qualifiers
REGION                 1..172
                       note = Synthetic
source                 1..172
                       mol_type = protein
                       organism = synthetic construct
SEQUENCE: 76
SGESQVRQNF KPEMEEKLNE QMNLELYSSL LYQQMSAWCS YHTFEGAAAF LRRHAQEEMT  60
HMQRLFDYLT DTGNLPRINT VESPFAEYSS LDELFQETYK HEQLITQKIN ELAHAAMTNQ  120
DYPTFNFLQW YVSEQHEEEK LFKSIIDKLS LAGKSGEGLY FIDKELSTLD GS  172
```

```
SEQ ID NO: 77          moltype = DNA  length = 516
FEATURE                Location/Qualifiers
misc_feature           1..516
                       note = Synthetic
source                 1..516
                       mol_type = other DNA
                       organism = synthetic construct
SEQUENCE: 77
ggatccgtcc aggtgctca gctccttgtc gatgaagtac aggccctcgc cgctcttgcc  60
ggccaggctc agcttgtcga tgatgctctt gaacagcttc tcctcctcgt gctgctcgct  120
cacgtaccac tgcaggaagt tgaaggtggg gtagcctgg ttggtcatgg cggcgtgggc  180
cagctcgttg atcttctggg tgatcagctg ctcgtgcttg taggtctcct ggaacagctc  240
```

-continued

```
gtccaggctg ctgtactcgg cgaaggggct ctccacggtg ttgatcctgg gcaggttgcc   300
ggtgtcggtc aggtagtcga acagcctctg catgtgggtc atctcctcct gggcgtgcct   360
cctcaggaag gcggcggcgc cctcgaaggt gtggtagctg caccaggcgc tcatctgctg   420
gtacagcagg ctgctgtaca gctccaggtt catctgctcg ttcagcttct cctccatctc   480
gggcttgaag ttctgcctca cctggctctc tccgga                             516

SEQ ID NO: 78          moltype = DNA   length = 792
FEATURE                Location/Qualifiers
source                 1..792
                       mol_type = genomic DNA
                       organism = Thermotoga maritima
SEQUENCE: 78
atggagttcc tgaagaggag cttcgcccct ctgaccgaga agcagtggca ggagatcgac   60
aacagggcca gggagatctt caagacccag ctgtacggca ggaagttcgt ggacgtggag   120
ggcccctacg gctgggagta cgccgcccac cccctgggcg aggtggaggt gctgagcgac   180
gagaacgagg tggtgaagtg gggcctgagg aagagcctgc ccctgatcga gctgagggcc   240
accttcaccc tggacctgtg ggagctggac aacctggaga ggggcaagcc caacgtggac   300
ctgagcagcc tggaggagac cgtgaggaag gtggccgagt tcgaggacga ggtgatcttc   360
aggggctgcg agaagagcgg cgtgaagggc ctgctgagct tcgaggagag gaagatcgag   420
tgcggcagca cccccaagga cctgctggag gccatcgtga gggccctgag catcttcagc   480
aaggacggca tcgagggccc ctacaccctg gtgatcaaca ccgacaggtg gatcaacttc   540
ctgaaggagg aggccggcca ctacccctg gagaagggag taggagagtg cctgaggggc   600
ggcaagatca tcaccacccc caggatcgag gacgccctgg tggtgagcga gaggggcggc   660
gacttcaagc tgatcctggg ccaggacctg agcatcggct acgaggacag ggagaaggac   720
gccgtgaggc tgttcatcac cgagaccttc accttccagg tggtgaaccc cgaggccctg   780
atcctgctga ag                                                       792

SEQ ID NO: 79          moltype = AA   length = 264
FEATURE                Location/Qualifiers
source                 1..264
                       mol_type = protein
                       organism = Thermotoga maritima
SEQUENCE: 79
MEFLKRSFAP LTEKQWQEID NRAREIFKTQ LYGRKFVDVE GPYGWEYAAH PLGEVEVLSD   60
ENEVVKWGLR KSLPLIELRA TFTLDLWELD NLERGKPNVD LSSLEETVRK VAEFEDEVIF   120
RGCEKSGVKG LLSFEERKIE CGSTPKDLLE AIVRALSIFS KDGIEGPYTL VINTDRWINF   180
LKEEAGHYPL EKRVEECLRG GKIITTPRIE DALVVSERGG DFKLILGQDL SIGYEDREKD   240
AVRLFITETF TFQVVNPEAL ILLK                                          264

SEQ ID NO: 80          moltype = DNA   length = 792
FEATURE                Location/Qualifiers
source                 1..792
                       mol_type = genomic DNA
                       organism = Thermotoga maritima
SEQUENCE: 80
cttcagcagg atcagggcct cggggttcac cacctggaag gtgaaggtct cggtgatgaa   60
cagcctcacg gcgtccttct ccctgtcctc gtagccgatg ctcaggtcct ggcccaggat   120
cagcttgaag tcgccgcccc tctcgctcac caccagggcg tcctcgatcc tggggggtggt   180
gatgatcttg ccgcccctca ggcactcctc caccctcttc tccagggggt agtggccggc   240
ctcctccttc aggaagttga tccacctgtc ggtgttgatc accagggtgt aggggccctc   300
gatgccgtcc ttgctgaaga tgctcagggc cctcacgatg gcctccagca ggtccttggg   360
ggtgctgccg cactcgatct tcctctcctc gaagctcagc aggcccttca cgccgctctt   420
ctcgcagccc ctgaagatca cctcgtcctc gaactcggcc accttcctca cggtctcctc   480
caggctgctc aggtccacgt tgggcttgcc cctctccagg ttgtccagct cccacaggtc   540
cagggtgaag gtggccctca gctcgatcag gggcaggctc ttcctcaggc cccacttcac   600
cacctcgttc tcgtcgctca gcacctccac ctcgcccagg gggtgggcgg cgtactccca   660
gccgtagggg ccctccacgt ccacgaactt cctgccgtac agctgggtct tgaagatctc   720
cctggccctg ttgtcgatct cctgccactg cttctcggtc agaggggcga agctcctctt   780
caggaactcc at                                                       792

SEQ ID NO: 81          moltype =    length =
SEQUENCE: 81
000

SEQ ID NO: 82          moltype = AA   length = 192
FEATURE                Location/Qualifiers
REGION                 1..192
                       note = Synthetic
source                 1..192
                       mol_type = protein
                       organism = synthetic construct
SEQUENCE: 82
MSQAIGILEL TSIAAGMELG DAMLKSANVD LLVSKTISPG KFLLMLGGDI GAIQQAIETG   60
TSQAGELLVD SLVLANIHPS VLPAISGLNS VDKRQAVGIV ETWSVAACIS AADRAVKGSN   120
VTLVRVHMAF GIGGKCYMVV AGDVSDVALA VTVASSSAGA YGLLVYASLI PRPHEAMWRQ   180
MVEGLEHHHH HH                                                       192

SEQ ID NO: 83          moltype =    length =
SEQUENCE: 83
```

-continued

```
000

SEQ ID NO: 84              moltype =   length =
SEQUENCE: 84
000

SEQ ID NO: 85              moltype = AA   length = 318
FEATURE                    Location/Qualifiers
SITE                       31
                           note = misc_feature - X can be any naturally occurring
                            amino acid
source                     1..318
                           mol_type = protein
                           organism = Acidianus ambivalens
SEQUENCE: 85
MPKPYVAINM AELKNEPKTF EMFASVGPKV XMVTARHPGF VGFQNHIQIG ILPFGNRYGG   60
AKMDMTKESS TVRVLQYTFW KDWKDHEEMH RQNWSYLFRL CYSCASQMIW GPWEPIYEII   120
YANMPINTEM TDFTAVVGKK FAEGKPLDIP VISQPYGKRV VAFAEHSVIP GKEKQFEDAI   180
VRTLEMLKKA PGFLGAMVLK EIGVSGIGSM QFGAKGFHQV LENPGSLEPD PNNVMYSVPE   240
AKNTPQQYIV HVEWANTDAL MFGMGRVLLY PELRQVHDEV LDTLVYGPYI RILNPMMEGT   300
FWREYLNEQA WRHPQFGG                                                 318

SEQ ID NO: 86              moltype =   length =
SEQUENCE: 86
000

SEQ ID NO: 87              moltype =   length =
SEQUENCE: 87
000

SEQ ID NO: 88              moltype = AA   length = 154
FEATURE                    Location/Qualifiers
source                     1..154
                           mol_type = protein
                           organism = Aquifex aeolicus
SEQUENCE: 88
MQIYEGKLTA EGLRFGIVAS RFNHALVDRL VEGAIDCIVR HGGREEDITL VRVPGSWEIP   60
VAAGELARKE DIDAVIAIGV LIRGATPHFD YIASEVSKGL ANLSLELRKP ITFGVITADT   120
LEQAIERAGT KHGNKGWEAA LSAIEMANLF KSLR                               154

SEQ ID NO: 89              moltype =   length =
SEQUENCE: 89
000

SEQ ID NO: 90              moltype =   length =
SEQUENCE: 90
000

SEQ ID NO: 91              moltype = AA   length = 242
FEATURE                    Location/Qualifiers
source                     1..242
                           mol_type = protein
                           organism = Bacillus stearothermophilus
SEQUENCE: 91
AAAKPATTEG EFPETREKMS GIRRAIAKAM VHSKHTAPHV TLMDEADVTK LVAHRKKFKA   60
IAAEKGIKLT FLPYVVKALV SALREYPVLN TSIDDETEEI IQKHYYNIGI AADTDRGLLV   120
PVIKHADRKP IFALAQEINE LAEKARDGKL TPGEMKGASC TITNIGSAGG QWFTPVINHP   180
EVAILGIGRI AEKPIVRDGE IVAAPMLALS LSFDHRMIDG ATAQKALNHI KRLLSDPELL   240
LM                                                                 242

SEQ ID NO: 92              moltype =   length =
SEQUENCE: 92
000

SEQ ID NO: 93              moltype = DNA   length = 3747
FEATURE                    Location/Qualifiers
source                     1..3747
                           mol_type = genomic DNA
                           organism = Chikungunya virus
SEQUENCE: 93
atggagttca tcccgacgca aactttctat aacagaaggt accaaccccg accctgggcc   60
ccacgcccta caattcaagt aattagacct agaccacgtc cacagaggca ggctgggcaa   120
ctcgcccagc tgatctccgc agtcaacaaa ttgaccatgc gcgcggtacc tcaacagaag   180
cctcgcagaa atcggaaaaa caagaagcaa aggcagaaga agcaggcgcc gcaaaacgac   240
ccaaagcaaa agaagcaacc accacaaaag aagccggctc aaaagaagaa gaaaccaggc   300
cgtaggggaga gaatgtgcat gaaaattgaa aatgattgca tcttcgaagt caagcatgaa   360
ggcaaagtga tgggctacgc atgcctggtg ggggataaag taatgaaacc agcacatgtg   420
aagggaacta tcgacaatgc cgatctggct aaactggcct ttaagcggtc gtctaaatac   480
gatcttgaat gtgcacagat accggtgcac atgaagtctg atgcctcgaa gtttacccac   540
```

```
gagaaacccg aggggtacta taactggcat cacggagcag tgcagtattc aggaggccgg    600
ttcactatcc cgacgggtgc aggcaagccg ggagacagcg gcagaccgat cttcgacaac    660
aaaggacggg tggtggccat cgtcctagga ggggccaacg aaggtgcccg cacggccctc    720
tccgtggtga cgtggaacaa agacatcgtc acaaaaatta cccctgaggg agccgaagag    780
tggagcctcg ccctcccggt cttgtgcctg ttggcaaaca ctacattccc ctgctctcag    840
ccgccttgca caccctgctg ctacgaaaag gaaccggaaa gcaccttgcg catgcttgag    900
gacaacgtga tgagaccggg atactaccag ctactaaaag catcgctgac ttgctctccc    960
caccgccaaa gacgcagtac taaggacaat tttaatgtct ataaagccac aagaccatat   1020
ctagctcatt gtcctgactg cggagaaggg cattcgtgcc acagccctat cgcattggag   1080
cgcatcagaa atgaagcaac ggacggaacg ctgaaaatcc aggtctcttt gcagatcggt   1140
ataaagacag atgacagcca cgattggacc aagctgcgct atatggatag ccatacgcca   1200
gcggacgcgg agcgagccgg attgcttgta aggacttcag caccgtgcac gatcaccggg   1260
accatgggac actttattct cgcccgatgc ccgaaaggag agacgctgac agtgggattt   1320
acggacagca gaaagatcag ccacacatgc acacacccgt tccatcatga accacctgtg   1380
ataggtaggg agaggttcca ctctcgacca caacatggta aagagttacc ttgcagcacg   1440
tacgtgcaga gcaccgctgc cactgctgag gagatagagg tgcatatgcc cccagatact   1500
cctgaccgca cgctgatgac gcagcagtct ggcaacgtga agatcacagt taatgggcag   1560
acggtgcggt acaagtgcaa ctgcggtggc tcaaacgagg gactgacaac cacagacaaa   1620
gtgatcaata actgcaaaat tgatcagtgc catgctgcag tcactaatca caagaattgg   1680
caatacaact cccctttagt cccgcgcaac gctgaactcg gggaccgtaa aggaaagatc   1740
cacatcccat tcccattggc aaacgtgact tgcagagtgc caaaagcaag aaaccctaca   1800
gtaacttacg gaaaaaacca agtcaccatg ctgctgtatc ctgaccatcc gacactcttg   1860
tcttaccgta acatgggaca ggaaccaaat taccacgagg agtgggtgac acacaagaag   1920
gaggttacct tgaccgtgcc tactgagggt ctggaggtca cttgggggcaa caacgaacca   1980
tacaagtact ggccgcagat gtctacgaac ggtactgctc atggtcaccc catgagata   2040
atcttgtact attatgagct gtaccccact atgactgtag tcattgtgtc ggtggccttg   2100
ttcgtgcttc tgtcgatggt gggcacagca gtgggaatgt gtgtgtgcgc acggcgcaga   2160
tgcattacac catatgaatt aacaccagga gccactgttc ccttcctgct cagcctgcta   2220
tgctgcgtca gaacgaccaa ggcggccaca tattacgagg ctgcggcata tctatggaac   2280
gaacagcagc ccctgttctg gttgcaggct cttatcccgc tggccgcctt gatcgtcctg   2340
tgcaactgtc tgaaactctt gccatgctgc tgtaagaccc tggcttttt agccgtaatg   2400
agcatcggtg cccacactgt gagcgcgtac gaacacgtaa cagtgatccc gaacacggtg   2460
ggagtaccgt ataagactct tgtcaacaga ccggggttaca gccccatggt gttggagatg   2520
gagctacaat cagtcacctt ggaaccaaca ctgtcacttg actacatcac gtgcgagtac   2580
aaaactgtca tcccctcccc gtacgtgaag tgctgtggta cagcagagtg caaggacaag   2640
agcctaccag actacagctg caaggtcttt actggagtct acccatttat gtggggcggc   2700
gcctactgct ttgcgacgc cgaaaatacg caattgagcg aggcacatgt agagaaatct   2760
gaatcttgca aaacagagtt tgcatcggcc tacagagccc acaccgcatc ggcgtcggcg   2820
aagctccgcg tcctttacca aggaaacaac attaccgtag ctgcctacgc taacggtgac   2880
catgccgtca cagtaaagga cgccaagttt gtcgtgggcc caatgtcctc cgcctggaca   2940
ccttttgaca caaaatcgt ggtgtacaaa ggcgacgtct acaacatgga ctacccacct   3000
tttggcgcag gaagaccagg acaatttggt gacattcaaa gtcgtacacc ggaaagtaaa   3060
gacgtttatg ccaacactca gttggtacta cagagggccag cggcaggccac ggtacatgta   3120
ccatactctc aggcaccatc tggcttcaag tattggctga aggaacgagg agcatcgcta   3180
cagcacacgg caccgttcgg ttgccagatt gcgacaaacc cggtaagagc tgtaaattgc   3240
gctgtgggga acataccaat ttccatcgac ataccggatg cggcctttac tagggttgtc   3300
gatgcaccct ctgtaacgga catgtcatgc gaagtacacg cctgcactca ctcctccgac   3360
tttgggggcg tcgccatcat caaatacaca gctagcaaga aggtaaatg tgcagtacat   3420
tcgatgacca acgccgttac cattcgagaa gccgacgtag aagtagaggg gaactcccag   3480
ctgcaaatat ccttctcaac agccctggca agcgccgagt ttcgcgtgca agtgtgctcc   3540
acacaagtac actgcgcagc cgcatgccac cctccaaaga accacatagt caattaccca   3600
gcatcacaca ccaccccttgg ggtccaggat atatccacaa cggcaatgtc ttgggtgcag   3660
aagattacgg gaggagtagg attaattgtt gctgttgctg ccttaatttt aattgtggtg   3720
ctatgcgtgt cgtttagcag gcactaa                                        3747
```

```
SEQ ID NO: 94            moltype = AA  length = 1248
FEATURE                  Location/Qualifiers
source                   1..1248
                         mol_type = protein
                         organism = Chikungunya virus
SEQUENCE: 94
MEFIPTQTFY NRRYQPRPWA PRPTIQVIRP RPRPQRQAGQ LAQLISAVNK LTMRAVPQQK    60
PRRNRKNKKQ RQKKQAPQND PKQKKQPPQK KPAQKKKKPG RRERMCMKIE NDCIFEVKHE   120
GKVMGYACLV GDKVMKPAHV KGTIDNADLA KLAFKRSSKY DLECAQIPVH MKSDASKFTH   180
EKPEGYYNWH HGAVQYSGGR FTIPTGAGKP GDSRPIFDN KGRVVAIVLG GANEGARTAL   240
SVVTWNKDIV TKITPEGAEE WSLALPVLCL LANTTFPCSQ PPCTPCCYEK EPESTLRMLE   300
DNVMRPGYYQ LLKASLTCSP HRQRRSTKDN FNVYKATRPY LAHCPDCGEG HSCHSPIALE   360
RIRNEATDGT LKIQVSLQIG IKTDDSHDWT KLRYMDSHTP ADAERAGLLV RTSAPCTITG   420
TMGHFILARC PKGETLTVGF TDSRKISHTC THPFHHEPPV IGRERFHSRP QHGKELPCST   480
YVQSTAATAE EIEVHMPPDT PDRTLMTQQS GNVKITVNGQ TVRYKCNCGG SNEGLTTTDK   540
VINNCKIDQC HAAVTNHKNW QYNSPLVPRN AELGDRKGKI HIPFPLANVT CRVPKARNPT   600
VTYGKNQVTM LLYPDHPTLL SYRNMGQEPN YHEEWVTHKK EVTLTVPTEG LEVTWGNNEP   660
YKYWPQMSTN GTAHGHPHEI ILYYYELYPT MTVVIVSVAS FVLLSMVGTA VGMCVCARRR   720
CITPYELTPG ATVPFLLSLL CCVRTTKAAT YYEAAAYLWN EQQPLFWLQA LIPLAALIVL   780
CNCLKLLPCC CKTLAFLAVM SIGAHTVSAY EHVTVIPNTV GVPYKTLVNR PGYSPMVLEM   840
ELQSVTLEPT LSLDYITCEY KTVIPSPYVK CCGTAECKDK SLPDYSCKVF TGVYPFMWGG   900
AYCFCDAENT QLSEAHVEKS ESCKTEFASA YRAHTASASA KLRVLYQGNN ITVAAYANGD   960
HAVTVKDAKF VVGPMSSAWT PFDNKIVVYK GDVYNMDYPP FGAGRPGQFG DIQSRTPESK  1020
DVYANTQLVL QRPAAGTVHV PYSQAPSGFK YWLKERGASL QHTAPFGCQI ATNPVRAVNC  1080
```

-continued

```
AVGNIPISID IPDAAFTRVV DAPSVTDMSC EVPACTHSSD FGGVAIIKYT ASKKGKCAVH 1140
SMTNAVTIRE ADVEVEGNSQ LQISFSTALA SAEFRVQVCS TQVHCAAACH PPKDHIVNYP 1200
ASHTTLGVQD ISTTAMSWVQ KITGGVGLIV AVAALILIVV LCVSFSRH             1248

SEQ ID NO: 95          moltype = DNA  length = 3747
FEATURE                Location/Qualifiers
source                 1..3747
                       mol_type = genomic DNA
                       organism = Chikungunya virus
SEQUENCE: 95
ttagtgcctg ctaaacgaca cgcatagcac cacaattaaa attaaggcag caacagcaac  60
aattaatcct actcctcccg taatcttctg cacccaagac attgccgttg tggatatatc  120
ctggacccca agggtggtgt gtgatgctgg gtaattgact atgtggtcct ttggagggtg  180
gcatgcgggct gcgcagtgta cttgtgtgga gcacacttgc acgcgaaact cggcgcttgc  240
cagggctgtt gagaaggata tttgcagctg ggagttcccc tctacttcta cgtcggcttc  300
tcgaatggta acggcgttgg tcatcgaatg tactgcacat ttacctttct tgctagctgt  360
gtatttgatg atggcgacgc ccccaaagtc ggaggagtga gtgcaggctg gtacttcgca  420
tgacatgtcc gttacagagg gtgcatcgac aaccctagta aaggccgcat ccggtatgtc  480
gatggaaatt ggtatgttcc ccacagcgca atttacagct cttaccgggt ttgtcgcaat  540
ctggcaaccg aacggtgccg tgtgctgtag cgatgctcct cgttccttca gccaatactt  600
gaagccagat ggtgcctgag agtatggtac atgtaccgtg cctgctgctg gcctctgtag  660
taccaactga gtgttggcat aaacgtcttt actttccggt gtacgacttt gaatgtcacc  720
aaattgtcct ggtcttcctg cgccaaaagg tgggtagtcc atgttgtaga cgtcgccttt  780
gtacaccacg attttgttgt caaaaggtgt ccaggcggag gacattgggc ccacgacaaa  840
cttggcgtcc tttactgtga cggcatggtc accgttagcg taggcagcta cggtaatgtt  900
gtttccttgg taaaggacgc ggagcttcgc cgacgccgat gcgtgtggg ctctgtaggc   960
cgatgcaaac tctgttttgc aagattcaga tttctctaca tgtgcctcgc tcaattgcgt  1020
attttcggcg tcgcaaaagc agtaggcgcc gccccacata aatgggtaga ctccagtaaa  1080
gaccttgcag ctgtagtctg gtaggctctt gtccttgcac tctgctgtac cacagcactt  1140
cacgtacggg gaggggatga cagttttgta ctcgcacgtg atgtagtcaa gtgacagtgt  1200
tggttccaag gtgactgatt gtagctccat ctccaacacc atggggctgt aacccggtct  1260
gttgacaaga gtcttatacg gtactccac cgtgttcggg atcactgtta cgtgttcgta   1320
cgcgctcaca gtgtgggcac cgatgctcat tacggctaaa aaagccaggg tcttacagca  1380
gcatggcaag agtttcagac agttgcacag gacgatcaag gcggccagcg ggataagagc  1440
ctgcaaccag aacaggggct gctgttcgtt ccatagatat gccgcagcct cgtaatatgt  1500
ggccgccttg gtcgttctga cgcagcatag caggctgagc aggaagggaa cagtggctcc  1560
tggtgttaat tcatatggtg taatgcatct gcgcgtgcg cacacacaca ttcccactgc   1620
tgtgcccacc atcgacagaa gcacgaacga ggccaccgac acaatgacta cagtcatagt  1680
ggggtacagc tcataaatagt acaagattat ctcatgtggg tgaccatgag cagtaccgtt  1740
cgtagacatc tgcggccagt acttgtatgg ttcgttgttg ccccaagtga cctccagacc  1800
ctcagtaggc acggtcaagg taacctcctt cttgtgtgtc acccactcct cgtggtaatt  1860
tggttcctgt cccatgttac ggtaagacaa gagtgtcgga tggtcaggat acagcagcat  1920
ggtgacttgg tttttttccgt aagttactgt agggtttctt ctctgcaagt 1980
cacgtttgcc aatgggaatg ggatgtggat cttttccttta cggtccccga gttcagcgtt  2040
gcgcgggact aaaggggagt tgtattgcca attcttgtga ttagtgactg cagcatggca  2100
ctgatcaatt ttgcagttat tgatcacttt gtctgtggtt gtcagtccct cgtttgagcc  2160
accgcagttg cacttgtacc gcaccgtctg cccattaact gtgatcttca cgttgccaga  2220
ctgctgcgtc atcagcgtgc ggtcaggagt atctgggggc atatgcacct ctatctcctc  2280
agcagtggca gcggtgctct gcacgtacgt gctgcaaggt aactctttac catgttgtgg  2340
tcgagagtgg aacctctccc tacctatcac aggtggttca tgatggaacg ggtgtgtgca  2400
tgtgtgggtg atctttctgc tgtccgtaaa tcccactgtc agcgtctctc ctttcgggca  2460
tcgggcgaga ataaagtgtc ccatggtccc ggtgatcgtg cacggtgctg aagtccttac  2520
aagcaatccg gctcgctccg cgtccgctgg cgtatggcta tccatatagc gcagcttggt  2580
ccaatcgtgg ctgtcatctg tctttatccc gatctgcaaa gagacctgga ttttcagcgt  2640
tccgtccgtt gcttcatttc tgatgcgctc caatgcgata gggctgtggc acgaatgccc  2700
ttctccgcag tcaggacaat gagctagata tggtcttgtg gctttataga cattaaaatt  2760
gtccttagta ctgcgtcttt ggcggtgggg agagcaagtc agcgatgctt ttagtagctg  2820
gtagtatccg ggtctcatca cgttgtcctc aagcatgcgc aaggtgcttt ccggttcctt  2880
ttcgtagcag cagggtgtgc aaggcggctg agagcagggg aatgtagtgt ttgccaacag  2940
gcacaagacc gggagggcga ggctccactc ttcggctccc tcaggggtaa tttttgtgac  3000
gatgtctttg ttccacgtca ccacggagag ggccgtgcgg gcaccttcgt tggcccctcc  3060
taggacgatg gccaccaccc gtcctttgtt gtcgaagatc ggtctgccgc tgtctcccgg  3120
cttgcctgca cccgtcggga tagtgaaccg gcctcctgaa tactgcactg ctccgtgatg  3180
ccagttatag tacccctcgg gtttctcgtg ggtaaacttc aggcatcag acttcatgtg   3240
caccggtatc tgtgcacatt caagatcgta tttagacgac cgcttaaagg ccagtttagc  3300
cagatcggca ttgtcgatag ttcccttcac atgtgctggt ttcattactt tatccccac   3360
caggcatgcg tagcccatca ctttgccttc atgcttgact tcgaagatgc aatcattttc  3420
aattttcatg cacattctct ccctacggcc tggtttcttc ttcttttgag ccggcttctt  3480
ttgtggtggt tgcttctttt gctttgggtc gttttgcggc gcctgcttct tctgcctttg  3540
cttcttgttt ttccgatttc tgcgaggctt ctgttgaggt accgcgcgca tggtcaattt  3600
gttgactgcg gagatcagct gggcgagttg cccagcctgc ctctgtggac gtggtctagg  3660
tctaattact tgaattgtag ggcgtggggc ccagggtcgg ggttggtacc ttctgttata  3720
gaaagtttgc gtcgggatga actccat                                      3747

SEQ ID NO: 96          moltype = DNA  length = 1266
FEATURE                Location/Qualifiers
misc_feature           1..1266
                       note = Synthetic
source                 1..1266
```

```
                        mol_type = other DNA
                        organism = synthetic construct
SEQUENCE: 96
atggacagca agggcagcag ccagaagggc agcagactgc tgctgctgct ggtggtgagc      60
aacctgctgc tgcctcaggg cgtgctagcc attgcccctc tgcagctggg caattgttct     120
gtggccggat ggattctggg caaccccgag tgtgagctgc tgatttctaa ggagagctgg     180
agctacatcg tggagacccc caatcctgag aatggcacct gctacctggg ctacttcgcc     240
gattacgagg agctgcgcga gcagctgtct agcgtgtcca gcttcgagag attcgagatc     300
ttccccaagg agtccagctg gcctaatcac acagtgacag gcgtgtctgc cagctgtagc     360
cacaacggca aaagcagctt ctaccggaac ctgctgtggc tgacaggcaa gaatggcctg     420
taccccaacc tgagcaagag ctacgtgaac aacaaggaaa aggaagtgct ggtgctgtgg     480
ggagtgcacc accctcccaa catcggaaat cagcgggccc tgtaccacac agagaacgcc     540
tatgtgagcg tggtgtccag ccactacagc agaagattca cccccgagat cgccaagaga     600
cccaaagtga gagaccagga gggccggatc aattactact ggaccctgct ggagcctgac     660
gataccatca tcttcgaggc caacggcaat ctgatcgccc cttggtatgc ctttgccctg     720
agcagaggcg cctccggaga gagccaggtg aggcagcagt tcagcaagga catcgagaag     780
ctgctgaacg agcaggtgaa caaggagatg cagagcagca acctgtacat gagcatgagc     840
agctggtgct acacccacag cctggacggc gccggcctgt tcctgttcga ccacgccgcc     900
gaggagtacg agcacgccaa gaagctgatc atcttcctga acgagaacaa cgtgcccgtg     960
cagctgacca gcatcagcgc ccccgagcac aagttcgagg gcctgaccca gatcttccag    1020
aaggcctacg agcacgagca gcacatcagc gagagcatca caacatcgt ggaccacgcc     1080
atcaagagca aggaccacgc caccttcaac ttcctgcagt ggtacgtcgc cgagcagcac    1140
gaggaggagg tgctgttcaa ggacatcctg gacaagtcag agctgatcgg caacgagaac    1200
cacgcctgt acctggccga ccagtacgtg aagggcatcg ccaagagcag gaagagcgga    1260
tcctag                                                               1266

SEQ ID NO: 97            moltype = AA  length = 421
FEATURE                 Location/Qualifiers
REGION                  1..421
                        note = Synthetic
source                  1..421
                        mol_type = protein
                        organism = synthetic construct
SEQUENCE: 97
MDSKGSSQKG SRLLLLLVVS NLLLPQGVLA IAPLQLGNCS VAGWILGNPE CELLISKESW      60
SYIVETPNPE NGTCYPGYFA DYEELREQLS SVSSFERFEI FPKESSWPNH TVTGVSASCS     120
HNGKSSFYRN LLWLTGKNGL YPNLSKSYVN NKEKEVLVLW GVHHPPNIGN QRALYHTENA     180
YVSVVSSHYS RRFTPEIAKR PKVRDQEGRI NYYWTLLEPG DTIIFEANGN LIAPWYAFAL     240
SRGASGESQV RQQFSKDIEK LLNEQVNKEM QSSNLYMSMS SWCYTHSLDG AGLFLFDHAA     300
EEYEHAKKLI IFLNENNVPV QLTSISAPEH KFEGLTQIFQ KAYEHEQHIS ESINNIVDHA     360
IKSKDHATFN FLQWYVAEQH EEEVLFKDIL DKIELIGNEN HGLYLADQYV KGIAKSRKSG     420
S                                                                     421

SEQ ID NO: 98            moltype = DNA  length = 1266
FEATURE                 Location/Qualifiers
misc_feature            1..1266
                        note = Synthetic
source                  1..1266
                        mol_type = other DNA
                        organism = synthetic construct
SEQUENCE: 98
ctaggatccg ctcttcctgc tcttggcgat gcccttcacg tactggtcgg ccaggtacag      60
gccgtggttc tcgttgccga tcagctcgat cttgtccagg atgtccttga acagcacctc     120
ctcctcgtgc tgctcggcca cgtaccactg caggaagttg aaggtggcgt ggtccttgct     180
cttgatggcg tggtccacga tgttgttgat gctctcgcta atgtgctgct cgtgctcgta     240
ggccttctgg aagatctggg tcaggccctc gaacttgtgc tcggggggcgc tgatgctggt     300
cagctgcacg ggcacgttgt tctcgttcag gaagatgatc agcttcttgg cgtgctcgta     360
ctcctcggcg gcgtggtcga acaggaacag gccggcgccg tccaggctgt gggtgtagca     420
ccagctgctc atgctcatgt acaggttgct gctctgcatc tccttgttca cctgctcgtt     480
cagcagcttc tcgatgtcct tgctgaactg ctgcctcacc tggctctctc cggaggcgcc     540
tctgctcagg gcaaaggcat accaaggggc gatcagattg ccgttggcct cgaagatgat     600
ggtatcgcca ggctccagca gggtccagta gtaattgatc cggcccctcc tggtctctcac    660
tttgggtctc ttggcgatct cggggggtgaa tcttctgctg tagtggctgg acaccacgct    720
cacataggcg ttctctgtgt ggtacagggc ccgctgattt ccgatgttgg gagggtggtg    780
cactccccac agcaccagca cttccttttc cttgttgttc acgtagctct tgctcaggtt     840
ggggtacagg ccattcttgc ctgtcagcca cagcaggttc cggtagaagc tgcttttgcc     900
gttgtggcta cagctggcag acacgcctgt cactgtgtga ttaggccagc tggactcctt     960
ggggaagatc tcgaatctct cgaagctgga cacgctagac agctgctcgc gcagctcctc    1020
gtaatcggcg aagtagccag ggtagcaggt gccattctca ggattggggg tctccacgat    1080
gtagctccag ctctccttag aaatcagcag ctcacactcg gggttgccca gaatccatcc    1140
ggccacagaa caattgccca gctgcagagg ggcaatggct agcacgccct gaggcagcag    1200
caggttgctc accaccagca gcagcagcag tctgctgccc ttctggctgc tgcccttgct    1260
gtccat                                                               1266

SEQ ID NO: 99            moltype = DNA  length = 1266
FEATURE                 Location/Qualifiers
misc_feature            1..1266
                        note = Synthetic
source                  1..1266
```

```
                         mol_type = other DNA
                         organism = synthetic construct
SEQUENCE: 99
atggacagca agggcagcag ccagaagggc agcagactgc tgctgctgct ggtggtgagc    60
aacctgctgc tgcctcaggg cgtgctagcc attgcccctc tgcagctggg caattgttct   120
gtggccggat ggattctggg caaccccgag tgtgagctgc tgatttctaa ggagagctgg   180
agctacatcg tggagacccc caatcctgag aatggcacct gcttccctgg ctacttcgcc   240
gattacgagg agctgcgcga gcagctgtct agcgtgtcca gcttcgagag attcgagatc   300
ttccccaagg agtccagctg gcctaatcac acagtgacag gcgtgtctgc cagctgtagc   360
cacaacggca aaagcagctt ctaccggaac ctgctgtggc tgacaggcaa gaatggcctg   420
taccccaacc tgagcaagag ctacgtgaac aacaaggaaa aggaagtgct ggtgctgtgg   480
ggagtgcacc accctcccaa catcggaaat cagcgggccc tgtaccacac agagaacgcc   540
tatgtgagcg tggtgtccag ccactacagc agaagattca cccccgagat cgccaagaga   600
cccaaagtga gagaccagga gggccggatc aattactact ggaccctgct ggagcctgac   660
gataccatca tcttcgaggc caacggcaat ctgatcgccc cttggtatgc ctttgccctg   720
agcagaggcg cctccggaga gagccaggtg aggcagcagt tcagcaagga catcgagaag   780
ctgctgaacg agcaggtgaa caaggagatg cagagcagca acctgtacat gagcatgagc   840
agctggtgct acacccacag cctggacggc gccggcctgt tcctgttcga ccacgccgcc   900
gaggagtacg agcacgccaa gaagctgatc atcttcctga acgagaacaa cgtgcccgtg   960
cagctgacca gcatcagcgc ccccgagcac aagttcgagg gcctgacccca gatcttccag  1020
aaggcctacg agcacgagca gcacatcagc gagagcatca caaacatcgt ggaccacgcc  1080
atcaagagca aggaccacgc caccttcaac ttcctgcagt ggtacgtggc cgagcagcac  1140
gaggaggagg tgctgttcaa ggacatcctg gacaagatcg agctgatcgg caacgagaac  1200
cacgcctgt acctggccga ccagtacgtg aagggcatcg ccaagagcag gaagagcgga  1260
tcctag                                                              1266

SEQ ID NO: 100           moltype = AA   length = 421
FEATURE                  Location/Qualifiers
REGION                   1..421
                         note = Synthetic
source                   1..421
                         mol_type = protein
                         organism = synthetic construct
SEQUENCE: 100
MDSKGSSQKG SRLLLLLVVS NLLLPQGVLA IAPLQLGNCS VAGWILGNPE CELLISKESW    60
SYIVETPNPE NGTCFPGYFA DYEELREQLS SVSSFERFEI FPKESSWPNH TVTGVSASCS   120
HNGKSSFYRN LLWLTGKNGL YPNLSKSYVN NKEKEVLVLW GVHHPPNIGN QRALYHTENA   180
YVSVVSSHYS RRFTPEIAKR PKVRDQEGRI NYYWTLLEPG DTIIFEANGN LIAPWYAFAL   240
SRGASGESQV RQQFSKDIEK LLNEQVNKEM QSSNLYMSMS SWCYTHSLDG AGLFLFDHAA   300
EEYEHAKKLI IFLNENNVPV QLTSISAPEH KFEGLTQIFQ KAYEHEQHIS ESINNIVDHA   360
IKSKDHATFN FLQWYVAEQH EEEVLFKDIL DKIELIGNEN HGLYLADQYV KGIAKSRKSG   420
S                                                                   421

SEQ ID NO: 101           moltype = DNA   length = 1266
FEATURE                  Location/Qualifiers
misc_feature             1..1266
                         note = Synthetic
source                   1..1266
                         mol_type = other DNA
                         organism = synthetic construct
SEQUENCE: 101
ctaggatccg ctcttcctgc tcttggcgat gcccttcacg tactggtcgg ccaggtacag    60
gccgtggttc tcgttgccga tcagctcgat cttgtccagg atgtccttga acagcacctc   120
ctcctcgtgc tgctcggcca cgtaccactg caggaagttg aaggtggcgt ggtccttgct   180
cttgatggcg tggtccacga tgttgttgat gctctcgctg atgtgctgct cgtgctcgta   240
ggccttctgg aagatctggg tcaggccctc gaacttgtgc tcgggggcgc tgatgctggt   300
cagctgcacg ggcacgttgt tctcgttcag gaagatgatc agcttcttgg cgtgctcgta   360
ctcctcggcg gcgtggtcga acaggaacag gccggcgccg tccaggctgt gggtgtagca   420
ccagctgctc atgctcatgt acaggttgct gctctgcatc tccttgttca cctgctcgtt   480
cagcagcttc tcgatgtcct tgctgaactg ctgcctcacc tggctctctc cggaggcgcc   540
tctgctcagg gcaaaggcat accaaggggc gatcagattg ccgttggcct cgaagatgat   600
ggtatcgcca ggctccagca gggtccagta gtaattgatc cggcccctcc tggtctctcac   660
tttgggtctc ttggcgatct cgggggtgaa tcttctgctg tagtggctgg acaccacgct   720
cacataggcg ttctctgtgt ggtacagggc ccgctgattt ccgatgttgg gagggtggtg   780
cactccccac agcaccagca cttccttttc cttgttgttc acgtagctct tgctcaggtt   840
ggggtacagg ccattcttgc ctgtcagcca cagcaggttc cggtagaagc tgcttttgcc   900
gttgtggcta cagctggcag acacgcctgt cactgtgtga ttaggccagc tggactcctt   960
ggggaagatc tcgaatctct cgaagctgga cacgctagac agctgctcgc gcagctcctc  1020
gtaatcggcg aagtagccag ggaagcaggt gccattctca ggatcggggg tctccacgat  1080
gtagctccag ctctccttag aaatcagcag ctcacactcg gggttgccca gaatccatcc  1140
ggccacagaa caattgccca gctgcagagg ggcaatggct agcacgccct gaggcagcag  1200
caggttgctc accaccagca gcagcagcag tctgctgccc ttctggctgc tgcccttgct  1260
gtccat                                                              1266

SEQ ID NO: 102           moltype = DNA   length = 1269
FEATURE                  Location/Qualifiers
misc_feature             1..1269
                         note = Synthetic
source                   1..1269
```

-continued

```
                         mol_type = other DNA
                         organism = synthetic construct
SEQUENCE: 102
atggacagca agggcagcag ccagaagggc agcagactgc tgctgctgct ggtggtgagc   60
aacctgctgc tgcctcaggg cgtgctagcc gtggcccccc tgcacctggg caagtgcaac  120
atcgccggct ggattctggg caaccccgag tgcgagagcc tgagcaccgc cagcagctgg  180
agctacatcg tggagacccc cagcagcgac aacggcacct gctaccccgg cgacttcatc  240
gactacgagg agctgcggga gcagctgagc agcgtgagca gcttcgagcg gttcgagatc  300
ttccccaaga ccagcagctg gcccaaccac gacagcaaca agggcgtgac cgccgcctgc  360
ccccacgccg gcgccaagag cttctacaag aacctgatct ggctggtgaa gaagggcaac  420
agctacccca gctgagcaa gagctacatc aacgacaagg caaggaggt gctggtgctg   480
tggggcatcc accaccccag caccagcgcc gaccagcaga gcctgtacca gaacgccgac  540
acctacgtgt tcgtgggcag cagccggtac agcaagaagt tcaagcccga gatcgccatc  600
cggcccaagg tgcgggacca ggagggccgg atgaactact actggaccct ggtggagccc  660
ggcgacaaga tcaccttcga ggccaccggc aacctggtgg tgccccggta cgccttcgcc  720
atggagcgga acgcctccgg agagagccag gtgaggcagc agttcagcaa ggacatcgag  780
aagctgctga acgagcaggt gaacaaggag atgcagagca gcaacctgta catgagcatg  840
agcagctggt gctacaccca cagcctggac ggcggcctgc tgttcctgtt cgaccacgcc  900
gccgaggagt acgagcacgc caagaagctg atcatcttcc tgaacgagaa caacgtgccc  960
gtgcagctga ccagcatcag cgccccccgag cacaagttcg agggcctgac ccagatcttc  1020
cagaaggcct acgagcacga gcagcacatc agcgagagca tcaacaacat cgtggaccac  1080
gccatcaaga gcaaggacca cgccaccttc aacttcctgc agtggtacgt ggccgagcag  1140
cacgaggagg aggtgctgtt caaggacatc ctggacaaga tcgagctgat cggcaacgag  1200
aaccacggcc tgtacctggc cgaccagtac gtgaagggca tcgccaagag caggaagagc  1260
ggatcctag                                                         1269

SEQ ID NO: 103          moltype = AA  length = 422
FEATURE                 Location/Qualifiers
REGION                  1..422
                        note = Synthetic
source                  1..422
                        mol_type = protein
                        organism = synthetic construct
SEQUENCE: 103
MDSKGSSQKG SRLLLLLVVS NLLLPQGVLA VAPLHLGKCN IAGWILGNPE CESLSTASSW   60
SYIVETPSSD NGTCYPGDFI DYEELREQLS SVSSFERFEI FPKTSSWPNH DSNKGVTAAC  120
PHAGAKSFYK NLIWLVKKGN SYPKLSKSYI NDKGKEVLVL WGIHHPSTSA DQQSLYQNAD  180
TYVFVGSSRY SKKFKPEIAI RPKVRDQEGR MNYYWTLVEP GDKITFEATG NLVVPRYAFA  240
MERNASGESQ VRQQFSKDIE KLLNEQVNKE MQSSNLYMSM SSWCYTHSLD GAGLFLFDHA  300
AEEYEHAKKL IIFLNENNVP VQLTSISAPE HKFEGLTQIF QKAYEHEQHI SESINNIVDH  360
AIKSKDHATF NFLQWYVAEQ HEEEVLFKDI LDKIELIGNE NHGLYLADQY VKGIAKSRKS  420
GS                                                                 422

SEQ ID NO: 104          moltype = DNA  length = 1269
FEATURE                 Location/Qualifiers
misc_feature            1..1269
                        note = Synthetic
source                  1..1269
                        mol_type = other DNA
                        organism = synthetic construct
SEQUENCE: 104
ctaggatccg ctcttcctgc tcttggcgat gcccttcacg tactggtcgg ccaggtacag   60
gccgtggttc tcgttgccga tcagctcgat cttgtccagg atgtccttga acagcacctc  120
ctcctcgtgc tgctcggcca cgtaccactg caggaagttg aaggtggcgt ggtccttgct  180
cttgatggcg tggtccacga tgttgttgat gctctcgctg atgtgctgct cgtgctcgta  240
ggccttctgg aagatctggg tcaggccctc gaacttgtgc tcggggggcgc tgatgctggt  300
cagctgcacg ggcacgttgt tctcgttcag gaagatgatc agcttcttgg cgtgctcgta  360
ctcctcggcg gcgtggtcga acaggaacag gccggcgccg tccaggctgt gggtgtagca  420
ccagctgctc atgctcatgt acaggttgct gctctgcatc tccttgttca cctgctcgtt  480
cagcagcttc tcgatgtcct tgctgaactg ctgcctcacc tggctctctc cggaggcgtt  540
ccgctccatg gcgaaggcgt accggggcac caccaggttg ccggtggcct cgaaggtgat  600
cttgtcgccg ggctccacca gggtccagta gtagttcatc cggcccctcc tggtcccgca  660
cttgggccgg atggcgatct cgggcttgaa cttcttgctg taccggctgc tgcccacgaa  720
cacgtaggtg tcggcgttct ggtacaggct ctgctggtcg gcgtggtgc tgggggtgggtg  780
gatgccccac agcaccagca cctccttgcc cttgtcgttg atgtagctct tgctcagctt  840
ggggtagctg ttgcccttct tcaccagcca gatcaggttc ttgtagaagc tcttggcgcc  900
ggcgtggggg caggcggcgg tcacgccctt gttgctgtcg tggttgggcc agctgctggt  960
cttgggggaag atctcgaacc gctcgaagct gctcacgctg ctcagctgct cccgcagctc  1020
ctcgtagtcg atgaagtcgc cggggtagca ggtgccgttg tcgctgctgg gggtctccac  1080
gatgtagctc cagctgctgg cggtgctcag gctctcgcac tcggggttgc ccagaatcca  1140
gccggcgatg ttgcacttgc ccaggtgcag ggggccacg gctagcacgc cctgaggcag  1200
cagcaggttg ctcaccacca gcagcagcag cagtctgctg cccttctggc tgctgccctt  1260
gctgtccat                                                         1269

SEQ ID NO: 105          moltype = DNA  length = 1269
FEATURE                 Location/Qualifiers
misc_feature            1..1269
                        note = Synthetic
source                  1..1269
```

```
                        mol_type = other DNA
                        organism = synthetic construct
SEQUENCE: 105
atggacagca agggcagcag ccagaagggc agcagactgc tgctgctgct ggtggtgagc    60
aacctgctgc tgcctcaggg cgtgctagcc gtggcccccc tgcacctggg caagtgcaac   120
atcgccggct ggattctggg caaccccgag tgcgagagcc tgagcaccgc cagcagctgg   180
agctacatcg tggagacccc cagcagcgac aacggcacct gcttccccgg cgacttcatc   240
gactacgagg agctgcggga gcagctgagc agcgtgagca gcttcgagcg gttcgagatc   300
ttccccaaga ccagcagctg gcccaaccac gacagcaaca agggcgtgac cgccgcctgc   360
ccccacgccg gcgccaagag cttctacaag aacctgatct ggctggtgaa gaagggcaac   420
agctacccca gctgagcaa gagctacatc aacgacaagg gcaaggaggt gctggtgctg   480
tggggcatcc accaccccag caccagcgcc gaccagcaga gcctgtacca gaacgccgac   540
acctacgtgt tcgtgggcag cagccggtac agcaagaagt tcaagcccga gatcgccatc   600
cggcccaagg tgcgggacca ggagggccgg atgaactact actggaccct ggtggagccc   660
ggcgacaaga tcaccttcga ggccaccggc aacctggtgg tgccccggta cgccttcgcc   720
atggagcgga acgcctccgg agagagccag gtgaggcagc agttcagcaa ggacatcgag   780
aagctgctga acgagcaggt gaacaaggag atgcagagca gcaacctgta catgagcatg   840
agcagctggt gctacaccca cagcctggac ggcgccggcc tgttcctgtt cgaccacgcc   900
gccgaggagt acgagcacgc caagaagctg atcatcttcc tgaacgagaa caacgtgccc   960
gtgcagctga ccagcatcag cgcccccgag cacaagttcg agggcctgac ccagatcttc   1020
cagaaggcct acgagcacga gcagcacatc agcgagagca tcaacaacat cgtggaccac   1080
gccatcaaga gcaaggacca cgccaccttc aacttcctgc agtggtacgt ggccgagcag   1140
cacgaggagg aggtgctgtt caaggacatc ctggacaaga tcgagctgat cggcaacgag   1200
aaccacggcc tgtacctggc cgaccagtac gtgaagggca tcgccaagag caggaagagc   1260
ggatcctag                                                           1269

SEQ ID NO: 106        moltype = AA  length = 422
FEATURE               Location/Qualifiers
REGION                1..422
                      note = Synthetic
source                1..422
                      mol_type = protein
                      organism = synthetic construct
SEQUENCE: 106
MDSKGSSQKG SRLLLLLVVS NLLLPQGVLA VAPLHLGKCN IAGWILGNPE CESLSTASSW    60
SYIVETPSSD NGTCFPGDFI DYEELREQLS SVSSFERFEI FPKTSSWPNH DSNKGVTAAC   120
PHAGAKSFYK NLIWLVKKGN SYPKLSKSYI NDKGKEVLVL WGIHHPSTSA DQQSLYQNAD   180
TYVFVGSSRY SKKFKPEIAI RPKVRDQEGR MNYYWTLVEP GDKITFEATG NLVVPRYAFA   240
MERNASGESQ VRQQFSKDIE KLLNEQVNKE MQSSNLYMSM SSWCYTHSLD GAGLFLFDHA   300
AEEYEHAKKL IIFLNENNVP VQLTSISAPE HKFEGLTQIF QKAYEHEQHI SESINNIVDH   360
AIKSKDHATF NFLQWYVAEQ HEEEVLFKDI LDKIELIGNE NHGLYLADQY VKGIAKSRKS   420
GS                                                                  422

SEQ ID NO: 107        moltype = DNA  length = 1269
FEATURE               Location/Qualifiers
misc_feature          1..1269
                      note = Synthetic
source                1..1269
                      mol_type = other DNA
                      organism = synthetic construct
SEQUENCE: 107
ctaggatccg ctcttcctgc tcttggcgat gcccttcacg tactggtcgg ccaggtacag    60
gccgtggttc tcgttgccga tcagctcgat cttgtccagg atgtccttga acagcacctc   120
ctcctcgtgc tgctcggcca cgtaccactg caggaagttg aaggtggcgt ggtccttgct   180
cttgatggcg tggtccacga tgttgttgat gctctcgctg atgtgctgct cgtgctcgta   240
ggccttctgg aagatctggg tcaggccctc gaacttgtgc tcggggcgc tgatgctggt   300
cagctgcacg gcacgttgt tctcgttcag gaagatgatc agcttcttgg cgtgctcgta   360
ctcctcggcg gcgtggtcga acaggaacag gccggcgccg tccaggctgt gggtgtagca   420
ccagctgctc atgctcatgt acaggttgct gctctgcatc tccttgttca cctgctcgtt   480
cagcagcttc tcgatgtcct tgctgaactg ctgcctcacc tggctctctc cggaggcgtt   540
ccgctccatg gcgaaggcgt accggggcac caccaggttg ccggtggcct cgaaggtgat   600
cttgtcgccg ggctccacca gggtccagta gtagttcatc cggccctcct ggtcccgcac   660
cttgggccgg atggcgatct cgggcttgaa cttcttgctg taccggctgc tgcccacgaa   720
cacgtaggtg tcggcgttct ggtacaggct ctgctggtcg gcgctggtgg tggggtgggtg   780
gatgccccac agcaccagca cctccttgcc cttgtcgttg atgtagctct tgctcagctt   840
ggggtagctg ttgcccttct tcaccagcca gatcaggttc ttgtagaagc tcttggcgcc   900
ggcgtggggg caggcggcgg tcacgccctt gttgctgtcg tggttgggcc agctgctggt   960
cttgggggaag atctcgaacc gctcgaagct gctcacgctg ctcagctgct cccgcagctc   1020
ctcgtagtcg atgaagtcgc cggggaagca ggtgccgttg tcgctgctgg gggtctccac   1080
gatgtagctc cagctgctgg cggtgctcag gctctcgcac tcggggttgc ccagaatcca   1140
gccggcgatg ttgcacttgc ccaggtgcag ggggccacg gctagcacgc cctgaggcag   1200
cagcaggttg ctcaccacca gcagcagcag cagtctgctg cccttctggc tgctgccctt   1260
gctgtccat                                                           1269

SEQ ID NO: 108        moltype = DNA  length = 1269
FEATURE               Location/Qualifiers
misc_feature          1..1269
                      note = Synthetic
source                1..1269
```

```
                          mol_type = other DNA
                          organism = synthetic construct
SEQUENCE: 108
atggacagca agggcagcag ccagaagggc agcagactgc tgctgctgct ggtggtgagc    60
aacctgctgc tgcctcaggg cgtgctagcc atcgcccctc tgcagctggg caagtgtaat   120
atcgccggat ggctgctggg aaaccccgag tgtgattctc tgctgcctgc caagagctgg   180
agctacatcg tggagacccc caattctgag aatggcgcct gcttccctgg cgacttcatc   240
gattacgagg agctgaagga gcagctgagt tctgtctcta gcctggagag attcgagatc   300
ttccccaagg agagcagctg gcccaatcac aataccctca agggagtgac agccgcctgt   360
agccacagag gcaagagcag cttctaccgg aatctgctgt ggctgaccaa gaccggcgat   420
agctacccca agctgaacaa cagctacgtg aacaacaagg gcaaggaagt gctggtgctg   480
tggggagtgc accaccctag cagcagcaat gagcagcaga gcctgtacca caacgtgaac   540
gcctatgtga gcgtggtgtc cagcaactac aaccggagat tcacccctga aatcgccgcc   600
agacccaaag tgagagacca gcccggcagg atgaattact actggaccct gctggagcct   660
ggcgatacca tcatctttga ggccaccggc aatctgattg cccccttggta cgcctttgcc   720
ctgagcagag gcgcctccgg agagagccag gtgaggcagc agttcagcaa ggacatcgag   780
aagctgctga cgagcaggt gaacaaggag atgcagagca gcaacctgta catgagcatg   840
agcagctggt gctacaccca cagcctggac ggcgccggcc tgttcctgtt cgaccacgcc   900
gccgaggagt acgagcacgc caagaagctg atcatcttcc tgaacgagaa caacgtgccc   960
gtgcagctga ccagcatcag cgccccccgag cacaagttcg agggcctgac ccagatcttc  1020
cagaaggcct acgagcacga gcagcacatc agcgagagca tcaacaacat cgtggaccac  1080
gccatcaaga gcaaggacca cgccaccttc aacttcctgc agtggtacgt ggccgagcag  1140
cacgaggagg aggtgctgtt caaggacatc ctggacaaga tcgagctgat cggcaacgag  1200
aaccacggcc tgtacctggc cgaccagtac gtgaagggca tcgccaagag caggaagagc  1260
ggatcctag                                                          1269

SEQ ID NO: 109         moltype = AA  length = 422
FEATURE                Location/Qualifiers
REGION                 1..422
                       note = Synthetic
source                 1..422
                       mol_type = protein
                       organism = synthetic construct
SEQUENCE: 109
MDSKGSSQKG SRLLLLLVVS NLLLPQGVLA IAPLQLGKCN IAGWLLGNPE CDSLLPAKSW    60
SYIVETPNSE NGACFPGDFI DYEELKEQLS SVSSLERFEI FPKESSWPNH NTLKGVTAAC   120
SHRGKSSFYR NLLWLTKTGD SYPKLNNSYV NNKGKEVLVL WGVHHPSSSN EQQSLYHVN N   180
AYVSVVSSNY NRRFTPEIAA RPKVRDQPGR MNYYWTLLEP GDTIIFEATG NLIAPWYAFA   240
LSRGASGESQ VRQQFSKDIE KLLNEQVNKE MQSSNLYMSM SSWCYTHSLD GAGLFLFDHA   300
AEEYEHAKKL IIFLNENNVP VQLTSISAPE HKFEGLTQIF QKAYEHEQHI SESINNIVDH   360
AIKSKDHATF NFLQWYVAEQ HEEEVLFKDI LDKIELIGNE NHGLYLADQY VKGIAKSRKS   420
GS                                                                  422

SEQ ID NO: 110         moltype = DNA  length = 1269
FEATURE                Location/Qualifiers
misc_feature           1..1269
                       note = Synthetic
source                 1..1269
                       mol_type = other DNA
                       organism = synthetic construct
SEQUENCE: 110
ctaggatccg ctcttcctgc tcttggcgat gcccttcacg tactggtcgg ccaggtacag    60
gccgtggttc tcgttgccga tcagctcgat cttgtccagg atgtccttga acagcacctc   120
ctcctcgtgt tgctcggcca cgtaccactg caggaagttg aaggtggcgt ggtccttgct   180
cttgatggcg tggtccacga tgttgttgat gctctcgctg atgtgctgct cgtgctcgta   240
ggccttctgg aagatctggg tcaggccctc gaacttgtgc tcggggcgcg tgatgctggt   300
cagctgcacg ggcacgttgt tctcgttcag gaagatgatc agcttcttgg cgtgctcgta   360
ctcctcggcg gcgtggtcga acaggaacag gccggcgccg tccaggctgt gggtgtagca   420
ccagctgctc atgctcatgt acaggttgct gctctgcatc tccttgttca cctgctcgtt   480
cagcagcttc tcgatgtcct tgctgaactg ctgcctcacc tggctctctc cggaggcgcc   540
tctgctcagg gcaaaggcgt accaaggggc aatcagattg ccggtggcct caaagatgat   600
ggtatcgcca ggtccagca gggtccagta gtaattcatc ctgccgggct ggtctctcac   660
tttgggtctg gcggcgattt cagggggtgaa tctccggttg tagttgctgg acaccacgct   720
cacataggcg ttcacgttgt ggtacaggct ctgctgctca ggggtctgac taggtggct   780
cactccccac agcaccagca cttccttgcc cttgttgttc acgtagcgt tgttcagctt   840
ggggtagcta tcgccggtct tggtcagcca cagcagattc cggtagaagc tgctcttgcc   900
tctgtggcta caggcggctg tcactccctt cagggtattg tgattgggcc agctgctctc   960
cttggggaag atctcgaatc tctccaggct agagacagaa ctcagctgct ccttcagctc  1020
ctcgtaatcg atgaagtcgc cagggaagca ggcgccattc tcagaattgg gggtctccac  1080
gatgtagctc cagctcttgg caggcagcag agaatcacac tcggggtttc ccagcagcca  1140
tccggcgata ttcacttgc ccagctgcag aggggcgatg ctagcacgc cctgaggcag  1200
cagcaggttg ctcaccacca gcagcagcag cagtctgctg cccttctggc tgctgccctt  1260
gctgtccat                                                          1269

SEQ ID NO: 111         moltype = DNA  length = 1269
FEATURE                Location/Qualifiers
misc_feature           1..1269
                       note = Synthetic
source                 1..1269
```

-continued

```
                         mol_type = other DNA
                         organism = synthetic construct
SEQUENCE: 111
atggacagca agggcagcag ccagaagggc agcagactgc tgctgctgct ggtggtgagc    60
aacctgctgc tgcctcaggg cgtgctagcc attgcccccc tgcagctggg caagtgcagc   120
attgccggct ggattctggg caaccccgag tgcgagagcc tgttcagcaa gaagagctgg    180
tcctacattg ccgagacacc caacagcgag aacggcacct gtttccccgg ctacttcgcc    240
gactacgagg aactgcggga gcagctgagc agcgtgtcca gcttcgagcg gttcgagatc    300
ttccccaaag agcggagctg gcccaagcac aacgtgacca gaggcgtgac cgccagctgc    360
tctcacaagg gcaagagcag cttctaccgg aacctgctgt ggctgaccga gaagaacggc    420
agctacccca acctgagcaa gagctacgtg aacaacaaag agaaagaggt cctggtcctc    480
tggggcgtgc accaccctag caacatcgag gaccagaaaa ccatctaccg gaaagaaaac    540
gcctacgtgt ccgtggtgtc cagcaactac aaccggcggt tcacccccga gatcgccgag    600
aggcctaaag tgcggggcca ggccggcaga atcaactact actggaccct gctggaaccc    660
ggcgacacca tcatcttcga ggccaacggc aacctgatcg cccttggca cgcctttgcc    720
ctgagcagag gcgcctccgg agagagccag gtgaggcagc agttcagcaa ggacatcgag    780
aagctgctga acgagcaggt gaacaaggag atgcagagca gcaacctgta catgagcatg    840
agcagctggt gctacaccca cagcctggac ggcgcccgggc tgttcctgtt cgaccacgcc    900
gccgaggagt acgagcacgc caagaagctg atcatcttcc tgaacgagaa caacgtgccc    960
gtgcagctga ccagcatcag cgcccccgag cacaagttcg agggcctgac ccagatcttc   1020
cagaaggcct acgagcacga gcagcacatc agcgagagca tcaacaacat cgtggaccac   1080
gccatcaaga gcaaggacca cgccaccttc aacttcctgc agtggtacgt ggccgagcag   1140
cacgaggagg aggtgctgtt caaggacatc ctggacaaga tcgagctgat cggcaacgag   1200
aaccacggcc tgtacctggc cgaccagtac gtgaagggca tcgccaagag caggaagagc   1260
ggatcctag                                                          1269

SEQ ID NO: 112        moltype = AA   length = 422
FEATURE               Location/Qualifiers
REGION                1..422
                      note = Synthetic
source                1..422
                      mol_type = protein
                      organism = synthetic construct
SEQUENCE: 112
MDSKGSSQKG SRLLLLLVVS NLLLPQGVLA IAPLQLGKCS IAGWILGNPE CESLFSKKSW    60
SYIAETPNSE NGTCFPGYFA DYEELREQLS SVSSFERFEI FPKERSWPKH NVTRGVTASC   120
SHKGKSSFYR NLLWLTEKNG SYPNLSKSYV NNKEKEVLVL WGVHHPSNIE DQKTIYRKEN   180
AYVSVVSSNY NRRFTPEIAE RPKVRGQAGR INYYWTLLEP GDTIIFEANG NLIAPWHAFA   240
LSRGASGESQ VRQQFSKDIE KLLNEQVNKE MQSSNLYMSM SSWCYTHSLD GAGLFLFDHA   300
AEEYEHAKKL IIFLNENNVP VQLTSISAPE HKFEGLTQIF QKAYEHEQHI SESINNIVDH   360
AIKSKDHATF NFLQWYVAEQ HEEEVLFKDI LDKIELIGNE NHGLYLADQY VKGIAKSRKS   420
GS                                                                 422

SEQ ID NO: 113        moltype = DNA   length = 1269
FEATURE               Location/Qualifiers
misc_feature          1..1269
                      note = Synthetic
source                1..1269
                      mol_type = other DNA
                      organism = synthetic construct
SEQUENCE: 113
ctaggatccg ctcttcctgc tcttggcgat gcccttcacg tactggtcgg ccaggtacag    60
gccgtggttc tcgttgccga tcagctcgat cttgtccagg atgtccttga acagcacctc   120
ctcctcgtgt tgctcggcca cgtaccactg caggaagttg aaggtggcgt ggtccttgct   180
cttgatggcg tggtccacga tgttgttgat gctctcgctg atgtgctgct cgtgctcgta   240
ggccttctgg aagatctggg tcaggccctc gaacttgtgc tcgggggcgc tgatgctggt   300
cagctgcacg ggcacgttgt tctcgttcag gaagatgatc agcttcttgg cgtgctcgta   360
ctcctcggcg gcgtggtcga acaggaacag gccggcgccg tccaggctgt gggtgtagca   420
ccagctgctc atgctcatgt acaggttgct gctctgcatc tccttgttca cctgctcgtt   480
cagcagcttc tcgatgtcct tgctgaactg ctgcctcacc tggctctctc cggaggcgcc   540
tctgctcagg gcaaaggcgt gccaaggggc gatcaggttg ccgttggcct cgaagatgat   600
ggtgtcgccg ggttccagca gggtccagta gtagttgatt ctgccggcct ggccccgcac   660
tttaggcctc tcggcgatct cggggggtgaa ccgccggttg tagttgctgg acaccacgga   720
cacgtaggcg ttttcttttcc ggtagatggt tttctggtcc tcgatgttg gtggtctcggc   780
cacgccccag aggaccagga cctctttctc tttgttgttc acgtagtcct tgctcaggtt   840
ggggtagctg ccgttcttct cggtcagcca cagcaggttc cggtagaagc tgctcttgcc   900
cttgtgagag cagctggcgg tcacgcctct ggtcacgttg tgcttgggcc agctccgctc   960
tttggggaag atctcgaacc gctcgaagct ggacacgctg ctcagctgct cccgcagttc   1020
ctcgtagtcg gcgaagtagc cggggaaaca ggtgccgttc tcgctgttgg gtgtctcggc   1080
aatgtaggac cagctcttct tgctgaacag gctctcgcac tcggggttgc ccagaatcca   1140
gccggcaatg ctgcacttgc ccagctgcag ggggcaatg gctagcacgc cctgaggcag   1200
cagcaggttg ctcaccacca gcagcagcag cagtctgctg cccttctggc tgctgccctt   1260
gctgtccat                                                          1269

SEQ ID NO: 114        moltype = DNA   length = 1269
FEATURE               Location/Qualifiers
misc_feature          1..1269
                      note = Synthetic
source                1..1269
```

```
                          mol_type = other DNA
                          organism = synthetic construct
SEQUENCE: 114
atggacagca agggcagcag ccagaagggc agcagactgc tgctgctgct ggtggtgagc    60
aacctgctgc tgcctcaggg cgtgctagcc atcgcccctc tgcagctggg caactgcagc   120
gtggctggct ggattctggg gaatccaaag tgtgagagtc tgttttcaaa agaatcttgg   180
agttacatcg cagagacccc caaccctgaa aatggaacat gcttccctgg ctatttcgcc   240
gattatgagg aactgaggga gcagctgagc tccgtgtcta gtttcgagcg ctttgaaatt   300
ttcccaaagg aatcaagctg gcccaaccac accgtgacaa aaggcgtcac cacatcatgt   360
agccataacg ggaagtcctc tttttaccgc aatctgctgt ggctgacaga gaagaacggc   420
ctgtacccaa atctgtccaa gtcttacgtg aacaataagg agaaggaagt gctggtcctg   480
tggggcgtcc accatcccag caacatccga gaccagcggg caatctacca cacagagaat   540
gcctatgtga gcgtggtcag ttcacattac agccggcggt tcaccccga  gatcgccaag   600
agaccaaaag tgaggggcca ggaagggcga attaactact attggactct gctggagcca   660
ggagatacca tcattttcga agccaacggc aatctgatcg ctccctggta tgcatttgcc   720
ctgtcccgcg gagcctccgg agagagccag gtgaggcagc agttcagcaa ggacatcgag   780
aagctgctga acgagcaggt gaacaaggag atgcagagca gcaacctgta catgagcatg   840
agcagctggt gctacaccca cagcctggac ggcggccggc tgttcctgtt cgaccacgcc   900
gccgaggagt acgagcacgc caagaagctg atcatcttcc tgaacgagaa caacgtgccc   960
gtgcagctga ccagcatcag cgcccccgag cacaagttcg agggcctgac ccagatcttc  1020
cagaaggcct acgagcacga gcagcacatc agcgagagca tcaacaacat cgtggaccac  1080
gccatcaaga gcaaggacca cgccaccttc aacttcctgc agtggtacgt ggccgagcag  1140
cacgaggagg aggtgctgtt caaggacatc ctggacaaga tcgagctgat cggcaacgag  1200
aaccacggcc tgtacctggc cgaccagtac gtgaagggca tcgccaagag caggaagagc  1260
ggatcctag                                                          1269

SEQ ID NO: 115          moltype = AA   length = 422
FEATURE                 Location/Qualifiers
REGION                  1..422
                        note = Synthetic
source                  1..422
                        mol_type = protein
                        organism = synthetic construct
SEQUENCE: 115
MDSKGSSQKG SRLLLLLVVS NLLLPQGVLA IAPLQLGNCS VAGWILGNPK CESLFSKESW    60
SYIAETPNPE NGTCFPGYFA DYEELREQLS SVSSFERFEI FPKESSWPNH TVTKGVTTSC   120
SHNGKSSFYR NLLWLTEKNG LYPNLSKSYV NNKEKEVLVL WGVHHPSNIR DQRAIYHTEN   180
AYVSVVSSHY SRRFTPEIAK RPKVRGQEGR INYYWTLLEP GDTIIFEANG NLIAPWYAFA   240
LSRGASGESQ VRQQFSKDIE KLLNEQVNKE MQSSNLYMSM SSWCYTHSLD GAGLFLFDHA   300
AEEYEHAKKL IIFLNENNVP VQLTSISAPE HKFEGLTQIF QKAYEHEQHI SESINNIVDH   360
AIKSKDHATF NFLQWYVAEQ HEEEVLFKDI LDKIELIGNE NHGLYLADQY VKGIAKSRKS   420
GS                                                                  422

SEQ ID NO: 116          moltype = DNA   length = 1269
FEATURE                 Location/Qualifiers
misc_feature            1..1269
                        note = Synthetic
source                  1..1269
                        mol_type = other DNA
                        organism = synthetic construct
SEQUENCE: 116
ctaggatccg ctcttcctgc tcttggcgat gcccttcacg tactggtcgg ccaggtacag    60
gccgtggttc tcgttgccga tcagctcgat cttgtccagg atgtccttga acagcacctc   120
ctcctcgtgt tgctcggcca cgtaccactg caggaagttg aaggtggcgt ggtccttgct   180
cttgatggcg tggtccacga tgttgttgat gctctcgctg atgtgctgct cgtgctcgta   240
ggccttctgg aagatctggg tcaggccctc gaacttgtgc tcggggggcgc tgatgctggt   300
cagctgcacg ggcacgttgt tctcgttcag gaagatgatc agcttcttgg cgtgctcgta   360
ctcctcggcg gcgtggtcga acaggaacag gccggcgccg tccaggctgt gggtgtagca   420
ccagctgctc atgctcatgt acaggttgct gctctgcatc tccttgttca cctgctcgtt   480
cagcagcttc tcgatgtcct tgctgaactg ctgcctcacc tggctctctc cggaggctcc   540
gcgggacagg gcaaatgcat accagggagc gatcagattg ccgttggctt cgaaaatgat   600
ggtatctcct ggctccagca gagtccaata gtagttaatt cgcccttcct ggcccctcac   660
ttttggtctc ttggcgatct cggggggtgaa ccgccggctg taatgtgaac tgaccacgct   720
cacataggca ttctctgtgt ggtagattgc ccgctggtct cggatgttgc tgggatgggtg   780
gacgccccac aggaccagca cttccttctc cttattgttc acgtaagact tggacagatt   840
tgggtacagg ccgttcttct ctgtcagcca cagcagattg cggtaaaaag aggacttccc   900
gttatggcta catgatgtgg tgacgccttt tgtcacggtg tggttgggcc agcttgattc   960
ctttgggaaa atttcaaagc gctcgaaact agacacggag ctcagctgct ccctcagttc  1020
ctcataatcg gcgaaatagc cagggaagca tgttccattt tcaggggttgg gggtctctgc  1080
gatgtaactc caagattctt ttgaaaacag actctcacac tttggattcc ccagaatcca  1140
gccagccacg ctgcagttgc ccagctgcag aggggcgatg gctagcacgc cctgaggcag  1200
cagcaggttg ctcaccacca gcagcagcag cagtctgctg cccttctggc tgctgccctt  1260
gctgtccat                                                          1269

SEQ ID NO: 117          moltype = DNA   length = 1269
FEATURE                 Location/Qualifiers
misc_feature            1..1269
                        note = Synthetic
source                  1..1269
```

```
                        mol_type = other DNA
                        organism = synthetic construct
SEQUENCE: 117
atggacagca  agggcagcag  ccagaagggc  agcagactgc  tgctgctgct  ggtggtgagc  60
aacctgctgc  tgcctcaggg  cgtgctagcc  attgcccctc  tgcagctggg  caattgttct  120
atcgccggct  ggattctggg  aaatcccgag  tgcgagagcc  tgttcagcaa  gaagtcctgg  180
tcctatatcg  ccgagacacc  caacagcgag  aatggcacct  gtttccctgg  ctacttcgcc  240
gattacgagg  aactgagaga  gcagctgtcc  tctgtctcca  gcttcgagcg  gttcgagatc  300
ttccccaaag  agtccagctg  gcccaatcac  acagtgacca  agggcgtgac  cgcctcttgc  360
agccacaagg  gcagaagcag  cttctaccgg  aacctgctgt  ggctgaccaa  gaagaacggc  420
agctacccca  atctgagcaa  gagctacgtg  aacaacaaag  aaaaagaggt  gctggtcctc  480
tggggagtgc  accaccctag  caacatcgga  gatcagcggg  ccatctacca  caccgagaac  540
gcctatgtgt  ccgtggtgtc  cagccactac  aacagaagat  tcaccccga   gatcgccaaa  600
agacccaaag  tgcgggacca  ggaaggcaga  atcaactact  actggacct   gctggaacct  660
ggcgacacca  tcatcttcga  ggccaacggc  aatctgatcg  cccttggta   tgcctttgcc  720
ctgagcagag  cgcctccgg   agagagccag  gtgaggcagc  agttcagcaa  ggacatcgag  780
aagctgctga  acgagcaggt  gaacaaggag  atgcagagca  gcaacctgta  catgagcatg  840
agcagctggt  gctacaccca  cagcctggac  ggcggcctgc  tgttcctgtt  cgaccacgcc  900
gccgaggagt  acgagcacgc  caagaagctg  atcatcttcc  tgaacgagaa  caacgtgccc  960
gtgcagctga  ccagcatcag  cgcccccgag  cacaagttcg  agggcctgac  ccagatcttc  1020
cagaaggcct  acgagcacga  gcagcacatc  agcgagagca  tcaacaacat  cgtggaccac  1080
gccatcaaga  gcaaggacca  cgccaccttc  aacttcctgc  agtggtacgt  ggccgagcag  1140
cacgaggagg  aggtgctgtt  caaggacatc  ctggacaaga  tcgagctgat  cggcaacgag  1200
aaccacggcc  tgtacctggc  cgaccagtac  gtgaagggca  tcgccaagag  caggaagagc  1260
ggatcctag                                                               1269

SEQ ID NO: 118          moltype = AA  length = 422
FEATURE                 Location/Qualifiers
REGION                  1..422
                        note = Synthetic
source                  1..422
                        mol_type = protein
                        organism = synthetic construct
SEQUENCE: 118
MDSKGSSQKG  SRLLLLLVVS  NLLLPQGVLA  IAPLQLGNCS  IAGWILGNPE  CESLFSKKSW  60
SYIAETPNSE  NGTCFPGYFA  DYEELREQLS  SVSSFERFEI  FPKESSWPNH  TVTKGVTASC  120
SHKGRSSFYR  NLLWLTKKNG  SYPNLSKSYV  NNKEKEVLVL  WGVHHPSNIG  DQRAIYHTEN  180
AYVSVVSSHY  NRRFTPEIAK  RPKVRDQEGR  INYYWTLLEP  GDTIIFEANG  NLIAPWYAFA  240
LSRGASGESQ  VRQQFSKDIE  KLLNEQVNKE  MQSSNLYMSM  SSWCYTHSLD  GAGLFLFDHA  300
AEEYEHAKKL  IIFLNENNVP  VQLTSISAPE  HKFEGLTQIF  QKAYEHEQHI  SESINNIVDH  360
AIKSKDHATF  NFLQWYVAEQ  HEEEVLFKDI  LDKIELIGNE  NHGLYLADQY  VKGIAKSRKS  420
GS                                                                      422

SEQ ID NO: 119          moltype = DNA  length = 1269
FEATURE                 Location/Qualifiers
misc_feature            1..1269
                        note = Synthetic
source                  1..1269
                        mol_type = other DNA
                        organism = synthetic construct
SEQUENCE: 119
ctaggatccg  ctcttcctgc  tcttggcgat  gcccttcacg  tactggtcgg  ccaggtacag  60
gccgtggttc  tcgttgccga  tcagctcgat  cttgtccagg  atgtccttga  acagcacctc  120
ctcctcgtgt  tgctcggcca  cgtaccactg  caggaagttg  aaggtggcgt  ggtccttgct  180
cttgatggcg  tggtccacga  tgttgttgat  gctctcgctg  atgtgctgct  cgtgctcgta  240
ggccttctgg  aagatctggg  tcaggccctc  gaacttgtgc  tcgggggcgc  tgatgctggt  300
cagctgcacg  ggcacgttgt  tctcgttcag  gaagatgatc  agcttcttgg  cgtgctcgta  360
ctcctcggcg  gcgtggtcga  acaggaacag  gccggcgccg  tccaggctgt  gggtgtagca  420
ccagctgctc  atgctcatgt  acaggttgct  gctctgcatc  tccttgttca  cctgctcgtt  480
cagcagcttc  tcgatgtcct  tgctgaactg  ctgcctcacc  tggctctctc  cggaggcgcc  540
tctgctcagg  gcaaaggcat  accaaggggc  gatcagattg  ccgttggcct  cgaagatgat  600
ggtgtcgcca  ggtccagca   gggtccagta  gtagttgatt  ctgccttcct  ggtcccgcac  660
tttgggtctt  ttggcgatct  cggggggtgaa  tcttctgttg  tagtggctgg  acaccacgga  720
cacataggcg  ttctcggtgt  ggtagatggc  ccgctgatct  ccgatgttgc  tagggtggtg  780
cactccccag  aggaccagca  cctctttttc  tttgttgttc  acgtagctct  tgctcagatt  840
ggggtagctg  ccgttcttct  tggtcagcca  cagcaggttc  cggtagaagc  tgcttctgcc  900
cttgtggcta  caagaggcgg  tcacgccctt  ggtcactgtg  tgattgggcc  agctggactc  960
tttggggaag  atctcgaacc  gctcgaagct  ggagacagag  gacagctgct  ctctcagttc  1020
ctcgtaatcg  gcgaagtagc  cagggaaaca  ggtgccattc  tcgctgttgg  gtgtctcggc  1080
gatataggac  caggacttct  tgctgaacag  gctctcgcac  tcgggatttc  ccagaatcca  1140
gccggcgata  aacaattgc   ccagctgcag  aggggcaatg  gctagcacgc  cctgaggcag  1200
cagcaggttg  ctcaccacca  gcagcagcag  cagtctgctg  cccttctggc  tgctgccctt  1260
gctgtccat                                                               1269

SEQ ID NO: 120          moltype = DNA  length = 1269
FEATURE                 Location/Qualifiers
misc_feature            1..1269
                        note = Synthetic
source                  1..1269
```

```
                             mol_type = other DNA
                             organism = synthetic construct
SEQUENCE: 120
atggacagca agggcagcag ccagaagggc agcagactgc tgctgctgct ggtggtgagc   60
aacctgctgc tgcctcaggg cgtgctagcc atcgctcctc tgcagctggg gaaatgcagc  120
atcgcagggt ggattctggg aaacccagag tgtgaaagtc tgttttcaaa gaaatcttgg  180
agttacattg ccgagacacc caacagcgaa aatggcactt gcttccctgg gtatttcgct  240
gattatgagg aactgcgcga gcagctgagc tccgtgtcta gtttcgagcg atttgaaatc  300
ttcccaaggg aatcaagctg gcctaagcac aacgtgaccca aaggggtcac agcctcatgt  360
agccataagg gaaaatcctc tttttaccgc aatctgctgt ggctgacaga gaagaacggg  420
tcctacccaa atctgtccaa gtcttacgtg aacaataagg agaaggaagt gctggtcctg  480
tggggcgtcc accatccctc taacatcgag gaccagaaga ctatctacag gaaagaaaac  540
gcatatgtga gtgtggtcag ttcacactac aatcggcggt tcacccccga gatcgccaag  600
aggcccaaag tgcgcaacca ggaaggccgc attaattact attggaccct gctggagcca  660
ggcgatacaa tcattttcga agccaacggg aatctgatcg ctccctggta tgcatttgcc  720
ctgtcccgag gagcctccgg agagagccag gtgaggcagc agttcagcaa ggacatcgag  780
aagctgctga cgagcaggt gaacaaggag atgcagagca gcaacctgta catgagcatg  840
agcagctggt gctacaccca cagcctggac ggcgccggcc tgttcctgtt cgaccacgcc  900
gccgaggagt acgagcacgc caagaagctg atcatcttcc tgaacgagaa caacgtgccc  960
gtgcagctga ccagcatcag cgcccccgag cacaagttcg agggcctgac ccagatcttc 1020
cagaaggcct acgagcacga gcagcacatc agcgagagca tcaacaacat cgtggaccac 1080
gccatcaaga gcaaggacca cgccaccttc aacttcctgc agtggtacgt ggccgagcag 1140
cacgaggagg aggtgctgtt caaggacatc ctggacaaga tcgagctgat cggcaacgag 1200
aaccacggcc tgtacctggc cgaccagtac gtgaagggca tcgccaagag caggaagagc 1260
ggatcctag                                                         1269

SEQ ID NO: 121           moltype = AA  length = 422
FEATURE                  Location/Qualifiers
REGION                   1..422
                         note = Synthetic
source                   1..422
                         mol_type = protein
                         organism = synthetic construct
SEQUENCE: 121
MDSKGSSQKG SRLLLLLVVS NLLLPQGVLA IAPLQLGKCS IAGWILGNPE CESLFSKKSW   60
SYIAETPNSE NGTCFPGYFA DYEELREQLS SVSSFERFEI FPKESSWPKH NVTKGVTASC  120
SHKGKSSFYR NLLWLTEKNG SYPNLSKSYV NNKEKEVLVL WGVHHPSNIE DQKTIYRKEN  180
AYVSVVSSHY NRRFTPEIAK RPKVRNQEGR INYYWTLLEP GDTIIFEANG NLIAPWYAFA  240
LSRGASGESQ VRQQFSKDIE KLLNEQVNKE MQSSNLYMSM SSWCYTHSLD GAGLFLFDHA  300
AEEYEHAKKL IIFLNENNVP VQLTSISAPE HKFEGLTQIF QKAYEHEQHI SESINNIVDH  360
AIKSKDHATF NFLQWYVAEQ HEEEVLFKDI LDKIELIGNE NHGLYLADQY VKGIAKSRKS  420
GS                                                                 422

SEQ ID NO: 122           moltype = DNA  length = 1269
FEATURE                  Location/Qualifiers
misc_feature             1..1269
                         note = Synthetic
source                   1..1269
                         mol_type = other DNA
                         organism = synthetic construct
SEQUENCE: 122
ctaggatccg ctcttcctgc tcttggcgat gcccttcacg tactggtcgg ccaggtacag   60
gccgtggttc tcgttgccga tcagctcgat cttgtccagg atgtccttga acagcacctc  120
ctcctcgtg tgctcggcca cgtaccactg caggaagttg aaggtggcgt ggtccttgct  180
cttgatggcg tggtccacga tgttgttgat gctctcgctg atgtgctgct cgtgctcgta  240
ggccttctgg aagatctggg tcaggccctc gaacttgtgc tcgggggcgc tgatgctggt  300
cagctgcacg ggcacgttgt tctcgttcag gaagatgatc agcttcttgg cgtgctcgta  360
ctcctcggcg gcgtggtcga acaggaacag gccggcgccg tccaggctgt gggtgtagca  420
ccagctgctc atgctcatgt acaggttgct gctctgcatc tccttgttca cctgctcgtt  480
cagcagcttc tcgatgtcct tgctgaactg ctgcctcacc tggctctctc cggaggctcc  540
tcgggacagg gcaaatgcat accagggagc gatcagattc ccgttggctt cgaaaatgat  600
tgtatcgcct ggctccagca gggtccaata gtaattaatg cggccttcct ggttgcgcac  660
tttgggcctc ttggcgatct cggggggtgaa ccgccgattg tagtgtgaac tgaccacact  720
cacatatgcg ttttctttcc tgtagatagt cttctggtcc tcgatgttag agggatggtg  780
gacgccccac aggaccagca cttccttctc cttattgttc acgtaagact tggacagatt  840
tgggtaggac ccgttcttct ctgtcagcca cagcagattc ggtaaaaag aggattttcc  900
cttatggcta catgaggctg tgacccttt ggtcacgttg tgcttaggcc agcttgattc  960
cttggggaag atttcaaatc gctcgaaact agacacggag ctcagctgct cgcgcagttg 1020
ctcataatca gcgaaatacc cagggaagca agtgccattt tcgctgttgg gtgtctcggc 1080
aatgtaactc caagatttct ttgaaaacag actttcacac tctgggtttc ccagaatcca 1140
ccctgcgatg ctgcatttcc ccagctgcag aggagcgatg ctagcacgc cctgaggcag 1200
cagcaggttg ctcaccacca gcagcagcag cagtctgctg cccttctggc tgctgccctt 1260
gctgtccat                                                         1269

SEQ ID NO: 123           moltype = DNA  length = 1269
FEATURE                  Location/Qualifiers
misc_feature             1..1269
                         note = Synthetic
source                   1..1269
```

```
                         mol_type = other DNA
                         organism = synthetic construct
SEQUENCE: 123
atggacagca agggcagcag ccagaagggc agcagactgc tgctgctgct ggtggtgagc  60
aacctgctgc tgcctcaggg cgtgctagcc atcgccccac tgcagctggg caagtgcaac  120
atcgctggct ggattctggg gaatcccgag tgtgaatcac tgctgagcaa ccgctcatcg  180
agctacatcg ctgagacccc taacagcgaa aatggaattt gcttcccagg cgactttgca  240
gattatgagg aactgcggga gcagctgagc tccgtgtcta gtttcgagag atttgaaatc  300
ttccccaaag aatcaagctg gcctaagcac aacattacca ggggcgtgac agtcgcctgt  360
agccatgcta agaaatcctc tttctacaag aacctgctgt ggctgacaga ggccaatggc  420
ctgtacccct ccctgtctaa aagttatgtg aatgaccgcg agaaggaagt gctggtcctg  480
tggggcgtcc accatcctag caacatcgag gatcagagga cactgtaccg caaggaaaat  540
gcctatgtga gcgtcgtcag ttcaaactac aatcggagat ttactccaga gattgctgaa  600
cgaccaaaag tgcgaggaca gcctggacga atgaactact attggacect gctggagcca  660
ggagataaga tcattttga agcaaacggc aatctgatcg cccctggta tgcattcgcc  720
ctgtcaagag gaccttccgg agagagccag gtgaggcagc agttcagcaa ggacatcgag  780
aagctgctga acgagcaggt gaacaaggag atgcagagca gcaacctgta catgagcatg  840
agcagctggt gctacaccca cagcctggac ggcgccgagc tgttcctgtt cgaccacgcc  900
gccgaggagt acgagcacgc caagaagctg atcatcttcc tgaacgagaa caacgtgccc  960
gtgcagctga ccagcatcag cgcccccgag cacaagttcg agggcctgac ccagatcttc  1020
cagaaggcct acgagcacga gcagcacatc agcgagagca tcaacaacat cgtggaccac  1080
gccatcaaga gcaaggacca cgccaccttc aacttcctgc agtggtacgt ggccgagcag  1140
cacgaggagg aggtgctgtt caaggacatc ctggacaaga tcgagctgat cggcaacgag  1200
aaccacggcc tgtacctggc cgaccagtac gtgaagggca tcgccaagag caggaagagc  1260
ggatcctag                                                         1269

SEQ ID NO: 124          moltype = AA  length = 422
FEATURE                 Location/Qualifiers
REGION                  1..422
                        note = Synthetic
source                  1..422
                        mol_type = protein
                        organism = synthetic construct
SEQUENCE: 124
MDSKGSSQKG SRLLLLLVVS NLLLPQGVLA IAPLQLGKCN IAGWILGNPE CESLLSNRSW  60
SYIAETPNSE NGICFPGDFA DYEELREQLS SVSSFERFEI FPKESSWPKH NITRGVTVAC  120
SHAKKSSFYK NLLWLTEANG LYPSLSKSYV NDREKEVLVL WGVHHPSNIE DQRTLYRKEN  180
AYVSVVSSNY NRRFTPEIAE RPKVRGQPGR MNYYWTLLEP GDKIIFEANG NLIAPWYAFA  240
LSRGPSGESQ VRQQFSKDIE KLLNEQVNKE MQSSNLYMSM SSWCYTHSLD GAGLFLFDHA  300
AEEYEHAKKL IIFLNENNVP VQLTSISAPE HKFEGLTQIF QKAYEHEQHI SESINNIVDH  360
AIKSKDHATF NFLQWYVAEQ HEEEVLFKDI LDKIELIGNE NHGLYLADQY VKGIAKSRKS  420
GS                                                                422

SEQ ID NO: 125          moltype = DNA  length = 1269
FEATURE                 Location/Qualifiers
misc_feature            1..1269
                        note = Synthetic
source                  1..1269
                        mol_type = other DNA
                        organism = synthetic construct
SEQUENCE: 125
ctaggatccg ctcttcctgc tcttggcgat gcccttcacg tactggtcgg ccaggtacag  60
gccgtggttc tcgttgccga tcagctcgat cttgtccagg atgtccttga acagcacctc  120
ctcctcgtgc tgctcggcca cgtaccactg caggaagttg aaggtggcgt ggtccttgct  180
cttgatggcg tggtccacga tgttgttgat gctctcgctg atgtgctgct cgtgctcgta  240
ggccttctgg aagatctggg tcaggccctc gaacttgtgc tcggggggcgc tgatgctggt  300
cagctgcacg ggcacgttgt tctcgttcag gaagatgatc agcttcttgg cgtgctcgta  360
ctcctcggcg gcgtggtcga acaggaacag gccggcgccg tccaggctgt gggtgtagca  420
ccagctgctc atgctcatgt acaggttgct gctctgcatc tccttgttca cctgctcgtt  480
cagcagcttc tcgatgtcct tgctgaactg ctgcctcacc tggctctctc cggaaggtcc  540
tcttgacagg gcgaatgcat accagggggc gatcagattg ccgtttgctt caaaaatgat  600
cttatctcct ggctccagca gggtccaata gtagttcatt cgtccaggct gtcctcgcac  660
ttttggtcgt tcagcaatct ctggagtaaa tctccgattg tagtttgaac tgacgacgct  720
cacataggca ttttccttgc ggtacagtgt cctctgatcc tcgatgttgc taggatggtg  780
gacgccccac aggaccagca cttccttctc gcggtcattc acataacttt tagacaggga  840
ggggtacagg ccattggcct ctgtcagcca cagcaggttc ttgtagaaag aggatttctt  900
agcatggcta caggcgactg tcacgcccct ggtaatgttg tgcttaggcc agcttgattc  960
tttggggaag atttcaaatc tctcgaaact agacacggag ctcacgctgc ccgcagttg  1020
ctcataatct gcaaagtcgc ctgggaagca aattccattt tcgctgttag gggtctcagc  1080
gatgtagctc catgagcggt tgctcagcag tgattcacac tcgggattcc ccagaatcca  1140
gccagcgatg ttgcacttgc ccagctgcag tggggcgatg gctagcacgc cctgaggcag  1200
cagcaggttg ctcaccacca gcagcagcag cagtctgctg cccttctggc tgctgccctt  1260
gctgtccat                                                         1269

SEQ ID NO: 126          moltype = DNA  length = 1266
FEATURE                 Location/Qualifiers
misc_feature            1..1266
                        note = Synthetic
source                  1..1266
```

```
                          mol_type = other DNA
                          organism = synthetic construct
SEQUENCE: 126
atggacagca agggcagcag ccagaagggc agcagactgc tgctgctgct ggtggtgagc    60
aacctgctgc tgcctcaggg cgtgctagcc atcgccccac tgcagctggg aaaatgcaac   120
atcgctggat ggattctggg caatcccgag tgtgaatcac tgctgagcga gcgctcttgg   180
agttacatcg tggagacccc taacagcgaa aatgggacat gcttcccagg agactttatt   240
gattatgagg aactgcgcga gcagctgagc tccgtgtcta gtttcgagcg atttgaaatc   300
ttctctaagg aatcaagctg gccaaaacac accacaggcg gggtgactgc cgcttgtagt   360
catgccggca agtcctcttt ctaccggaac ctgctgtggc tgaccgagaa agacgggtcc   420
taccccaacc tgaacaactc ttacgtgaat aagaagggca aggaagtgct ggtcctgtgg   480
ggggtccacc atcctagcaa catcaaggat cagcagacac tgtaccagaa agagaatgcc   540
tatgtgtccg tggtcagttc aaactacaat cggcggttca cccccgagat cgctgaaagg   600
cctaaggtcc gcggacaggc aggccgaatt aactactatt ggacctctgct gaaacccggg   660
gacaccatca tgttcgaggc aaacggaaat ctgattgccc cttggtatgc ttttgcactg   720
tctcgcgggg cctccggaga gagccaggtg aggcagcagt tcagcaagga catcgagaag   780
ctgctgaacg agcaggtgaa caaggagatg cagagcagca acctgtacat gagcatgagc   840
agctggtgct acacccacag cctggacggc gccggcctgc tcctgttcga ccacgccgcc   900
gaggagtacg agcacgccaa gaagctgatc atcttcctga acgagaacaa cgtgcccgtg   960
cagctgacca gcatcagcgc ccccgagcac aagttcgagg gcctgaccca gatcttccag   1020
aaggcctacg agcacgagca gcacatcagc gagagcatca caacatcgt ggaccacgcc   1080
atcaagagca aggaccacgc caccttcaac ttcctgcagt ggtacgtggc cgagcagcac   1140
gaggaggagg tgctgttcaa ggacatcctg acaagtccg agctgatcgg caacgagaac   1200
cacggcctgt acctggccga ccagtacgtg aagggcatcg ccaagagcag gaagagcgga   1260
tcctag                                                             1266

SEQ ID NO: 127        moltype = AA  length = 421
FEATURE               Location/Qualifiers
REGION                1..421
                      note = Synthetic
source                1..421
                      mol_type = protein
                      organism = synthetic construct
SEQUENCE: 127
MDSKGSSQKG SRLLLLLVVS NLLLPQGVLA IAPLQLGKCN IAGWILGNPE CESLLSERSW    60
SYIVETPNSE NGTCFPGDFI DYEELREQLS SVSSFERFEI FSKESSWPKH TTGGVTAACS   120
HAGKSSFYRN LLWLTEKDGS YPNLNNSYVN KKGKEVLVLW GVHHPSNIKD QQTLYQKENA   180
YVSVVSSNYN RRFTPEIAER PKVRGQAGRI NYYWTLLKPG DTIMFEANGN LIAPWYAFAL   240
SRGASGESQV RQQFSKDIEK LLNEQVNKEM QSSNLYMSMS SWCYTHSLDG AGLFLFDHAA   300
EEYEHAKKLI IFLNENNVPV QLTSISAPEH KFEGLTQIFQ KAYEHEQHIS ESINNIVDHA   360
IKSKDHATFN FLQWYVAEQH EEEVLFKDIL DKIELIGNEN HGLYLADQYV KGIAKSRKSG   420
S                                                                   421

SEQ ID NO: 128        moltype = DNA  length = 1266
FEATURE               Location/Qualifiers
misc_feature          1..1266
                      note = Synthetic
source                1..1266
                      mol_type = other DNA
                      organism = synthetic construct
SEQUENCE: 128
ctaggatccg ctcttcctgc tcttggcgat gcccttcacg tactggtcgg ccaggtacag    60
gccgtggttc tcgttgccga tcagctcgat cttgtccagg atgtccttga acagcacctc   120
ctcctcgtgc tgctcggcca cgtaccactg caggaagttg aaggtggcgt ggtccttgct   180
cttgatggcg tggtccacga tgttgttgat gctctcgcta atgtgctgct cgtgctcgta   240
ggccttctgg aagatctggg tcaggccctc gaacttgtgc tcggggggcgc tgatgctggt   300
cagctgcacg ggcacgttgt tctcgttcag gaagatgatc agcttcttgg cgtgctcgta   360
ctcctcggcg gcgtggtcga acaggaacag gccggcgccg tccaggctgt gggtgtagca   420
ccagctgctc atgctcatgt acaggttgct gctctgcatc tccttgttca cctgctcgtt   480
cagcagcttc tcgatgtcct tgctgaactg ctgcctcacc tggctctctc cggaggcccc   540
gcgagacagt gcaaaagcat accaaggggc aatcagattt ccgtttgcct cgaacatgat   600
ggtgtccccg ggtttcagca gagtccaata gtagttaatt cggcctgcct gtccgcggac   660
cttaggcctt tcagcgatct cggggggtgaa ccgccgattg tagtttgaac tgaccaccgga  720
cacataggca ttctctttct ggtacagtgt ctgctgatcc ttgatgttgc taggatggtg   780
gaccccccac aggaccagca cttccttgcc cttcttattc acgtaagagt tgttcaggtt   840
ggggtaggac ccgtctttct cggtcagcca cagcaggttc cggtagaaag aggacttgcc   900
ggcatgacta caagcggcag tcaccccgcc tgtggtgtgt tttggccagc ttgattcctt   960
agagaagatt tcaaatcgct cgaaactaga cacggagctc agctgctcgc gcagttcctc  1020
ataatcaata agtctcctg ggaagcatgt cccattttcg tcgttagggg tctccacgat   1080
gtaactccaa gagcgctcgc tcagcagtga ttcacactcg ggattgccca gaatccatcc   1140
agcgatgttg catttccca gctgcagtgg ggcgatggct agcacgccct gaggcagcag   1200
caggttgctc accaccagca gcagcagcag tctgctgccc ttctggctgc tgcccttgct   1260
gtccat                                                             1266

SEQ ID NO: 129        moltype = DNA  length = 1269
FEATURE               Location/Qualifiers
misc_feature          1..1269
                      note = Synthetic
source                1..1269
```

```
                            mol_type = other DNA
                            organism = synthetic construct
SEQUENCE: 129
atggacagca agggcagcag ccagaagggc agcagactgc tgctgctgct ggtggtgagc   60
aacctgctgc tgcctcaggg cgtgctagcc atcgcccctc tgcagctggg caagtgctct  120
atcgctggct ggattctggg gaatccagag tgtgaaagtc tgttttcaaa gaaatcttgg  180
agttacattg ctgagacccc caacagcgaa aatggaacat gcttccctgg ctatttcgca  240
gattatgagg aactgaggga gcagctgagc tccgtgtcta gtttcgagag atttgaaatc  300
ttccccaaag aaaggagctg gcctaagcac aacgtgaccc ggggagtcac agcctcatgt  360
agccataagg gcaaatcaag cttttacaga aatctgctgt ggctgacaga gaaaaacggg  420
tcctacccaa atctgtccaa gtcttatgtg aacaataagg agaaagaagt gctggtcctg  480
tggggcgtcc accatcccag caacatcgag gaccagaaga ctatttaccg aaaagaaaat  540
gcctatgtgt ccgtggtctc ctctaactac aatcggagat ttacccccaga gatcgctgaa  600
aggccaaagg tgcgaggaca ggcaggacga attaactact attggactct gctggagcca  660
ggggatacca tcattttcga agccaacgga aatctgatcg ctccctggta tgcatttgcc  720
ctgagtcggg gagcctccgg agagagccag gtgaggcagc agttcagcaa ggacatcgag  780
aagctgctga acgagcaggt gaacaaggag atgcagagca gcaacctgta catgagcatg  840
agcagctggt gctacaccca cagcctggac ggcgccggcc tgttcctgtt cgaccacgcc  900
gccgaggagt acgagcacgc caagaagctg atcatcttcc tgaacgagaa caacgtgccc  960
gtgcagctga ccagcatcag cgcccccgag cacaagttcg agggcctgac ccagatcttc 1020
cagaaggcct acgagcacga gcagcacatc agcgagagca tcaacaacat cgtggaccac 1080
gccatcaaga gcaaggacca cgccaccttc aacttcctgc agtggtacgt ggccgagcag 1140
cacgaggagg aggtgctgtt caaggacatc ctggacaaga tcgagctgat cggcaacgag 1200
aaccacggcc tgtacctggc cgaccagtac gtgaagggca tcgccaagag caggaagagc 1260
ggatcctag                                                         1269

SEQ ID NO: 130          moltype = AA  length = 422
FEATURE                 Location/Qualifiers
REGION                  1..422
                        note = Synthetic
source                  1..422
                        mol_type = protein
                        organism = synthetic construct
SEQUENCE: 130
MDSKGSSQKG SRLLLLLVVS NLLLPQGVLA IAPLQLGKCS IAGWILGNPE CESLFSKKSW   60
SYIAETPNSE NGTCFPGYFA DYEELREQLS SVSSFERFEI FPKERSWPKH NVTRGVTASC  120
SHKGKSSFYR NLLWLTEKNG SYPNLSKSYV NNKEKEVLVL WGVHHPSNIE DQKTIYRKEN  180
AYVSVVSSNY NRRFTPEIAE RPKVRGQAGR INYYWTLLEP GDTIIFEANG NLIAPWYAFA  240
LSRGASGESQ VRQQFSKDIE KLLNEQVNKE MQSSNLYMSM SSWCYTHSLD GAGLFLFDHA  300
AEEYEHAKKL IIFLNENNVP VQLTSISAPE HKFEGLTQIF QKAYEHEQHI SESINNIVDH  360
AIKSKDHATF NFLQWYVAEQ HEEEVLFKDI LDKIELIGNE NHGLYLADQY VKGIAKSRKS  420
GS                                                                 422

SEQ ID NO: 131          moltype = DNA  length = 1269
FEATURE                 Location/Qualifiers
misc_feature            1..1269
                        note = Synthetic
source                  1..1269
                        mol_type = other DNA
                        organism = synthetic construct
SEQUENCE: 131
ctaggatccg ctcttcctgc tcttggcgat gcccttcacg tactggtcgg ccaggtacag   60
gccgtggttc tcgttgccga tcagctcgat cttgtccagg atgtccttga acagcacctc  120
ctcctcgtgt tgctcggcca cgtaccactg caggaagttg aaggtggcgt ggtccttgct  180
cttgatggcg tggtccacga tgttgttgat gctctcgctg atgtgctgct cgtgctcgta  240
ggccttctgg aagatctggg tcaggccctc gaacttgtgc tcggggggcgc tgatgctggt  300
cagctgcacg ggcacgttgt tctcgttcag gaagatgatc agcttcttgg cgtgctcgta  360
ctcctcggcg gcgtggtcga acaggaacag gccggcgccg tccaggctgt gggtgtagca  420
ccagctgctc atgctcatgt acaggttgct gctctgcatc tccttgttca cctgctcgtt  480
cagcagcttc tcgatgtcct tgctgaactg ctgcctcacc tggctctctc cggaggctcc  540
ccgactcagg gcaaatgcat accagggagc gatcagattt ccgttggctt cgaaaatgat  600
ggtatcccct ggctccagca gagtccaata gtagttaatt cgtcctgcct gtcctcgcac  660
ctttggcctt tcagcgatct ctggggtaaa tctccgattg tagttagagg agaccacgga  720
cacataggca ttttcttttc ggtaaatagt cttctggtcc tcgatgttgc tgggatggtg  780
gacgccccac aggaccagca cttctttctc cttattgttc acataagact tggacagatt  840
tgggtaggac ccgttttct ctgtcagcca cagcagattt ctgtaaaagc ttgatttgcc  900
cttatggcta catgaggctg tgactccccg ggtcacgttg tgcttaggcc agctcctttc  960
tttggggaag atttcaaatc tctcgaaact agacacggag ctcagctgct ccctcagttg 1020
ctcataatct gcgaaatagc caggaagca tgttccatc tcgctgttgg gggtctcagc 1080
aatgtaactc caagatttct ttgaaaacag actttcacac tctggattcc ccagaatcca 1140
gccagcgata gagcacttgc ccagctgcag aggggcgatg gctagcacgc cctgaggcag 1200
cagcaggttg ctcaccacca gcagcagcag cagtctgctg cccttctggc tgctgccctt 1260
gctgtccat                                                         1269

SEQ ID NO: 132          moltype = DNA  length = 1269
FEATURE                 Location/Qualifiers
misc_feature            1..1269
                        note = Synthetic
source                  1..1269
```

-continued

```
                         mol_type = other DNA
                         organism = synthetic construct
SEQUENCE: 132
atggacagca agggcagcag ccagaagggc agcagactgc tgctgctgct ggtggtgagc    60
aacctgctgc tgcctcaggg cgtgctagcc atcgctcctc tgcagctggg aaagtgcaac   120
atcgcaggat ggattctggg caatccagag tgtgaatccc tgctgtctaa acggtcttgg   180
agttacattg ccgagacacc caactctgaa aatggggcct gcttccctgg agactttgct   240
gattatgagg aactgagaga gcagctgagc tccgtgtcta gtttcgagag atttgaaatc   300
ttccccaagg aaaggtcctg gcctaaacac aacattacta gggggggtgac cgccgcttgt   360
tctcatgccg gaaaatcaag cttctacaag aatctgctgt ggctgacaga gactgacggc   420
tcctacccaa agctgtcaaa aagctatgtg aacaataagg agaaagaagt gctggtcctg   480
tggggcgtcc accatcccag taacatcgag gatcagaaaa ctctgtaccg caaggaaaat   540
gcttatgtga gcgtggtctc ctctaactac aatcggagat ttaccccaga gatcgcagaa   600
aggccaaagg tgcgaggaca ggcaggacga attaactact attggactct gctggagcca   660
ggcgacacca tcattttcga agcaaacggg aatctgatcg cccctggta tgcttttgca    720
ctgtcccgcg atgcctccgg agagagccag gtgaggcagc agttcagcaa ggacatcgag   780
aagctgctga cgagcaggt gaacaaggag atgcagagca gcaacctgta catgagcatg   840
agcagctggt gctacacca cagcctggac ggcgccggcc tgttcctgtt cgaccacgcc   900
gccgaggagt acgagcacgc caagaagctg atcatcttcc tgaacgagaa caacgtgccc   960
gtgcagctga ccagcatcag cgcccccgag cacaagttcg agggcctgac ccagatcttc   1020
cagaaggcct acgagcacga gcagcacatc agcgagagca tcaacaacat cgtggaccac   1080
gccatcaaga gcaaggacca cgccaccttc aacttcctgc agtggtacgt ggccgagcag   1140
cacgaggagg aggtgctgtt caaggacatc ctggacaaga tcgagctgat cggcaacgag   1200
aaccacggcc tgtacctggc cgaccagtac gtgaagggca tcgccaagag caggaagagc   1260
ggatcctag                                                          1269

SEQ ID NO: 133        moltype = AA   length = 422
FEATURE               Location/Qualifiers
REGION                1..422
                      note = Synthetic
source                1..422
                      mol_type = protein
                      organism = synthetic construct
SEQUENCE: 133
MDSKGSSQKG SRLLLLLVVS NLLLPQGVLA IAPLQLGKCN IAGWILGNPE CESLLSKRSW    60
SYIAETPNSE NGACFPGDFA DYEELREQLS SVSSFERFEI FPKERSWPKH NITRGVTAAC   120
SHAGKSSFYK NLLWLTETDG SYPKLSKSYV NNKEKEVLVL WGVHHPSNIE DQKTLYRKEN   180
AYVSVVSSNY NRRFTPEIAE RPKVRGQAGR INYYWTLLEP GDTIIFEANG NLIAPWYAFA   240
LSRDASGESQ VRQQFSKDIE KLLNEQVNKE MQSSNLYMSM SSWCYTHSLD GAGLFLFDHA   300
AEEYEHAKKL IIFLNENNVP VQLTSISAPE HKFEGLTQIF QKAYEHEQHI SESINNIVDH   360
AIKSKDHATF NFLQWYVAEQ HEEEVLFKDI LDKIELIGNE NHGLYLADQY VKGIAKSRKS   420
GS                                                                  422

SEQ ID NO: 134        moltype = DNA   length = 1269
FEATURE               Location/Qualifiers
misc_feature          1..1269
                      note = Synthetic
source                1..1269
                      mol_type = other DNA
                      organism = synthetic construct
SEQUENCE: 134
ctaggatccg ctcttcctgc tcttggcgat gcccttcacg tactggtcgg ccaggtacag    60
gccgtggttc tcgttgccga tcagctcgat cttgtccagg atgtccttga acagcacctc   120
ctcctcgtgt tgctcggcca cgtaccactg caggaagttg aaggtggcgt ggtccttgct   180
cttgatggcg tggtccacga tgttgttgat gctctcgatc atgtgctgct cgtgctcgta   240
ggccttctgg aagatctggg tcaggccctc gaacttgtgc tcgggggcgc tgatgctggt   300
cagctgcacg gcacgttgt tctcgttcag gaagatgatc agcttcttgg cgtgctcgta   360
ctcctcggcg gcgtggtcga acaggaacag gccggcgccg tccaggctgt gggtgtagca   420
ccagctgctc atgctcatgt acaggttgct gctctgcatc tccttgttca cctgctcgtt   480
cagcagcttc tcgatgtcct tgctgaactg ctgcctcacc tggctctctc cggaggcatc   540
gcgggacagt gcaaaagcat accaggggc gatcagattc ccgtttgctt cgaaaatgat   600
ggtgtcgcct ggctccagca gagtccaata gtagttaatt cgtcctgcct gtcctcgcac   660
ctttggcctt tctgcgatct ctggggtaaa tctccgattg tagttagagg agaccacgct   720
cacataagca ttttccttgc ggtacagagt tttctgatcc tcgatgttac tgggatggtg   780
gacgccccac aggaccagca cttctttctc cttattgttc acatagcttt ttgacagctt   840
tgggtaggag ccgtcagtct ctgtcagcca cagcagattc ttgtagaagc ttgattttcc   900
ggcatgagaa caagcggcgg tcacccccct agtaatgttg tgtttaggcc aggacctttc   960
cttgggaag atttcaaatc tctcgaaact agacacggag ctcagctgct ctctcagttg   1020
ctcataatca gcaaagtctc cagggaagca ggcccctttc tcagagttgg gtgtctcggc   1080
aatgtaactc caagaccgtt tagacagcag ggattcacac tctggattgc ccagaatcca   1140
tcctgcgatg ttgcactttc ccagctgcag aggagcgatg gctagcacgc cctgaggcag   1200
cagcaggttg ctcaccacca gcagcagcag cagtctgctg cccttctggc tgctgccctt   1260
gctgtccat                                                          1269

SEQ ID NO: 135        moltype = DNA   length = 1266
FEATURE               Location/Qualifiers
misc_feature          1..1266
                      note = Synthetic
source                1..1266
```

```
                             mol_type = other DNA
                             organism = synthetic construct
SEQUENCE: 135
atggacagca agggcagcag ccagaagggc agcagactgc tgctgctgct ggtggtgagc    60
aacctgctgc tgcctcaggg cgtgctagcc attgcccctc tgcagctggg aaattgtagc   120
gtggccggct ggattctggg caatcctgag tgcgagctgc tgatttccaa agagtcctgg   180
tcctacatcg tggagaagcc caaccctgag aatggcacct gcttccctgg ccacttcgcc   240
gattacgagg aactgagaga acagctgtcc agcgtgtcca gcttcgagag attcgagatc   300
ttccccaaag agagcagctg gcccaatcat acagtgaccg gcgtgagcgc ctcttgtagc   360
cacaatggcg agagcagctt ctacagaaac ctgctgtggc tgaccggcaa gaacggcctg   420
taccccaacc tgagcaagag ctacgccaac aacaaagaaa agaagtgct ggtcctctgg    480
ggagtgcacc accctcctaa catcggcatc cagaaggccc tgtaccacac cgagaatgcc   540
tacgtgtccg tggtgtccag ccactacagc agaaagttca cccccgagat cgccaaaaga   600
cccaaagtgc gggaccagga aggcagaatc aactactact ggaccctgct ggaacctggc   660
gacaccatca tcttcgaggc caacggcaat ctgatcgccc ctagatacg ctttgccctg     720
agcagaggc cctccggaga gagccaggtg aggcagcagt tcagcaagga catcgagaag     780
ctgctgaacg agcaggtgaa caaggagatg cagagcagca acctgtacat gagcatgagc   840
agctggtgct acacccacag cctggacggc gccggcctgt tcctgttcga ccacgccgcc   900
gaggagtacg agcacgccaa gaagctgatc atcttcctga acgagaacaa cgtgcccgtg   960
cagctgacca gcatcagcgc ccccgagcac aagttcgagg gcctgaccca gatcttccag  1020
aaggcctacg agcacgagca gcacatcagc gagagcatca acaacatcgt ggaccacgcc  1080
atcaagagca aggaccacgc caccttcaac ttcctgcagt ggtacgtggc cgagcagcac  1140
gaggaggagg tgctgttcaa ggacatcctg gacaagatcg agctgatcgg caacgagaac  1200
cacggcctgt acctggccga ccagtacgtg aagggcatcg ccaagagcag gaagagcgga  1260
tcctag                                                            1266

SEQ ID NO: 136          moltype = AA  length = 421
FEATURE                 Location/Qualifiers
REGION                  1..421
                        note = Synthetic
source                  1..421
                        mol_type = protein
                        organism = synthetic construct
SEQUENCE: 136
MDSKGSSQKG SRLLLLLVVS NLLLPQGVLA IAPLQLGNCS VAGWILGNPE CELLISKESW    60
SYIVEKPNPE NGTCFPGHFA DYEELREQLS SVSSFERFEI FPKESSWPNH TVTGVSASCS   120
HNGESSFYRN LLWLTGKNGL YPNLSKSYAN NKEKEVLVLW GVHHPPNIGI QKALYHTENA   180
YVSVVSSHYS RKFTPEIAKR PKVRDQEGRI NYYWTLLEPG DTIIFEANGN LIAPRYAFAL   240
SRGASGESQV RQQFSKDIEK LLNEQVNKEM QSSNLYMSMS SWCYTHSLDG AGLFLFDHAA   300
EEYEHAKKLI IFLNENNVPV QLTSISAPEH KFEGLTQIFQ KAYEHEQHIS ESINNIVDHA   360
IKSKDHATFN FLQWYVAEQH EEEVLFKDIL DKIELIGNEN HGLYLADQYV KGIAKSRKSG   420
S                                                                 421

SEQ ID NO: 137          moltype = DNA  length = 1266
FEATURE                 Location/Qualifiers
misc_feature            1..1266
                        note = Synthetic
source                  1..1266
                        mol_type = other DNA
                        organism = synthetic construct
SEQUENCE: 137
ctaggatccg ctcttcctgc tcttggcgat gcccttcacg tactggtcgg ccaggtacag    60
gccgtggttc tcgttgccga tcagctcgat cttgtccagg atgtccttga acagcacctc   120
ctcctcgtgc tgctcggcca cgtaccactg caggaagttg aaggtggcgt ggtccttgct   180
cttgatggcg tggtccacga tgttgttgat gctctcgctg atgtgctgct cgtgctcgta   240
ggccttctgg aagatctggg tcaggccctc gaacttgtgc tcgggggcgc tgatgctggt   300
cagctgcacg ggcacgttgt tctcgttcag gaagatgatc agcttcttgg cgtgctcgta   360
ctcctcggcg gcgtggtcga acaggaacag gccggcgccg tccaggctgt gggtgtagca   420
ccagctgctc atgctcatgt acaggttgct gctctgcatc tccttgttca cctgctcgtt   480
cagcagcttc tcgatgtcct tgctgaactg ctgcctcacc tggctctctc cggaggcgcc   540
tctgctcagg gcaaaggcgt atctaggggc gatcagattg ccgttggcct cgaagatgat   600
ggtgtcgcca ggtccagca gggtccagta gtagttgatc ctgccttcct ggtcccgcac     660
tttgggtctt ttggcgatct cggggtgaa ctttctgctg tagtggctgg acaccacgga     720
cacgtaggca ttctcggtgt ggtacagggc cttctggatg ccgatgttag gaggtggtg     780
cactccccag aggaccagca cttctttttc tttgttgttg gcgtagctct tgctcaggtt   840
ggggtacagg ccgttcttgc cggtcagcca cagcaggttt ctgtagaagc tgctctcgcc   900
attgtggcta caagaggcgc tcacgccggt cactgtatga ttgggccagc tgctctcttt   960
ggggaagatc tcgaatctct cgaagctgga cacgctggac agcgttctc tcagttcctc   1020
gtaatcggcg aagtggccag ggaagcaggt gccattctca gggttgggct tctccacgat  1080
gtaggaccag gactctttgg aaatcagcag ctcgcactca ggattgccca gaatccagcc  1140
ggccacgcta caatttccca gctgcagagg ggcaatggct agcacgccct gaggcagcag  1200
caggttgctc accaccagca gcagcagcag tctgctgccc ttctggctgc tgcccttgct  1260
gtccat                                                            1266

SEQ ID NO: 138          moltype = DNA  length = 1269
FEATURE                 Location/Qualifiers
misc_feature            1..1269
                        note = Synthetic
source                  1..1269
```

```
                        mol_type = other DNA
                        organism = synthetic construct
SEQUENCE: 138
atggacagca agggcagcag ccagaagggc agcagactgc tgctgctgct ggtggtgagc   60
aacctgctgc tgcctcaggg cgtgctagcc atcgctcctc tgcagctggg gaagtgcagc  120
atcgcagggt ggattctggg aaatccagag tgtgaatccc tgttttctaa gaaaagctgg  180
tcctacattg ccgagacacc caactccgaa aatggcactt gtttccctgg gtatttcgct  240
gattatgagg aactgcgcga gcagctgagc tccgtgtcta gtttcgagcg atttgaaatc  300
ttccccaagg aatcaagctg gcctaaacac aacgtgaccc ggggggtcac agcctcttgc  360
agtcataagg gaaaatgttc tttctacaga aatctgctgt ggctgacaga gaagaacggg  420
agttacccaa atctgtcaaa gagctacgtg aacaataagg agaaagaagt gctggtcctg  480
tggggcgtcc accatccctc taacatcgag gaccagaaga ctatctaccg aaaagaaaac  540
gcatatgtga gcgtggtctc ctctcactac aatcggcggt tcacccccga gatcgccaag  600
aggcccaaag tgcgcgacca ggaaggccgc attaactact attggaccct gctggagcca  660
ggcgatacaa tcattttcga gccaacgggg aatctgatcg ctccctggta tgcatttgcc  720
ctgtcaagag gagcctccgg agagagccag gtgaggcagc agttcagcaa ggacatcgag  780
aagctgctga acgagcaggt gaacaaggag atgcagagca gcaacctgta catgagcatg  840
agcagctggt gctacaccca cagcctggac ggcgccggcc tgttcctgtt cgaccacgcc  900
gccgaggagt acgagcacgc caagaagctg atcatcttcc tgaacgagaa caacgtgccc  960
gtgcagctga ccagcatcag cgcccccgag cacaagttcg agggcctgac ccagatcttc 1020
cagaaggcct acgagcacga gcagcacatc agcgagagca tcaacaacat cgtggaccac 1080
gccatcaaga gcaaggacca cgccaccttc aacttcctgc agtggtacgt ggccgagcag 1140
cacgaggagg aggtgctgtt caaggacatc ctggacaaga tcgagctgat cggcaacgag 1200
aaccacggcc tgtacctggc cgaccagtac gtgaagggca tcgccaagag caggaagagc 1260
ggatcctag                                                          1269

SEQ ID NO: 139         moltype = AA  length = 422
FEATURE                Location/Qualifiers
REGION                 1..422
                       note = Synthetic
source                 1..422
                       mol_type = protein
                       organism = synthetic construct
SEQUENCE: 139
MDSKGSSQKG SRLLLLLVVS NLLLPQGVLA IAPLQLGKCS IAGWILGNPE CESLFSKKSW   60
SYIAETPNSE NGTCFPGYFA DYEELREQLS SVSSFERFEI FPKESSWPKH NVTRGVTASC  120
SHKGKCSFYR NLLWLTEKNG SYPNLSKSYV NNKEKEVLVL WGVHHPSNIE DQKTIYRKEN  180
AYVSVVSSHY NRRFTPEIAK RPKVRDQEGR INYYWTLLEP GDTIIFEANG NLIAPWYAFA  240
LSRGASGESQ VRQQFSKDIE KLLNEQVNKE MQSSNLYMSM SSWCYTHSLD GAGLFLFDHA  300
AEEYEHAKKL IIFLNENNVP VQLTSISAPE HKFEGLTQIF QKAYEHEQHI SESINNIVDH  360
AIKSKDHATF NFLQWYVAEQ HEEEVLFKDI LDKIELIGNE NHGLYLADQY VKGIAKSRKS  420
GS                                                                  422

SEQ ID NO: 140         moltype = DNA  length = 1269
FEATURE                Location/Qualifiers
misc_feature           1..1269
                       note = Synthetic
source                 1..1269
                       mol_type = other DNA
                       organism = synthetic construct
SEQUENCE: 140
ctaggatccg ctcttcctgc tcttggcgat gcccttcacg tactggtcgg ccaggtacag   60
gccgtggttc tcgttgccga tcagctcgat cttgtccagg atgtccttga acagcacctc  120
ctcctcgtgc tgctcggcca cgtaccactg caggaagttg aaggtggcgt ggtccttgct  180
cttgatggcg tggtccacga tgttgttgat gctctcgctg atgtgctgct cgtgctcgta  240
ggccttctgg aagatctggg tcaggccctc gaacttgtgc tcggggggcgc tgatgctggt  300
cagctgcacg ggcacgttgt tctcgttcag gaagatgatc agcttcttgg cgtgctcgta  360
ctcctcggcg gcgtggtcga acaggaacag gccggcgccg tccaggctgt gggtgtagca  420
ccagctgctc atgctcatgt acaggttgct gctctgcatc tccttgttca cctgctcgtt  480
cagcagcttc tcgatgtcct tgctgaactg ctgcctcacc tggctctctc cggaggctcc  540
tcttgacagg gcaaatgcat accagggagc gatcagattc ccgttggctt cgaaaatgat  600
tgtatcgcct ggctccagca gggtccaata gtagttaatg cggccttcct ggtcgcgcac  660
tttgggcctc ttggcgatct cgggggtgaa ccgccgattg tagtgagagg agaccacgct  720
cacatatgcg ttttcttttc ggtagatagt cttctggtcc tcgatgttag agggatggtg  780
gacgccccac aggaccagca cttctttctc cttattgttc acgtagctct ttgacagatt  840
tgggtaactc ccgttcttct ctgtcagcca cagcagattt ctgtagaaag aacattttcc  900
cttatgactc aagaggctg tgacccccccg ggtcacgttg tgtttaggcc agcttgattc  960
cttggggaag atttcaaatc gctcgaaact agacacggag ctcagctgct cgcgcagttc 1020
ctcataatca gcgaaatacc cagggaaaca agtgccattt tcggagttgg gtgtctcggc 1080
aatgtaggac cagcttttct tagaaaacag ggattcacac tctggatttc cagaatcca 1140
ccctgcgatg ctgcacttcc ccagctgcag aggagcgatg ctagcacgc cctgaggcag 1200
cagcaggttg ctcaccacca gcagcagcag cagtctgctg cccttctggc tgctgccctt 1260
gctgtccat                                                          1269

SEQ ID NO: 141         moltype = DNA  length = 1269
FEATURE                Location/Qualifiers
misc_feature           1..1269
                       note = Synthetic
source                 1..1269
```

```
                          mol_type = other DNA
                          organism = synthetic construct
SEQUENCE: 141
atggacagca  agggcagcag  ccagaagggc  agcagactgc  tgctgctgct  ggtggtgagc    60
aacctgctgc  tgcctcaggg  cgtgctagcc  atcgcccctc  tgcagctggg  caagtgcaac   120
atcgctggct  ggattctggg  gaatccagag  tgtgaatctc  tgtttagtaa  gaaaagctgg   180
tcctacattg  ctgagacccc  caacagcgaa  aatggaacat  gcttccctgg  ctatttcgca   240
gattatgagg  aactgaggga  gcagctgagc  tccgtgtcta  gtttcgagag  atttgaaatc   300
ttccccaagg  aaaggtcttg  gcctaaacac  aacattacac  ggggcgtgac  agccgcttgt   360
agtcataagg  ggaaatcaag  cttttacaga  aacctgctgt  ggctgacaga  gaagaatggc   420
tcatacccaa  acctgaacaa  gagctatgtg  aacaataagg  agaaagaagt  gctggtcctg   480
tggggcgtcc  accatccctc  taacatcgag  gaccagaaga  ctctgtaccg  aaaagaaaat   540
gcctatgtgt  ccgtggtctc  tctctaactac  aatcggcggt  tcaccccccga  gatcgctgaa   600
aggccaaagg  tgcgcgggaca  ggcaggacgc  attaactact  attggacttct  gctggagcca   660
ggagatacca  tcattttcga  agcaaacggc  aatctgatcg  cccctggca  cgcttttgca   720
ctgagccggg  gagcctccgg  agagagccag  gtgaggcagc  agttcagcaa  ggacatcgag   780
aagctgctga  acgagcaggt  gaacaaggag  atgcagagca  gcaacctgta  catgagcatg   840
agcagctggt  gctacaccca  cagcctggac  ggcgccgggc  tgttcctgtt  cgaccacgcc   900
gccgaggagt  acgagcacgc  caagaagctg  atcatcttcc  tgaacgagaa  caacgtgccc   960
gtgcagctga  ccagcatcag  cgcccccgag  cacaagttcg  agggcctgac  ccagatcttc  1020
cagaaggcct  acgagcacga  gcagcacatc  agcgagagca  tcaacaacat  cgtggaccac  1080
gccatcaaga  gcaaggacca  cgccaccttc  aacttcctgc  agtggtacgt  ggcgagcag  1140
cacgaggagg  aggtgctgtt  caaggacatc  ctggacaaga  tcgagctgat  cggcaacgag  1200
aaccacggcc  tgtacctggc  cgaccagtac  gtgaagggca  tcgccaagag  caggaagagc  1260
ggatcctag                                                             1269

SEQ ID NO: 142          moltype = AA  length = 422
FEATURE                 Location/Qualifiers
REGION                  1..422
                        note = Synthetic
source                  1..422
                        mol_type = protein
                        organism = synthetic construct
SEQUENCE: 142
MDSKGSSQKG  SRLLLLLVVS  NLLLPQGVLA  IAPLQLGKCN  IAGWILGNPE  CESLFSKKSW    60
SYIAETPNSE  NGTCFPGYFA  DYEELREQLS  SVSSFERFEI  FPKERSWPKH  NITRGVTAAC   120
SHKGKSSFYR  NLLWLTEKNG  SYPNLNKSYV  NNKEKEVLVL  WGVHHPSNIE  DQKTLYRKEN   180
AYVSVVSSNY  NRRFTPEIAE  RPKVRGQAGR  INYYWTLLEP  GDTIIFEANG  NLIAPWHAFA   240
LSRGASGESQ  VRQQFSKDIE  KLLNEQVNKE  MQSSNLYMSM  SSWCYTHSLD  GAGLFLFDHA   300
AEEYEHAKKL  IIFLNENNVP  VQLTSISAPE  HKFEGLTQIF  QKAYEHEQHI  SESINNIVDH   360
AIKSKDHATF  NFLQWYVAEQ  HEEEVLFKDI  LDKIELIGNE  NHGLYLADQY  VKGIAKSRKS   420
GS                                                                     422

SEQ ID NO: 143          moltype = DNA  length = 1269
FEATURE                 Location/Qualifiers
misc_feature            1..1269
                        note = Synthetic
source                  1..1269
                        mol_type = other DNA
                        organism = synthetic construct
SEQUENCE: 143
ctaggatccg  ctcttcctgc  tcttggcgat  gcccttcacg  tactggtcgg  ccaggtacag    60
gccgtggttc  tcgttgccga  tcagctcgat  cttgtccagg  atgtccttga  acagcacctc   120
ctcctcgtgc  tgctcggcca  cgtaccactg  caggaagttg  aaggtggcgt  ggtccttgct   180
cttgatggcg  tggtccacga  tgttgttgat  gctctcgcta  atgtgctgct  cgtgctcgta   240
ggccttctgg  aagatctggg  tcaggccctc  gaacttgtgc  tcggggggcgc  tgatgctggt   300
cagctgcacg  ggcacgttgt  tctcgttcag  gaagatgatc  agcttcttgg  cgtgctcgta   360
ctcctcggcg  gcgtggtcga  acaggaacag  gccggcgccg  tccaggctgt  gggtgtagca   420
ccagctgctc  atgctcatgt  acaggttgct  gctctgcatc  tccttgttca  cctgctcgtt   480
cagcagcttc  tcgatgtcct  tgctgaactg  ctgcctcacc  tggctctctc  cggaggctcc   540
ccggctcagt  gcaaaagcgt  gccaggggggc  gatcagattg  ccgtttgctt  cgaaaatgat   600
ggtatctcct  ggctccagca  gagtccaata  gtagttaatg  cgtcctgcct  gtccgcgcac   660
ctttggcctt  tcagcgatct  cgggggtgaa  ccgcgcgattg  tagttagagg  agaccacgga   720
cacataggca  ttttcttttc  ggtacagagt  cttctggtcc  tcgatgttag  agggatgggt   780
gacgcccac  aggaccagca  cttctttctc  ttattgttc  acatagctct  tgttcaggtt   840
tgggtatgag  ccattcttct  ctgtcagcca  cagcaggttt  ctgtaaaagc  ttgatttccc   900
cttatgacta  caagcggctg  tcacgccccg  ggtaatgttg  tgtttaggcc  aagacctttc   960
cttggggaag  atttcaaatc  tctcgaaact  agacacggag  ctcagctgct  ccctcagttc  1020
ctcataatct  gcgaaatagc  caggggaagca  tgttccattt  tcgctgttgg  gggtctcagc  1080
aatgtaggac  cagctttttct  tactaaacag  agattcacac  tctggattcc  ccagaatcca  1140
gccagcgatg  ttgcacttgc  ccagctgcag  aggggcgatg  gctagcacgc  cctgaggcag  1200
cagcaggttg  ctcaccacca  gcagcagcag  cagtctgctg  cccttctggc  tgctgccctt  1260
gctgtccat                                                             1269

SEQ ID NO: 144          moltype = DNA  length = 1266
FEATURE                 Location/Qualifiers
misc_feature            1..1266
                        note = Synthetic
source                  1..1266
```

-continued

```
                            mol_type = other DNA
                            organism = synthetic construct
SEQUENCE: 144
atggacagca agggcagcag ccagaagggc agcagactgc tgctgctgct ggtggtgagc    60
aacctgctgc tgcctcaggg cgtgctagcc gtgaagcctc tgatcctgag agattgtagc   120
gtggctggat ggctgctggg caaccctatg tgcgacgagt tcatcaacgt gcccgagtgg   180
agctatatcg tggagaaggc caaccccacc aacgatctgt gtttccccgg cagcttcaac   240
gattacgagg aactgaagca cctgctgtcc cggatcaacc acttcgagaa gatccagatc   300
atccccaagt cctcttggag cgatcacgaa gcctctagcg gagtgtctag cgcctgtcct   360
tacctgggca gccccagctt cttcagaaac gtggtgtggc tgatcaagaa gaacagcacc   420
taccccacca tcaagaagag ctacaacaac accaaccagg aagatctgct ggtcctgtgg   480
ggaatccacc accctaatga tgccgccgag cagaccagc tgtaccagaa ccccaccacc   540
tatatcagca tcggcaccag caccctgaat cagagactgg tgcccaagat cgccaccaga   600
tccaaggtga acggccagag cggcaggatg gaattcttct ggaccatcct gaagcccaac   660
gacgccatca acttcgagag caacggcaac tttatcgccc ctgagtacgc ctacaagatc   720
gtgaagaagg gctccggaga gagccaggtg aggcagcagt tcagcaagga catcgagaag   780
ctgctgaacg agcaggtgaa caaggagatg cagagcagca acctgtacat gagcatgagc   840
agctggtgct acacccacag cctggacggc gccggcctgt tcctgttcga ccacgccgcc   900
gaggagtacg agcacgccaa gaagctgatc atcttcctga acgagaacaa cgtgcccgtg   960
cagctgacca gcatcagcgc ccccgagcac aagttcgagg gcctgaccca gatcttccag  1020
aaggcctacg agcacgagca gcacatcagc gagagcatca acaacatcgt ggaccacgcc  1080
atcaagagca aggaccacgc caccttcaac ttcctgcagt ggtacgtggc cgagcagcac  1140
gaggaggagg tgctgttcaa ggacatcctg acaagtgag agctgatcgg caacgagaac  1200
cacgcctgt acctggccga ccagtacgtg aagggcatcg ccaagagcag gaagagcgga  1260
tcctag                                                              1266

SEQ ID NO: 145           moltype = AA  length = 421
FEATURE                  Location/Qualifiers
REGION                   1..421
                         note = Synthetic
source                   1..421
                         mol_type = protein
                         organism = synthetic construct
SEQUENCE: 145
MDSKGSSQKG SRLLLLLVVS NLLLPQGVLA VKPLILRDCS VAGWLLGNPM CDEFINVPEW    60
SYIVEKANPT NDLCFPGSFN DYEELKHLLS RINHFEKIQI IPKSSWSDHE ASSGVSSACP   120
YLGSPSFFRN VVWLIKKNST YPTIKKSYNN TNQEDLLVLW GIHHPNDAAE QTRLYQNPTT   180
YISIGTSTLN QRLVPKIATR SKVNGQSGRM EFFWTILKPN DAINFESNGN FIAPEYAYKI   240
VKKGSGESQV RQQFSKDIEK LLNEQVNKEM QSSNLYMSMS SWCYTHSLDG AGLFLFDHAA   300
EEYEHAKKLI IFLNENNVPV QLTSISAPEH KFEGLTQIFQ KAYEHEQHIS ESINNIVDHA   360
IKSKDHATFN FLQWYVAEQH EEEVLFKDIL DKIELIGNEN HGLYLADQYV KGIAKSRKSG   420
S                                                                   421

SEQ ID NO: 146           moltype = DNA  length = 1266
FEATURE                  Location/Qualifiers
misc_feature             1..1266
                         note = Synthetic
source                   1..1266
                         mol_type = other DNA
                         organism = synthetic construct
SEQUENCE: 146
ctaggatccg ctcttcctgc tcttggcgat gcccttcacg tactggtcgg ccaggtacag    60
gccgtggttc tcgttgccga tcagctcgat cttgtccagg atgtccttga acagcacctc   120
ctcctcgtgc tgctcggcca cgtaccactg caggaagttg aaggtggcgt ggtccttgct   180
cttgatggcg tggtccacga tgttgttgat gctctcgcta atgtgctgct cgtgctcgta   240
ggccttctgg aagatctggg tcaggccctc gaacttgtgc tcgggggcgc tgatgctggt   300
cagctgcacg ggcacgttgt tctcgttcag gaagatgatc agcttcttgg cgtgctcgta   360
ctcctcggcg gcgtggtcga acaggaacag gccggcgccg tccaggctgt gggtgtagca   420
ccagctgctc atgctcatgt acaggttgct gctctgcatc tccttgttca cctgctcgtt   480
cagcagcttc tcgatgtcct tgctgaactg ctgcctcacc tggctctctc cggagcccctt   540
cttcacgatc ttgtaggcgt actcaggggc gataaagttg ccgttgctct cgaagttgat   600
ggcgtcgttg ggcttcagga tggtccagaa gaattccatc ctgccgctct ggccgttcac   660
cttggatctg gtggcgatct tgggcaccag tctctgattc agggtgctgg tgccgatgct   720
gatataggtg gtggggttct ggtacagtct ggtctgctcg gcggcatcat taggtggtg   780
gattccccac aggaccagca gatcttcctg gttggtgttg ttgtagctct tcttgatggt   840
ggggtaggtg ctgttcttct tgatcagcca caccacgttt ctgaagaagc tggggctgcc   900
caggtaagga caggcgctag acactccgct agaggcttcg tgatcgctcc aagaggactt   960
ggggatgatc tggatcttct cgaagtggtt gatccgggac agcaggtgct tcagttcctc  1020
gtaatcgttg aagctgccgg ggaaacacag atcgttggtg gggttggcct tctccacgat  1080
atagctccac tcgggcacgt tgatgaactc gtcgcacata gggttgccca gcagccatcc  1140
agccacgcta caatctctca ggatcagagg cttcacggct agcacgccct gaggcagcag  1200
caggttgctc accaccagca gcagcagcag tctgctgccc ttctggctgc tgcccttgct  1260
gtccat                                                              1266

SEQ ID NO: 147           moltype = DNA  length = 1263
FEATURE                  Location/Qualifiers
misc_feature             1..1263
                         note = Synthetic
source                   1..1263
```

```
                          mol_type = other DNA
                          organism = synthetic construct
SEQUENCE: 147
atggacagta aggggtcttc acagaaaggg tcacggctgc tgctgctgct ggtcgtcagt    60
aacctgctgc tgcctcaggg agtgctagcc gtgaaacctg tgattctgcg cgactgtagc   120
gtggccggat ggctgctggg caaccctatg tgccgatgagt ttattaacgt ccctgagtgg   180
agctacatcg tggagaaggc atccccagcc aacgacctgt gcttccccgg caacttcaat   240
gattatgagg aactgaaaca cctgctgtct cgaatcaacc atttcgaaaa gatccagatc   300
atcccaaaga gctcctggag caatcacgac gcctctagtg gagtctcaag cgcttgtccc   360
tatctgggcc ggtcctcttt ctttagaaac gtggtctggc tgatcaagaa aaattctgcc   420
taccctacaa ttaagagaag ttacaacaac actaatcagg aggacctgct ggtgctgtgg   480
ggcgtccacc atcctaacga tgccgctgaa cagaccaaac tgtaccagaa tccaaccaca   540
tatatcagtg tggggacttc aaccctgaac cagaggctgg tgcccgagat tgcaacccgc   600
cctaaggtca atggccagtc cgggcggatg gaattctttt ggacaatcct gaaacccaac   660
gatgctatta atttcgagag caacgggaat tttatcgctc ctgaatacgc atataagatt   720
gtgaagaaag gctccggaga aagtcaggtg aggcagcagt tcagtaagga tatcgagaaa   780
ctgctgaacg aacaggtgaa caaggagatg cagtctagta acctgtacat gagtatgtca   840
agctggtgtt atacccactc actggacgga gccggcctgt tcctgtttga tcacgcagcg   900
gaggaatacg aacatgctaa gaaactgatc attttttctga acgagaacaa cgtcccagtg   960
cagctgacaa gtatctcagc ccccgagcat aagttcgaag gcctgactca gatctttcag  1020
aaagcctacg aacacgagca gcatattagc gagtccatca caatattgt ggaccacgca  1080
attaagagca aagatcatgc caccttcaat tttctgcagt ggtacgtggc cgagcagcac  1140
gaggaagagg tgctgttcaa ggacatcctg gataaaatcg aactgattgg caacgagaat  1200
catgggctgt acctggcaga ccagtatgtg aagggcattg ctaagtcaag aaaaagctga  1260
tga                                                                1263

SEQ ID NO: 148       moltype = AA   length = 419
FEATURE              Location/Qualifiers
REGION               1..419
                     note = Synthetic
source               1..419
                     mol_type = protein
                     organism = synthetic construct
SEQUENCE: 148
MDSKGSSQKG SRLLLLLVVS NLLLPQGVLA VKPLILRDCS VAGWLLGNPM CDEFINVPEW    60
SYIVEKASPA NDLCFPGNFN DYEELKHLLS RINHFEKIQI IPKSSWSNHD ASSGVSSACP   120
YLGRSSFFRN VVWLIKKNSA YPTIKRSYNN TNQEDLLVLW GVHHPNDAAE QTKLYQNPTT   180
YISVGTSTLN QRLVPEIATR PKVNGQSGRM EFFWTILKPN DAINFESNGN FIAPEYAYKI   240
VKKGSGESQV RQQFSKDIEK LLNEQVNKEM QSSNLYMSMS SWCYTHSLDG AGLFLFDHAA   300
EEYEHAKKLI IFLNENNVPV QLTSISAPEH KFEGLTQIFQ KAYEHEQHIS ESINNIVDHA   360
IKSKDHATFN FLQWYVAEQH EEEVLFKDIL DKIELIGNEN HGLYLADQYV KGIAKSRKS    419

SEQ ID NO: 149       moltype = DNA   length = 1263
FEATURE              Location/Qualifiers
misc_feature         1..1263
                     note = Synthetic
source               1..1263
                     mol_type = other DNA
                     organism = synthetic construct
SEQUENCE: 149
tcatcagctt tttcttgact tagcaatgcc cttcacatac tggtctgcca ggtacagccc    60
atgattctcg ttgccaatca gttcgatttt atccaggatg tccttgaaca gcacctcttc   120
ctcgtgctgc tcggccacgt accactgcag aaaattgaag gtggcatgat ctttgctctt   180
aattgcgtgg tccacaatat tgttgatgga ctcgctaata tgctgctcgt gttcgtaggc   240
tttctgaaag atctgagtca ggccttcgaa cttatgctcg ggggctgaga tacttgtcag   300
ctgcactggg acgttgttct cgttcagaaa aatgatcagt ttcttagcat gttcgtattc   360
ctcggctgcg tgatcaaaca ggaacaggcc ggctccgtcc agtgagtggg tataacacca   420
gcttgacata ctcatgtaca ggttactaga ctgcatctcc ttgttcacct gttcgttcag   480
cagtttctcg atatccttac tgaactgctg cctcacctga ctttctccgg agcctttct   540
cacaatcatta tatgcgtatt caggagcgat aaaattcccg ttgctctcga aattaatagc   600
atcgttgggt ttcaggattg tccaaaagaa ttccatccgc ccggactggc cattgacctt   660
agggcgggtt gcaatctcgg gcaccagcct ctggttcagg gttgaagtcc ccacactgat   720
atatgtggtt ggattctggt acagtttggt ctgttcagcg gcatcgttag gatggtggac   780
gccccacagc accagcaggt cctcctgatt agtgttgttg taacttctct taattgtagg   840
gtaggcagaa ttttttcttga tcagccagac cacgtttcta aagaaagagg accggcccag   900
ataggacaa cgcgcttgaga ctccactaga ggcgtcgtga ttgctccagg agctctttgg   960
gatgatctgg atcttttcga aatggttgat tcgagacagc aggtgtttca gttcctcata  1020
atcattgaag ttgccgggga agcacaggtc gttggctggg gatgccttct ccacgatgta  1080
gctccactca gggacgttaa taaatcatc gcacataggg ttgcccagca gcatcccggc  1140
cacgctacag tcgcgcagaa tcaggggttt cacggctagc actccctgag gcagcagcag  1200
gttactgacg accagcagca gcagcagccg tgacccctttc tgtgaagacc ccttactgtc  1260
cat                                                                1263

SEQ ID NO: 150       moltype = DNA   length = 1263
FEATURE              Location/Qualifiers
misc_feature         1..1263
                     note = Synthetic
source               1..1263
                     mol_type = other DNA
```

```
                         organism = synthetic construct
SEQUENCE: 150
atggacagta aggggtcttc acagaaaggg tcacggctgc tgctgctgct ggtcgtcagt   60
aacctgctgc tgcctcaggg agtgctagcc gtgaagcctc tgattctgaa agactgctcc  120
gtcgctggat ggctgctggg gaaccctatg tgtgatgagt ttattaacgt gcctgagtgg  180
agctacatcg tggagaaggc caaccccgct aatgacctgt gcttccctgg caacttcaat  240
gattatgagg aactgaaaca cctgctgagc cgaatcaacc attttgagaa gattcagatc  300
attcccaaag actcatggag cgatcacgaa gcttccctgg gagtgagctc cgcatgtcct  360
tatcagggca actctagttt ctttagaaat gtggtctggc tgatcaagaa aggcaacgcc  420
tacccaacaa ttaagaaatc ttacaacaac actaatcagg aagacctgct ggtcctgtgg  480
ggcatccacc atccaaacga tgaggccgaa cagaccaggc tgtaccagaa tcccaccaca  540
tatatctcca ttggcacttc taccctgaac cagcggctgg tgcccaagat cgccaccaga  600
agtaaagtca atggccagtc agggcgcatc gacttctttt ggacaattct gaagcctaac  660
gatgctatta atttcgagtc caacgggaat tttatcgcac cagaatacgc ctataagatt  720
gtgaagaaag gctccggaga aagtcaggtg aggcagcagt tcagtaagga tatcgagaaa  780
ctgctgaacg aacaggtgaa caaggagatg cagtctagta acctgtacat gagtatgtca  840
agctggtgtt atacccactc actggacgga gccggcctgt tcctgtttga tcacgcagcc  900
gaggaatacg aacatgctaa gaaactgatc atttttctga acgagaacaa cgtcccagtg  960
cagctgacaa gtatctcagc ccccgagcat aagttcgaag gcctgactca gatctttcag 1020
aaagcctacg aacacgagca gcatattagc gagtccatca acaatattgt ggaccacgca 1080
attaagagca aagatcatgc caccttcaat tttctgcagt ggtacgtggc cgagcagcac 1140
gaggaagagg tgctgttcaa ggacatcctg gataaaatcg aactgattgg caacgagaat 1200
catgggctgt acctggcaga ccagtatgtg aagggcattg ctaagtcaag aaaaagctga 1260
tga                                                               1263

SEQ ID NO: 151        moltype = AA   length = 419
FEATURE               Location/Qualifiers
REGION                1..419
                      note = Synthetic
source                1..419
                      mol_type = protein
                      organism = synthetic construct
SEQUENCE: 151
MDSKGSSQKG SRLLLLLVVS NLLLPQGVLA VKPLILKDCS VAGWLLGNPM CDEFINVPEW   60
SYIVEKANPA NDLCFPGNFN DYEELKHLLS RINHFEKIQI IPKDSWSDHE ASLGVSSACP  120
YQGNSSFFRN VVWLIKKGNA YPTIKKSYNN TNQEDLLVLW GIHHPNDEAE QTRLYQNPTT  180
YISIGTSTLN QRLVPKIATR SKVNGQSGRI DFFWTILKPN DAINFESNGN FIAPEYAYKI  240
VKKGSGESQV RQQFSKDIEK LLNEQVNKEM QSSNLYMSMS SWCYTHSLDG AGLFLFDHAA  300
EEYEHAKKLI IFLNENNVPV QLTSISAPEH KFEGLTQIFQ KAYEHEQHIS ESINNIVDHA  360
IKSKDHATFN FLQWYVAEQH EEEVLFKDIL DKIELIGNEN HGLYLADQYV KGIAKSRKS   419

SEQ ID NO: 152        moltype = DNA   length = 1263
FEATURE               Location/Qualifiers
misc_feature          1..1263
                      note = Synthetic
source                1..1263
                      mol_type = other DNA
                      organism = synthetic construct
SEQUENCE: 152
tcatcagctt tttcttgact tagcaatgcc cttcacatac tggtctgcca ggtacagccc   60
atgattctcg ttgccaatca gttcgatttt atccaggatg tccttgaaca gcacctcttc  120
ctcgtgctgc tcggccacgt accactgcag aaaattgaag gtggcatgat ctttgctctt  180
aattgcgtgg tccacaatat tgttgatgga ctcgctaata tgctgctcgt gttcgtaggc  240
tttctgaaag atctgagtca ggccttcgaa cttatgctcg ggggctgaga tacttgtcag  300
ctgcactggg acgttgttct cgttcagaaa aatgatcagt ttcttagcat gttcgtattc  360
ctcggctgcg tgatcaaaca ggaacaggcc ggctccgtcc agtgagtggg tataacacca  420
gcttgacata tcatgtaca ggttactaga ctgcatctcc ttgttcacct gttcgttcag  480
cagtttctcg atatccttac tgaactgctg cctcacctga ctttctccgg agcctttctt  540
cacaatctta taggcgtatt ctggtgcgat aaaattcccg ttggactcga aattaatagc  600
atcgttaggc ttcagaattg tccaaaagaa gtcgatgcgc cctgactggc cattgacttt  660
acttctggtg gcgatcttgg gcaccagccg ctggttcagg gtagaagtgc caatggagat  720
atatgtggtg ggattctggt acagcctggt ctgttcggcc tcatcgtttg atggtggat  780
gccccacagg accagcaggt cttcctgatt agtgttgttg taagatttct taattgttgg  840
gtaggcgttg cctttcttga tcagccagac cacatttcat aagaaactag agttgccctg  900
ataaggacat gcggagctca ctcccaggga agcttcgtga tcgctccatg agtctttggg  960
aatgatctga atcttctcaa aatggttgat tcggctcagc aggtgtttca gttcctcata 1020
atcattgaag ttgccaggga agcacaggtc attagcgggg ttggccttct ccacgatgta 1080
gctccactca ggcacgttaa taaactcatc acacataggt ttcccagca gccatccagc 1140
gacggagcag tctttcagaa tcagaggctt cacggctagc actccctgag gcagcagcag 1200
gttactgacg accagcagca gcagcagccg tgacccttct tgtgaagacc ccttactgtc 1260
cat                                                               1263

SEQ ID NO: 153        moltype = DNA   length = 1260
FEATURE               Location/Qualifiers
misc_feature          1..1260
                      note = Synthetic
source                1..1260
                      mol_type = other DNA
                      organism = synthetic construct
```

```
SEQUENCE: 153
atggacagta aggggtcttc acagaaaggg tcacggctgc tgctgctgct ggtcgtcagt    60
aacctgctgc tgcctcaggg agtgctagcc gtgaaacccc tgattctgaa agactgctct   120
gtggctggat ggctgctggg caaccctatg tgcgatgagt tcctgaatgt gtccgaatgg   180
tcttacatcg tggagaaggc cagtccagct aacggactgt gcttccccgg cgacttcaat   240
gattatgagg aactgaagca cctgctgtct aggatcaacc atttcgagaa gatcaagatc   300
atcccaaaga gctcctggtc caatcacgaa gcttctgggg tgtctagtgc atgtagttat   360
ctgggaaagc cctcattctt tcgcaacctg gtctggctga tcaagaaaaa caatacttac   420
cccccatca aggtcaatta tactaacacc aatcaggaag acctgctggt cctgtggggc    480
atccaccatc ctaacgatga gacagaacag gtgaagatct accagaatcc aaccacatat   540
atttcagtcg gcacaagcac tctgaaccag cggctggtgc ctaagattgc caccagaagc   600
aaagtcaatg gccagtccgg gcgaatggag ttcttttgga caatcctgaa gcccaacgac   660
gctattaatt tcgatagcaa cggcaacttc atcgcacctg aatacgccta taaaattgtg   720
aagaaagggt ccggagaaag tcaggtgagg cagcagttca gtaaggatat cgagaaactg   780
ctgaacgaac aggtgaacaa ggagatgcag tctagtaacc tgtacatgag tatgtcaagc   840
tggtgttata cccactcact ggacggagcc ggcctgttcc tgtttgatca cgcagccgag   900
gaatacgaac atgctaagaa actgatcatt tttctgaacg agaacaacgt cccagtgcag   960
ctgacaagta tctcagcccc cgagcataag ttcgaaggcc tgactcagat ctttcagaaa  1020
gcctacgaac acgagcagca tattagcgag tccatcaaca atattgtgga ccacgcaatt  1080
aagagcaaaa tcatgccac cttcaatttt ctgcagtggt acgtggccga gcagcacgag  1140
gaagaggtgc tgttcaagga catcctggat aaaatcgaac tgattggcaa cgagaatcat  1200
gggctgtacc tggcagacca gtatgtgaag ggcattgcta agtcaagaaa aagctgatga  1260
```

```
SEQ ID NO: 154          moltype = AA   length = 418
FEATURE                 Location/Qualifiers
REGION                  1..418
                        note = Synthetic
source                  1..418
                        mol_type = protein
                        organism = synthetic construct
SEQUENCE: 154
MDSKGSSQKG SRLLLLLVVS NLLLPQGVLA VKPLILKDCS VAGWLLGNPM CDEFLNVSEW    60
SYIVEKASPA NGLCFPGDFN DYEELKHLLS RINHFEKIKI IPKSSWSNHE ASGVSSACSY   120
LGKPSFFRNL VWLIKKNNTY PPIKVNYTNT NQEDLLVLWG IHHPNDETEQ VKIYQNPTTY   180
ISVGTSTLNQ RLVPKIATRS KVNGQSGRME FFWTILKPND AINFDSNGNF IAPEYAYKIV   240
KKGSGESQVR QQFSKDIEKL LNEQVNKEMQ SSNLYMSMSS WCYTHSLDGA GLFLFDHAAE   300
EYEHAKKLII FLNENNVPVQ LTSISAPEHK FEGLTQIFQK AYEHEQHISE SINNIVDHAI   360
KSKDHATFNF LQWYVAEQHE EEVLFKDILD KIELIGNENH GLYLADQYVK GIAKSRKS     418
```

```
SEQ ID NO: 155          moltype = DNA   length = 1260
FEATURE                 Location/Qualifiers
misc_feature            1..1260
                        note = Synthetic
source                  1..1260
                        mol_type = other DNA
                        organism = synthetic construct
SEQUENCE: 155
tcatcagctt tttcttgact tagcaatgcc cttcacatac tggtctgcca ggtacagccc    60
atgattctcg ttgccaatca gttcgatttt atccaggatg tccttgaaca gcacctcttc   120
ctcgtgctgc tcggccacgt accactgcag aaaattgaag gtggcatgat ctttgctctt   180
aattgcgtgg tccacaatat tgttgatgga ctcgctaata tgctgctcgt gttcgtaggc   240
tttctgaaag atctgagtca ggccttcgaa cttatgctcg ggggctgaga tacttgtcag   300
ctgcactggg acgttgttct cgttcagaaa aatgatcagt ttcttagcat gttcgtattc   360
ctcggctgcg tgatcaaaca ggaacaggcc ggctccgtcc agtgagtggg tataacacca   420
gcttgacata ctcatgtaca ggttactaga ctgcatctcc ttgttcacct gttcgttcag   480
cagtttctcg atatccttac tgaactgctg cctcacctga ctttctccgg accctttctt   540
cacaattttta taggcgtatt caggtgcgat gaagttgccg ttgctatcga aattaatagc   600
gtcgttgggc ttcaggattg tccaaaagaa ctccattcgc ccggactggc cattgacttt   660
gcttctggtg gcaatcttag gcaccagccg ctggttcaga gtgcttgtgc cgactgaaat   720
atatgtggtt ggattctggt agatcttcac ctgttctgtc tcatcgttag gatggtggat   780
gccccacagg accagcaggt cttcctgatt ggtgttagta taattgacct tgatggggg   840
gtaagtattg tttttcttga tcagccagac caggttgcga agaatgagg ctttcccag    900
ataactacat gcactagaca ccccagaagc ttcgtgattg gaccaggagc tctttgggat   960
gatcttgatc ttctcgaaat ggttgatcct agacagcagg tgcttcagtt cctcataatc  1020
attgaagtcg ccggggaagc acagtccgtt agctggactg gccttctcca cgatgtaaga  1080
ccattcggac acattcagga actcatcgca catggggttg cccagcagcc atccagccac  1140
agagcagtct ttcagaatca ggggtttcac ggctagcact ccctgaggca gcagcaggtt  1200
actgacgacc agcagcagca gcagccgtga ccctttctgt gaagacccct tactgtccat  1260
```

```
SEQ ID NO: 156          moltype = DNA   length = 1263
FEATURE                 Location/Qualifiers
misc_feature            1..1263
                        note = Synthetic
source                  1..1263
                        mol_type = other DNA
                        organism = synthetic construct
SEQUENCE: 156
atggacagta aggggtcttc acagaaaggg tcacggctgc tgctgctgct ggtcgtcagt    60
aacctgctgc tgcctcaggg agtgctagcc gtcaaacccc tgattctgag agattgtagt   120
```

```
gtcgctggct ggctgctggg caaccctatg tgtgatgagt ttattaacgt ccctgaatgg    180
tcttacatcg tggagaaagc aagtcccgcc aacgacctgt gcttccctgg cgacttcaat    240
gattatgagg aactgaaaca cctgctgtcc cgaatcaacc attttgagaa gattcagatc    300
attcccaaaa gctcctggtc taatcacgaa gcctctagtg gagtctcaag cgcttgtcct    360
tatctgggca agtcctcttt ctttaggaac gtggtctgca tgatcaagaa aaattcaaca    420
tacccaacca tcaagcgcag ttataacaat actaaccagg aggacctgct ggtgctgtgg    480
ggcatccacc atccaaacga tgccgctgaa cagacaaagc tgtaccagaa tcccaccaca    540
tatatcagtg tcgggacttc aaccctgaac cagcggctgg tgcccaagat tgccaccaga    600
agcaaagtca atggccagtc cgggagaatg gaattctttt ggacaatcct gaagcctaac    660
gatgccatta atttcgagag caacgggaat tttatcgctc cagaatacgc atataaaatt    720
gtgaagaaag gctccggaga aagtcaggtg aggcagcagt tcagtaagga tatcgagaaa    780
ctgctgaacg aacaggtgaa caaggagatg cagtctagta acctgtacat gagtatgtca    840
agctggtgtt atacccactc actggacgga gccggcctgt tcctgtttga tcacgcagcc    900
gaggaatacg aacatgctaa gaaactgatc attttctgta acgagaacaa cgtcccagtg    960
cagctgacaa gtatctcagc ccccgagcat aagttcgaag gcctgactca gatctttcag   1020
aaagcctacg aacacgagca gcatattagc gagtccatca acaatattgt ggaccacgca   1080
attaagagca aagatcatgc caccttcaat tttctgcagt ggtacgtggc cgagcagcac   1140
gaggaagagg tgctgttcaa ggacatcctg gataaaatcg aactgattgg caacgagaat   1200
catgggctgt acctggcaga ccagtatgtg aagggcattg ctaagtcaag aaaaagctga   1260
tga                                                                 1263

SEQ ID NO: 157            moltype = AA  length = 419
FEATURE                   Location/Qualifiers
REGION                    1..419
                          note = Synthetic
source                    1..419
                          mol_type = protein
                          organism = synthetic construct
SEQUENCE: 157
MDSKGSSQKG SRLLLLLVVS NLLLLPQGVLA VKPLILRDCS VAGWLLGNPM CDEFINVPEW     60
SYIVEKASPA NDLCFPGDFN DYEELKHLLS RINHFEKIQI IPKSSWSNHE ASSGVSSACP    120
YLGKSSFFRN VVWLIKKNST YPTIKRSYNN TNQEDLLVLW GIHHPNDAAE QTKLYQNPTT    180
YISVGTSTLN QRLVPKIATR SKVNGQSGRM EFFWTILKPN DAINFESNGN FIAPEYAYKI    240
VKKGSGESQV RQQFSKDIEK LLNEQVNKEM QSSNLYMSMS SWCYTHSLDG AGLFLFDHAA    300
EEYEHAKKLI IFLNENNVPV QLTSISAPEH KFEGLTQIFQ KAYEHEQHIS ESINNIVDHA    360
IKSKDHATFN FLQWYVAEQH EEEVLFKDIL DKIELIGNEN HGLYLADQYV KGIAKSRKS     419

SEQ ID NO: 158            moltype = DNA  length = 1263
FEATURE                   Location/Qualifiers
misc_feature              1..1263
                          note = Synthetic
source                    1..1263
                          mol_type = other DNA
                          organism = synthetic construct
SEQUENCE: 158
tcatcagctt tttcttgact tagcaatgcc cttcacatac tggtctgcca ggtacagccc     60
atgattctcg ttgccaatca gttcgatttt atccaggatg tccttgaaca gcacctcttc    120
ctcgtgctgc tcggccacgt accactgcag aaaattgaag gtggcatgat ctttgctctt    180
aattgcgtgg tccacaatat tgttgatgga ctcgctaata tgctgctcgt gttcgtaggc    240
tttctgaaag atctgagtca ggccttcgaa cttatgctcg ggggctgaga tacttgtcag    300
ctgcactggg acgttgttct cgttcagaaa aatgatcagt ttcttagcat gttcgtattc    360
ctcggctgcg tgatcaaaca ggaacaggcc ggctccgtcc agtgagtggg tataacacca    420
gcttgacata ctcatgtaca ggttactaga ctgcatctcc ttgttcacct gttcgttcag    480
cagtttctcg atatccttac tgaactgctg cctcacctga ctttctccgg agcctttctt    540
cacaatttta tatgcgtatt ctggagcgat aaaattcccg ttgctctcga aattaatggc    600
atcgttaggc ttcaggattg tccaaaagaa ttccattctc ccggactggc cattgacttt    660
gcttctggtg gcaatcttgg gcaccagccg ctggttcagg gttgaagtcc cgacactgat    720
atatgtggtg ggattctggt acagctttgt ctgttcagcg gcatcgtttg atggtggat    780
gccccacagc accagcaggt cctcctggtt agtattgtta taactgcgct tgatggttgg    840
gtatgttgaa tttttcttga tcagccagac cacgttccta aagaaagagg acttgcccag    900
ataaggacaa gcgcttgaga ctccactaga ggcttcgtga ttagaccagg agcttttggg    960
aatgatctga atcttctcaa aatggttgat tcgggacagc aggtgtttca gttcctcata   1020
atcattgaag tcgccaggga agcacaggtc gttggcggga cttgctttct ccacgatgta   1080
agaccattca gggacgttaa taaactcatc acacatgggt ttgcccagca gccagccacc   1140
gacactacaa tctctcagaa tcaggggttt gacggctagc actccctgag gcagcagcag   1200
gttactgacg accagcagca gcagcagccg tgaccctttc tgtgaagacc ccttactgtc   1260
cat                                                                 1263

SEQ ID NO: 159            moltype = DNA  length = 1263
FEATURE                   Location/Qualifiers
misc_feature              1..1263
                          note = Synthetic
source                    1..1263
                          mol_type = other DNA
                          organism = synthetic construct
SEQUENCE: 159
atggacagta aggggtcttc acagaaaggg tcacggctgc tgctgctgct ggtcgtcagt     60
aacctgctgc tgcctcaggg agtgctagcc gtcaaacctc tgattctgag agactgttcc    120
gtggctggat ggctgctggg caaccctatg tgcgatgagt ttatcaatgt ccccgagtgg    180
```

```
tcttacatcg tggagaaagc aagtcccgcc aacggactgt gcttccctgg cgacttcaat   240
gattatgagg aactgaaaca cctgctgtcc cggatcaacc attttgagaa gattcagatc   300
attcccaaaa gctcctggtc taatcacgaa gcctctagtg gggtctcaag cgcttgtcct   360
tatcaggaa  agtcctcttt ctttaggaac gtggtctggc tgatcaagaa aaattcaaca   420
tacccaacca tcaagcgcag ttataacaat actaaccagg aggacctgct ggtgctgtgg   480
ggcatccacc atccaaacga tgccgctgaa cagacacgac tgtaccagaa tcccaccaca   540
tatatcagtg tcggcacttc aaccctgaac cagcggctgg tgcccaagat tgccaccaga   600
agcaaagtca atggccagtc cgggagaatg gaattctttt ggacaatcct gaagcctaac   660
gacgccatta tttcgagag  caacggcaat tttatcgctc cagaatacgc atataagatt   720
gtgaagaaag ggtccggaga aagtcaggtg aggcagcagt tcagtaagga tatcgagaaa   780
ctgctgaacg aacaggtgaa caaggagatg cagtctagta acctgtacat gagtatgtca   840
agctggtgtt atacccactc actggacgga gccggcctgt tcctgtttga tcacgcagcc   900
gaggaatacg aacatgctaa gaaactgatc attttctga  acgagaacaa cgtcccagtg   960
cagctgacaa gtatctcagc ccccgagcat aagttcgaag gcctgactca gatctttcag  1020
aaagcctacg aacacgagca gcatattagc gagtccatca caatattgt  ggaccacgca  1080
attaagagca aagatcatgc caccttcaat tttctgcagt ggtacgtggc cgagcagcac  1140
gaggaagagg tgctgttcaa ggacatcctg gataaaatcg aactgattgg caacgagaat  1200
catgggctgt acctggcaga ccagtatgtg aagggcattg ctaagtcaag aaaaagctga  1260
tga                                                                 1263
```

```
SEQ ID NO: 160          moltype = AA   length = 419
FEATURE                 Location/Qualifiers
REGION                  1..419
                        note = Synthetic
source                  1..419
                        mol_type = protein
                        organism = synthetic construct
SEQUENCE: 160
MDSKGSSQKG SRLLLLLVVS NLLLLPQGVLA VKPLILRDCS VAGWLLGNPM CDEFINVPEW    60
SYIVEKASPA NGLCFPGDFN DYEELKHLLS RINHFEKIQI IPKSSWSNHE ASSGVSSACP   120
YQGKSSFFRN VVWLIKKNST YPTIKRSYNN TNQEDLLVLW GIHHPNDAAE QTRLYQNPTT   180
YISVGTSTLN QRLVPKIATR SKVNGQSGRM EFFWTILKPN DAINFESNGN FIAPEYAYKI   240
VKKGSGESQV RQQFSKDIEK LLNEQVNKEM QSSNLYMSMS SWCYTHSLDG AGLFLFDHAA   300
EEYEHAKKLI IFLNENNVPV QLTSISAPEH KFEGLTQIFQ KAYEHEQHIS ESINNIVDHA   360
IKSKDHATFN FLQWYVAEQH EEEVLFKDIL DKIELIGNEN HGLYLADQYV KGIAKSRKS    419
```

```
SEQ ID NO: 161          moltype = DNA   length = 1263
FEATURE                 Location/Qualifiers
misc_feature            1..1263
                        note = Synthetic
source                  1..1263
                        mol_type = other DNA
                        organism = synthetic construct
SEQUENCE: 161
tcatcagctt tttcttgact tagcaatgcc cttcacatac tggtctgcca ggtacagccc    60
atgattctgt tgccaatca  gttcgatttt atccaggatg tccttgaaca gcacctcttc   120
ctcgtgctgc tcggccacgt accactgcag aaaattgaag gtggcatgat ctttgctctt   180
aattgcgtgg tccacaatat tgttgatgga ctcgctaata tgctgctcgt gttcgtaggc   240
tttctgaaag atctgagtca ggccttcgaa cttatgctcg ggggctgaga tacttgtcag   300
ctgcactggg acgttgttct cgttcagaaa atgatcagt  ttcttagcat gttcgtattc   360
ctcggctgcg tgatcaaaca ggaacaggcc ggctccgtcc agtgagtggg tataacacca   420
gcttgacata ctcatgtaca ggttactaga ctgcatctcc ttgttcacct gttcgttcag   480
cagtttctcg atatccttac tgaactgctg cctcacctga ctttctccgg acctttctt    540
cacaatctta tatgcgtatt ctggagcgat aaaattgccg ttgctctcga attaatggc    600
gtcgttaggc ttcaggattg tccaaaagaa ttccattctc ccggactggc cattgacttt   660
gcttctggtg gcaatcttgg gcaccagccg ctggttcagg gttgaagtgc cgacactgat   720
atatgtggtg ggattctggt acagtcgtgt ctgttcagcg gcatcgtttg gatggtggat   780
gccccacagc accagcaggt cctcctggtt agtattgtta taactgcgct tgatggttgg   840
gtatgttgaa ttttcttga  tcagccagac cacgttccta aagaaagagg acttcccctg   900
ataaggacaa gcgcttgaga ccccactaga ggcttcgtga ttagaccagg agcttttggg   960
aatgatctga atcttctcaa aatggttgat ccgggacagc aggtgtttca gttcctcata  1020
atcattgaag tcgccaggga agcacagtcc gttggcggga cttgctttct ccacgatgta  1080
agaccactcg gggacattga taaactcatc gcacataggt tgcccagca  gccatccagc  1140
cacggaacag tctctcagaa tcagaggttt gacggctagc actccctgag gcagcagcag  1200
gttactgacg accagcagca gcagcagccg tgacccttc  tgtgaagacc cctactgtc   1260
cat                                                                 1263
```

```
SEQ ID NO: 162          moltype = DNA   length = 1251
FEATURE                 Location/Qualifiers
misc_feature            1..1251
                        note = Synthetic
source                  1..1251
                        mol_type = other DNA
                        organism = synthetic construct
SEQUENCE: 162
atggacagca aggcagcag  ccagaagggc agcagactgc tgctgctgct ggtggtgagc    60
aacctgctgc tgcctcaggg cgtgctagcc accagatcc  tggatggcga aaactgtaca   120
ctgattgacg ctctgctggg agaccctcag tgcgatggct ccagaataa  gaaatgggat   180
ctgtttgtgg agaggtctaa ggcatacagt aactgtttcc cctatgacgt gcctgattat   240
```

```
gcaagcctgc gctccctggt cgcctctagt ggcacactgg agttcaacaa tgaaagcttt  300
aattggacag gggtgactca gaacggaact tcaagcgcct gcatccggag atctaacaac  360
agtttctttt caagactgaa ctggctgacc cagctgaatt tcaagtaccc tgctctgaac  420
gtgacaatgc caaacaatga gcagtttgac aagctgtata tctggggcgt gcaccatccc  480
gtcaccgaca aagatcagat cttcctgtac gcacagtcct ctggcaggat taccgtgtca  540
acaaagcgca gccagcaggc cgtcatccct aatattgggt acaggccacg catccgaaac  600
attcccagcc gcatctccat ctactggact atcgtgaaac caggcgatat cctgctgatt  660
aactccaccg gaaatctgat tgccccccgg ggctatttca agattagaag tggggcctcc  720
ggagagagca aggtgaggca gcagttcagc aaggacatcg agaagctgct gaacgagcag  780
gtgaacaagg agatgcagag cagcaacctg tacatgagca tgagcagctg gtgctacacc  840
cacagcctgg acggcgccgg cctgttcctg ttcgaccacg ccgccgagga gtacgagcac  900
gccaagaagc tgatcatctt cctgaacgag aacaacgtgc ccgtgcagct gaccagcatc  960
agcgcccccg agcacaagtt cgagggcctg acccagatct tccagaaggc ctacgagcac  1020
gagcagcaca tcagcgagag catcaacaac atcgtggacc acgccatcaa gagcaaggac  1080
cacgccacct tcaacttcct gcagtggtac gtggccgagc agcacgagga ggaggtgctg  1140
ttcaaggaca tcctggacaa gatcgagctg atcggcaacg agaaccacgg cctgtacctg  1200
gccgaccagt acgtgaaggg catcgccaag agcaggaaga gcggatccta g  1251
```

SEQ ID NO: 163                     moltype = AA  length = 416
FEATURE                            Location/Qualifiers
REGION                             1..416
                                   note = Synthetic
source                             1..416
                                   mol_type = protein
                                   organism = synthetic construct
SEQUENCE: 163

```
MDSKGSSQKG SRLLLLLVVS NLLLPQGVLA HQILDGENCT LIDALLGDPQ CDGFQNKKWD  60
LFVERSKAYS NCFPYDVPDY ASLRSLVASS GTLEFNNESF NWTGVTQNGT SSACIRRSNN  120
SFFSRLNWLT QLNFKYPALN VTMPNNEQFD KLYIWGVHHP VTDKDQIFLY AQSSGRITVS  180
TKRSQQAVIP NIGYRPRIRN IPSRISIYWT IVKPGDILLI NSTGNLIAPR GYFKIRSGAS  240
GESQVRQQFS KDIEKLLNEQ VNKEMQSSNL YMSMSSWCYT HSLDGAGLFL FDHAAEEYEH  300
AKKLIIFLNE NNVPVQLTSI SAPEHKFEGL TQIFQKAYEH EQHISESINN IVDHAIKSKD  360
HATFNFLQWY VAEQHEEEVL FKDILDKIEL IGNENHGLYL ADQYVKGIAK SRKSGS  416
```

SEQ ID NO: 164                     moltype = DNA  length = 1251
FEATURE                            Location/Qualifiers
misc_feature                       1..1251
                                   note = Synthetic
source                             1..1251
                                   mol_type = other DNA
                                   organism = synthetic construct
SEQUENCE: 164

```
ctaggatccg ctcttcctgc tcttggcgat gcccttcacg tactggtcgg ccaggtacag  60
gccgtggttc tcgttgccga tcagctcgat cttgtccagg atgtccttga acagcacctc  120
ctcctcgtgc tgctcggcca cgtaccactg caggaagttg aaggtggcgt ggtccttgct  180
cttgatggcg tggtccacga tgttgttgat gctctcgctg atgtgctgct cgtgctcgta  240
ggccttctgg aagatctggg tcaggccctc gaacttgtgc tcggggggcc tgatgctggt  300
cagctgcacg ggcacgttgt tctcgttcag gaagatgatc agcttcttgg cgtgctcgta  360
ctcctcggcg gcgtggtcga acaggaacag gccggcgccg tccaggctgt gggtgtagca  420
ccagctgctc atgctcatgt acaggttgct gctctgcatc tccttgttca cctgctcgtt  480
cagcagcttc tcgatgtcct tgctgaactg ctgcctcacc tggctctctc cggaggcccc  540
acttctaatc ttgaaatagc cccggggggc aatcagattt ccggtggagt taatcagcag  600
gatatcgcct ggtttcacga tagtccagta gatggagatg cggctgggaa tgtttccggt  660
gcgtggcctg tacccaatat tagggatgac ggcctgctgg ctgcgctttg ttgacacggt  720
aatcctgcca gaggactgtg cgtacaggaa gatctgatct ttgtcggtga cgggatggtg  780
cacgccccag atatacagct tgtcaaactg ctcattgttt ggcattgtca cgttcgagag  840
agggtacttg aaattcagct gggtcagcca gttcagtctt gaaaagaaac tgttgttaga  900
tctccggatg caggcgcttg aagttccgtt ctgagtcacc cctgtccaat aaagctttc   960
attgttgaac tccagtgtgc cactagaggc gaccagggag cgcagccttg cataatcagg  1020
cacgtcatag gggaaacagt tactgtatgc cttagacctc tccacaaaca gatcccattt  1080
cttattctgg aagccatcgc actgagggtc tcccagcaga gcgtcaatca gtgtacagtt  1140
ttcgccatcc aggatctggt gggctagcac gccctgaggc agcagcaggt tgctcaccac  1200
cagcagcagc agcagtctgc tgcccttctg gctgctgccc ttgctgtcca t  1251
```

SEQ ID NO: 165                     moltype = DNA  length = 1320
FEATURE                            Location/Qualifiers
misc_feature                       1..1320
                                   note = Synthetic
source                             1..1320
                                   mol_type = other DNA
                                   organism = synthetic construct
SEQUENCE: 165

```
atggacagca agggcagcag ccagaagggc agcagactgc tgctgctgct ggtggtgagc  60
aacctgctgc tgcctcaggg cgtgctagcc aaaacacgcg gaaaactgtg ccccgactgt  120
ctgaactgca ccgacctgga tgtggcactg gacgaccta tgtgtgtcgg aaccacacca  180
tccgcaaaag cctctattct gcacgaggtg cggcccgtca cttctggctg cttccctatc  240
atgcatgacc ggaccaagat tagacagctg gccaacctgc tgaggggggta cgaaaatatc  300
cgcctgtcca cacagaacgt gattgatgct gagaaggcac caggaggacc atatcgcctg  360
ggaacctccg ggtcttgtcc caatgctaca agtaaatcag gcttctttgc aactatggct  420
```

```
tgggcagtgc ctaaggacaa caacaagaac gctacaaatc ccctgactgt ggaagtccct  480
tacatctgcg cagaggggga agaccagatt accgtgtggg gatttcactc tgacgataag  540
acacagatga aaaacctgta cggggatagt aatcctcaga agttcaccag ctccgccaac  600
ggagtgacta cccattatgt cagtcagatc ggaggcttcc cagaccagac tgaggatggg  660
ggactgcccc agtcaggcag aatcgtggtc gactacatga tgcagaagcc tggaaaaact  720
ggcaccattg tgtatcagag aggagtcctg ctgccacaga aagtgtggtg tgcatcaggc  780
aggagctccg gagagagcca ggtgaggcag cagttcagca aggacatcga gaagctgctg  840
aacgagcagg tgaacaagga gatgcagagc agcaacctgt acatgagcat gagcagctgg  900
tgctacaccc acagcctgga cggcgccggc ctgttcctgt tcgaccacgc cgccgaggag  960
tacgagcacg ccaagaagct gatcatcttc ctgaacgaga acaacgtgcc cgtgcagctg  1020
accagcatca gcgcccccga gcacaagttc gagggcctga cccagatctt ccagaaggcc  1080
tacgagcacg agcagcacat cagcgagagc atcaacaaca tcgtggacca cgccatcaag  1140
agcaaggacc acgccacctt caacttcctg cagtggtacg tggccgagca gcacgaggag  1200
gaggtgctgt tcaaggacat cctggacaag atcgagctga tcggcaacga gaaccacggc  1260
ctgtacctgg ccgaccagta cgtgaagggc atcgccaaga gcaggaagag cggatcctag  1320
```

SEQ ID NO: 166    moltype = AA  length = 439
FEATURE          Location/Qualifiers
REGION           1..439
                    note = Synthetic
source           1..439
                    mol_type = protein
                    organism = synthetic construct

```
SEQUENCE: 166
MDSKGSSQKG SRLLLLLVVS NLLLLPQGVLA KTRGKLCPDC LNCTDLDVAL GRPMCVGTTP  60
SAKASILHEV RPVTSGCFPI MHDRTKIRQL ANLLRGYENI RLSTQNVIDA EKAPGGPYRL  120
GTSGSCPNAT SKSGFFATMA WAVPKDNNKN ATNPLTVEVP YICAEGEDQI TVWGFHSDDK  180
TQMKNLYGDS NPQKFTSSAN GVTTHYVSQI GGFPDQTEDG GLPQSGRIVV DYMMQKPGKT  240
GTIVYQRGVL LPQKVWCASG RSSGESQVRQ QFSKDIEKLL NEQVNKEMQS SNLYMSMSSW  300
CYTHSLDGAG LFLFDHAAEE YEHAKKLIIF LNENNVPVQL TSISAPEHKF EGLTQIFQKA  360
YEHEQHISES INNIVDHAIK SKDHATFNFL QWYVAEQHEE EVLFKDILDK IELIGNENHG  420
LYLADQYVKG IAKSRKSGS  439
```

SEQ ID NO: 167    moltype = DNA  length = 1320
FEATURE          Location/Qualifiers
misc_feature      1..1320
                    note = Synthetic
source           1..1320
                    mol_type = other DNA
                    organism = synthetic construct

```
SEQUENCE: 167
ctaggatccg ctcttcctgc tcttggcgat gcccttcacg tactggtcgg ccaggtacag  60
gccgtggttc tcgttgccga tcagctcgat cttgtccagg atgtccttga acagcacctc  120
ctcctcgtgc tgctcggcca cgtaccactg caggaagttg aaggtggcgt ggtccttgct  180
cttgatggcg tggtccacga tgttgttgat gctctcgctg atgtgctgct cgtgctcgta  240
ggccttctgg aagatctggg tcaggccctc gaacttgtgc tcgggggcgc tgatgctggt  300
cagctgcacg ggcacgttgt tctcgttcag gaagatgatc agcttcttgg cgtgctcgta  360
ctcctcggcg gcgtggtcga acaggaacag gccggcgccg tccaggctgt gggtgtagca  420
ccagctgctc atgctcatgt acaggttgct gctctgcatc tccttgttca cctgctcgtt  480
cagcagcttc tcgatgtcct tgctgaactg ctgcctcacc tggctctctc cggagctcct  540
gcctgatgca caccacactt tctgtggcag caggactcct ctctgataca caatggtgcc  600
agtttttcca ggcttctgca tcatgtagtc gaccacgatt ctgcctgact ggggcagtgc  660
cccatcctca gtctggtctg ggaagcctcc gatcgactg acataatggg tagtcactcc  720
gttggcggag ctggtgaact tctgaggatt actatccccg tacaggtttt tcatctgtgt  780
cttatcgtca gagtgaaatc cccacacggt aatctggtct tcccccctg cgcagatgta  840
agggacttcc acagtcaggg gatttgtagc gttcttgttg ttgtccttag gcactgccca  900
agccatagtt gcaaagaagc ctgatttact tgtagcattg ggacaagacc cggaggttcc  960
caggcgatat ggtcctcctg gtgccttctc agcatcaatc acgttctgtg tggacaggcg  1020
gatattttcg tacccctca gcaggttggc cagctgtca atcttggtcc ggtcatgcat  1080
gatagggaag cagccagaag tgacgggccg cacctcgtgc agaatagagg cttttgcgga  1140
tggtgtggtt ccgacacaca taggtcgtca cagtgccaca tccaggtcgg tgcagttcag  1200
acagtcgggg cacagttttc cgcgtgtttt ggctagcacg ccctgaggca gcagcaggtt  1260
gctcaccacc agcagcagca gcagtctgct gcccttctgg ctgctgccct tgctgtccat  1320
```

SEQ ID NO: 168    moltype = DNA  length = 1323
FEATURE          Location/Qualifiers
misc_feature      1..1323
                    note = Synthetic
source            1..1323
                    mol_type = other DNA
                    organism = synthetic construct

```
SEQUENCE: 168
atggacagca agggcagcag ccagaagggc agcagactgc tgctgctgct ggtggtgagc  60
aacctgctgc tgcctcaggg cgtgctagcc gagacaagag gcaagctgtg ccccaagtgc  120
ctgaactgta ccgatctgga tgtggccctg ggcagaccta gtgtaccggg caagatccct  180
agcgccagag tgtctatcct gcacgaagtg cggcctgtga ccagcggctg cttccccatc  240
atgcacgacc ggaccaagat cagacagctg cccaatctgc tgagaggcta cgagcacatc  300
agactgagca cccacaacgt gatcaatgcc gagaatgccc tggcggccc ttacaagatc  360
ggcacctccg gcagctgtcc caacatcacc aacggcaacg gctttttgc cacaatggcc  420
```

-continued

```
tgggccgtgc ctaagaacga caagaacaag accgccacca accctctgac aatcgaggtg   480
ccctacatct gtaccgaggg cgaggatcag atcacagtgt ggggcttcca cagcgacaac   540
gagactcaga tggccaagct gtacggcgac agcaagcccc agaagtttac cagcagcgcc   600
aatggcgtga ccacccacta cgtgtctcag atcggcggct ccctaatca gacagaggat   660
ggcggcctgc ctcagagcgg cagaatcgtg gtggactaca tggtgcagaa gtccggcaag   720
accggcacca tcacctacca gagaggcatc ctgctgcctc agaaagtgtg gtgtgccagc   780
ggcagatcct ccggagagag ccaggtgagg cagcagttca gcaaggacat cgagaagctg   840
ctgaacgagc aggtgaacaa ggagatgcag agcagcaacc tgtacatgag catgagcagc   900
tggtgctaca cccacagcct ggacggcgcc ggcctgttcc tgttcgacca cgccgccgag   960
gagtacgagc acgccaagaa gctgatcatc ttcctgaacg agaacaacgt gcccgtgcag  1020
ctgaccagca tcagcgcccc cgagcacaag ttcgagggcc tgacccagat cttccagaag  1080
gcctacgagc acgagcagca catcagcgag agcatcaaca acatcgtgga ccacgccatc  1140
aagagcaagg accacgccac cttcaacttc ctgcagtggt acgtggccga gcagcacgag  1200
gaggaggtgc tgttcaagga catcctggac aagatcgagc tgatcggcaa cgagaaccac  1260
ggcctgtacc tggccgacca gtacgtgaag ggcatcgcca gagcaggaa gagcggatcc  1320
tag                                                                1323
```

```
SEQ ID NO: 169       moltype = AA   length = 440
FEATURE              Location/Qualifiers
REGION               1..440
                     note = Synthetic
source               1..440
                     mol_type = protein
                     organism = synthetic construct
SEQUENCE: 169
MDSKGSSQKG SRLLLLLVVS NLLLPQGVLA ETRGKLCPKC LNCTDLDVAL GRPKCTGKIP   60
SARVSILHEV RPVTSGCFPI MHDRTKIRQL PNLLRGYEHI RLSTHNVINA ENAPGGPYKI  120
GTSGSCPNIT NGNGFFATMA WAVPKNDKNK TATNPLTIEV PYICTEGEDQ ITVWGFHSDN  180
ETQMAKLYGD SKPQKFTSSA NGVTTHYVSQ IGGFPNQTED GGLPQSGRIV VDYMVQKSGK  240
TGTITYQRGI LLPQKVWCAS GRSSGESQVR QQFSKDIEKL LNEQVNKEMQ SSNLYMSMSS  300
WCYTHSLDGA GLFLFDHAAE EYEHAKKLII FLNENNVPVQ LTSISAPEHK FEGLTQIFQK  360
AYEHEQHISE SINNIVDHAI KSKDHATFNF LQWYVAEQHE EEVLFKDILD KIELIGNENH  420
GLYLADQYVK GIAKSRKSGS                                              440
```

```
SEQ ID NO: 170       moltype = DNA   length = 1323
FEATURE              Location/Qualifiers
misc_feature         1..1323
                     note = Synthetic
source               1..1323
                     mol_type = other DNA
                     organism = synthetic construct
SEQUENCE: 170
ctaggatccg ctcttcctgc tcttggcgat gcccttcacg tactggtcgg ccaggtacag   60
gccgtggttc tcgttgccga tcagctcgat cttgtccagg atgtccttga acagcacctc  120
ctcctcgtgc tgctcggcca cgtaccactg caggaagttg aaggtggcgt ggtccttgct  180
cttgatggcg tggtccacga tgttgttgat gctctcgctg atgtgctgct cgtgctcgta  240
ggccttctgg aagatctggg tcaggccctc gaacttgtgc tgggggtcgc tgatgctggt  300
cagctgcacg ggcacgttgt tctcgttcag gaagatgatc agcttcttgg cgtgctcgta  360
ctcctcggcg gcgtggtcga acaggaacag gccggcgccg tccaggctgt gggtgtagca  420
ccagctgctc atgctcatgt acaggttgct gctctgcatc tccttgttca cctgctcgtt  480
cagcagcttc tcgatgtcct tgctgaactg ctgcctcacc tggctctctc cggaggatct  540
gccgctggca caccacactt tctgaggcag caggatgcct ctctggtagg tgatggtgcc  600
ggtcttgccg gacttctgca ccatgtagtc caccacgatt ctgccgctct gaggcaggcc  660
gccatcctct gtctgattag ggaagccgcc gatctgagac acgtagtggg tggtcacgcc  720
attggcgctg ctggtaaact tctggggctt gctgtcgccg tacagcttgg ccatctgagt  780
ctcgttgtcg ctgtggaagc cccacactgt gatctgatcc tcgccctcgg tacagatgta  840
gggcacctcg attgtcagag ggttggtggc ggtcttgttc ttgtcgttct taggcacggc  900
ccaggccatt gtggcaaaaa agccgttgcc gttggtgatg ttgggacagc tgccggaggt  960
gccgatcttg taagggccgc cagggggcatt ctcggcattg atcacgttgt gggtgctcag  1020
tctgatgtgc tcgtagcctc tcagcagatt gggcagctgt ctgatcttgg tccggtcgtg  1080
catgatgggg aagcagccgc tggtcacagg ccgcacttcg tgcaggatag acactctggc  1140
gctaggatc ttgccggtac acttaggtct gcccagggcc acatccagat cggtacagtt  1200
caggcacttg gggcacagct tgcctcttgt ctcggctagc acgccctgag gcagcagcag  1260
gttgctcacc accagcagca gcagcagtct gctgcccttc tggctgctgc ccttgctgtc  1320
cat                                                                1323
```

```
SEQ ID NO: 171       moltype = DNA   length = 2604
FEATURE              Location/Qualifiers
misc_feature         1..2604
                     note = Synthetic
source               1..2604
                     mol_type = other DNA
                     organism = synthetic construct
SEQUENCE: 171
atggacagca agggcagcag ccagaagggc tccagactgc tgctgctcct ggtggtgtcc   60
aacctcctgc tgcctcaggg cgtgctagcc gtggctcctc tgcacctggg caagtgcaat  120
atcgccggct ggattctggg caaccccgag tgcgagagcc tgagcacagc cagcagctgg  180
tcctacatct tggaaacccc tagcagcgac aacggcaccc gtttccccgg cgacttcatc  240
gactacgagg aactgcgcga gcagctgagc agcgtgtcca gcttcgagag attcgagatc  300
```

```
ttccccaaga cctccagctg gcccaaccac gacagcaaca aaggcgtgac cgccgcctgt   360
cctcacgctg gcgccaagag ctttctacaag aacctgatct ggctggtcaa gaagggcaac   420
agctacccca agctgagcaa gagctacatc aacgacaagg gcaaagaggt gctggtcctc   480
tggggcatcc accaccctag cacaagcgcc gaccagcaga gcctgtacca gaacgccgac   540
gcctacgtgt tcgtgggcag ctcccggtac agcaagaagt tcaagcccga gatcgccatc   600
cggcccaaag tgcgggacca ggaaggccgg atgaactact actggaccct ggtggaaccc   660
ggcgacaaga tcaccttcga ggccaccggc aatctggtgg tgcccagata cgccttcgcc   720
atggaaagaa acgccagcgg cgagagccaa gtccgacagc agttcagcaa ggacatcgag   780
aagctgctga acgagcaggt caacaaagag atgcagagca gcaacctgta catgagcatg   840
tccagctggt gttacaccca cagcctggac ggcgctggcc tgttcctgtt tgatcacgcc   900
gccgaggaat acgagcacgc caagaagctg atcatcttcc tgaacgagaa caacgtgccc   960
gtgcagctga ccagcatcag cgccccagag cacaagttcg agggcctgac ccagatcttc  1020
cagaaggcct acgaacacga gcagcacatc agcgagagca tcaacaatat cgtggaccac  1080
gccatcaaga gcaaggatca cgccaccttc aactttctgc aatggtacgt ggccgaacag  1140
cacgaggaag aagtgctgtt taaggacatc ctggacaaga tcgagctgat cggcaacag  1200
aaccacggcc tgtacctggc cgaccagtac gtgaagggca ttgccaagag cagaaagagc  1260
cggaagcgga gatctggcag cggcgctcct gtgaagcaga ccctgaactt cgacctgctg  1320
aagctggccg gcgacgtgga aagcaaccct gggcccatgg actccaaggg ctcctcccag  1380
aaaggatctc ggctgctcct cctgctcgtg gtgtctaatc tgctgctgcc acagggtgtc  1440
ctggcccacc agatcctgga tggcgagaac tgcaccctga tcgacgccct gctgggcgac  1500
cctcagtgcg acggcttcca gaacaagaag tgggacctgt tcgtcgagcg gagcaaggcc  1560
tacagcaact gcttcccta cgacgtgccc gactacgcca gcctgagaag cctggtggcc  1620
agcagcggca ccctggaatt caacaacgag agcttcaact ggaacggcgt gacccagaac  1680
ggcaccagct ccgcctgcat cagaagaagc aacaacagct tcttctcccg gctgaactgg  1740
ctgacccacc tgaatttcaa gtaccccgcc ctgaacgtga ccatgcccaa caatgagcag  1800
ttcgacaagc tgtacatctg gggagtgcac caccccgtga ccgacaagga ccagatcttt  1860
ctgtacgccc agcccagcgg ccggatcacc gtgtctacca agagaagcca gcaggccgtg  1920
atccccaaca tcggcttccg gcccaggatc agaaacatcc ccagccggat cagcatctac  1980
tggacaatcg tgaagcctgg cgacatcctg ctgatcaaca gcaccggcaa cctgatcgcc  2040
cctcggggcct acttcaagat cagaagcggc gcctccggag aatctcaagt ccgccagcag  2100
ttttctaagg acatcgaaaa gctgctcaat gaacaggtca acaaagagat gcagtcctct  2160
aacctgtata tgagtatgag ttcctggtgc tataccact ctctcgacgg tgcagggctg  2220
ttcctcttcg accacgctgc agaggaatat gaacatgcta agaaactgat tatctttctc  2280
aacgaaaaca acgtgccagt ccagctcacc agtatctctg cccctgaaca taagtttgag  2340
gggctcactc agatctttca gaaagcttac gagcacgagc agcatatctc tgagtctatt  2400
aacaacatcg tcgaccatgc tatcaaatct aaagaccacg ctactttta ctttctccaa  2460
tggtacgtcg cagagcagca tgaggaagag gtcctcttca aggacattct cgacaaaatt  2520
gaactcatcg gaaacgaaaa ccatgggctc tacctggctg atcagtacgt caagggaatc  2580
gcaaaaagcc ggaagtcttg atga                                          2604
```

SEQ ID NO: 172              moltype = AA  length = 865
FEATURE                    Location/Qualifiers
REGION                     1..865
                           note = Synthetic
source                     1..865
                           mol_type = protein
                           organism = synthetic construct
SEQUENCE: 172

```
DSKGSSQKGS RLLLLLVVSN LLLPQGVLAV APLHLGKCNI AGWILGNPEC ESLSTASSWS   60
YIVETPSSDN GTCFPGDFID YEELREQLSS VSSFERFEIF PKTSSWPNHD SNKGVTAACP  120
HAGAKSFYKN LIWLVKKGNS YPKLSKSYIN DKGKEVLVLW GIHHPSTSAD QQSLYQNADA  180
YVFVGSSRYS KKFKPEIAIR PKVRDQEGRM NYYWTLVEPG DKITFEATGN LVVPRYAFAM  240
ERNASGESQV RQQFSKDIEK LLNEQVNKEM QSSNLYMSMS SWCYTHSLDG AGLFLFDHAA  300
EEYEHAKKLI IFLNENNVPV QLTSISAPEH KFEGLTQIFQ KAYEHEQHIS ESINNIVDHA  360
IKSKDHATFN FLQWYVAEQH EEEVLFKDIL DKIELIGNEN HGLYLADQYV KGIAKSRKSR  420
KRRSGSGAPV KQTLNFDLLK LAGDVESNPG PMDSKGSSQK GSRLLLLLVV SNLLLPQGVL  480
AHQILDGENC TLIDALLGDP QCDGFQNKKW DLFVERSKAY SNCFPYDVPD YASLRSLVAS  540
SGTLEFNNES FNWNGVTQNG TSSACIRRSN NSFFSRLNWL THLNFKYPAL NVTMPNNEQF  600
DKLYIWGVHH PVTDKDQIFL YAQPSGRITV STKRSQQAVI PNIGFRPRIR NIPSRISIYW  660
TIVKPGDILL INSTGNLIAP RGYFKIRSGA SGESQVRQQF SKDIEKLLNE QVNKEMQSSN  720
LYMSMSSWCY THSLDGAGLF LFDHAAEEYE HAKKLIIFLN ENNVPVQLTS ISAPEHKFEG  780
LTQIFQKAYE HEQHISESIN NIVDHAIKSK DHATFNFLQW YVAEQHEEEV LFKDILDKIE  840
LIGNENHGLY LADQYVKGIA KSRKS                                         865
```

SEQ ID NO: 173              moltype = DNA  length = 2604
FEATURE                    Location/Qualifiers
misc_feature               1..2604
                           note = Synthetic
source                     1..2604
                           mol_type = other DNA
                           organism = synthetic construct
SEQUENCE: 173

```
tcatcaagac ttccggcttt ttgcgattcc cttgacgtac tgatcagcca ggtagagccc   60
atggttttcg tttccgaatga gttcaatttt gtcgagaatg tccttgaaga ggacctcttc  120
ctcatgctgc tctgcgacgt accattggag aaagttaaaa gtagcgtggt ctttagattt  180
gatagcatgg tcgacgatgt tgttaataga ctcagagata tgctgctcgt gctcgtaagc  240
tttctgaaat atctgagtga gcccctcaaa cttatgttca ggggcagaga tactggtgag  300
ctggactggc acgttgtttt cgttgagaaa gataatcagt ttcttagcat gttcatattc  360
ctctgcagcg tggtcgaaga ggaacagccc tgcaccgtcg agagagtggg tatagcacca  420
```

-continued

```
ggaactcata ctcatataca ggttagagga ctgcatctct ttgttgacct gttcattgag   480
cagcttttcg atgtccttag aaaactgctg gcggacttga gattctccgg aggcgccgct   540
tctgatcttg aagtagcccc gagggcgat caggttgccg gtgctgttga tcagcaggat    600
gtcgccaggc ttcacgattg tccagtagat gctgatccgg ctgggatgt ttctgatcct    660
gggccggaag ccgatgttgg ggatcacggc ctgctgctt ctcttggtag acacggtgat    720
ccggccgctg ggctgggcgt acagaaagat ctggtccttg tcggtcacgg ggtggtgcac    780
tccccagatg tacagcttgt cgaactgctc attgttgggc atggtcacgt tcagggcggg    840
gtacttgaaa ttcaggtggg tcagccagtt cagccgggag aagaagctgt tgttgcttct    900
tctgatgcag gcggagctgg tgccgttctg ggtcacgccg ttccagttga agctctcgtt    960
gttgaattcc agggtgccgc tgctggccac caggcttctc aggctggcgt agtcgggcac   1020
gtcgtagggg aagcagttgc tgtaggcctt gctccgctcg acgaacaggt cccacttctt   1080
gttctggaag ccgtcgcact gagggtcgcc cagcagggcg tcgatcaggg tgcagttctc   1140
gccatccagg atctggtggg ccaggacacc ctgtggcagc agcagattag acaccacgag   1200
caggaggagc agccgagatc ctttctggga ggagcccttg gagtccatgg gcccagggtt   1260
gctttccacg tcgccggcca gcttcagcag gtcgaagttc agggtctgct tcacaggagc   1320
gccgctgcca gatctccgct tccggctctt tctgctcttg gcaatgccct tcacgtactg   1380
gtcggccagg tacaggccgt ggttctcgtt gccgatcagc tcgatcttgt ccaggatgtc   1440
cttaaacagc acttcttcct cgtgctgttc ggccacgtac cattgcagaa agttgaaggt   1500
ggcgtgatcc ttgctcttga tggcgtggtc cacgatattg ttgatgctct cgctgatgtg   1560
ctgctcgtgt tcgtaggcct tctggaagat ctgggtcagg ccctcgaact tgtgctctgg   1620
ggcgctgatg ctggtcagct gcacgggcac gttgttctcg ttcaggaaga tgatcagctt   1680
cttggcgtgc tcgtattcct cggcggcgtg atcaaacagg aacaggccag cgccgtccag   1740
gctgtgggtg taacaccagc tggacatgct catgtacagg ttgctgctct gcatctcttt   1800
gttgacctgc tcgttcagca gcttctcgat gtccttgctg aactgctgtc ggacttggct   1860
ctcgccgctg gcgtttcttt ccatggcgaa ggcgtatctg ggcaccacca gattgccggt   1920
ggcctcgaag gtgatcttgt cgccgggttc caccagggtc cagtagtagt tcatccggcc   1980
ttcctggtcc cgcactttgg gccggatggc gatctcgggc ttgaacttct tgctgtaccg   2040
ggagctgccc acgaacacgt aggcgtcggc gttctggtac aggctctgct ggtcggcgct   2100
tgtgctaggg tggtggatgc cccagaggac cagcacctct ttgcccttgt cgttgatgta   2160
gctcttgctc agcttggggt agctgttgcc cttcttgacc agccagatca ggttcttgta   2220
gaagctcttg gcgccagcgt gaggacaggc ggcggtcacg cctttgttgc tgtcgtggtt   2280
gggccagctg gaggtcttgg ggaagatctc gaatctctcg aagctggaca cgctgctcag   2340
ctgctcgcgc agttcctcgt agtcgatgaa gtcgccgggg aaacaggtgc cgttgtcgct   2400
gctaggggtt tccacgatgt aggaccagct gctggctgtg ctcaggctct cgcactcggg   2460
gttgcccaga atccagccgg cgatattgca cttgcccagg tgcagaggag ccacggctag   2520
cacgccctga ggcagcagga ggttggacac caccaggagc agcagcagtc tggagccctt   2580
ctggctgctg cccttgctgt ccat                                           2604
```

```
SEQ ID NO: 174        moltype = DNA  length = 2727
FEATURE               Location/Qualifiers
misc_feature          1..2727
                      note = Synthetic
source                1..2727
                      mol_type = other DNA
                      organism = synthetic construct
SEQUENCE: 174
atggacagca agggcagcag ccagaagggc tccagactgc tgctgctcct ggtggtgtcc   60
aacctcctgc tgcctcaggg cgtgctagcc gagacaagag gcaagctgtg ccccaagtgc  120
ctgaactgca ccgacctgga tgtggccctg ggcagaccta agtgcaccgg caagatcccc  180
agcgccagag tgtccatcct gcacgaagtg cggcctgtga ccagcggctg cttccccatc  240
atgcagacc ggaccaagat cagacagctg cccaacctgc tgcggggcta cgagcacatc  300
agactgagca cccacaacgt gatcaacgcc gagaatgccc ctggcggccc ttacaagatc  360
ggcaccagcg gaagctgccc caacatcacc aacggcaacg gcttttttcgc caccatggcc  420
tgggccgtgc ccaagaacga caagaacaag accgccacca accctctgac catcgaggtg  480
ccctacatct gcaccgaggg cgaggaccag atcaccgtgt ggggcttcca cagcgacgac  540
gagactcaga tggccaagct gtacggcgac agcaagcccc agaagttcac cagcagcgcc  600
aacggcgtga ccacccacta tgtgtcccag atcggcggct ccctaaccca gacagaggat  660
ggcggcctgc cccagagcgg cagaatcgtg gtggactaca tggtgcagaa gtccggcaag  720
accggcacaa tcacctacca gagaggcatc ctgctgcctc agaaagtgtg gtgcgccagc  780
ggcagatcta gcggcgaatc tcaagtccga cagcagttca gcaaggacat cgagaagctg  840
ctgaacgagc aggtcaacaa agagatgcag agcagcaacc tgtacatgag catgagcagc  900
tggtgctaca cccacagcct ggacggcgct ggcctgttcc tgtttgatca cgccgccgag  960
gaatacgagc acgccaagaa gctgatcatc ttcctgaacg agaacaacgt gcccgtgcag 1020
ctgaccagca tcagcgcccc tgagcacaag ttcgagcacg tgacccagat cttccagaag 1080
gcctacgaac acgagcagca catctccgag agcatcaaca acatcgtgga ccacgccatc 1140
aagagcaagg atcacgccac cttcaacttt ctgcagtggt acgtggccga acagcacgag 1200
gaagaggtgc tgtttaagga catcctggac aagatcgagc tgatcggcaa cgagaaccac 1260
ggcctgtacc tggccgacca gtacgtgaag ggaatcgcca gagcagaaa gagccggaag 1320
cggagatctg gcagcggcgc tcctgtgaag cagaccctga acttcgacct gctgaagctg 1380
gccggcgacg tggaatctaa tcctgggccc atggatagca aaggctctag ccagaaaggc 1440
agccgactcc tgctcctgct ggtcgtcagt aacctgctgc tgcccagggg cgtcctcgcc 1500
aagacaagag gcaagctgtg ccccgactgc ctgaattgca ccgacctgga tgtggccctg 1560
ggcagaccta tgtgcgtggg cacaaacacct agcgccaagg ccagcatcct gcacgaagtg 1620
cggcctgtga ccagcggctg cttccctatc atgcagacc atgcagacct caggcagctg 1680
gccaatctgc tgagaggcta cgagaacatc cggctgagca cccagaatgt gatcgatgcc 1740
gagaaggccc ctgccggccc ttacagactg ggcacaagcg gcagctgtcc caacgccacc 1800
agcaagagcg gctttttcgc cacaatggcc tgggccgtgc ccaaggacaa caacaagaat 1860
gccaccaacc ctctgaccgt ggaagtgccc tacatctgcg ccgagggcga ggatcagatc 1920
acagtgtggg gcttccacag cgacgacaag acccagatga gagaacctgta cggcgacagc 1980
```

```
aatccccaga agttcacctc cagcgccaat ggcgtgacca cccactacgt gtcccagatc   2040
ggcggcttcc ccgatcagac agaggatggc ggactgcccc agtccggcag aatcgtggtg   2100
gactacatga tgcagaagcc cggcaagacc ggcaccatcg tgtaccagag aggcgtgctg   2160
ctccctcaga aagtgtggtg cgcctctggc agaagctccg gagaatctca agtccgccag   2220
cagttttcta aggacatcga aaagctgctc aatgaacagg tcaacaaaga gatgcagtcc   2280
tctaacctgt atatgagtat gagttcctgg tgctataccc actctctcga cggtgcaggg   2340
ctgttcctct tcgaccacgc tgcagaggaa tatgaacatg ctaagaaact gattatcttt   2400
ctcaacgaaa acaacgtgcc agtccagctc accagtatct ctgcccctga acataagttt   2460
gaggggctca ctcagatctt tcagaaagct tacgagcacg agcagcatat ctctgagtct   2520
attaacaaca tcgtcgacca tgctatcaaa tctaaagacc acgctacttt taactttctc   2580
caatggtacg tcgcagagca gcatgaggaa gaggtcctct tcaaggacat tctcgacaaa   2640
attgaactca tcggaaacga aaaccatggg ctctacctgg ctgatcagta cgtcaaggga   2700
atcgcaaaaa gccggaagtc ttgatga                                       2727
```

SEQ ID NO: 175             moltype = AA  length = 907
FEATURE                    Location/Qualifiers
REGION                     1..907
                           note = Synthetic
source                     1..907
                           mol_type = protein
                           organism = synthetic construct
SEQUENCE: 175
```
MDSKGSSQKG SRLLLLLVVS NLLLPQGVLA ETRGKLCPKC LNCTDLDVAL GRPKCTGKIP   60
SARVSILHEV RPVTSGCFPI MHDRTKIRQL PNLLRGYEHI RLSTHNVINA ENAPGGPYKI   120
GTSGSCPNIT NGNGFFATMA WAVPKNDKNK TATNPLTIEV PYICTEGEDQ ITVWGFHSDD   180
ETQMAKLYGD SKPQKFTSSA NGVTTHYVSQ IGGFPNQTED GGLPQSGRIV VDYMVQKSGK   240
TGTITYQRGI LLPQKVWCAS GRSSGESQVR QQFSKDIEKL LNEQVNKEMQ SSNLYMSMSS   300
WCYTHSLDGA GLFLFDHAAE EYEHAKKLII FLNENNVPVQ LTSISAPEHK FEGLTQIFQK   360
AYEHEQHISE SINNIVDHAI KSKDHATFNF LQWYVAEQHE EEVLFKDILD KIELIGNENH   420
GLYLADQYVK GIAKSRKSRK RRSGSGAPVK QTLNFDLLKL AGDVESNPGP MDSKGSSQKG   480
SRLLLLLVVS NLLLPQGVLA KTRGKLCPDC LNCTDLDVAL GRPMCVGTTP SAKASILHEV   540
RPVTSGCFPI MHDRTKIRQL ANLLRGYENI RLSTQNVIDA EKAPGGPYRL GTSGSCPNAT   600
SKSGFFATMA WAVPKDNNKN ATNPLTVEVP YICAEGEDQI TVWGFHSDDK TQMKNLYGDS   660
NPQKFTSSAN GVTTHYVSQI GGFPDQTEDG GLPQSGRIVV DYMMQKPGKT GTIVYQRGVL   720
LPQKVWCASG RSSGESQVRQ QFSKDIEKLL NEQVNKEMQS SNLYMSMSSW CYTHSLDGAG   780
LFLFDHAAEE YEHAKKLIIF LNENNVPVQL TSISAPEHKF EGLTQIFQKA YEHEQHISES   840
INNIVDHAIK SKDHATFNFL QWYVAEQHEE EVLFKDILDK IELIGNENHG LYLADQYVKG   900
IAKSRKS                                                             907
```

SEQ ID NO: 176             moltype = DNA  length = 2727
FEATURE                    Location/Qualifiers
misc_feature               1..2727
                           note = Synthetic
source                     1..2727
                           mol_type = other DNA
                           organism = synthetic construct
SEQUENCE: 176
```
tcatcaagac ttccggcttt ttgcgattcc cttgacgtac tgatcagcca ggtagagccc   60
atggttttcg tttccgatga gttcaatttt gtcgagaatg tccttgaaga ggacctcttc   120
ctcatgctgc tctgcgacgt accattggag aaagttaaaa gtagcgtggt ctttagattt   180
gatagcatgg tcgacgatgt tgttaataga ctcagaatta tgctgctcgt gctcgtaagc   240
tttctgaaag atctgagtga gccccctcaaa cttatgttca ggggcagaga tactggtgag   300
ctggactggc acgttgtttt cgttgagaaa gataatcagt ttcttagcat gttcatattc   360
ctctgcagcg tggtcgaaga ggaacagccc tgcaccgtcg agagagtggg tatagcacca   420
ggaactcata ctcatataca ggttagagga ctgcatctct ttgttgacct gttcattgag   480
cagctttcg atgtccttag aaaaactgctg gcggacttga gattctccgg agcttctgcc   540
agaggcgcac cacactttct gagggagcag cacgcctctc tggtacacga tggtgccggt   600
cttgccgggc ttctgcatca tgtagtccac cacgattctg ccggactggg gcagtccgcc   660
atcctctgtc tgatcgggga agccgccgat ctgggacacg tagtgggtgg tcacgccatt   720
ggcgctggag gtgaacttct ggggattgct gtcgccgtac aggttcttca tctgggtgtt   780
gtcgtcgctg tggaagcccc acactgtgat ctgatcctcg ccctcggcgc agatgtaggg   840
cacttccacg tcagagggt tggtggcatt cttgttgttg tccttgggca cggcccaggc   900
cattgtggcg aaaaagccgc tcttgctggt ggcgttggga cagctgccgc ttgtgcccag   960
tctgtaaggg ccgccagggg cctttctggc atcgatcaca ttctgggtgc tcagccggat   1020
gttctcgtag cctctcagca gattggccag ctgcctgatc ttggtccggt cgtgcatgat   1080
agggaagcag ccgctggtca caggccgcac ttcgtgcagg atgctggcct tggcgctagg   1140
tgttgtgccc acgcacatag gtctgcccag gccacatcc aggtcggtgc aattcaggca   1200
gtcggggcac agcttgcctc ttgtcttggc gaggacgccc tggggcagca gcaggttact   1260
gacgaccagc aggagcagga gtcggctgcc tttctggcta gagcctttgc tatccatggg   1320
cccaggatta gattccacgt cgccggccag cttcagcagg tcgaagttca gggtctgctt   1380
cacaggagcc ccgctgccag atctccgctt ccggctcttt ctgctcttgg cgattccctt   1440
cacgtactgg tcggccaggt acaggccgtg gttctcgttg ccgatcagct cgatcttgtc   1500
caggatgtcc ttaaacagca cctcttcctc gtgctgttcg gccacgtacc actcagaaa   1560
gttgaaggtg gcgtgatcct tgctcttgat ggcgtgtcc acagtgttgt tgatgctctc   1620
ggagatgtgc tgctcgtgtt cgtaggcctt ctggaagatc tgggtcaggc cctcgaactt   1680
gtgctcaggg cgctgatgc tggtcagctg cacgggcacg ttgttctcgt tcaggaagat   1740
gatcagcttt ttggcgtgct cgtattcctc ggcggcgtga tcaaacagga acaggccagc   1800
gccgtccagg ctgtgggtgt agcaccagct gctcatgctc atgtacaggt tgctgctctg   1860
catctctttg ttgacctgct cgttcagcag cttctcgatg tccttgctga actgctgtcg   1920
```

```
gacttgagat tcgccgctag atctgccgct ggcgcaccac actttctgag gcagcaggat  1980
gcctctctgg taggtgattg tgccggtctt gccggacttc tgcaccatgt agtccaccac  2040
gattctgccg ctctgggca ggccgccatc ctctgtctgg ttagggaagc cgccgatctg  2100
ggacacatag tgggtggtca cgccgttggc gctgctggtg aacttctggg gcttgctgtc  2160
gccgtacagc ttggccatct gagtctcgtc gtcgctgtgg aagccccaca cggtgatctg  2220
gtcctcgccc tcggtgcaga tgtagggcac ctcgatggtc agagggttgg tggcggtctt  2280
gttcttgtcg ttcttgggca cggcccaggc catggtggcg aaaaagccgt tgccgttggt  2340
gatgttgggg cagcttccgc tggtgccgat cttgtaaggg ccgccagggg cattctcggc  2400
gttgatcacg ttgtgggtgc tcagtctgat gtgctcgtag ccccgcagca ggttgggcag  2460
ctgtctgatc ttggtccggt cgtgcatgat ggggaagcag ccgctggtca caggccgcac  2520
ttcgtgcagg atggacactc tggcgctggg gatcttgccg gtgcacttag gtctgcccag  2580
ggccacatcc aggtcggtgc agttcaggca cttgggcac agcttgcctc ttgtctcggc  2640
tagcacgccc tgaggcagca ggaggttgga caccaccagg agcagcagca gtctggagcc  2700
cttctggctg ctgcccttgc tgtccat                                       2727

SEQ ID NO: 177          moltype = DNA   length = 4011
FEATURE                 Location/Qualifiers
misc_feature            1..4011
                        note = Synthetic
source                  1..4011
                        mol_type = other DNA
                        organism = synthetic construct
SEQUENCE: 177
atggacagca agggcagcag ccagaagggc tccagactgc tgctgctcct ggtggtgtcc  60
aacctcctgc tgcctcaggg cgtgctagcc gtggctcctc tgcacctggg caagtgcaat  120
atcgccggct ggattctggg caaccccgag tgcgagagcc tgagcacagc cagcagctgg  180
tcctacatcg tggaaacccc tagcagcgac aacggcacct gtttccccgg cgacttcatc  240
gactacgagg aactgcgcga gcagctgagc agcgtgtcca gcttcgagag attcgagatc  300
ttccccaaga cctccagctg gcccaaccac gacagcaaca aaggcgtgac cgccgcctgt  360
cctcacgctg gcgccaagag cttctacaag aacctgatct ggctggtcaa gaagggcaac  420
agctacccca agctgagcaa gagctacatc aacgacaagg gcaaagaggt gctggtcctc  480
tggggcatcc accaccctag cacaagcgcc gaccagcaga gcctgtacca gaacgccgac  540
gcctacgtgt tcgtgggcag ctcccggtac agcaagaagt tcaagcccga gatcgccatc  600
cggcccaaag tgcgggacca ggaaggccgg atgaactact actggaccct ggtggaaccc  660
ggcgacaaga tcaccttcga ggccaccggc aatctggtgg tgcccagata cgccttcgcc  720
atggaaagaa acgccagcgg cgagagccaa gtccgacagc agttcagcaa ggacatcgag  780
aagctgctga cgagcaggt caacaaagag atgcagagca gcaacctgta catgagcatg  840
tccagctggt gttacaccca cagcctggac ggcgctggcc tgttcctgtt tgatcacgcc  900
gccgaggaat acgagcacgc caagaagctg atcatcttcc tgaacgagaa caacgtgccc  960
gtgcagctga ccagcatcag cgccccagag cacaagttcg agggcctgac ccagatcttc  1020
cagaaggcct acgaacacga gcagcacatc agcgagagca tcaacaatat cgtggaccac  1080
gccatcaaga gcaaggatca cgccaccttc aactttctgc aatggtacgt ggccgaacag  1140
cacgagaag aagtgctgtt taaggacatc ctggacaaga tcgagctgat cggcaacgag  1200
aaccacggcc tgtacctggc cgaccagtac gtgaagggca ttgccaagag cagaaagagc  1260
cggaagcgga gatctggcag cggcgctcct gtgaagcaga ccctgaactt cgacctgctg  1320
aagctggccg gcgacgtgga aagcaaccct gggcccatgg actccaaggg ctcctcccag  1380
aaaggatctc ggctgaatcc cctgctcgtg gtgtctaatc tgctgctgcc acagggtgtc  1440
ctggcccacc agatcctgga tggcgagaac tgcaccctga tcgacgccct gctgggcgac  1500
cctcagtgcg acggcttcca gaacaagaag tgggacctgt tcgtcgagcg gagcaaggcc  1560
tacagcaact gcttcccta cgacgtgccc gactacgcca gcctgagaag cctggtggcc  1620
agcagcggca ccctggaatt caacaacgag agcttcaac ggaacggcgt gacccagaac  1680
ggcaccagct ccgcctgcat cagaagaagc aacaacagct tcttctcccg gctgaactg  1740
ctgacccacc tgaatttcaa gtaccccgcc ctgaacgtga ccatgcccaa caatgagcag  1800
ttcgacaagc tgtacatctg gggagtgcac caccccgtga ccgacaagga ccagatcttt  1860
ctgtacgccc agccagcgg ccggatcacc gtgtctacca agagaagcca gcaggccgtg  1920
atccccaaca tcggcttccg gcccaggatc agaaacatcc ccagccggat cagcatctac  1980
tggacaatcg tgaagcctgg cgacatcctg ctgatcaaca gcaccggcaa cctgatcgcc  2040
cctcggggct acttcaagat cagaagcggc gcctccggag agtcccaagt cgcgccagcag  2100
ttttccaagg atattgagaa actcctcaat gaacaggtca acaaggaaat gcagtcctcc  2160
aacctctaca tgtctatgtc ctcttggtgc tacacacact ccctggatgg ggccggactg  2220
tttctgttcg accatgccgc tgaagagtat gaacacgcca aaaaactcat cattttctc  2280
aatgagaaca atgtccctgt ccagctcacc tccatctccg ctcccgagca caaatttgaa  2340
ggactcacac agattttca gaaagcctat gagcatgaac agcacatttc cgagtccatc  2400
aacaacattg tcgatcatgc cattaagtcc aaggaccatg ctacattcaa tttcctccaa  2460
tggtatgtcg ctgagcagca tgaagaggaa gtcctgttca aagatatcct cgataagatc  2520
gaactcattg ggaatgagaa tcacgggctc tatctgccg atcagtatgt gaaagggatc  2580
gctaagtccc ggaagtccag aaagcggaga agcggctctg gcgccccagt caaacagaca  2640
ctgaattttg atctgctcaa gctcgctggg gacgtcgagt ccaatccagg gcccatggat  2700
agcaaaggct ctagccagaa aggcagccga ctcctgctcc tgctggtcgt cagtaacctg  2760
ctgctgcccc agggcgtcct cgccaagaca agaggcaagc tgtgcccga ctgcctgaat  2820
tgcaccgacc tggatgtggc cctgggcaga cctatgtgcg tgggcacaac acctagcgcc  2880
aaggccagca tcctgcacga agtgcggcct gtgaccagcg gctgcttccc tatcatgcac  2940
gaccggacca agatcaggtc gctggccaat ctgctgagag ctacgagaa catccggctg  3000
agcaccgaga atgtgatcga tgccgagaag gccctgggcg gccttacag actgggcaca  3060
agcggcagct gtcccaacgc caccagcaag agcggctttt cgccacaat ggcctgggcc  3120
gtgcccaagg acaacaacaa gaatgccacc aaccctctga ccgtggaagt gcctacatc  3180
tgcgccgagg cgaggatca gatcacagtg tggggcttcc acagcgacga caagacccag  3240
atgaagaacc tgtacggcga cagcaatccc cagaagttca cctccagcgc caatggcgtg  3300
accacccact acgtgtccca gatcggcggc ttccccgatc agacagagga tggcggactg  3360
```

```
ccccagtccg gcagaatcgt ggtggactac atgatgcaga agcccggcaa gaccggcacc   3420
atcgtgtacc agagaggcgt gctgctcct cagaaagtgt ggtgcgcctc tggcagaagc   3480
tccggagaat ctcaagtccg ccagcagttt tctaaggaca tcgaaaagct gctcaatgaa   3540
caggtcaaca aagagatgca gtcctctaac ctgtatatga gtatgagttc ctggtgctat   3600
acccactctc tcgacggtgc agggctgttc ctcttcgacc acgctgcaga ggaatatgaa   3660
catgctaaga aactgattat ctttctcaac gaaaacaacg tgccagtcca gctcaccagt   3720
atctctgccc ctgaacataa gtttgagggg ctcactcaga tctttcagaa agcttacgag   3780
cacgagcagc atatctctga gtctattaac aacatcgtcg accatgctat caaatctaaa   3840
gaccacgcta cttttaactt tctccaatgg tacgtcgcag agcagcatga ggaagaggtc   3900
ctcttcaagg acattctcga caaaattgaa ctcatcggaa acgaaaacca tgggctctac   3960
ctggctgatc agtacgtcaa gggaatcgca aaaagccgga agtcttgatg a             4011
```

SEQ ID NO: 178          moltype = AA   length = 1335
FEATURE                 Location/Qualifiers
REGION                  1..1335
                        note = Synthetic
source                  1..1335
                        mol_type = protein
                        organism = synthetic construct
SEQUENCE: 178
MDSKGSSQKG SRLLLLLVVS NLLLPQGVLA VAPLHLGKCN IAGWILGNPE CESLSTASSW    60
SYIVETPSSD NGTCFPGDFI DYEELREQLS SVSSFERFEI FPKTSSWPNH DSNKGVTAAC   120
PHAGAKSFYK NLIWLVKKGN SYPKLSKSYI NDKGKEVLVL WGIHHPSTSA DQQSLYQNAD   180
AYVFVGSSRY SKKFKPEIAI RPKVRDQEGR MNYYWTLVEP GDKITFEATG NLVVPRYAFA   240
MERNASGESQ VRQQFSKDIE KLLNEQVNKE MQSSNLYMSM SSWCYTHSLD GAGLFLFDHA   300
AEEYEHAKKL IIFLNENNVP VQLTSISAPE HKFEGLTQIF QKAYEHEQHI SESINNIVDH   360
AIKSKDHATF NFLQWYVAEQ HEEEVLFKDI LDKIELIGNE NHGLYLADQY VKGIAKSRKS   420
RKRRSGSGAP VKQTLNFDLL KLAGDVESNP GPMDSKGSSQ KGSRLLLLLV VSNLLLPQGV   480
LAHQILDGEN CTLIDALLGD PQCDGFQNKK WDLFVERSKA YSNCFPYDVP DYASLRSLVA   540
SSGTLEFNNE SFNWNGVTQN GTSSACIRRS NNSFFSRLNW LTHLNFKYPA LNVTMPNNEQ   600
FDKLYIWGVH HPVTDKDQIF LYAQPSGRIT VSTKRSQQAV IPNIGFRPRI RNIPSRISIY   660
WTIVKPGDIL LINSTGNLIA PRGYFKIRSG ASGESQVRQQ FSKDIEKLLN EQVNKEMQSS   720
NLYMSMSSWC YTHSLDGAGL FLFDHAAEEY EHAKKLIIFL NENNVPVQLT SISAPEHKFE   780
GLTQIFQKAY EHEQHISESI NNIVDHAIKS KDHATFNFLQ WYVAEQHEEE VLFKDILDKI   840
ELIGNENHGL YLADQYVKGI AKSRKSRKRR SGSGAPVKQT LNFDLLKLAG DVESNPGPMD   900
SKGSSQKGSR LLLLLVVSNL LLPQGVLAKT RGKLCPDCLN CTDLDVALGR PMCVGTTPSA   960
KASILHEVRP VTSGCFPIMH DRTKIRQLAN LLRGYENIRL STQNVIDAEK APGGPYRLGT  1020
SGSCPNATSK SGFFATMAWA VPKDNNKNAT NPLTVEVPYI CAEGEDQITV WGFHSDDKTQ  1080
MKNLYGDSNP QKFTSSANGV TTHYVSQIGG FPDQTEDGGL PQSGRIVVDY MMQKPGKTGT  1140
IVYQRGVLLP QKVWCASGRS SGESQVRQQF SKDIEKLLNE QVNKEMQSSN LYMSMSSWCY  1200
THSLDGAGLF LFDHAAEEYE HAKKLIIFLN ENNVPVQLTS ISAPEHKFEG LTQIFQKAYE  1260
HEQHISESIN NIVDHAIKSK DHATFNFLQW YVAEQHEEEV LFKDILDKIE LIGNENHGLY  1320
LADQYVKGIA KSRKS                                                   1335

SEQ ID NO: 179          moltype = DNA   length = 4011
FEATURE                 Location/Qualifiers
misc_feature            1..4011
                        note = Synthetic
source                  1..4011
                        mol_type = other DNA
                        organism = synthetic construct
SEQUENCE: 179
tcatcaagac ttccggcttt ttgcgattcc cttgacgtac tgatcagcca ggtagagccc    60
atggttttcg tttccgatga gttcaatttt gtcgagaatg tccttgaaga ggacctcttc   120
ctcatgctgc tctgcgacgt accattggag aaagtgataa gtagcgtggt ctttagattt   180
gatagcatgg tcgacgatgt tgttaataga ctcagataga tgctgctcgt gctcgtaagc   240
tttctgaaag atctgagtga gcccctcaaa cttatgttca ggggcagaga tactggtgag   300
ctggactggc acgttgtttt cgttgagaaa gataatcagt ttcttagcat gttcatattc   360
ctctgcagcg tggtcgaaga ggaacagccc tgcaccgtcg agagagtggg tatagcacca   420
ggaactcata ctcatataca ggttagagga ctgcatctgt ttgttgacct gttcattgag   480
cagctttcg atgtccttag aaaactgctg gcggacttga gattctccgg agcttctgcc   540
agaggcgcac cacactttct gagggagcag cacgcctctc tggtacacga tggtgccggt   600
cttgccgggc ttctgcatca tgtagtccac cacgattctg ccggactggg gcagtccgcc   660
atcctctgtc tgatcgggga agccgccgat ctgggacatg tagggggtgg tcacgccatt   720
ggcgctggag gtgaacttct ggggattgct gtcgccgtac aggttcttca tctgggtctt   780
gtcgtcgctg tggaagcccc acactgtgat ctgatcctcg ccctcggcgc agatgtaggg   840
cacttccacg tcagagggt tggtggcatt cttgttgttg tccttgggca cggcccaggc   900
cattgtggcg aaaaagccgc tcttgctggt ggcgttggga cagctgccgc ttgtgcccag   960
tctgtaaggg ccgccagggg cctttctggc atcgatcaca ttctgggtgc tcagccggat  1020
gttctcgtag cctctcagca gattggccag ctgcctgatc ttggtccggt cgtgcatgat  1080
agggaagcag ccgctggtca caggccgcac ttcgtgcagg atgctggcct ggcgctagg   1140
tgttgtgccc acgcacatag gtctgcccag ggccacatcc aggtcggtgc aattcaggca  1200
gtcggggcac agcttgcctc ttgtcttggc gaggacgccc tggggcagca gcaggttact  1260
gacgaccagg aggagcagga gtcggctgcc tttctggcag ggccctttgc tatccatggg  1320
ccctggattg gactcgacgt ccccagcgag cttgagcaga tcaaaattca gtgtctgttt  1380
gactgggcg ccagagccgc ttcttccgct tctggacttc cgggacttag cgatcccttt   1440
cacatactga tcgcgagat agagcccgtg attctcattc ccaatgagtt cgatcttatc  1500
gaggatatct ttgaacagga cttcctcttc atgctgctca gcgacatacc attggaggaa  1560
attgaatgta gcatggtcct tggacttaat ggcatgatcg acaatgttgt tgatggactc  1620
```

```
ggaaatgtgc tgttcatgct cataggcttt ctgaaaaatc tgtgtgagtc cttcaaattt  1680
gtgctcggga gcggagatgg aggtgagctg gacagggaca ttgttctcat tgagaaaaat  1740
gatgagtttt ttggcgtgtt catactcttc agcggcatgg tcgaacagaa acagtccggc  1800
cccatccagg gagtgtgtgt agcaccaaga ggacatagac atgtagaggt tggaggactg  1860
catttccttg ttgacctgtt cattgaggag tttctcaata tccttggaaa atgctcggcg  1920
cacttgggac tctccggagg cgccgcttct gatcttgaag tagccccgag gggcgatcag  1980
gttgccggtg ctgttgatca gcaggatgtc gccaggcttc acgattgtcc agtagatgct  2040
gatccggctg gggatgtttc tgatcctggg ccggaagccg atgttgggga tcacggcctg  2100
ctggcttctc ttggtagaca cggtgatccg gccgctgggc tgggcgtaca gaaagatctg  2160
gtccttgtcg gtcacgtggt ggtgcactcc ccagatgtac agcttgtcga actgctcatt  2220
gttgggcatg gtcacgttca gggcgggta cttgaaattc aggtgggtca gccagttcag  2280
ccgggagaag aagctgttgt tgcttcttct gatgcaggcg gagctggtgc cgttctgggt  2340
cacgccgttc cagttgaagc tctcgttgtt gaattccagg gtgccgctgc tggccaccag  2400
gcttctcagg ctggcgtagt cgggcacgtc gtaggggaag cagttgctgt aggccttgct  2460
ccgctcgacg aacaggtccc acttcttgtt ctggaagccg tcgcactgag ggtcgcccag  2520
cagggcgtcg atcagggtgc agttctcgcc atccaggatc tggtgggcca ggacaccctg  2580
tggcagcagc agattagaca ccacgagcag gaggagcagc cgagatcctt tctgggagga  2640
gcccttggag tccatgggcc cagggttgct ttccacgtcg ccggccagct tcagcaggtc  2700
gaagttcagg gtctgcttca caggagcgcc gctgccagat ctccgcttcc ggctcttttct  2760
gctcttggca atgcccttca cgtactggtc ggccaggtac aggccgtggt tctcgttgcc  2820
gatcagctcg atcttgtcca ggatgtcctt aaacagcact tcttcctcgt gctgttcggc  2880
cacgtaccat tgcagaaagt tgaaggtggc gtgatccttg ctcttgatgg cgggtccac  2940
gatattgttg atgctctcgc tgatgtgctg ctcgtgttcg taggccttct ggaagatctg  3000
ggtcaggccc tcgaacttgt gctctggggc gctgatgctg gtcagctgca cgggcacgtt  3060
gttctcgttc aggaagatga tcagcttctt ggcgtgctcg tattcctcgg cggcgtgatc  3120
aaacaggaac aggccagcgc cgtccaggct gtgggtgtaa caccagctgg acatgctcat  3180
gtacaggttg ctgctctgca tctctttgtt gacctgctcg ttcagcagct tctcgatgtc  3240
cttgctgaac tgctgtcgga cttggctctc gccgctggcg tttctttcca tggcgaaggc  3300
gtatctgggc accaccagat tgccggtggc ctcgaaggtg atcttgtcgc cgggttccac  3360
cagggtccag tagtagttca tccggccttc ctggtcccgc acttgggcc ggatggcgat  3420
ctcgggcttg aacttcttgc tgtaccggga gctgcccacg aacacgtagg cgtcggcgtt  3480
ctggtacagg ctctgctggt cggcgcttgt gctagggtgg tggatgcccc agaggaccag  3540
cacctctttg cccttgtcgt tgatgtagct cttgctcagc ttggggtagc tgttgccctt  3600
cttgaccagc cagatcaggt tcttgtagaa gctcttggcg ccagcgtgag gacaggcggc  3660
ggtcacgcct ttgttgctgt cgtggttggg ccagctggag gtcttgggga agatctcgaa  3720
tctctcgaag ctggacacgc tgctcagctg ctcgcgcagt tcctcgtagt cgatgaagtc  3780
gccggggaaa caggtgccgt tgtcgctgct aggggtttcc acgatgtagg accagctgct  3840
ggctgtgctc aggctctcgc actcggggtt gcccagaatc cagccggcga tattgcactt  3900
gcccaggtgc agaggagcca cggctagcac gccctgaggc agcaggaggt tggacaccac  3960
caggacgagc agcagtctgg agcccttctg gctgctgccc ttgctgtcca t             4011
```

```
SEQ ID NO: 180            moltype = DNA  length = 1518
FEATURE                   Location/Qualifiers
misc_feature             1..1518
                          note = Synthetic
source                   1..1518
                          mol_type = other DNA
                          organism = synthetic construct
SEQUENCE: 180
atgcccatgg gcagcctgca gcccctggcc accctgtacc tgctgggcat gctggtggct  60
agcgtgctgg ccatggagtt cctgaagagg agcttcgccc tctctgaccga gaagcagttg  120
caggagatcg acaacagggc cagggagatc ttcaagaccc agctgtacgg caggaagttc  180
gtggacgtgg agggcccccta cggctgggag tacgccgccc accccctggg cgaggtggag  240
gtgctgagcg acgagaacga ggtggtgaag tggggcctga ggaagagcct gcccctgatc  300
gagctgaggg ccaccttcac cctggacctg tgggagctgg acaacctgga gaggggcaag  360
cccaacgtgg acctgagcag cctggaggag accgtgagga aggtggccga gttcgaggac  420
gaggtgatct tcaggggctg cgagaagagc ggcgtgaagg gcctgctgag cttcgaggag  480
aggaagatcg agtgcggcag cacccccaag gacctgctgg aggccatcgt gagggccctg  540
agcatcttca gcaaggacgg catcgagggc ccctacaccc tggtgatcaa caccgacagg  600
tggatcaact cctgaagga ggaggccggc cactacccc tggagaagag ggtggaggag  660
tgcctgaggg cgcgcaagat catcaccacc cccaggatcg aggacgccct ggtggtgagc  720
gagaggggc gcgacttcaa gctgatcctg gccaggacc tgagcatcgg ctacgaggac  780
agggagaagg acgccgtgag gctgttcatc accgagacct tcaccttcca ggtggtgaac  840
cccgaggccc tgatcctgct gaagtccgga attgccctc tgcagctgga caattgttct  900
gtggccggat ggattctggg caaccccgag tgtgagctgc tgatttctaa ggagagctgg  960
agctacatcg tggagacccc caatcctgag aatggcacct gctaccctgg ctacttcgcc  1020
gattacgagg agctgcgcga gcagctgtct agcgtgtcca gcttcgagag attcgagatc  1080
ttccccaagg agtccagctg gcctaatcac acagtgacag gcgtgtctgc cagctgtagc  1140
cacaacggca aaagcagctt ctaccggaac ctgctgtggc tgacaggcaa gaatggcctg  1200
taccccaacc tgagcaagag ctacgtgaac aacaaggaaa aggaagtgct ggtgctgtgg  1260
ggagtgcacc accctcccaa catcggaaat cagcgggccc tgtaccacac agagaacgcc  1320
tatgtgagcg tggtgtccag ccactacagc agaagattca ccccgagat cgccaagaga  1380
cccaaagtga gagaccagga gggccggatc aattactact ggaccctgct ggagcctggc  1440
gataccatca tcttcgaggc caacggcaat ctgatcgccc cttggtatgc ctttgccctg  1500
agcagaggcg cctgatga                                                 1518
```

```
SEQ ID NO: 181            moltype = AA  length = 504
FEATURE                   Location/Qualifiers
REGION                   1..504
```

-continued

```
                         note = Synthetic
source                   1..504
                         mol_type = protein
                         organism = synthetic construct
SEQUENCE: 181
MPMGSLQPLA TLYLLGMLVA SVLAMEFLKR SFAPLTEKQW QEIDNRAREI FKTQLYGRKF    60
VDVEGPYGWE YAAHPLGEVE VLSDENEVVK WGLRKSLPLI ELRATFTLDL WELDNLERGK   120
PNVDLSSLEE TVRKVAEFED EVIFRGCEKS GVKGLLSFEE RKIECGSTPK DLLEAIVRAL   180
SIFSKDGIEG PYTLVINTDR WINFLKEEAG HYPLEKRVEE CLRGGKIITT PRIEDALVVS   240
ERGGDFKLIL GQDLSIGYED REKDAVRLFI TETFTFQVVN PEALILLKSG IAPLQLGNCS   300
VAGWILGNPE CELLISKESW SYIVETPNPE NGTCYPGYFA DYEELREQLS SVSSFERFEI   360
FPKESSWPNH TVTGVSASCS HNGKSSFYRN LLWLTGKNGL YPNLSKSYVN NKEKEVLVLW   420
GVHHPPNIGN QRALYHTENA YVSVVSSHYS RRFTPEIAKR PKVRDQEGRI NYYWTLLEPG   480
DTIIFEANGN LIAPWYAFAL SRGA                                          504

SEQ ID NO: 182        moltype = DNA   length = 1518
FEATURE               Location/Qualifiers
misc_feature          1..1518
                      note = Synthetic
source                1..1518
                      mol_type = other DNA
                      organism = synthetic construct
SEQUENCE: 182
tcatcaggcg cctctgctca gggcaaaggc ataccaaggg gcgatcagat tgccgttggc    60
ctcgaagatg atggtatcgc caggctccag cagggtccag tagtaattga tccggccctc   120
ctggtctctc actttgggtc tcttggcgat ctcggggtg aatcttctgc tgtagtggct   180
ggacaccacg ctcacatagg cgttctctgt gtggtacagg gcccgctgat ttccgatgtt   240
gggagggtgg tgcactcccc acagcaccag cacttccttt tccttgttgt tcacgtagct   300
cttgctcagg ttggggtaca ggccattctt gcctgtcagc cacagcaggt tccggtagaa   360
gctgcttttg ccgttgtggc tacagctggc agacacgcct gtcactgtgt gattaggcca   420
gctggactcc ttggggaaga tctcgaatct ctcgaagctg gacacgctag acagctgctc   480
gcgcagctcc tcgtaatcgg cgaagtagcc agggtagcag gtgccattct caggattggg   540
ggtctccacg atgtagctcc agctctcctt agaaatcagc agctcacact cggggttgcc   600
cagaatccat ccggccacag aacaattgcc cagctgcaga ggggcaattc cggacttcag   660
caggatcagg gcctcgggt tcaccacctg gaaggtgaag gtctcggtga tgaacagcct   720
cacggcgtcc ttctccctgt cctcgtagcc gatgctcagg tcctggccca ggatcagctt   780
gaagtcgccg ccctctcgc tcaccaccag ggcgtcctcg atcctggggg tggtgatgat   840
cttgccgccc ctcaggcact cctccaccct cttctccagg gggtagtggc cggcctcctc   900
cttcaggaag ttgatccacc tgtcggtgtt gatcaccagg gtgtagggc cctcgatgcc   960
gtccttgctg aagatgctca gggccctcac gatggcctcc agcaggtcct gggggggtgct  1020
gccgcactcg atcttcctct cctcgaagct cagcaggccc ttcacgccgc tcttctcgca  1080
gccctgaag atcacctcgt cctcgaactc ggccacctc ctcacggtct cctccaggct   1140
gctcaggtcc acgttgggct tgccctctc caggttgtcc agtcccaca ggtccagggt   1200
gaaggtggcc ctcagctcga tcaggggcag gctcttcctc aggccccact tcaccacctc  1260
gttctcgtcg ctcagcacct ccacctgcc caggggtgg gcggcgtact cccagccgta   1320
ggggccctcc acgtccacga acttcctgcc gtacagctgg gtcttgaaga tctccctggc  1380
cctgttgtcg atctcctgcc actgcttctc ggtcagaggg gcgaagctcc tcttcaggaa  1440
ctccatggcc agcacgctag ccaccagcat gcccagcagg tacagggtgg ccaggggctg  1500
caggctgccc atgggcat                                                1518

SEQ ID NO: 183        moltype = DNA   length = 1521
FEATURE               Location/Qualifiers
misc_feature          1..1521
                      note = Synthetic
source                1..1521
                      mol_type = other DNA
                      organism = synthetic construct
SEQUENCE: 183
atgcccatgg gcagcctgca gcccctggcc accctgtacc tgctgggcat gctggtggct    60
agcgtgctgg ccatggagtt cctgaagagg agcttcgccc tctgaccga gaagcagtgg   120
caggagatcg acaacagggc cagggagatc ttcaagaccc agctgtacgg caggaagttc   180
gtggacgtgg agggccccta cggctgggag tacgccgccc accccctggg cgaggtggag   240
gtgctgagcg acgagaacga ggtggtgaag tggggcctga ggaagagcct gcccctgatc   300
gagctgaggg ccaccttcac cctggacctg tgggagctgg acaacctgga gaggggcaag   360
cccaacgtgg acctgagcag cctggaggag accgtgagga aggtggccga gttcgaggac   420
gaggtgatct tcaggggctg cgagaagagc ggcgtgaagg gcctgctgag cttcgaggag   480
aggaagatcg agtgcggcag caccccccaag gacctgctgg aggccatcgt gagggccctg   540
agcatcttca gcaaggacgg catcgagggc ccctacaccc tggtgatcaa caccgacagg   600
tggatcaact tcctgaagga ggaggccggc cactacccc tggagaagag ggtggaggag   660
tgcctgaggg gcggcaagat catcaccacc cccaggatcg aggacgccct ggtggtgagc   720
gagaggggcg gcgacttcaa gctgatcctg ggccaggacc tgagcatcgg ctacgaggac   780
agggagaagg acgccgtgag gctgttcatc accgagacct tcaccttcca ggtggtgaac   840
cccgaggccc tgatcctgct gaagtccgga gtggcccccc tgcacctggg caagtgcaac   900
atcgccggct ggattctggg caaccccgag tgcgagagc tgagcaagc cagcagctgg   960
agctacatcg tggagacccc cagcagcgac aacggcacct gctacccgg cgacttcatc  1020
gactacgagg agctgcggga gcagctgagc agcgtgagca gcttcgagcg gttcgagatc  1080
ttccccaaga ccagcagctg gcccaaccac gacagcaaca agggcgtgac cgccgcctgc  1140
ccccacgccg cgccaagag cttctacaag aacctgatct ggctggtgaa gaagggcaac  1200
agctacccca agctgagcaa gagctacatc aacgacaagg caggaggt gctggtgctg   1260
```

-continued

```
tggggcatcc accaccccag caccagcgcc gaccagcaga gcctgtacca gaacgccgac   1320
acctacgtgt tcgtgggcag cagccggtac agcaagaagt tcaagcccga gatcgccatc   1380
cggcccaagg tgcgggacca ggagggccgg atgaactact actggaccct ggtggagccc   1440
ggcgacaaga tcaccttcga ggccaccggc aacctggtgg tgccccggta cgccttcgcc   1500
atggagcgga acgcctgatg a                                             1521

SEQ ID NO: 184             moltype = AA   length = 505
FEATURE                    Location/Qualifiers
REGION                     1..505
                           note = Synthetic
source                     1..505
                           mol_type = protein
                           organism = synthetic construct
SEQUENCE: 184
MPMGSLQPLA TLYLLGMLVA SVLAMEFLKR SFAPLTEKQW QEIDNRAREI FKTQLYGRKF   60
VDVEGPYGWE YAAHPLGEVE VLSDENEVVK WGLRKSLPLI ELRATFTLDL WELDNLERGK   120
PNVDLSSLEE TVRKVAEFED EVIFRGCEKS GVKGLLSFEE RKIECGSTPK DLLEAIVRAL   180
SIFSKDGIEG PYTLVINTDR WINFLKEEAG HYPLEKRVEE CLRGGKIITT PRIEDALVVS   240
ERGGDFKLIL GQDLSIGYED REKDAVRLFI TETFTFQVVN PEALILLKSG VAPLHLGKCN   300
IAGWILGNPE CESLSTASSW SYIVETPSSD NGTCYPGDFI DYEELREQLS SVSSFERFEI   360
FPKTSSWPNH DSNKGVTAAC PHAGAKSFYK NLIWLVKKGN SYPKLSKSYI NDKGKEVLVL   420
WGIHHPSTSA DQQSLYQNAD TYVFVGSSRY SKKFKPEIAI RPKVRDQEGR MNYYWTLVEP   480
GDKITFEATG NLVVPRYAFA MERNA                                         505

SEQ ID NO: 185             moltype = DNA   length = 1521
FEATURE                    Location/Qualifiers
misc_feature               1..1521
                           note = Synthetic
source                     1..1521
                           mol_type = other DNA
                           organism = synthetic construct
SEQUENCE: 185
tcatcaggcg ttccgctcca tggcgaaggc gtaccggggc accaccaggt tgccggtggc   60
ctcgaaggtg atcttgtcgc cgggctccac cagggtccag tagtagttca tccggccctc   120
ctggtcccgc accttgggcc ggatggcgat ctcgggcttg aacttcttgc tgtaccggct   180
gctgcccacg aacacgtagg tgtcggcgtt ctggtacagg ctctgctggt cggcgctggt   240
gctggggtgg tggatgcccc acagcaccag cacctccttg cccttgtcgt tgatgtagct   300
cttgctcagc ttgggtagc tgttgccctt cttccaccagc cagatcaggt tcttgtagaa   360
gctcttgacg ccggcgtggg ggcaggcggc ggtcacgccc ttgttgctgt cgtggttgag   420
ccagctgctg gtcttgggga agatctcgaa ccgctcgaag ctgctcacgc tgctcagctg   480
ctcccgcagc tcctcgtagt cgatgaagtc gccggggtag caggtgccgt tgtcgctgct   540
gggggtctcc acgatgtagc tccagctgct ggcggtgctc aggctctcgc actcggggtt   600
gcccagaatc cagccggcga tgttgcactt gcccaggtgc aggggggcca ctccggactt   660
cagcaggatc agggcctcgg ggttcaccac ctggaaggtg aaggtctcgg tgatgaacag   720
cctcacggcg tccttctccc tgtcctcgta gccgatgctc aggtcctggc ccaggatcag   780
cttgaagtcg ccgcccctct cgctcaccac cagggcgtcc tcgatcctgg gggtggtgat   840
gatcttgccg cccctcaggc actcctccac cctcttcctc acggggtagt ggccggcctc   900
ctccttcagg aagttgatcc acctgtcggt gttgatcacc agggtgtagg ggccctcgat   960
gccgtccttg ctgaagatgc tcagggccct cacgatggcc tccagcaggt ccttgggggt   1020
gctgccgcac tcgatcttcc tctcctcgaa gctcagcagg cccttcacgc cgctcttctc   1080
gcagcccatc aagatcacct cgtcctcgaa ctcggccaca ttcctcacgg tctcctccag   1140
gctgctcagg tccacgttgg gcttgcccct ctccaggttg tccagctccc acaggtccag   1200
ggtgaaggtg gccctcagct cgatcagggg caggctcttc ctcaggcccc acttcaccac   1260
ctcgttctcg tcgctcagca cctccacctc gcccaggggg tgggcggcgt actcccagcc   1320
gtaggggccc tccacgtcca cgaacttcct gccgtacagc tgggtcttga agatctccct   1380
ggccctgttg tcgatctcct gccactgctt ctcggtcaga ggggcgaagc tcctcttcag   1440
gaactccatg gccagcacgc tagccaccag catgcccagc aggtacaggg tggccagggg   1500
ctgcaggctg cccatgggca t                                             1521

SEQ ID NO: 186             moltype = DNA   length = 4359
FEATURE                    Location/Qualifiers
misc_feature               1..4359
                           note = Synthetic
source                     1..4359
                           mol_type = other DNA
                           organism = synthetic construct
SEQUENCE: 186
atggagttca tcccgacgca aactttctat aacagaaggt accaacccg acccctgggcc   60
ccacgcccta caattcaagt aattagacct agaccacgtc cacagaggca ggctgggcaa   120
ctcgcccagc tgatctccgc agtcaacaaa ttgaccatgc gcgcggtacc tcaacagaag   180
cctcgcagaa atcggaaaaa caagaagcaa aggcagaaga agcaggcgcc gcaaaacgac   240
ccaaagcaaa agaagcaacc accacaaaag aagccggctc aaaagaagaa gaaaccaggc   300
cgtagggaga gaatgtgcat gaaaattgaa aatgattgca tcttcgaagt caagcatgaa   360
ggcaaagtga tgggctacga atgcctggtg ggggataaag taatgaaacc agcacatgtg   420
aaggaactca tcgacaatgc cgatctggct aaactggcct ttaagcggtc gtctaaaatac   480
gatcttgaat gtgcacagat accggtgcac atgaagtctg atgcctcgaa gtttacccac   540
gagaaacccg aggggtacta taactggcat cacggagcag tgcagtattc aggaggccgg   600
ttcactatcc gacgggtgc aggcaagccg ggagacagcg gcagaccgat cttcgacaac   660
aaaggacggg tggtggccat cgtcctagga ggggccaacg aaggtgcccg cacggccctc   720
```

```
tccgtggtga cgtggaacaa agacatcgtc acaaaaatta cccctgaggg agccgaagag  780
tggagcctcg ccctcccggt cttgtgcctg ttggcaaaca ctacattccc ctgctctcag  840
ccgccttgca cacctgctg ctacgaaaag gaaccggaaa gcaccttgcg catgcttgag  900
gacaacgtga tgagacccgg atactaccag ctactaaaag catcgctgac ttgccgccaa  960
agacgcctgc agctgggga ttgttctgtg gccggatgga ttctgggcaa ccccgagtgt  1020
gagctgctga tttctaagga gagctggagc tacatcgtgg agacccccaa tcctgagaat  1080
ggcacctgct tccctggcta cttcgccgat tacgaggagc tgcgcgagca gctgtctagc  1140
gtgtccagct tcgagagatt cgagatcttc cccaaggagt ccagctggcc taatcacaca  1200
gtgacaggcg tgtctgccag ctgtagccac aacggcaaaa gcagcttcta ccggaacctg  1260
ctgtggctga caggcaagaa tggcctgtac cccaacctga gcaagagcta cgtgaacaac  1320
aaggaaaagg aagtgctggt gctgtgggga gtgcaccacc ctcccaacat cggaaatcag  1380
cgggccctgt accacacaga gaacgcctat gtgagcgtgg tgtccagcca ctacagcaga  1440
agattcaccc ccgagatcgc caagagaccc aaagtgagag accaggaggg ccggatcaat  1500
tactactgga ccctgctgga gcctggcgat accatcatct tcgaggccaa cggcaatctg  1560
atcgcccctt ggtatgcctt tgccctgagc agaggcgcca attttaatgt ctataaagcc  1620
acaagaccat atctagctca ttgtcctgac tgcggagaag ggcattcgtg ccacagccct  1680
atcgcattgg agcgcatcag aaatgaagca acggacggaa cgctgaaaat ccaggtctct  1740
ttgcagatcg ggataaagac agatgacagc cacgattgga ccaagctgcg ctatatggat  1800
agccatacgc cagcggacgc ggagcgagcc ggattgcttg taaggacttc agcaccgtgc  1860
acgatcaccg ggaccatggg acactttatt ctcgcccgat gcccgaaagg agagacgctg  1920
acagtgggat ttacggacag cagaaagatc agccacacat gcacacaccc gttccatcat  1980
gaaccacctg tgataggcag ggagaggttc cactctcgac tcaacatgg taaagagtta  2040
ccttgcagca cgtacgtgca gagcaccgct gccactgctg aggagataga ggtgcatatg  2100
cccccagata ctcctgaccg cacgctgatg acgcagcagt ctggcaacgt gaagatcaca  2160
gttaatgggc agacggtgcg gtacaagtgc aactgcggtg gctcaaacga gggactgaca  2220
accacagaca aagtgatcaa taactgcaaa attgatcagt gccatgctgc agtcactaat  2280
cacaagaatt ggcaatacaa ctccccttta gtcccgcgca acgctgaact cggggaccgt  2340
aaaggaaaga tccacatccc attcccattg gcaaacgtga cttgcagagt gccaaaagca  2400
agaaaccctca cagtaactta cggaaaaaac caagtcacca tgctgctgta tcctgaccat  2460
ccgacactct tgtcttaccg taacatggga caggaaccaa attaccacga ggagtgggtg  2520
acacacaaga aggaggttac cttgaccgtg cctactgagg gtctggaggt cacttggggc  2580
aacaacgaac catacaagta ctggccgcag atgtctacga acggtactgc tcatggtcac  2640
ccacatgaga taatcttgta ctattatgag ctgtacccca ctatgactgt agtcattgtg  2700
tcggtggcct cgttcgtgct tctgtcgatg gtgggcacag cagtgggaat gtgtgtgtgc  2760
gcacggcgca gatgcattac accatatgaa ttaacaccag gagccactgc tcccttcctg  2820
ctcagcctgc tatgctgcgt cagaacgacc aaggcggcca catattacga ggctgcggca  2880
tatctatgga acgaacagca gccctgttc tggttgcagg ctcttatcc gctggccgcc  2940
ttgatcgtcc tgtgtcaactg tctgaaactc ttgccatgct gctgtaagac cctggctttt  3000
ttagccgtaa tgagcatcgg tgcccacact gtgagcgcgt acgaacacgt aacagtgatc  3060
ccgaacacgg tgggagtacc gtataagact cttgtcaaca gaccgggtta cagccccatg  3120
gtgttggaga tggagctaca atcagtcacc ttggaaccaa cactgtcact tgactacatc  3180
acgtgcgagt acaaaactgt catcccctcc ccgtacgtga agtgctgtgg tacagcagag  3240
tgcaaggaca agagcctacc agactacagc tgcaaggtct ttactggagt ctacccattt  3300
atgtggggcg cgcgcctactg cttttgcgac gccgaaaata cgcaattgag cgaggcacat  3360
gtagagaaat ctgaatcttg caaaacagag tttgcatcgg cctacagagc ccacaccgca  3420
tcggcgtcg cgaagctccg cgtcctttac caaggaaaca acattaccgt agctgcctac  3480
gctaacggtg accatgccgt cacagtaaag gacgccaagt ttgtcgtggg cccaatgtcc  3540
tccgcctgga caccttttga caacaaaatc gtggtgtaca aaggcgacgt ctacaacatg  3600
gactacccac ctttttggcgc aggaagacca ggacaatttg gtgacattca aagtcgtaca  3660
ccggaaagta aagacgttta tgccaacact cagttggtac tacagaggcc agcagcaggc  3720
acggtacatg taccatactc tcaggcacca tctggcttca agtattggct gaaggaacga  3780
ggagcatcgc tacagcacac ggcaccgttc ggttgccaga ttgcgacaaa cccggtaaga  3840
gctgaaatt gcgctgtggg gaacatacca atttccatcg acataccgga tgcggccttt  3900
actagggttg tcgatgcacc ctctgtaacg gacatgtcat gcgaagtacc agcctgcact  3960
cactcctccg actttgggg cgtcgccatc atcaaataca cagctagcaa gaaaggtaaa  4020
tgtgcagtac attcgatgac caacgccgtt accattcgaa aagccgacgt agaagtagag  4080
gggaactccc agctgcaaat atccttctca acagccctgg caagcgccga gtttcgcgtg  4140
caagtgtgct ccacacaagt acactgcgca gccgcatgcc accctccaaa ggaccacata  4200
gtcaattacc cagcatcaca caccacctt gggtccagg atatatccac aacggcaatg  4260
tcttgggtgc agaagattac gggaggagta ggattaattg ttgctgttgc tgccttaatt  4320
ttaattgtgg tgctatgcgt gtcgtttagc aggcactaa                        4359
```

```
SEQ ID NO: 187       moltype = AA  length = 1452
FEATURE              Location/Qualifiers
REGION               1..1452
                     note = Synthetic
source               1..1452
                     mol_type = protein
                     organism = synthetic construct
SEQUENCE: 187
MEFIPTQTFY NRRYQPRPWA PRPTIQVIRP RPRPQRQAGQ LAQLISAVNK LTMRAVPQQK  60
PRRNRKNKKQ RQKKQAPQND PKQKKQPPQK KPAQKKKKPG RRERMCMKIE NDCIFEVKHE  120
GKVMGYACLV GDKVMKPAHV KGTIDNADLA KLAFKRSSKY DLECAQIPVH MKSDASKFTH  180
EKPEGYYNWH HGAVQYSGGR FTIPTGAGKP GDSGRPIFDN KGRVVAIVLG GANEGARTAL  240
SVVTWNKDIV TKITPEGAEE WSLALPVLCL LANTTFPCSQ PPCTPCCYEK EPESTLRMLE  300
DNVMRPGYYQ LLKASLTCRQ RRLQLGNCSV AGWILGNPEC ELLISKESWS YIVETPNPEN  360
GTCFPGYFAD YEELREQLSS VSSFERFEIF PKESSWPNHT VTGVSASCSH NGKSSFYRNL  420
LWLTGKNGLY PNLSKSYVNN KEKEVLVLWG VHHPPNIGNQ RALYHTENAY VSVVSSHYSR  480
RFTPEIAKRP KVRDQEGRIN YYWTLLEPGD TIIFEANGNL IAPWYAFALS RGANFNVYKA  540
```

```
TRPYLAHCPD CGEGHSCHSP IALERIRNEA TDGTLKIQVS LQIGIKTDDS HDWTKLRYMD   600
SHTPADAERA GLLVRTSAPC TITGTMGHFI LARCPKGETL TVGFTDSRKI SHTCTHPFHH   660
EPPVIGRERF HSRPQHGKEL PCSTYVQSTA ATAEEIEVHM PPDTPDRTLM TQQSGNVKIT   720
VNGQTVRYKC NCGGSNEGLT TTDKVINNCK IDQCHAAVTN HKNWQYNSPL VPRNAELGDR   780
KGKIHIPFPL ANVTCRVPKA RNPTVTYGKN QVTMLLYPDH PTLLSYRNMG QEPNYHEEWV   840
THKKEVTLTV PTEGLEVTWG NNEPYKYWPQ MSTNGTAHGH PHEIILYYYE LYPTMTVVIV   900
SVASFVLLSM VGTAVGMCVC ARRRCITPYE LTPGATVPFL LSLLCCVRTT KAATYYEAAA   960
YLWNEQQPLF WLQALIPLAA LIVLCNCLKL LPCCCKTLAF LAVMSIGAHT VSAYEHVTVI  1020
PNTVGVPYKT LVNRPGYSPM VLEMELQSVT LEPTLSLDYI TCEYKTVIPS PYVKCCGTAE  1080
CKDKSLPDYS CKVFTGVYPF MWGGAYCFCD AENTQLSEAH VEKSESCKTE FASAYRAHTA  1140
SASAKLRVLY QGNNITVAAY ANGDHAVTVK DAKFVVGPMS SAWTPFDNKI VVYKGDVYNM  1200
DYPPFGAGRP GQFGDIQSRT PESKDVYANT QLVLQRPAAG TVHVPYSQAP SGFKYWLKER  1260
GASLQHTAPF GCQIATNPVR AVNCAVGNIP ISIDIPDAAF TRVVDAPSVT DMSCEVPACT  1320
HSSDFGGVAI IKYTASKKGK CAVHSMTNAV TIREADVEVE GNSQLQISFS TALASAEFRV  1380
QVCSTQVHCA AACHPPKDHI VNYPASHTTL GVQDISTTAM SWVQKITGGV GLIVAVAALI  1440
LIVVLCVSFS RH                                                     1452

SEQ ID NO: 188         moltype = DNA   length = 4359
FEATURE                Location/Qualifiers
misc_feature           1..4359
                       note = Synthetic
source                 1..4359
                       mol_type = other DNA
                       organism = synthetic construct
SEQUENCE: 188
ttagtgcctg ctaaacgaca cgcatagcac cacaattaaa attaaggcag caacagcaac   60
aattaatcct actcctcccg taatcttctg cacccaagac attgccgttg tggatatatc  120
ctggacccca agggtggtgt gtgatgctgg gtaattgact atgtggtcct ttggagggtg  180
gcatgcggct gcgcagtgta cttgtgtgga gcacacttgc acgcgaaact cggcgcttgc  240
cagggctgtt gagaaggata tttgcagctg ggagttcccc tctacttcta cgtcggcttc  300
tcgaatggta acggcgttgg tcatcgaatg tactgcacat ttacctttct tgctagctgt  360
gtatttgatg atggcgacgc ccccaaagtc ggaggagtga gtgcaggctg tacttcgca  420
tgacatgtcc gttacagagg gtgcatcgac aaccctagta aaggccgcat ccggtatgtc  480
gatggaaatt ggtatgttcc ccacagcgca atttacagct cttaccggtt ttgtcgcaat  540
ctggcaaccg aacggtgccg tgtgctgtag cgatgctcct cgttccttca gccaatactt  600
gaagccagat ggtgcctgag agtatggtac atgtaccgtg cctgctgctg gcctctgtag  660
taccaactga gtgttggcat aaacgtcttt actttccggt gtacgacttt gaatgtcacc  720
aaattgtcct ggtcttcctg cgccaaaagg tgggtagtcc atgttgtaga cgtcgccttt  780
gtacaccacg attttgttgt caaaaggtgt ccaggcggac gcattgggc ccacgacaaa  840
cttggcgtcc tttactgtga cggcatggtc accgttagcg taggcagcta cggtaatgtt  900
gtttccttgg taaaggacgc ggagcttcgc cgacgccgat gcggtgtggg ctctgtaggc  960
cgatgcaaac tctgttttgc aagattcaga tttctctaca tgtgcctcgc tcaattgcgt 1020
attttcggcg tcgcaaaagc aatgaggcgcc gccccacata aatgggtaga ctccagtaaa 1080
gaccttgcag ctgtagtctg gtaggctctt gtccttgcac tctgctgtac cacagcactt 1140
cacgtacggg gaggggatga cagttttgta ctcgcacgtg atgtagtcaa gtgacagtgt 1200
tggttccaag gtgactgatt gtagctccat ctccaacacc atggggctgt aacccggtct 1260
gttgacaaga gtcttatacg gtactcccac cgtgttcagg atcactgtta cgtgttcgta 1320
cgcgctcaca gtgtgggcac cgatgctcat tacggctaaa aaagccaggg tcttacagca 1380
gcatggcaag agtttcagac agttgcacag gacgatcaag cgggcagcg ggataagagc 1440
ctgcaaccag aacaggggct gctgttcgtt ccatagatat gccgcagcct cgtaaatgt 1500
ggccgccttg gtcgttctga cgcagcatag caggctgagc aggaaggaa cagtggctcc 1560
tggtgttaat tcatatggtg taatgcatct cgcgccgtgcg cacacacaca ttcccactgc 1620
tgtgcccacc atcgacagaa gcacgaacga ggccaccgac acaatgacta cagtcatagt 1680
ggggtacagc tcataatagt acaagattat ctcatgtggg tgaccatgag cagtaccgtt 1740
cgtagacatc tgcggccagt acttgtatgg ttcgttgttg ccccaagtga cctccagacc 1800
ctcagtaggc acggtcaagg taacctcctt cttgtgtgtc acccactcct cgtggtaatt 1860
tggttcctgt cccatgttac ggtaagacaa gagtgtcgga tggtcaggat acagcagcat 1920
ggtgacttgg ttttttccgt aagttactgt agggtttctt gcttttggca ctctgcaagt 1980
cacgtttgcc aatgggaatg ggatgtggat ctttccttta cggtccccga gttcagcgtt 2040
gcgcgggact aaaggggagt tgtattgcca attcttgtga ttagtgactg cagcatggca 2100
ctgatcaatt ttgcagttat tgatcacttt gtctgtggtt gtcagtccct cgtttgagcc 2160
accgcagttg cacttgtacc gcaccgtctg cccattaact gtgatcttca cgttgccaga 2220
ctgctgcgtc atcagcgtgc ggtcaggagt atctgggggc atatgcacct ctatctcctc 2280
agcagtggca gcggtgctct gcacgtacgt gctgcaaggt aactctttac catgttgtga 2340
tcgagagtgg aacctctccc tacctatcac aggtggttca tgatggaacg ggtgtgtgca 2400
tgtgtggctg atctttctgc tgtccgtaaa tcccactgtc agcgtctctc ctttcgggca 2460
tcgggcgaga ataaagtgtc ccatggtccc ggtgatcgtg caccggtgctg aagtccttac 2520
aagcaatccg gctcgctccg cgtccgctgg cgtatggcta tccatatagc gcagcttggt 2580
ccaatcgtgg ctgtcatctg tctttatccc gatctgcaaa gagacctgga tttcagcgt 2640
tccgtccgtt gcttcatttc tgatgcgctc caatgcgata gggctgtggc acgaatgccc 2700
ttctccgcag tcaggacaat gagctagata tggtcttgtg gctttataga cattaaaatt 2760
ggcgcctctc ctcagggcaa aggcatacca aggggcgatc agattgccgt tggcctcgaa 2820
gatgatggta tcgccaggct ccagcagggt ccagtagtaa ttgatccggc cctcctggtc 2880
tctcactttg ggtctcttgg gtgatctcggg ggtgaatctt ctgctgtagt ctggctggacac 2940
cacgctcaca taggcgttct ctgtgtggta cagggcccgc tgatttccga tgttgggagg 3000
gtggtgcact cccacagca ccagcacttc cttttccttg ttgttcacgt agctcttgct 3060
caggttgggg tacaggccat tcttgcctgt cagccacagc aggttccggt agaagctgct 3120
tttgccgttg tggctacagc tggcagacac gcctgtcact gtgtgattag gccagctgga 3180
ctccttgggg aagatctcga atctctcgaa gctggacacg ctagacagct gctcgcgcag 3240
```

```
ctcctcgtaa tcggcgaagt agccagggaa gcaggtgcca ttctcaggat tgggggtctc    3300
cacgatgtag ctccagctct ccttagaaat cagcagctca cactcggggt tgcccagaat    3360
ccatccggcc acagaacaat tccccagctg caggcgtctt tggcggcaag tcagcgatgc    3420
ttttagtagc tggtagtatc cgggtctcat cacgttgtcc tcaagcatgc gcaaggtgct    3480
ttccggttcc tttttcgtagc agcagggtgt gcaaggcggc tgagagcagg ggaatgtagt    3540
gtttgccaac aggcacaaga ccgggagggc gaggctccac tcttcggctc cctcaggggt    3600
aattttttgtg acgatgtctt tgttccacgt caccacggag agggccgtgc gggcaccttc    3660
gttggcccct cctaggacga tggccaccac ccgtcctttg ttgtcgaaga tcggtctgcc    3720
gctgtctccc ggcttgcctg cacccgtcgg gatagtgaac cggcctcctg aatactgcac    3780
tgctccgtga tgccagttat agtacccctc gggtttctcg tgggtaaact tcgaggcatc    3840
agacttcatg tgcaccggta tctgtgcaca ttcaagatcg tatttagacg accgcttaaa    3900
ggccagttta gccagatcgg cattgtcgat agttcccttc acatgtgctg gtttcattac    3960
tttatccccc accaggcatg cgtagcccat cactttgcct tcatgcttga cttcgaagat    4020
gcaatcattt tcaattttca tgcacattct ctccctacgg cctggtttct tcttcttttg    4080
agccggcttc ttttgtggtg gttgcttctt ttgcttgggg tcgttttgcg gcgcctgctt    4140
cttctgcctt tgcttcttgt ttttccgatt tctgcgaggc ttctgttgag gtaccgcgcg    4200
catggtcaat ttgttgactg cggagatcag ctgggcgagt gcccagcct gcctctgtgg     4260
acgtggtcta ggtctaatta cttgaattgt agggcgtggg gcccagggtc ggggttggta    4320
ccttctgtta tagaaagttt gcgtcgggat gaactccat                            4359
```

SEQ ID NO: 189                moltype = DNA   length = 4362
FEATURE                       Location/Qualifiers
misc_feature                  1..4362
                              note = Synthetic
source                        1..4362
                              mol_type = other DNA
                              organism = synthetic construct
SEQUENCE: 189

```
atggagttca tcccgacgca aactttctat aacagaaggt accaaccccg accctgggcc    60
ccacgcccta caattcaagt aattagacct agaccacgtc cacagaggca ggctgggcaa    120
ctcgcccagc tgatctccgc agtcaacaaa ttgaccatgc gcgcggtacc tcaacagaag    180
cctcgcagaa atcggaaaaa caagaagcaa aggcagaaga agcaggcgcc gcaaaacgac    240
ccaaagcaaa agaagcaacc accacaaaag aagccggctc aaaagaagaa gaaaccaggc    300
cgtagggaga gaatgtgcat gaaaattgaa aatgattgca tcttcgaagt caagcatgaa    360
ggcaaagtga tgggctacgc atgcctggtg ggggataaag taatgaaacc agcacatgtg    420
aagggaacta tcgacaatgc cgatctggct aaactggcct ttaagcggtc gtctaaatac    480
gatcttgaat gtgcacagat accggtgcac atgaagtctg atgcctcgaa gtttacccac    540
gagaaacccg aggggtacta taactggcat cacggagcag tgcagtattc aggaggccgg    600
ttcactatcc cgacgggtgc aggcaagccg ggagcaagcg gcagaccgat cttcgacaac    660
aaaggacggg tggtggccat cgtcctagga ggggccaacg aaggtgcccg cacggccctc    720
tccgtggtga cgtggaacaa agacatcgtc acaaaaatta cccctgaggg agccgaagag    780
tggagcctcg ccctcccggt cttgtgcctg ttggcaaaca ctacattccc ctgctctcag    840
ccgccttgca caccctgctg ctacgaaaag gaaccgaaac gcaccttgcg catgcttgag    900
gacaacgtga tgagacccgg atactaccag ctactaaaag catcgctgac ttgccgccaa    960
agacgcctgc aacctgggca agtgcaacatc gccggctgga ttctgggcaa ccccgagtgc    1020
gagagcctga gcaccgccag cagctggagc tacatcgtgg agacccccag cagcgacaac    1080
ggcacctgct tccccggcga cttcatcgac tacgaggagc tgcgggagca gctgagcgag    1140
gtgagcagct cgagcggtt cgagatcttc cccaagacca gcagctggcc caaccacgac    1200
agcaacaagg gcgtgaccgc cgcctgcccc cacgccggcg ccaagagctt ctacaagaac    1260
ctgatctggc tggtgaagaa gggcaacagc taccccaagc tgagcaagag ctacatcaac    1320
gacaagggca aggaggtgct ggtgctgtgg ggcatccacc accccagcac cagcgccgac    1380
cagcagagcc tgtaccagaa cgccgacacc tacgtgttcg tgggcagcag ccggtacagc    1440
aagaagttca gcccgagat cgccatccgg cccaaggtgc gggaccagga gggccggatg    1500
aactactact ggaccctggt ggagcccggc gacaagatca ccttcgaggc caccggcaac    1560
ctggtggtgc cccggtacgc cttcgccatg gagcggaacg ccaattttaa tgtctataaa    1620
gccacaagac catatctagc tcattgtcct gactgcggag aagggcattc gtgccacagc    1680
cctatcgcat tggagcgcat cagaaatgaa gcaacgacg gaacgctgaa aatccaggtc    1740
tctttgcaga tcgggataaa gacagatgac agccacgatt ggaccaagct gcgctatatg    1800
gatagccata cgccagcgga cgcggaacga gccggattgc ttgtaaggac ttcagcaccg    1860
tgcacgatca ccgggaccat gggacacttt attctcgccg gatgcccgaa aggagagacg    1920
ctgacagtgg gatttacgga cagcagaaag atcagccaca catgcacaca cccgttccat    1980
catgaaccac ctgtgatagg tagggagagg ttccactctc gaccacaaca tggtaaaagag    2040
ttaccttgca gcacgtacgt gcagagcacc gctgccactg ctgaggagat agaggtgcat    2100
atgcccccag atactcctga ccgcacgctg atgacgcagc agtctggcaa cgtgaagatc    2160
acagttaatg ggcagacggt gcggtacaag tgcaactgcg gtggctcaaa cgagggactg    2220
acaaccacag acaaagtgat caataactgc aaaattgatc agtgccatgc tgcagtcact    2280
aatcacaaga attggcaata caactcccct ttagtcccgc gcaacgctga actcgggac     2340
cgtaaaggaa agatccacat cccattccca ttggcaaacg tgacttgcag agtgccaaaa    2400
gcaagaaacc ctacagtaac ttacggaaaa aaccaagtca ccatgctgct gtatcctgac    2460
catccgacac tcttgtctta ccgtaacatg ggacaggaac caaattacca cgaggagtgg    2520
gtgacacaca agaaggaggt taccttgacc gtgcctactg agggtctgga ggtcacttgg    2580
ggcaacaacg aaccatacaa gtactggccg cagatgtcta cgaacggtac tgctcatggt    2640
cacccacatg agataatctt gtactattat gagctgtacc ccactatgac tgtagtcatt    2700
gtgtcggtgg cctcgttcgt gcttctgtcg atggtgggca actatgtgtg aatgtgtgtg    2760
tgcgcacgtg gcagatgcat tacaccatat gaattaacac caggagccac tgttcccttc    2820
ctgctcagcc tgctatgctg cgtcagacg accaaggcgg ccacatatta cgaggctgcg     2880
gcatatctat ggaacgaaca gcagccctg ttctggttgc aggctcttat cccgctggcc     2940
gccttgatcg tcctgtgcaa ctgtctgaaa ctcttgccat gctgctgtaa gaccctggct    3000
ttttttagccg taatgagcat cggtgcccac actgtgagcg cgtacgaaca cgtaacagtg    3060
```

```
atcccgaaca cggtgggagt accgtataag actcttgtca acagaccggg ttacagcccc   3120
atggtgttgg agatggagct acaatcagtc accttggaac caacactgtc acttgactac   3180
atcacgtgcg agtacaaaac tgtcatcccc tccccgtacg tgaagtgctg tggtacagca   3240
gagtgcaagg acaagagcct accagactac agctgcaagg tctttactgg agtctaccca   3300
tttatgtggg gcggcgccta ctgcttttgc gacgccgaaa atacgcaatt gagcgaggca   3360
catgtagaga aatctgaatc ttgcaaaaca gagtttgcat cggcctacag agcccacacc   3420
gcatcggcgt cggcgaagct ccgcgtcctt taccaaggaa acaacattac cgtagctgcc   3480
tacgctaacg gtgaccatgc cgtcacagta aaggacgcca agtttgtcgt gggcccaatg   3540
tcctccgcct ggacaccttt tgacaacaaa atcgtggtgt acaaaggcga cgtctacaac   3600
atggactacc cacctttttgg cgcaggaaga ccaggacaat ttggtgacat tcaaagtcgt   3660
acaccggaaa gtaaagacgt ttatgccaac actcagttgg tactacagag gccagcagca   3720
ggcacggtac atgtaccata ctctcaggca ccatctggct tcaagtattg gctgaaggaa   3780
cgaggagcat cgctcagca cacggcaccg ttcggttgcc agattgcgac aaacccggta   3840
agagctgtaa attgcgctgt ggggaacata ccaatttcca tcgacatacc ggatgcggcc   3900
tttactaggg ttgtcgatgc accctctgta acggacatgt catgcgaagt accagcctgc   3960
actcactcct ccgactttgg gggcgtcgcc atcatcaaat acacagctag caagaaaggt   4020
aaatgtgcag tacattcgat gaccaacgcc gttaccattc gagaagccga cgtagaagta   4080
gaggggaact cccagctgca aatatccttc tcaacagccc tggcaagcgc cgagtttcgc   4140
gtgcaagtgt gctccacaca agtacactgc gcagccgcat gccaccctcc aaaggaccac   4200
atagtcaatt acccagcatc acacaccacc cttggggtcc aggatatatc cacaacggca   4260
atgtcttggg tgcagaagat tacgggagga gtaggattaa ttgttgctgt tgctgcctta   4320
attttaattg tggtgctatg cgtgtcgttt agcaggcact aa                      4362
```

```
SEQ ID NO: 190              moltype = AA   length = 1453
FEATURE                     Location/Qualifiers
REGION                      1..1453
                            note = Synthetic
source                      1..1453
                            mol_type = protein
                            organism = synthetic construct
SEQUENCE: 190
MEFIPTQTFY NRRYQPRPWA PRPTIQVIRP RPRPQRQAGQ LAQLISAVNK LTMRAVPQQK   60
PRRNRKNKKQ RQKKQAPQND PKQKKQPPQK KPAQKKKKPG RRERMCMKIE NDCIFEVKHE   120
GKVMGYACLV GDKVMKPAHV KGTIDNADLA KLAFKRSSKY DLECAQIPVH MKSDASKFTH   180
EKPEGYYNWH HGAVQYSGGR FTIPTGAGKP GDSGRPIFDN KGRVVAIVLG GANEGARTAL   240
SVVTWNKDIV TKITPEGAEE WSLALPVLCL LANTTFPCSQ PPCTPCCYEK EPESTLRMLE   300
DNVMRPGYYQ LLKASLTCRQ RRLHLGKCNI AGWILGNPEC ESLSTASSWS YIVETPSSDN   360
GTCFPGDFID YEELREQLSS VSSFERFEIF PKTSSWPNHD SNKGVTAACP HAGAKSFYKN   420
LIWLVKKGNS YPKLSKSYIN DKGKEVLVLW GIHHPSTSAD QQSLYQNADT YVFVGSSRYS   480
KKFKPEIAIR PKVRDQEGRM NYYWTLVEPG DKITFEATGN LVVPRYAFAM ERNANFNVYK   540
ATRPYLAHCP DCGEGHSCHS PIALERIRNE ATDGTLKIQV SLQIGIKTDD SHDWTKLRYM   600
DSHTPADAER AGLLVRTSAP CTITGTMGHF ILARCPKGET LTVGFTDSRK ISHTCTHPFH   660
HEPPVIGRER FHSRPQHGKE LPCSTYVQST AATAEEIEVH MPPDTPDRTL MTQQSGNVKI   720
TVNGQTVRYK CNCGGSNEGL TTTDKVINNC KIDQCHAAVT NHKNWQYNSP LVPRNAELGD   780
RKGKIHIPFP LANVTCRVPK ARNPTVTYGK NQVTMLLYPD HPTLLSYRNM GQEPNYHEEW   840
VTHKKEVTLT VPTEGLEVTW GNNEPYKYWP QMSTNGTAHG HPHEIILYYY ELYPTMTVVI   900
VSVASFVLLS MVGTAVGMCV CARRRCITPY ELTPGATVPF LLSLLCCVRT TKAATYYEAA   960
AYLWNEQQPL FWLQALIPLA ALIVLCNCLK LLPCCCKTLA FLAVMSIGAH TVSAYEHVTV   1020
IPNTVGVPYK TLVNRPGYSP MVLEMELQSV TLEPTLSLDY ITCEYKTVIP SPYVKCCGTA   1080
ECKDKSLPDY SCKVFTGVYP FMWGGAYCFC DAENTQLSEA HVEKSESCKT EFASAYRAHT   1140
ASASAKLRVL YQGNNITVAA YANGDHAVTV KDAKFVVGPM SSAWTPFDNK IVVYKGDVYN   1200
MDYPPFGAGR PGQFGDIQSR TPESKDVYAN TQLVLQRPAA GTVHVPYSQA PSGFKYWLKE   1260
RGASLQHTAP FGCQIATNPV RAVNCAVGNI PISIDIPDAA FTRVVDAPSV TDMSCEVPAC   1320
THSSDFGGVA IIKYTASKKG KCAVHSMTNA VTIREADVEV EGNSQLQISF STALASAEFR   1380
VQVCSTQVHC AAACHPPKDH IVNYPASHTT LGVQDISTTA MSWVQKITGG VGLIVAVAAL   1440
ILIVVLCVSF SRH                                                      1453
```

```
SEQ ID NO: 191              moltype = DNA   length = 4362
FEATURE                     Location/Qualifiers
misc_feature                1..4362
                            note = Synthetic
source                      1..4362
                            mol_type = other DNA
                            organism = synthetic construct
SEQUENCE: 191
ttagtgcctg ctaaacgaca cgcatagcac cacaattaaa attaaggcag caacagcaac   60
aattaatcct actcctcccg taatcttctg cacccaagac attgccgttg tggatatatc   120
ctggacccca aggtggtgt gtgatgctgg gtaattgact atgtggtcct ttggagggtg   180
gcatgcggct gcgcagtgta cttgtgtgga gcacacttgc acgcgaaact cggcgcttgc   240
cagggctgtt gagaaggata tttgcagctg ggagttcccc tctacttcta cgtcggcttc   300
tcgaatggta acgcgttgg tcatcgaatg tactgcacat ttacctttct tgctagctgt   360
gtatttgatg atggcgacgc ccccaaagtc ggaggagtga gtgcaggctg gtacttcgca   420
tgacatgtcc gttacagagg gtgcatcgac aaccctagta aaggccgcat ccggtatgtc   480
gatggaaatt ggtatgttcc ccacagcgca atttacagct cttaccgggt ttgtcgcaat   540
```

-continued

```
ctggcaaccg aacggtgccg tgtgctgtag cgatgctcct cgttccttca gccaatactt   600
gaagccagat ggtgcctgag agtatggtac atgtaccgtg cctgctgctg gcctctgtag   660
taccaactga gtgttggcat aaacgtcttt actttccggt gtacgacttt gaatgtcacc   720
aaaattgtcct ggtcttcctg cgccaaaagg tgggtagtcc atgttgtaga cgtcgccttt   780
gtacaccacg attttgttgt caaaaggtgt ccaggcggag gacattgggc ccacgacaaa   840
cttggcgtcc tttactgtga cggcatggtc accgttagcg taggcagcta cggtaatgtt   900
gtttccttgg taaaggacgc ggagcttcgc cgacgccgat gcggtgtggg ctctgtaggc   960
cgatgcaaac tctgtttttgc aagattcaga tttctctaca tgtgcctcgc tcaattgcgt  1020
attttcggcg tcgcaaaagc agtaggcgcc gccccacata aatgggtaga ctccagtaaa  1080
gaccttgcag ctgtagtctg gtaggctctt gtccttgcac tctgctgtac cacagcactt  1140
cacgtacggg gaggggatga cagtttttgta ctcgcacgtg atgtagtcaa gtgacagtgt  1200
tggttccaag gtgactgatt gtagctccat ctccaacacc atggggctgt aacccggtct  1260
gttgacaaga gtcttatacg gtactcccac cgtgttcggg atcactgtta cgtgttcgta  1320
cgcgctcaca gtgtgggcac cgatgctcat tacggctaaa aaagccaggg tcttacagca  1380
gcatggcaag agtttcagac agttgcacag gacgatcaag gcggccagcg ggataagagc  1440
ctgcaaccag aacaggggct gctgttcgtt ccatagatat gccgcagcct cgtaatatgt  1500
ggccgccttg gtcgttctga cgcagcatag caggctgagc aggaagggaa cagtggctcc  1560
tggtgttaat tcatatggtg taatgcatct gcgccgtgcg cacacacaca ttcccactgc  1620
tgtgcccacc atcgacagaa gcacgaacga ggccaccgac acaatgacta cagtcatagt  1680
ggggtacagc tcataatagt acaagattat ctcatgtggg tgaccatgag cagtaccgtt  1740
cgtagacatc tgcggccagt acttgtatgg ttcgttgttg ccccaagtga cctccagacc  1800
ctcagtaggc acggtcaagg taacctcctt cttgtgtgtc acccactcct cgtggtaatt  1860
tggttcctgt cccatgttac ggtaagacaa gagtgtcgga tggtcaggat acagcagcat  1920
ggtgacttgg ttttttccgt aagttactgt agggtttctt gcttttggca ctctgcaagt  1980
cacgtttgcc aatgggaatg ggatgtggat cttttccttta cggtccccga gttcagcgtt  2040
gcgcgggact aaaggggagt tgtattgcca attcttgtga ttagtgactg cagcatggca  2100
ctgatcaatt ttgcagttat tgatcacttt gtctgtggtt gtcagtccct cgtttgagcc  2160
accgcagttg cacttgtacc gcaccgtctg cccattaact gtgatcttca cgttgccaga  2220
ctgctgcgtc atcagcgtgc ggtcaggagt atctggggggc atatgcacct ctatctcctc  2280
agcagtggca gcggtgctct gcacgtacgt gctgcaaggt aactctttac catgttgtgg  2340
tcgagagtgg aacctctccc tacctatcac aggtggttca tgatggaacg ggtgtgtgca  2400
tgtgtggctg atctttctgc tgtccgtaaa tcccactgtc agcgtctctc ctttcgggca  2460
tcgggcgaga ataaagtgtc ccatggtccc ggtgatcgtg cacggtgctg aagtccttac  2520
aagcaatccg gctcgctccg cgtccgctgg cgtatggcta tccatatagc gcagcttggt  2580
ccaatcgtgg ctgtcatctg tctttatccc gatctgcaaa gagacctgga ttttcagcgt  2640
tccgtccgtt gcttcatttc tgatgcgctc caatgcgata gggctgtggc acgaatgccc  2700
ttctccgcag tcaggacaat gagctagata tggtcttgtg gctttataga cattaaaatt  2760
ggcgttccgc tccatggcga aggcgtaccg gggcaccacc aggttgccgg tggcctcgaa  2820
ggtgatcttg tcgccgggct ccaccagggt ccagtagtag ttcatccggc cctcctggtc  2880
ccgcaccttg ggccggatgg cgatctcggg cttgaacttc ttgctgtacc ggctgctgcc  2940
cacgaacacg taggtgtcgg cgttctggta caggctctgc tggtcggcgc tggtgctggg  3000
gtggtggatg ccccacagca ccagcacctc cttgcccttg tcgttgatgt agctcttgct  3060
cagcttgggg tagctgttgc ccttcttcac cagccagatc aggttcttgt agaagctctt  3120
ggcgccggcg tgggggcagg cggcggtcac gcccttgttg ctgtcgtggt tgggccagct  3180
gctggtcttg gggaagatct cgaaccgctc gaagctgctc acgctgctca gctgctcccg  3240
cagctcctcg tagtcgatga agtcgccggg gaagcaggtg ccgttgtcgc tgctggggt  3300
ctccacgatg tagctccagc tgctggcggt gctcaggctc ggttgcccag  3360
aatccagccg gcgatgttgc acttgcccag gtgcaggcgt ctttggcggc aagtcagcga  3420
tgctttttagt agctggtagt atccgggtct catcacgttg tcctcaagca tgcgcaaggt  3480
gctttccggt tccttttcgt agcagcaggg tgtgcaaggc ggctgagagc aggggaatgt  3540
agtgtttgcc aacaggcaca agaccgggag ggcgaggctc cactcttcgg ctccctcagg  3600
ggtaattttt gtgacgatgt ctttgttcca cgtcaccacg gagagggccg tgcgggcacc  3660
ttcgttggcc cctcctagga cgatggccac cacccgtcct ttgttgtcga agatcggtct  3720
gccgctgtct cccggcttgc ctgcacccgt cgggatagtg aaccggcctc ctgaatactg  3780
cactgctccg tgatgccagt tatagtaccc ctcgggtttc tcgtgggtaa acttcgaggc  3840
atcagacttc atgtgcaccg gtatctgtgc acattcaaga tcgtatttag acgaccgctt  3900
aaaggccagt ttagccagat cggcattgtc gatagttccc ttcacatgtg ctggtttcat  3960
tactttatcc cccaccaggc atgcgtagcc catcactttg ccttcatgct tgacttcgaa  4020
gatgcaatca ttttcaattt tcatgcacat tctctcccta cggcctggtt tcttcttctt  4080
ttgagccggc ttcttttgtg tggttgctt cttttgcttt gggtcgtttt gcggcgcctg  4140
cttcttctgc ctttgcttct tgtttttccg atttctgcga ggcttctgtt gaggtaccgc  4200
gcgcatggtc aatttgttga ctgcggagat cagctgggcg agttgcccag cctgcctctg  4260
tggacgtggt ctaggtctaa ttacttgaat tgtagggcgt ggggcccagg tcggggttg  4320
gtaccttctg ttatagaaag tttgcgtcgg gatgaactcc at                      4362
```

```
SEQ ID NO: 192            moltype = AA  length = 30
FEATURE                   Location/Qualifiers
source                    1..30
                          mol_type = protein
                          organism = synthetic construct
SEQUENCE: 192
MDSKGSSQKG SRLLLLLVVS NLLLPQGVLA                                       30
```

1

MULTIVALENT NANOPARTICLE-BASED VACCINES

CROSS-REFERENCE TO RELATED APPLICATIONS

This is a divisional of U.S. Non-Provisional patent application Ser. No. 17/519,142, filed on Nov. 4, 2021, which is a divisional of U.S. Non-Provisional patent application Ser. No. 15/540,898, filed on Jun. 29, 2017, now U.S. Pat. No. 11,191,727, which is the U.S. National Stage of International Application No. PCT/US2015/068272, filed on Dec. 31, 2015, which was published in English under PCT Article 21(2), which in turn claims the benefit of U.S. Provisional Application No. 62/098,755, filed on Dec. 31, 2014. Each of the above-listed applications is incorporated by reference herein in its entirety.

REFERENCE TO SEQUENCE LISTING

This application contains a Sequence Listing submitted as an XML file in the form of the filed name "4239-104866-21_Sequence.xml" (358,480-bytes), which was created on Jan. 14, 2026, which is incorporated by reference herein.

SUMMARY OF THE INVENTION

The present invention provides novel, nanoparticle-based vaccines that are easily manufactured, potent, and which elicit broadly neutralizing antibodies against infectious agents, such as influenza virus, HIV and human papilloma virus. In particular, the present invention provides novel nanoparticles (nps), the surfaces of which display a heterogeneous population of immunogenic portions of proteins from infectious agents. Such nanoparticles comprise fusion proteins, each of which comprises a monomeric subunit of ferritin joined to one or more immunogenic portions of proteins from infectious agents. When such nanoparticles are administered to an individual, they elicit an immune response to proteins from a broad range of infectious agents.

In one embodiment, the invention is a nanoparticle comprising fusion proteins, wherein the surface of the nanoparticle displays immunogenic portions of corresponding proteins from at least two infectious agents, wherein the at least two infectious agents are from different corresponding taxonomic groups within the same taxonomic family. In certain aspects of the invention, the fusion proteins comprise at least a portion of a self-assembling, monomeric subunit joined to at least one immunogenic portion of a protein from an infectious agent.

In one embodiment, the invention is a nanoparticle comprising at least a first fusion protein and a second fusion protein, each fusion protein comprising at least a portion of a self-assembling, monomeric subunit joined to at least one immunogenic portion of a protein from an infectious agent, wherein the immunogenic portion of the first fusion protein is from a protein from a first infectious agent; wherein the immunogenic portion of the second fusion protein is from a protein from a second infectious agent; wherein the proteins from the first and second infectious agents are corresponding proteins; and wherein the first and second infectious agents are from different corresponding taxonomic groups within the same taxonomic family.

In the above embodiments, the corresponding taxonomic groups can be genera, types, subtypes, species or strains. In certain aspects, the monomeric subunit can be a monomeric ferritin subunit protein, a monomeric encapsulin protein, a monomeric 03-33 protein, a monomeric SOR protein, a monomeric LS protein, a monomeric PDC protein or a Chikungunya virus structural polyprotein. In certain aspects the infectious agents are viruses. In certain aspects, the infectious agents can be, for example, influenza viruses, human immunodeficiency viruses (HIV), flaviviruses (e.g., hepatitis virus, dengue virus, etc.), human papillomaviruses (HPV), rhinoviruses, coronaviruses, enteroviruses, polyomaviruses, respiratory synctial viruses (RSV), human metapneumoviruses, ebola viruses, Marburg viruses, alphaviruses (e.g., Chikungunya virus, Ross River virus, Semliki Forest virus, Sindbis virus, Mayaro virus, etc), Porcine Epidemic Diarrhea, Porcine reproductive and respiratory syndrome virus and foot and mouth disease virus.

In one embodiment, nanoparticles of the above embodiments can be produced by introducing into a cell one or more nucleic acid molecules encoding fusion proteins comprising at least a portion of a self-assembling, monomeric subunit joined to at least one immunogenic portion of a protein from an infectious agent, and incubating the cell under conditions suitable for expression of the encoded proteins to form nanoparticles. In certain embodiments, such a method can comprise further purification and/or isolation of the nanoparticles.

In one embodiment of the invention, nanoparticles of the embodiments listed above are used to prepare a medicament for protecting an individual from an infectious agent. In such embodiments, the nanoparticles comprise immunogenic portions of proteins from infectious agents in the same taxonomic family as the infectious agent against which the individual is being protected. In certain embodiments, the medicament is used to vaccinate the individual.

One embodiment of the invention is a method to elicit a protective immune response against an infectious agent, the method comprising administering to an individual a nanoparticle of the embodiments of the invention, or a composition or medicament comprising embodiments of the invention, wherein the nanoparticles comprise immunogenic portions of proteins from infectious agents in the same taxonomic family as the infectious agent against which the protective immune response is being elicited.

One embodiment of the invention is a method to elicit neutralizing antibodies against an infectious agent, the method comprising administering to an individual a nanoparticle of the embodiments of the invention, or a composition or medicament comprising embodiments of the invention, wherein the nanoparticles comprise immunogenic portions of proteins from infectious agents in the same taxonomic family as the infectious agent against which the neutralizing antibodies are desired.

In one embodiment, the invention is a nanoparticle that comprises self-assembling fusion proteins, and in this embodiment the nanoparticle displays on its surface a heterogeneous population of immunogenic portions from HA proteins from one or more Type, Group, subtype and/or strain of influenza virus.

In another embodiment, the invention is a nanoparticle that comprises a heterogeneous population of fusion proteins, and in this embodiment each fusion protein comprises at least a portion of a monomeric subunit protein capable of self-assembling into a nanoparticle joined to at least one immunogenic portion from an influenza virus hemagglutinin protein, such that the heterogeneous population comprises at least two different species of fusion proteins, and such that the difference between two species of fusion proteins is due, at least in part, to sequence differences in the immunogenic portion from an influenza virus HA protein.

In yet another embodiment, the invention is a nanoparticle that comprises at least two species of fusion proteins, and in this embodiment each fusion protein comprises at least a portion of a monomeric subunit protein capable of self-assembling into a nanoparticle joined to at least one immunogenic portion from an influenza virus HA protein, such that the species of fusion protein differ from one another due, at least in part, to differences in the sequences of the immunogenic portion from an influenza virus hemagglutinin protein.

In still another embodiment, the invention is a nanoparticle that comprises at least a first species of fusion protein and a second species of fusion protein, and in this embodiment the fusion proteins comprise at least a portion of a monomeric subunit protein capable of self-assembling into a nanoparticle joined to at least one immunogenic portion from an influenza virus hemagglutinin protein, such that the species of fusion proteins differ from one another due, at least in part, to differences in the sequences of the immunogenic portion from an influenza virus hemagglutinin protein.

In the above embodiments, the different species of fusion proteins contain immunogenic portions from HA proteins of influenza viruses in different taxonomic groups within the orthomyxoviridae family.

In the above embodiments, ferritin-based nanoparticle can form an octahedron, which can consist of 24 subunits. Further, the immunogenic portions of the influenza HA proteins can be displayed on the surface of the nanoparticle with a spacing range in the range of about 50 Å to about 100 Å. Additionally, the monomeric subunit protein can be selected from a monomeric ferritin subunit protein, a monomeric encapsulin protein, a monomeric 03-33 protein, a monomeric SOR protein, a monomeric LS protein, a monomeric PDC protein and Chikungunya virus envelope protein. The monomeric ferritin subunit protein can be selected from the a bacterial ferritin, a plant ferritin, an algal ferritin, an insect ferritin, a fungal ferritin and a mammalian ferritin and in preferred embodiments, is selected from a monomeric subunit of a *Helicobacter pylori* ferritin protein, a monomeric subunit of a *Escherichia coli* ferritin protein and a monomeric subunit of a bullfrog ferritin protein. In still another preferred embodiment, the monomeric ferritin subunit protein can be a hybrid protein that comprises at least a portion of a bullfrog ferritin protein joined to at least a portion of a ferritin protein selected from a *Helicobacter pylori* ferritin protein and an *Escherichia coli* ferritin protein.

In one aspect of the embodiments of the invention, the monomeric subunit protein can comprise at least 25 contiguous amino acids from a protein selected from a monomeric ferritin subunit protein, a monomeric encapsulin protein, a monomeric 03-33 protein, a monomeric SOR protein, a monomeric LS protein, a monomeric PDC protein and Chikungunya virus envelope protein.

In still another aspect of the embodiments of the invention, the monomeric subunit protein can comprise at least 25 contiguous amino acids from an amino acid sequence selected from a sequence selected from SEQ ID NO:64, SEQ ID NO:67, SEQ ID NO:70, SEQ ID NO:73, SEQ ID NO:76, SEQ ID NO: 79, SEQ ID NO:82, SEQ ID NO:85, SEQ ID NO:88, SEQ ID NO:91 and SEQ ID NO:94. Alternatively, the monomeric subunit protein can comprise an amino acid sequence at least about 80% identical to an amino acid sequence selected from SEQ ID NO:64, SEQ ID NO:67, SEQ ID NO:70, SEQ ID NO:73, SEQ ID NO:76, SEQ ID NO:79, SEQ ID NO:82, SEQ ID NO:85, SEQ ID NO:88, SEQ ID NO:91 and SEQ ID NO:94. Also, the monomeric subunit protein can comprise an amino acid sequence selected from SEQ ID NO:64, SEQ ID NO:67, SEQ ID NO:70, SEQ ID NO:73, SEQ ID NO:76, SEQ ID NO:79, SEQ ID NO:82, SEQ ID NO: 85, SEQ ID NO: 88, SEQ ID NO:91 and SEQ ID NO:94.

In one aspect of the embodiments of the invention, the HA protein can be from a virus selected from A/New Caledonia/20/1999 (H1N1), A/California/04/2009 (H1N1), A/Singapore/1/1957 (H2N2), A/Hong Kong/1/1968 (H3N2), A/Brisbane/10/2007 (H3N2), A/Indonesia/05/2005 (H5N1), B/Florida/4/2006 (influenza B), A/Perth/16/2009 (H3N2), A/Brisbane/59/2007 (H1N1), B/Brisbane/60/2008 (influenza B), A/Wilson-Smith/33 (H1N1), A/Tientsin/78/77 (H1N1), A/Texas/36/91 (H1N1), A/Singapore/6/86 (H1N1), A/Memphis/39/83 (H1N1), A/Malaysia/54 (H1N1), A/Iowa/43 (H1N1), A/Hong Kong/117/77 (H1N1), A/Fort Monmouth/1/47 (H1N1), A/Brisbane/59/07 (H1N1), A/Baylor/4052/81 (H1N1), A/Albany/4835/48 (H1N1), A/Hong Kong/156/97 (H5N1), A/common magpie/Hong Kong/5052/07 (H5N1), A/chicken/Shanxi/2/06 (H5N1), A/silky chicken/Hong Kong/SF189/01 (H5N1), A/chicken/Henan/16/04 (H5N1), A/Victoria/361/11 (H3N2), B/Massachusetts/2/12 (influenza B), B/Brisbane/60/08 (influenza B) and A/Texas/50/12 (H3N2).

In yet another aspect of the embodiments of the invention, the HA protein can comprise at least 25 contiguous amino acids from the hemagglutinin protein of an influenza virus selected from the group consisting of A/New Caledonia/20/1999 (H1N1), A/California/04/2009 (H1N1), A/Singapore/1/1957 (H2N2), A/Hong Kong/1/1968 (H3N2), A/Brisbane/10/2007 (H3N2), A/Indonesia/05/2005 (H5N1), B/Florida/4/2006 (influenza B), A/Perth/16/2009 (H3N2), A/Brisbane/59/2007 (H1N1), B/Brisbane/60/2008 (influenza B), A/Wilson-Smith/33 (H1N1), A/Tientsin/78/77 (H1N1), A/Texas/36/91 (H1N1), A/Singapore/6/86 (H1N1), A/Memphis/39/83 (H1N1), A/Malaysia/54 (H1N1), A/Iowa/43 (H1N1), A/Hong Kong/117/77 (H1N1), A/Fort Monmouth/1/47 (H1N1), A/Brisbane/59/07 (H1N1), A/Baylor/4052/81 (H1N1), A/Albany/4835/48 (H1N1), A/Hong Kong/156/97 (H5N1), A/common magpie/Hong Kong/5052/07 (H5N1), A/chicken/Shanxi/2/06 (H5N1), A/silky chicken/Hong Kong/SF189/01 (H5N1), A/chicken/Henan/16/04 (H5N1), A/Victoria/361/11 (H3N2), B/Massachusetts/2/12 (influenza B), B/Brisbane/60/08 (influenza B) and A/Texas/50/12 (H3N2).

In yet another aspect of the embodiments of the invention, the HA protein can comprise at least 25 contiguous amino acids from a sequence selected from SEQ ID NOs: 1-62. The HA protein can comprise an amino acid sequence at least about 80% identical to an amino acid sequence selected from SEQ ID NOs: 1-62. Also, the hemagglutinin protein can comprise an amino acid sequence selected from SEQ ID NOs: 1-62.

In still another aspect of the embodiments of the invention, the HA protein can be capable of eliciting an immune response to a protein comprising an amino acid sequence selected from SEQ ID NOs: 1-62.

In another aspect of the embodiments of the invention, the immunogenic portion can comprise the receptor-binding domain of an influenza HA protein. Further, the immunogenic portion can be selected from amino acid residues 56-264 of a sequence selected from SEQ ID NOs: 1-62.

In yet another aspect of the embodiments of the invention, the at least two species of fusion proteins can comprise immunogenic portions obtained from HA proteins from two different strains of influenza virus. Also, the at least two species of fusion proteins can comprise immunogenic portions obtained from HA protein from two different subtypes of influenza virus.

In still another aspect of the embodiments of the invention, at least one species of fusion protein can comprise a linker sequence.

In another aspect of the embodiments of the invention, the nanoparticle can elicit an immune response against the RBD region of an influenza HA protein. In one aspect, the nanoparticle can elicit an immune response to an influenza virus strain that is heterologous to the strains of influenza viruses from which the HA immunogenic portions were obtained. In still another aspect, the nanoparticle can elicit an immune response to an influenza virus that is antigenically divergent from the influenza virus from which the hemagglutinin proteins were obtained.

In still another aspect of the embodiments of the invention, the heterogeneous population can comprise between 2 and 60 species of fusion proteins. In still another aspect of the embodiments of the invention, the heterogeneous population can comprise between 2 and 240 species of fusion proteins.

Another embodiment of the present invention is a fusion protein comprising an amino acid sequence at least 80% identical to a sequence selected from SEQ ID NO:97, SEQ ID NO:100, SEQ ID NO: 103, SEQ ID NO: 106, SEQ ID NO: 109, SEQ ID NO: 112, SEQ ID NO:115, SEQ ID NO: 118, SEQ ID NO: 121, SEQ ID NO: 124, SEQ ID NO: 127, SEQ ID NO:130, SEQ ID NO: 133, SEQ ID NO: 136, SEQ ID NO:139, SEQ ID NO: 142, SEQ ID NO:145, SEQ ID NO:148, SEQ ID NO: 151, SEQ ID NO: 154, SEQ ID NO: 157, SEQ ID NO:160, SEQ ID NO:163, SEQ ID NO: 166, SEQ ID NO:169, SEQ ID NO: 172, SEQ ID NO:175, SEQ ID NO:178, SEQ ID NO: 181, SEQ ID NO: 184, SEQ ID NO: 187 and SEQ ID NO:190. The fusion protein can also comprise an amino acid sequence selected from SEQ ID NO:97, SEQ ID NO: 100, SEQ ID NO: 103, SEQ ID NO: 106, SEQ ID NO: 109, SEQ ID NO: 112, SEQ ID NO:115, SEQ ID NO:118, SEQ ID NO: 121, SEQ ID NO:124, SEQ ID NO:127, SEQ ID NO: 130, SEQ ID NO: 133, SEQ ID NO:136, SEQ ID NO:139, SEQ ID NO: 142, SEQ ID NO:145, SEQ ID NO: 148, SEQ ID NO: 151, SEQ ID NO: 154, SEQ ID NO: 157, SEQ ID NO:160, SEQ ID NO: 163, SEQ ID NO: 166, SEQ ID NO: 169, SEQ ID NO: 172, SEQ ID NO:175, SEQ ID NO: 178, SEQ ID NO: 181, SEQ ID NO: 184, SEQ ID NO: 187 and SEQ ID NO:190.

A further embodiment is a nucleic acid molecule encoding any of the fusion proteins described above. In this embodiment, the nucleic acid sequence can be at least 80% identical to a sequence selected from SEQ ID NO:96, SEQ ID NO:99, SEQ ID NO: 102, SEQ ID NO: 105, SEQ ID NO: 108, SEQ ID NO: 111, SEQ ID NO: 114, SEQ ID NO: 117, SEQ ID NO: 120, SEQ ID NO:123, SEQ ID NO: 126, SEQ ID NO:129, SEQ ID NO: 132, SEQ ID NO: 135, SEQ ID NO:138, SEQ ID NO:141, SEQ ID NO:144, SEQ ID NO: 147, SEQ ID NO: 150, SEQ ID NO:153, SEQ ID NO:156, SEQ ID NO: 159, SEQ ID NO: 162, SEQ ID NO: 165, SEQ ID NO:168, SEQ ID NO:171, SEQ ID NO:174, SEQ ID NO: 177, SEQ ID NO: 180, SEQ ID NO:183, SEQ ID NO:186 and SEQ ID NO:189. In still another aspect, the nucleic acid sequence can comprise a sequence selected from SEQ ID NO:96, SEQ ID NO:99, SEQ ID NO: 102, SEQ ID NO: 105, SEQ ID NO: 108, SEQ ID NO: 111, SEQ ID NO: 114, SEQ ID NO:117, SEQ ID NO:120, SEQ ID NO: 123, SEQ ID NO: 126, SEQ ID NO: 129, SEQ ID NO:132, SEQ ID NO: 135, SEQ ID NO: 138, SEQ ID NO: 141, SEQ ID NO: 144, SEQ ID NO:147, SEQ ID NO:150, SEQ ID NO: 153, SEQ ID NO: 156, SEQ ID NO: 159, SEQ ID NO:162, SEQ ID NO: 165, SEQ ID NO: 168, SEQ ID NO: 171, SEQ ID NO: 174, SEQ ID NO:177, SEQ ID NO: 180, SEQ ID NO: 183, SEQ ID NO: 186 and SEQ ID NO: 189. Further in this embodiment, a plasmid can comprise the nucleic acid molecule of any of the nucleic acid molecules described above.

Another embodiment of the present invention is a method for producing a nanoparticle of any of the nanoparticles described above, the method comprising introducing one or more nucleic acid molecules encoding fusion proteins, wherein each fusion protein can comprise at least a portion of a monomeric subunit protein capable of self-assembling into a nanoparticle joined to at least one immunogenic portion from an influenza virus hemagglutinin protein; and incubating the cell under conditions suitable for expressing the encoded proteins and forming nanoparticles. A further aspect of this embodiment can comprise isolating the nanoparticles from the cell.

Another embodiment of the present invention is a method of eliciting an immune response against influenza virus, the method comprising administering to an individual a nanoparticle as described above.

Another embodiment of the present invention is a method of vaccinating an individual against influenza virus, such that the method can comprise administering to the individual a nanoparticle as described above. Accordingly, another embodiment of the present invention is an immunogenic composition comprising a nanoparticle of the invention. Another embodiment of the invention is a medicament for use in vaccinating an individual, or electing an immune response, against influenza virus, the medicament comprising a nanoparticle of the present invention.

A further embodiment of the present invention is a kit. The kit can comprise a nanoparticle as described above, compositions and medicaments comprising such nanoparticles, a fusion protein and/or a nucleic acid molecule as described above.

BACKGROUND

Protective immune responses induced by vaccination against influenza virus are primarily directed to the viral hemagglutinin (HA) protein, which is a glycoprotein on the surface of the virus responsible for interaction of the virus with host cell receptors. HA proteins on the virus surface are trimers of hemagglutinin protein monomers that are enzymatically cleaved to yield amino-terminal HA1 and carboxy-terminal HA2 polypeptides. The globular head consists exclusively of the major portion of the HA1 polypeptide, whereas the stem that anchors the hemagglutinin protein into the viral lipid envelope is comprised of HA2 and part of HA1. The globular head of a hemagglutinin protein includes two domains: the receptor binding domain (RBD), an ~148-amino acid residue domain that includes the sialic acid-binding site, and the vestigial esterase domain, a smaller ~75-amino acid residue region just below the RBD. The top part of the RBD adjacent to the 2,6-sialic acid recognition sites includes a large region (amino acids 131-143, 170-182, 205-215 and 257-262, 1918 numbering) (referred to herein as the RBD-A region) of over 6000 $\text{Å}^2$ per trimer that is 95% conserved between A/South Carolina/1/ 1918 (1918 SC) and A/California/04/2009 (2009 CA) pandemic strains. The globular head includes several antigenic sites that include immunodominant epitopes. Examples include the Sa, Sb, $Ca_1$, $Ca_2$ and Cb antigenic sites (see, for example, Caton A J et al, 1982, Cell 31, 417-427). The RBD-A region includes the Sa antigenic site and part of the Sb antigenic site.

Antibodies against influenza often target variable antigenic sites in the globular head of HA, which surround a conserved sialic acid binding site, and thus, neutralize only antigenically closely related viruses. The variability of the HA head is due to the constant antigenic drift of influenza viruses and is responsible for seasonal endemics of influenza. In contrast, gene segments of the viral genome can undergo reassortment (antigenic shift) in host species, creating new viruses with altered antigenicity that are capable of becoming pandemics [Salomon, R. et al. *Cell* 136, 402-410 (2009)]. Until now, each year, influenza vaccine is updated to reflect the predicted HA and neuraminidase (NA) for upcoming circulating viruses.

Current vaccine strategies for influenza use either a chemically inactivated or a live attenuated influenza virus. Both vaccines are generally produced in embryonated eggs which present major manufacturing limitations due to the time consuming process and limited production capacity. Another more critical limitation of current vaccines is its highly strain-specific efficacy. These challenges became glaring obvious during emergence of the 2009 H1N1 pandemic, thus validating the necessity for new vaccine platforms capable of overcoming these limitations. Virus-like particles represent one of such alternative approaches and are currently being evaluated in clinical trials [Roldao, A. et al. *Expert Rev Vaccines* 9, 1149-1176 (2010); Sheridan, C. *Nat Biotechnol* 27, 489-491 (2009)]. Instead of embryonated eggs, VLPs comprising HA, NA and matrix protein 1 (M1) can be mass-produced in mammalian or insect cell expression systems [Haynes, J. R. *Expert Rev Vaccines* 8, 435-445 (2009)]. The advantages of this approach are its particulate, multivalent nature and the authentic display of properly folded HA proteins that faithfully mimic the infectious virion. In contrast, by the nature of its assembly, the enveloped VLPs contain a small but finite host cell component that may present potential safety, immunogenicity challenges following repeated use of this platform [Wu, C. Y. et al. *PLOS One* 5, c9784 (2010)]. Moreover, the immunity induced by the VLPs is essentially the same as the immunity induced by current vaccines, and thus, does not likely improve both potency and breadth of vaccine-induced protective immunity. In addition to VLPs, a recombinant HA protein has also been evaluated in humans [Treanor, J. J. et al. *Vaccine* 19, 1732-1737 (2001); Treanor, J. J. *JAMA* 297, 1577-1582 (2007)], though the ability to induce protective neutralizing antibody titers are limited. The recombinant HA proteins used in those trials were produced in insect cells and might not form native trimer preferentially [Stevens, *J. Science* 303, 1866-1870 (2004)].

Recently, entirely new classes of broadly neutralizing antibodies against influenza viruses were isolated. One class of antibodies recognizes the highly conserved HA stem [Corti, D. et al. *J Clin Invest* 120, 1663-1673 (2010); Ekiert, D. C. et al. *Science* 324, 246-251 (2009); Kashyap, A. K. et al. *Proc Natl Acad Sci USA* 105, 5986-5991 (2008); Okuno, Y. et al. *J Virol* 67, 2552-2558 (1993); Sui, J. et al. *Nat Struct Mol Biol* 16, 265-273 (2009); Ekiert, D. C. et al. *Science* 333, 843-850 (2011); Corti, D. et al. *Science* 333, 850-856 (2011)], and another class of antibodies precisely recognizes the sialic acid binding site of the RBD on the variable HA head [Whittle, J. R. et al. *Proc Natl Acad Sci USA* 108, 14216-14221 (2011); Krause, J. C. et al. *J Virol* 85, 10905-10908 (2011)]. Unlike strain-specific antibodies, those antibodies are capable of neutralizing multiple antigenically distinct viruses, and hence inducing such antibodies has been a focus of next generation universal vaccine [Nabel, G. J. et al. *Nat Med* 16, 1389-1391 (2010)]. However, robustly eliciting these antibodies with such heterologous neutralizing profile by vaccination has been difficult [Steel, J. et al. *MBio* 1, e0018 (2010); Wang, T. T. et al. *PLOS* Pathog 6, e1000796 (2010); Wei, C. J. et al. *Science* 329, 1060-1064 (2010)].

Despite several alternatives to conventional influenza vaccines, advances in biotechnology in past decades have allowed engineering of biological materials to be exploited for the generation of novel vaccine platforms. Ferritin, an iron storage protein found in almost all living organisms, is an example which has been extensively studied and engineered for a number of potential biochemical/biomedical purposes [Iwahori, K. U.S. Patent 2009/0233377 (2009); Meldrum, F. C. et al. Science 257, 522-523 (1992); Naitou, M. et al. U.S. Patent Publication No. 2011/0038025 (2011); Yamashita, I. Biochim Biophys Acta 1800, 846-857 (2010)], including a potential vaccine platform for displaying exogenous epitope peptides [Carter, D. C. et al. U.S. Patent Publication No. 2006/0251679 (2006); Li, C. Q. et al. Industrial Biotechnol 2, 143-147 (2006)]. Its use as a vaccine platform is particularly interesting because of its self-assembly and multivalent presentation of antigen which induces stronger B cell responses than monovalent form as well as induce T-cell independent antibody responses [Bachmann, M. F. et al. *Annu Rev Immunol* 15, 235-270 (1997); Dintzis, H. M. et al. *Proc Natl Acad Sci USA* 73, 3671-3675 (1976)]. Further, the molecular architecture of ferritin, which consists of 24 subunits assembling into an octahedral cage with 432 symmetry has the potential to display multimeric antigens on its surface.

There remains a need for an efficacious influenza vaccine that provides robust protection against influenza virus. There particularly remains a need for an influenza vaccine that elicits broadly a neutralizing immune response, thereby protecting individuals from heterologous strains of influenza virus, including evolving seasonal and pandemic influenza virus strains of the future. The present invention meets this need by providing a novel, multivalent nanoparticle-based, influenza vaccine that is easily manufactured, potent, and elicits broadly neutralizing influenza antibodies.

BRIEF DESCRIPTION OF THE FIGURES

FIG. 1. Theoretical model of immune triggering by a supernatural heterogeneous antigen array on particulate immunogen. (Left Images) Immune triggering upon natural homogeneous antigen array. Particulate homogeneous antigens are built by an antigenically identical subunit and thereby displaying antigenically homogeneous antigens to immune system. B cells harboring B cell receptor (BCR) specific to an antigen displayed on the homogeneous array are stimulated strongly upon encountering the "matched" antigenic stimulation (left middle). B cells harboring more BCR with broader specificity are also stimulated by the homogeneous antigen array but lesser extent presumably the binding affinity of broader specific BCR to the antigen is not as tight as narrower specific BCR to the "matched" antigen (left bottom). The weaker affinity of broader specific BCR to antigen may partly be due to its cross-reactivity because the BCR recognizes other antigenically distinct antigens and thus avoids contacting antigenically heterogeneous parts on antigens (smaller antibody footprint on antigens). (Right Images) Immune triggering upon supernatural heterogeneous antigen array. Particulate heterogeneous antigens are synthetically built using antigenically heterogeneous sub-units, which display antigenically heterogeneous antigens to immune system. Upon stimulation with the heterogeneous antigen array, BCRs having narrow specificity only recognize a subset of antigens on the particulate antigen and thus are not stimulated by this antigen (middle right); BCRs having broader specificity recognize larger numbers of antigens on the particulate antigen and thus are stimulated by this antigen (bottom right). In this situation, the B cells harboring BCR with broader specificity have a better chance to outcompete B cells harboring BCR with narrower specificity, therefore selecting cross-reactive B cells otherwise being overcast by others.

(Left panel) Neutralization titer of sera from mice immunized with monovalent nanoparticles (NC99) or mixtures of monovalent nanoparticles (Admix 2, 4 or 6). (Middle panel) Neutralization titer of sera from mice immunized with monovalent nanoparticles (NC99) or multivalent nanoparticles (CoAsmbl2, 4, 6, or 8). (Right panel) Side by Side comparison, using the data from the left and middle panels, comparing the neutralization titers generated by immunizing mice with either admixed monovalent nanoparticles or multivalent nanoparticles displaying corresponding influenza HA proteins. All sera was collected at 2 weeks following the second immunization and tested for hemagluttination inhibition activity. Each dot indicates individual serum sample and is plotted as box-and-whiskers graph. P values were calculated by Student's t-test.

Figure 9:
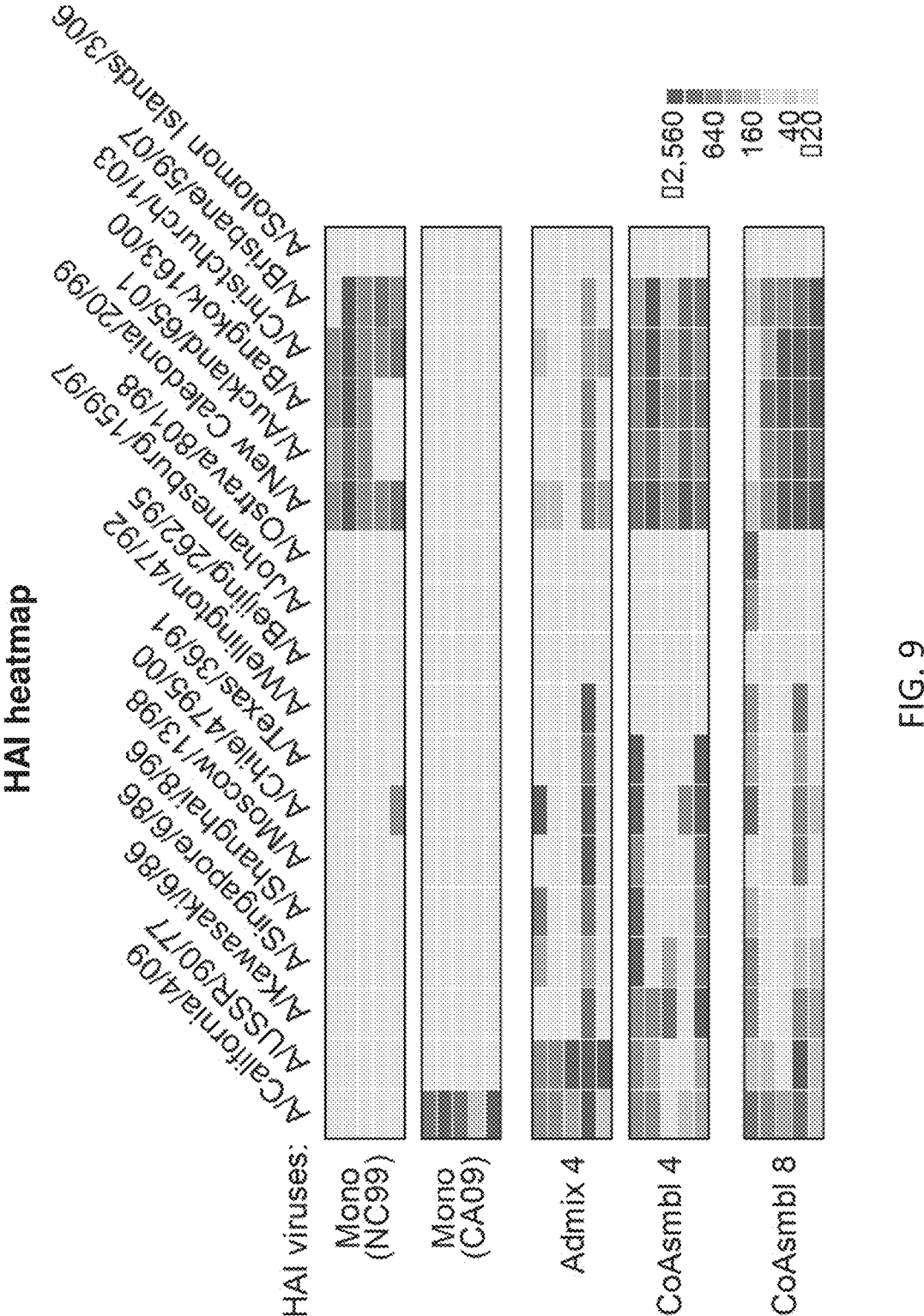

FIG. 9. Neutralization breadth of immune serum. Heatmap representation of HAI titers from mice immunized with either monovalent nanoparticles against NC99 or CA09, admixed monovalent nanoparticles (Admix 4), or multivalent, co-assembled nanoparticles (CoAsmbl 4 or CoAsmbl 8). Each row indicates an individual mouse.

Figure 10:
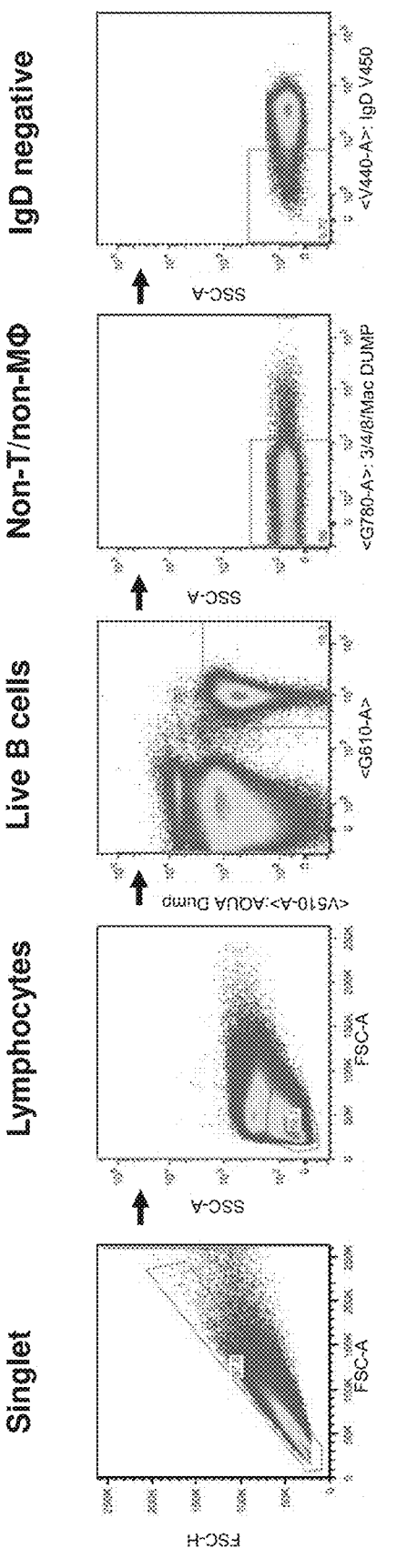
Figure 10:
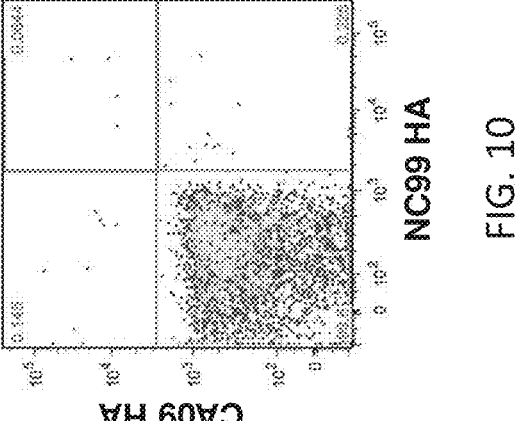

FIG. 10. Detection of HA-specific cross-reactive B cells in peripheral blood cells in HA RBD-nanoparticle-immunized mice. (Upper panels). Gating strategy of mouse whole blood cells. (Bottom panel) FACs analysis using anti-CD3, anti-CD14, anti-CD19, anti-IgD to identify non-naïve B-cell populations in peripheral blood from mice immunized with monovalent nanoparticles against NC99 or CA09, admixed particles (Admix 2, Admix 4 or Admix 6), or multivalent (CoAsmbl 2, CoAsmbl 4, CoAsmbl 6 or CoAsmbl 8). Each dot indicates individual sample.

Figure 11:
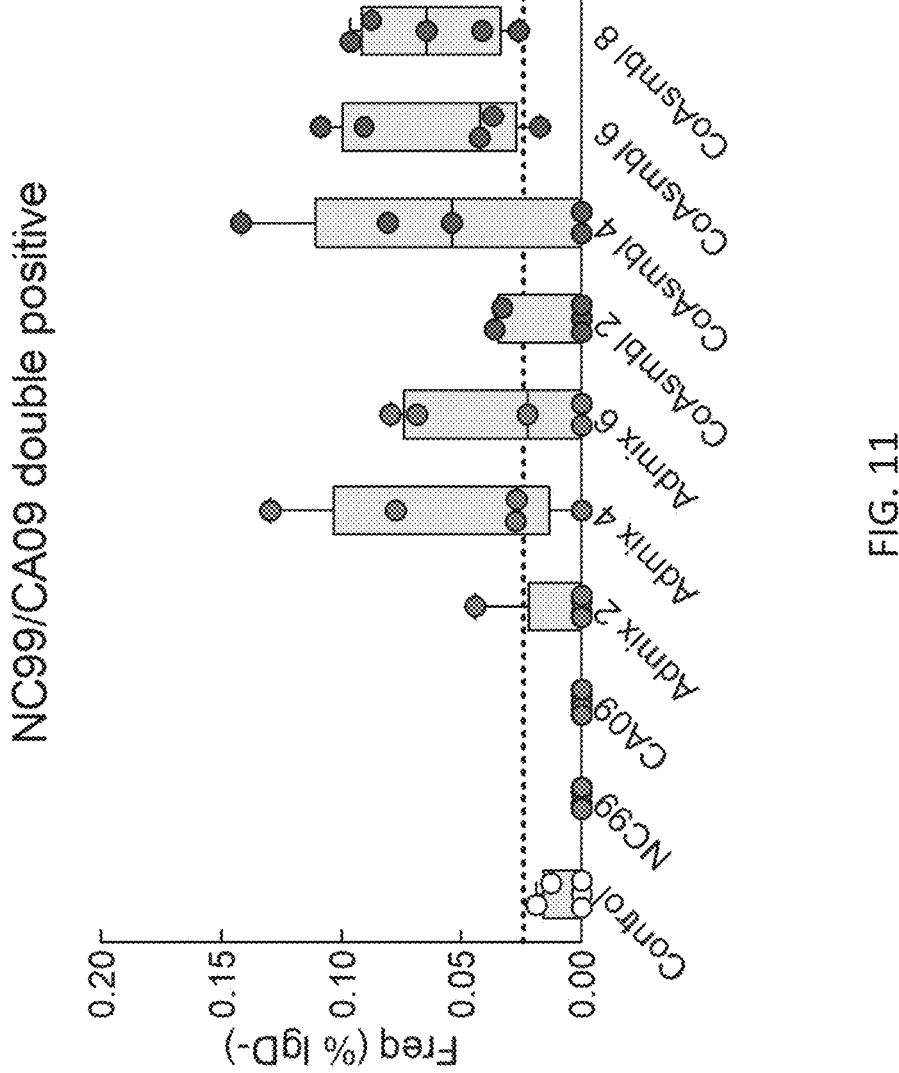

FIG. 11. Box-and-whiskers plot of FACS data from lower panel in FIG. 10.

Figure 12:
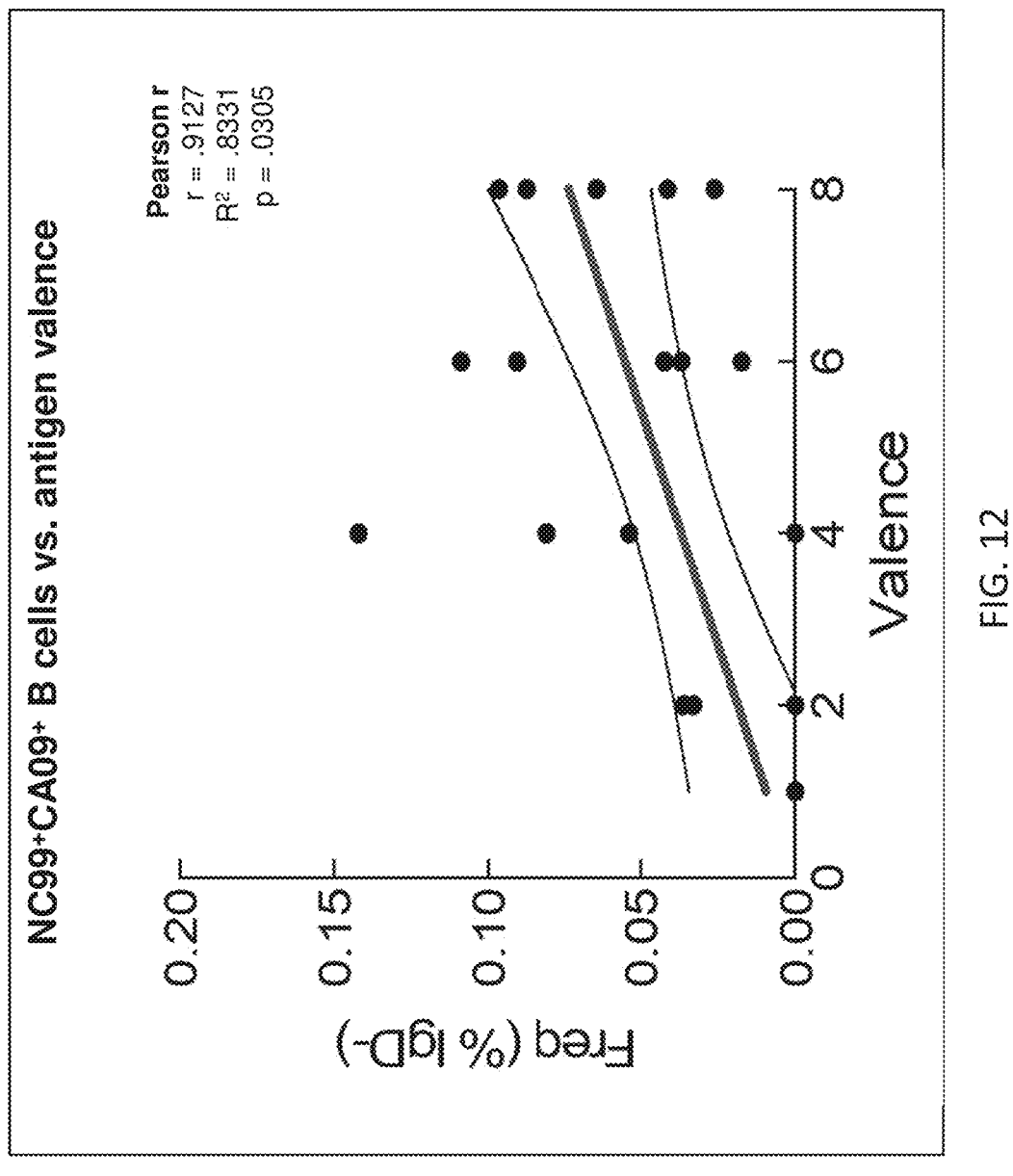

FIG. 12. Correlation of NC99/CA09 cross-reactive B cell frequency and antigenic heterogeneity of co-assembled RBD-nanoparticles. X-axis represents antigenic heterogeneity (number of different HA RBD on a single RBD-nanoparticle). Y-axis represents cross-reactive B cell frequency. Pearson correlation was calculated using GraphPad Prism 6.

Figure 13:
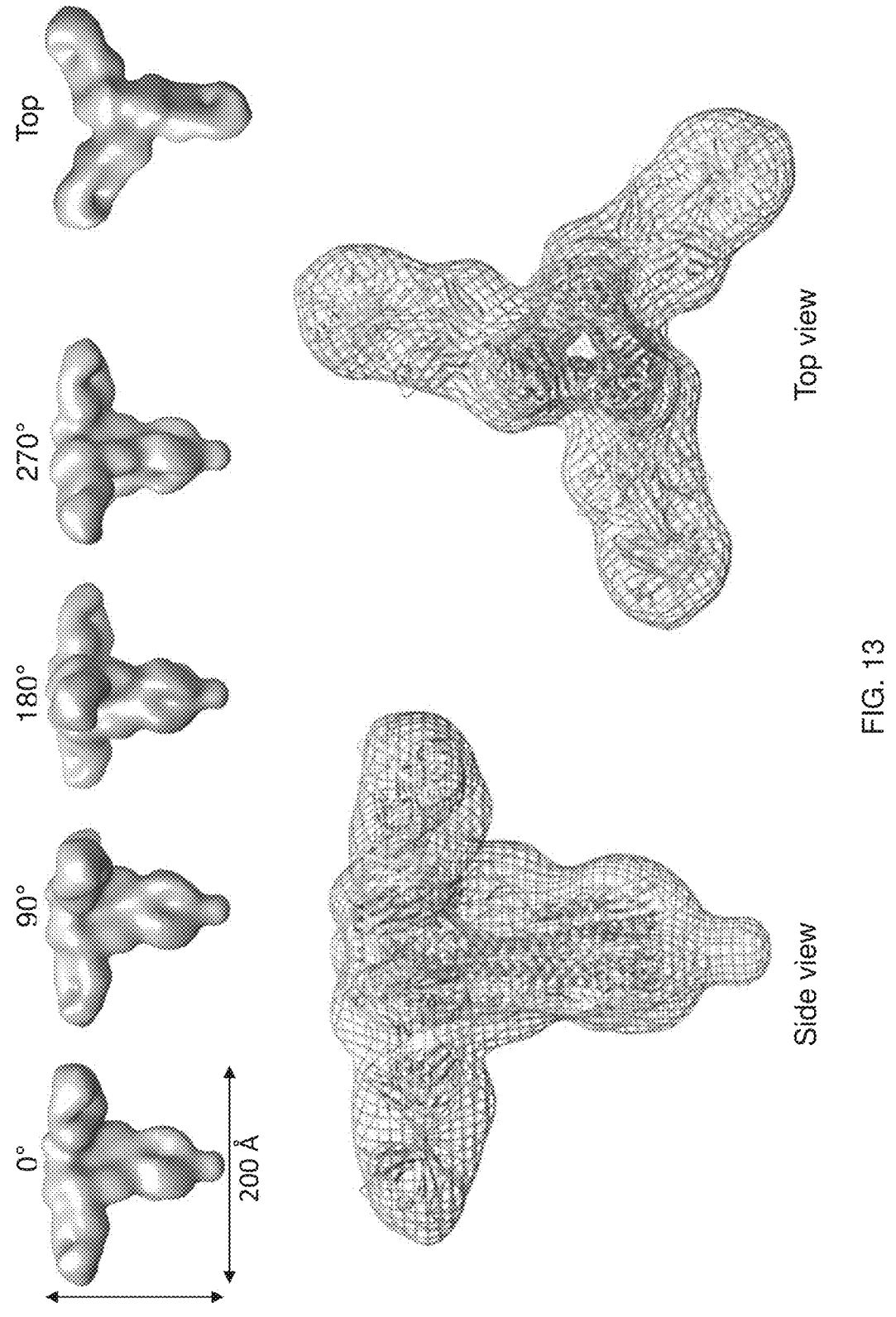

FIG. 13. Three dimensional reconstruction model of HA trimer in complex with Fab 441D6. (Upper panels) Rotational and top views for reconstructed model of HA:Fab441D6 complex. (Lower panels) Electron microscopy density maps of HA:Fab441D6 complex. Resolution of the final model was ~18.5 Å.

DETAILED DESCRIPTION OF THE INVENTION

The present invention relates to a novel, nanoparticle-based, multivalent vaccine that can be used to produce a broadly neutralizing immune response to various infectious agents, such as influenza virus and human immunodeficiency virus (HIV). The present invention builds on previous work showing that monovalent, nanoparticle-based vaccines can be used to induce a protective immune response against a limited number of closely related infectious agents. For example, previous work in the field of influenza vaccines demonstrated that fusion proteins comprising an immunogenic portion of an influenza virus hemagglutinin (HA) protein joined to a self-assembly (SA) protein, to produce an HA-SA fusion protein, will self-assemble into nanoparticles displaying the immunogenic portion of the influenza HA protein on their surface. Moreover, when such nanoparticles are administered to an individual, they elicit a robust, neutralizing immune response to influenza virus. The construction and use of such nanoparticles has been described in U.S. Patent Publication No. 2014-0302079A1, which is incorporated herein by reference in its entirety. Similarly, nanoparticle-based vaccines for Epstein-Barr Virus have been described in International Patent Application No. PCT/US14/60142, which is incorporated herein by reference in its entirety. The present inventors have now discovered that nanoparticles displaying immunogenic portions of proteins from more than one genera, Type, Group, subtype or strain of infectious agent (e.g., influenza virus) can be used as a vaccine to elicit an immune response that neutralizes a variety, including a heterogeneous population, of different, but related, infectious agents. Moreover, the inventors have found that, surprisingly, such multivalent nanoparticles elicit a greater immune response than do vaccines comprising a single species of monovalent nanoparticles, or a mixture of two or more species of monovalent nanoparticles. Thus, a general embodiment of the invention is a nanoparticle made from self-assembling fusion proteins, wherein the surface of the nanoparticle displays a heterogeneous population of immunogenic portions of proteins from two or more infectious agents of the same taxonomic family. In specific embodiments, the two or more infectious agents are divergent enough such that the amino acid sequence of the immunogenic portions of corresponding proteins from the two or more infectious agents differ by at least one amino acid. In certain embodiments, the infectious agents are from different taxonomic groups within the same taxonomic family.

Before the present invention is further described, it is to be understood that this invention is not limited to particular embodiments described herein, as such may, of course, vary. It is also to be understood that the terminology used herein is for the purpose of describing particular embodiments only, and is not intended to be limiting on the finally claimed invention, since the scope of the invention will be limited only by the claims. It should also be understood that while elements of the invention appear in specific locations in the application, the present invention encompasses any combination of the elements disclosed herein.

It must be noted that as used herein and in the appended claims, the singular forms "a," "an," and "the" include plural referents unless the context clearly dictates otherwise. For example, a nucleic acid molecule refers to one or more nucleic acid molecules. As such, the terms "a", "an", "one or more" and "at least one" can be used interchangeably. Similarly the terms "comprising", "including" and "having" can be used interchangeably. It is further noted that the claims may be drafted to exclude any optional element. As such, this statement is intended to serve as antecedent basis for use of such exclusive terminology as "solely," "only" and the like, in connection with the recitation of claim elements, or use of a "negative" limitation.

Figure 1:
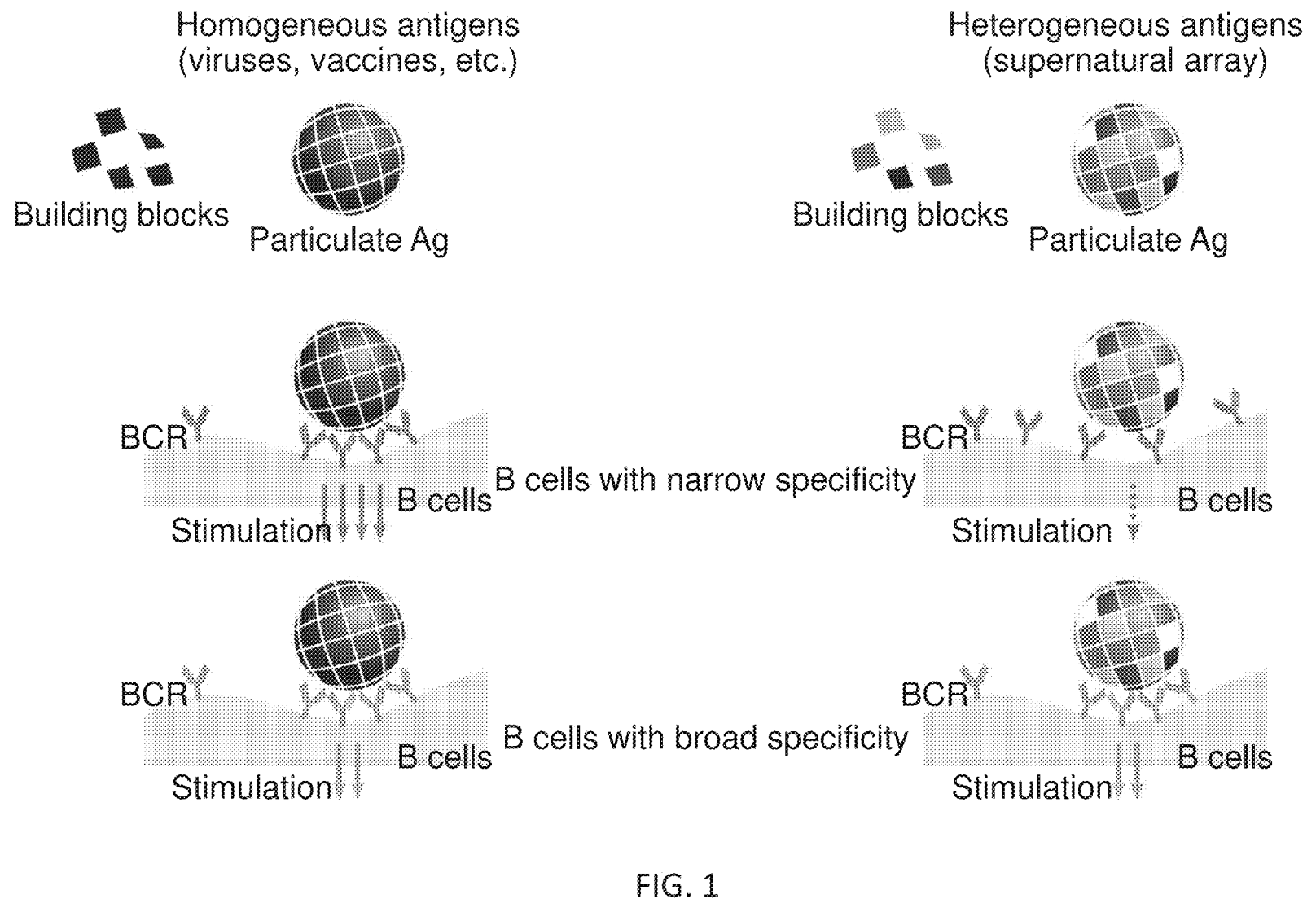

As used herein, a nanoparticle refers to a particle formed from self-assembling, monomeric subunit proteins. For example, ferritin subunit proteins self-assemble into ferritin nanoparticles. Nanoparticles of the present invention are generally spherical, or spheroid, in shape, although other shapes, for example, rod, cube, sheet, oblong, ovoid, and the like, are also useful for practicing the present invention. While nanoparticles of the present invention can vary in size, preferred nanoparticles are those in which the distance between the displayed immunogenic portions of the HA protein globular head region is such that two adjacent immunogenic portions displayed on the nanoparticle can fit the distance of the two antigenic-binding sites of a single B-cell receptor, or about 50-100 Å apart. Such spacing allows each of the two adjacent immunogenic portions to interact with one of the two, identical antigen-binding sites in the same B-cell receptor. Binding of a single B-cell receptor to heterologous immunogenic portions that are adjacent on the surface of the nanoparticle is desirable since it allows for the selection of cross-reactive immune responses. While not intending to be bound by theory, the inventors believe that this is due to the fact that high affinity binding of one antigenic site to an immunogenic portion allows stabilization of low-affinity binding of the other antigenic binding site to a heterologous immunogenic portion. Thus, B-cells are selected that produce cross-reactive antibodies. This concept is illustrated in FIG. 1. It is understood by those skilled in the art that the antigenic binding sites of a B-cell receptor are approximately 50-100 angstroms (Å) apart. Thus, in certain embodiments, the immunogenic portions displayed on the surface of the nanoparticle are separated by about 50-100 Å. In specific embodiment, the immunogenic portions displayed on the surface of the nanoparticle are separated by about 50 Å, by about 60 Å, by about 70 Å, by about 80 Å, by about 90 Å, by about 100 Å. With respect to the spacing of immunogenic portions on the surface of a nanoparticle, the term about refers to a variation of no more than 20%.

According to the present invention, a self-assembling monomeric subunit protein, monomeric subunit protein, self-assembly (SA) protein, self-assembling subunit protein, and the like, of the present invention is a full length, monomeric polypeptide, or any portion or variant thereof, which, is capable of directing self-assembly of monomeric self-assembling subunit proteins into a nanoparticle. Such proteins are known to those skilled in the art. Examples of self-assembly proteins useful for producing nanoparticles of the present invention include, but are not limited to, ferritin, encapsulin, sulfur oxygenase reductase (SOR), lumazine synthase (LS), pyruvate dehydrogenase complex (PDC) dihydrolipoamide acetyltransferase (E2) and the envelope (Env) proteins of alphaviruses such as Chikungunya virus. Representative examples of such proteins are listed below in Table 1.

As used herein, a fusion protein is a recombinant protein containing amino acid sequences from at least two unrelated proteins that have been joined together, via a peptide bond, to make a single protein. The unrelated amino acid sequences can be joined directly to each other or they can be joined using a linker sequence. As used herein, proteins are unrelated, if their amino acid sequences are not normally found joined together via a peptide bond in their natural environment (e.g., inside a cell). For example, the amino acid sequences of monomeric subunits of ferritin, and the amino acid sequences of influenza hemagglutinin proteins are not normally found joined together via a peptide bond and thus, these two proteins would be considered unrelated. Similarly, the amino acid sequences of monomeric subunits of encapsulin and the amino acid sequences of influenza hemagglutinin proteins or HIV envelope proteins are not normally found joined together via a peptide bond and thus, encapsulin and influenza HA, or encapsulin and HIV envelope protein, would be considered unrelated.

As used herein, a heterogeneous population of immunogenic portions refers a nanoparticle that displays more than one species of immunogenic portion of a protein on its surface. A species of immunogenic portion of a protein of the invention is defined by the specific amino acid sequence of the immunogenic portion. Accordingly, two immunogenic portions having identical amino acid sequences would be considered the same species of immunogenic portion. It should be noted that two fusion proteins comprising the same species of immunogenic portions may or may not vary in regions of amino acid sequences other than the immunogenic portion. If such fusion proteins are identical throughout their entire sequence, they would be considered the same species of fusion protein. Thus, it should be apparent that species of immunogenic portions are defined by variations in their immunogenic portions. Such variation can be due to natural or man-made changes in the amino acid sequence of the immunogenic portion. For example, a new species of immunogenic portion can be made by altering (mutating) the sequence of an existing immunogenic portion through means such as recombinant DNA technology. Methods of making such alterations are known to those skilled in the art.

Alternatively, fusion proteins having different species of immunogenic portions can be made using corresponding proteins, or useful portions thereof, (or nucleic acid molecules encoding such proteins or portions) from unique, but related, infectious agents. For example, it is known that viruses often produce progeny virus having mutations in their envelope (or capsid) protein, the result being that some percentage of the progeny virus avoid detection by the host immune system. Similarly repeated cycles of progeny production result in a heterogeneous population of viruses, with various individual viruses in the population differing in the sequence of their envelope (or capsid) proteins. Such a process eventually results in the production of closely related, but genetically divergent viruses. These divergent viruses are referred to strains, species and subtypes. As these strains, species and subtypes become more divergent, they are further classified into types, generas and/or families. Such classifications can be referred to as taxonomic groups. For examples, a taxonomic group can be a family, a genus, a type, a subtype, a strain or a species. Classification of viruses into various taxonomic groups is well understood by those skilled in the art. With regard to the present invention, preferred nanoparticles are those comprising immunogenic portions from two or more infectious agents within the same family.

As used herein, corresponding proteins are proteins having a similar function in two (or more) different organisms. Corresponding proteins may or may not have identical amino acid sequences, but generally share some sequence homology. In the examples above, the envelope (or capsid) proteins from two closely related viruses are corresponding proteins. As a further example, envelope proteins from different strains of HIV would be considered corresponding proteins, as would hemagglutinin (HA) protein from different strains, subtypes, or genera of influenza virus. In certain embodiments, proteins having the same function in two different infectious agents from the same taxonomic family would be considered corresponding proteins. In certain embodiments, such proteins have at least 50% sequence homology. In certain embodiments, such proteins have at least 50% sequence identity, at least 60% sequence identity, at least 70% sequence identity, at least 80% sequence identity, at least 85% sequence identity, at least 95% sequence identity, at least 97% sequence identity, or at least 99% sequence identity.

As used herein, the term infectious agent refers to any microorganism capable of infecting a mammal. Preferred infectious agents are those which cause illness. Examples of infectious agents include, but are not limited to, viruses, bacteria and parasites. Examples of useful viruses for practicing methods of the present invention include, but are not limited to, viruses from a family selected from the group consisting of orthomyxoviridae, retroviridae, flaviviridae, filoviridae, coronoviridae, paramyxoviridae, picornoviridae, retroviridae, papillomaviridae, togaviridae, and polyomaviridae. More specific examples of useful viruses for practicing methods of the present invention include, but are not limited to, influenza viruses, human immunodeficiency viruses (HIV), flaviviruses (e.g., hepatitis virus, dengue virus, etc.), human papillomaviruses (HPV), rhinoviruses, coronaviruses, enteroviruses, polyomaviruses, respiratory synctial viruses (RSV), human metapneumoviruses, ebola viruses, Marburg viruses, alphaviruses (e.g., Chikungunya virus, Ross River virus, Semliki Forest virus, Sindbis virus, Mayaro virus, etc), Porcine Epidemic Diarrhea virus, Porcine reproductive and respiratory syndrome virus, and foot and mouth disease virus.

Proteins from infectious agents can be any protein useful for generating an immune response against an infectious agent comprising the protein. Useful proteins are those that elicit a protective immune response, such as the production of neutralizing antibodies. A particularly desirable protein is one that elicits the production of broadly neutralizing antibodies. One example of a useful protein with which to practice the present invention is the HIV envelope glycoprotein protein (Gp120). The ability of GP120 to elicit an antibody response, as well as useful mutants thereof, as well as other useful HIV proteins are described in U.S. Patent Publication Nos. US20140322269, US 20040052821, US20030064361, US20030158134, all of which are incorporated herein by reference in their entirety. Another example of a useful protein with which to practice the present invention is the flavivirus envelope protein, which is described in U.S. Patent Publication No. 20110059131, U.S. Patent Publication No. 20090311287, and U.S. Patent Publication No. 20040009469, all of which are incorporated herein by reference in their entirety. Another example of a useful protein with which to practice the present invention is the HCV capsid protein, which is described in U.S. Patent Publication No. 20020107360, U.S. Patent Publication No. 20020119495, and U.S. Patent Publication No. 20050233316, all of which are incorporated herein by reference in their entirety. Other useful proteins with which to practice the present invention are human Papillomavirus (HPV) proteins such as E2. The use of such proteins is described in U.S. Patent Publication No. 20100143408 and U.S. Patent Publication No. 20100183648, both of which are incorporated herein by reference in their entirety. Other useful proteins are disclosed in U.S. Patent Publication No. 20140161833, U.S. Patent Publication No. 20090202583, U.S. Patent Publication No. 20060182762, U.S. Patent Publication No. 20050053622, U.S. Patent Publication No. 20040175395, U.S. Patent Publication No. 20090162395, U.S. Patent Publication No. 20030224015, U.S. Patent Publication No. 20050255123, U.S. Patent Publication No. US 2012-0003266 and U.S. Patent Publication No. 20120315270, all of which are incorporated herein by reference in their entirety.

As used herein, broadly neutralizing antibodies are antibodies that neutralize an infectious agent from a taxonomic group that differs from the taxonomic groups of the infectious agents from which the immunogenic portions used to elicit the antibodies (used produce the nanoparticles) were derived. In preferred embodiments, nanoparticles of the invention elicit broadly neutralizing antibodies that neutralize at least one infectious agent from a genera, type, subtype, species and/or strain that differs from the genera, type, subtype, species and/or strain of the infectious agents from which immunogenic portions were derived in order to produce the nanoparticle. For example, if a nanoparticle is constructed using immunogenic portions of HA proteins from influenza A/Hong Kong/1/1968 (H3N2) and influenza A/Indonesia/05/2005 (H5N1), antibodies elicited by such nanoparticle and that that are broadly neutralizing would be able to neutralize one or more influenza viruses of genera, types, subtypes, species and/or strains other than influenza A/Hong Kong/1/1968 (H3N2) and influenza A/Indonesia/ 05/2005 (H5N1).

One embodiment of the present invention is a nanoparticle comprising fusion proteins, wherein the surface of the nanoparticle displays immunogenic portions of corresponding proteins from at least two infectious agents, wherein the at least two infectious agents are from different corresponding taxonomic groups within the same taxonomic family. In on embodiment, each fusion protein comprises at least a portion of a self-assembling, monomeric subunit joined to at least one portion of an immunogenic portion of a protein from an infectious agent. In one embodiment, the portion of the self-assembling, monomeric subunit comprises at least 25 amino acids, at least 50 amino acids, at least 75 amino acids, at least 100 amino acids or at least 150 amino acids from a monomeric subunit protein selected from the group consisting of a monomeric ferritin subunit protein, a monomeric encapsulin protein, a monomeric 03-33 protein, a monomeric SOR protein, a monomeric LS protein, a monomeric PDC protein and a Chikungunya virus structural polyprotein. In one embodiment, each fusion protein comprises a monomeric subunit protein selected from the group consisting of a monomeric ferritin subunit protein, a monomeric encapsulin protein, a monomeric 03-33 protein, a monomeric SOR protein, a monomeric LS protein, a monomeric PDC protein and a Chikungunya virus structural polyprotein.

In one embodiment, the infectious agents are viruses. Any virus capable of infecting a mammal can be used in constructing nanoparticles of the present invention. Examples of useful viruses for practicing methods of the present invention include, but are not limited to, viruses from a family selected from the group consisting of orthomyxoviridae, retroviridae, flaviviridae, filoviridae, coronoviridae, paramyxoviridae, picornoviridae, retroviridae, papillomaviridae, togaviridae, and polyomaviridae. Examples of useful viruses include, but are not limited to, influenza viruses, human immunodeficiency viruses (HIV), flaviviruses (e.g., hepatitis virus, dengue virus, etc.), human papillomaviruses (HPV), rhinoviruses, coronaviruses, enteroviruses, polyomaviruses, respiratory synctial viruses (RSV), human metapneumoviruses, ebola viruses, Marburg viruses, alphaviruses (e.g., Chikungunya virus, Ross River virus, Semliki Forest virus, Sindbis virus, Mayaro virus, etc), Porcine Epidemic Diarrhea virus, Porcine reproductive and respiratory syndrome virus and foot and mouth disease virus.

In one embodiment, the at least two infectious agents are from different genera within the same family. In one embodiment, the at least two infectious agents are from different species within the same family. In one embodiment, the at least two infectious agents are from different Types within the same family. In one embodiment, the at least two infectious agents are from different subtypes within the same family. In one embodiment, the at least two infectious agents are different strains within the same family.

One embodiment of the present invention is a nanoparticle comprising a first fusion protein and a second fusion protein, each fusion protein comprising at least a portion of a self-assembling, monomeric subunit joined to at least one immunogenic portion of a protein from an infectious agent, wherein the immunogenic portion of the first fusion protein is from a protein from a first infectious agent; wherein the immunogenic portion of the second fusion protein is from a protein from a second infectious agent; wherein the proteins from the first and second infectious agents are corresponding proteins; and wherein the first and second infectious agents are from different corresponding taxonomic groups within the same taxonomic family.

In one embodiment, the infectious agents are viruses. Any virus capable of infecting a mammal can be used in constructing nanoparticles of the present invention. Examples of useful viruses for practicing methods of the present invention include, but are not limited to, viruses from a family selected from the group consisting of orthomyxoviridae, retroviridae, flaviviridae, filoviridae, coronoviridae, paramyxoviridae, picornoviridae, retroviridae, papillomaviridae, togaviridae, and polyomaviridae. Examples of useful viruses include, but are not limited to, influenza viruses, human immunodeficiency viruses (HIV), flaviviruses (e.g., hepatitis virus, dengue virus, etc.), human papillomaviruses (HPV), rhinoviruses, coronaviruses, enteroviruses, polyomaviruses, respiratory synctial viruses (RSV), human metapneumoviruses, ebola viruses, Marburg viruses, alphaviruses (e.g., Chikungunya virus, Ross River virus, Semliki Forest virus, Sindbis virus, Mayaro virus, etc), Porcine Epidemic Diarrhea, Porcine reproductive and respiratory syndrome virus and foot and mouth disease virus.

In one embodiment, the at least two infectious agents are from different genera within the same family. In one embodiment, the at least two infectious agents are from different species within the same family. In one embodiment, the at least two infectious agents are from different Types within the same family. In one embodiment, the at least two infectious agents are from different subtypes within the same family. In one embodiment, the at least two infectious agents are different strains within the same family.

One embodiment of the present invention is a nanoparticle comprising at least two species of fusion protein, each species of fusion protein comprising at least a portion of a self-assembling, monomeric subunit joined to at least one immunogenic portion of a protein from a unique infectious agent, wherein the proteins in the unique infectious agents correspond to one another, and; wherein each unique infectious agent is from a different corresponding taxonomic group within the same taxonomic family.

As used herein, a unique infectious agent refers to infectious agents from the same taxonomic family, such as orthomyoviridae or retroviridae, which are genetically distinct from one another. Thus, infectious agents that are unique from one another would belong to different taxonomic groups. For example, two different strains of influenza virus would be considered unique from one another. Likewise, two different subtypes of influenza virus would be considered unique from one another.

While not intending to be limited to a specific embodiment, the inventors have chosen to utilize influenza virus to demonstrate the general principles and concepts of the present invention. Thus, with regard to certain embodiments of the present invention, all nomenclature used herein to classify influenza virus is that commonly used by those skilled in the art. Thus, a Type of influenza virus refers to influenza Type A, influenza Type B or influenza type C. It is understood by those skilled in the art that the designation of a virus as a specific Type relates to sequence difference in the respective M1 (matrix) protein or NP (nucleoprotein). Type A influenza viruses are further divided into Group1 and Group 2. These Groups are further divided into subtypes, a designation that refers to classification of a virus based on the sequence of its HA protein. Examples of current commonly recognized subtypes are H1, H2, H3, H4, H5, H6, H7, H8, H9, H10, H11, H12, H13, H14, H15, H16, H17 or H18. Group 1 influenza subtypes are H1, H2, H5, H6, H8, H9, H11, H12, H13, H16, H17 and H18. Group 2 influenza subtypes are H3, H4, H7, H10, H14 and H15. Finally, the term strain refers to viruses within a subtype that differ from one another due to small, genetic variations in their genome.

Such genetic variations may, or may not, result in amino acid changes in the encoded influenza protein(s).

As used herein, an influenza hemagglutinin protein, or HA protein, refers the hemagglutinin glycoprotein present on the surface of influenza virus. Influenza virus HA proteins are able to bind sialic acid on the surface of cells, an activity responsible for the viruses ability to cause red blood cells to agglutinate. Influenza virus HA proteins are also responsible for fusion of the influenza virus membrane with the endosome membrane following infection of a cell by influenza virus. Such proteins, and their activities, are known to those skilled in the art. With specific regard to the present invention, an HA protein refers to a full-length influenza virus hemagglutinin protein or any portion thereof, that is, at least, capable of eliciting an immune response. Exemplary influenza proteins useful for producing nanoparticles of the present invention are listed below in Table 1.

TABLE 1

| SEQ ID NOs. | ORGANISM | DESCRIPTION |
|---|---|---|
| | | Ectodomains |
| 1 | Influenza Virus | Amino acid sequence of ectodomain from the hemagglutinin protein from A/New Caledonia/20/1999 (H1N1). |
| 2 | Influenza Virus | Amino acid sequence of ectodomain from the hemagglutinin protein from A/California/04/2009 (H1N1) |
| 3 | Influenza Virus | Amino acid sequence of ectodomain from the hemagglutinin protein from A/Singapore/1/1957 (H2N2) |
| 4 | Influenza Virus | Amino acid sequence of ectodomain from the hemagglutinin protein from A/Hong Kong/1/1968 (H3N2) |
| 5 | Influenza Virus | Amino acid sequence of ectodomain from the hemagglutinin protein from A/Brisbane/10/2007 (H3N2) |
| 6 | Influenza Virus | Amino acid sequence of ectodomain from the hemagglutinin protein from A/Indonesia/05/2005 (H5N1) |
| 7 | Influenza Virus | Amino acid sequence of ectodomain from the hemagglutinin protein from B/Florida/4/2006 (influenza B) |
| 8 | Influenza Virus | Amino acid sequence of ectodomain from the hemagglutinin protein from A/Perth/16/2009 (H3N2) |
| 9 | Influenza Virus | Amino acid sequence of ectodomain from the hemagglutinin protein from A/Brisbane/59/2007 (H1N1) |
| 10 | Influenza Virus | Amino acid sequence of ectodomain from the hemagglutinin protein from B/Brisbane/60/2008 (influenza B) |
| 11 | Influenza Virus | Amino acid sequence of ectodomain from the hemagglutinin protein from A/Wilson-Smith/33 (H1N1) |
| 12 | Influenza Virus | Amino acid sequence of ectodomain from the hemagglutinin protein from A/Tientsin/78/77 (H1N1) |
| 13 | Influenza Virus | Amino acid sequence of ectodomain from the hemagglutinin protein from A/Texas/36/91 (H1N1) |
| 14 | Influenza Virus | Amino acid sequence of ectodomain from the hemagglutinin protein from A/Singapore/6/86 (H1N1) |
| 15 | Influenza Virus | Amino acid sequence of ectodomain from the hemagglutinin protein from A/Memphis/39/83 (H1N1) |
| 16 | Influenza Virus | Amino acid sequence of ectodomain from the hemagglutinin protein from A/Malaysia/54 (H1N1) |
| 17 | Influenza Virus | Amino acid sequence of ectodomain from the hemagglutinin protein from A/Iowa/43 (H1N1) |
| 18 | Influenza Virus | Amino acid sequence of ectodomain from the hemagglutinin protein from A/Hong Kong/117/77 (H1N1) |
| 19 | Influenza virus | Amino acid sequence of ectodomain from the hemagglutinin protein from A/Fort Monmouth/1/47 (H1N1) |
| 20 | Influenza virus | Amino acid sequence of ectodomain from the hemagglutinin protein from A/Brisbane/59/07 (H1N1) |
| 21 | Influenza Virus | Amino acid sequence of ectodomain from the hemagglutinin protein from A/Baylor/4052/81 (H1N1) |
| 22 | Influenza Virus | Amino acid sequence of ectodomain from the hemagglutinin protein from A/Albany/4835/48 (H1N1) |
| 23 | Influenza Virus | Amino acid sequence of ectodomain from the hemagglutinin protein from A/Hong Kong/156/97 (H5N1) |
| 24 | Influenza Virus | Amino acid sequence of ectodomain from the hemagglutinin protein from A/common magpie/Hong Kong/5052/07 (H5N1) |
| 25 | Influenza Virus | Amino acid sequence of ectodomain from the hemagglutinin protein from A/chicken/Shanxi/2/06 (H5N1) |

TABLE 1-continued

| SEQ ID NOs. | ORGANISM | DESCRIPTION |
|---|---|---|
| 26 | Influenza Virus | Amino acid sequence of ectodomain from the hemagglutinin protein from A/silky chicken/Hong Kong/SF189/01 (H5N1) |
| 27 | Influenza Virus | Amino acid sequence of ectodomain from the hemagglutinin protein from A/chicken/Henan/16/04 (H5N1) |
| 28 | Influenza Virus | Amino acid sequence of ectodomain from the hemagglutinin protein from A/Victoria/361/11 (H3N2) |
| 29 | Influenza Virus | Amino acid sequence of ectodomain from the hemagglutinin protein from B/Massachusetts/2/12 (Influenza B) |
| 30 | Influenza Virus | Amino acid sequence of ectodomain from the hemagglutinin protein from B/Brisbane/60/08 (Influenza B) |
| 31 | Influenza Virus | Amino acid sequence of ectodomain from the hemagglutinin protein from A/Texas/50/12 (H3N2) Receptor Binding Domains |
| 32 | Influenza Virus | Amino acid sequence of RBD from hemagglutinin protein of A/New Caledonia/20/1999 (H1N1); (56-264, F264A) |
| 33 | Influenza Virus | Amino acid sequence of RBD from hemagglutinin protein of A/New Caledonia/20/1999 (H1N1); (56-264, Y98F, F264A) |
| 34 | Influenza Virus | Amino acid sequence of RBD from hemagglutinin protein of A/California/04/2009 (H1N1); (56-264) |
| 35 | Influenza Virus | Amino acid sequence of RBD from hemagglutinin protein of A/California/04/2009 (H1N1); (56-264, Y98F) |
| 36 | Influenza Virus | Amino acid sequence of RBD from hemagglutinin protein of A/Singapore/1/1957 (H2N2) |
| 37 | Influenza Virus | Amino acid sequence of RBD from hemagglutinin protein of A/Hong Kong/1/1968 (H3N2) |
| 38 | Influenza Virus | Amino acid sequence of RBD from hemagglutinin protein of A/Brisbane/10/2007 (H3N2) |
| 39 | Influenza Virus | Amino acid sequence of RBD from hemagglutinin protein of B/Florida/4/2006 (influenza B) |
| 40 | Influenza Virus | Amino acid sequence of RBD from hemagglutinin protein of A/Perth/16/2009 (H3N2) |
| 41 | Influenza Virus | Amino acid sequence of RBD from hemagglutinin protein of A/Wilson-Smith/33 (H1N1) (56-264, Y98F, F264A) |
| 42 | Influenza Virus | Amino acid sequence of RBD from hemagglutinin protein of A/Tientsin/78/77 (H1N1) (56-264, Y98F, F264A) |
| 43 | Influenza Virus | Amino acid sequence of RBD from hemagglutinin protein of A/Texas/36/91 (H1N1) (56-264, Y98F, F264A) |
| 44 | Influenza Virus | Amino acid sequence of RBD from hemagglutinin protein of A/Singapore/6/86 (H1N1) (56-264, Y98F, F264A) |
| 45 | Influenza Virus | Amino acid sequence of RBD from hemagglutinin protein of A/Memphis/39/83 (H1N1) (56-264, Y98F, F264A) |
| 46 | Influenza Virus | Amino acid sequence of RBD from hemagglutinin protein of A/Malaysia/54 (H1N1) (56-264, Y98F) (56-264, Y98F) |
| 47 | Influenza Virus | Amino acid sequence of RBD from hemagglutinin protein of A/Iowa/43 (H1N1) (56-264, Y98F, F264A) |
| 48 | Influenza Virus | Amino acid sequence of RBD from hemagglutinin protein of A/Hong Kong/117/77 (H1N1) (56-264, Y98F, F264A) |
| 49 | Influenza Virus | Amino acid sequence of RBD from hemagglutinin protein of Fort Monmouth/1/47 (H1N1) (56-264, Y98F, F264A) |
| 50 | Influenza virus | Amino acid sequence of RBD from hemagglutinin protein of Brisbane/59/07 (H1N1) (56-264, Y98F, F264A) |
| 51 | Influenza Virus | Amino acid sequence of RBD from hemagglutinin protein of A/Baylor/4052/81 (H1N1) (56-264, Y98F, F264A) |
| 52 | Influenza Virus | Amino acid sequence of RBD from hemagglutinin protein of A/Albany/4835/48 (H1N1) (56-264, Y98F, F264A) |
| 53 | Influenza virus | Amino acid sequence of RBD from hemagglutinin protein of Indonesia/05/05 (H5N1) (56-264, Y98F) |
| 54 | Influenza Virus | Amino acid sequence of RBD from hemagglutinin protein of A/Hong Kong/156/97 (H5N1) (56-264, Y98F) |
| 55 | Influenza Virus | Amino acid sequence of RBD from hemagglutinin protein of A/common magpie/Hong Kong/5052/07 (H5N1) (56-264, Y98F) |
| 56 | Influenza Virus | Amino acid sequence of RBD from hemagglutinin protein of A/chicken/Shanxi/2/06 (H5N1) (56-264, Y98F) |
| 57 | Influenza Virus | Amino acid sequence of RBD from hemagglutinin protein of A/silky chicken/Hong Kong/SF189/01 (H5N1) (56-264, Y98F) |
| 58 | Influenza Virus | Amino acid sequence of RBD from hemagglutinin protein of A/chicken/Henan/16/04 (H5N1) (56-264, Y98F) |
| 59 | Influenza Virus | Amino acid sequence of RBD from hemagglutinin protein of A/Victoria/361/11 (H3N2) (56-264, Y98F, K264A)) |
| 60 | Influenza Virus | Amino acid sequence of RBD from hemagglutinin protein of B/Massachusetts/2/12 (Influenza B) (63-294) |
| 61 | Influenza Virus | Amino acid sequence of RBD from hemagglutinin protein of B/Brisbane/60/08 (Influenza B) (63-294) |
| 62 | Influenza Virus | Amino acid sequence of RBD from hemagglutinin protein of A/Texas/50/12 (H3N2) Self-Assembly Proteins |

TABLE 1-continued

| SEQ ID NOs. | ORGANISM | DESCRIPTION |
|---|---|---|
| | | Ferritin Proteins |
| 63 | *Helicobacter pylori* | Coding sequence for ferritin monomeric subunit protein from *H. pylori* |
| 64 | *Helicobacter pylori* | Amino acid sequence encoded by SEQ ID NO: 63 |
| 65 | *Helicobacter pylori* | Complement of SEQ ID NO: 63 |
| 66 | *Escherichia coli* | Coding sequence for ferritin monomeric subunit protein from *E. coli* (gi 446839951_WP_000917207.1) |
| 67 | *Escherichia coli* | Amino acid sequence encoded by SEQ ID NO: 66 |
| 68 | *Escherichia coli* | Complement of SEQ ID NO: 66 |
| 69 | Rana catesbeiana | Coding sequence for bullfrog ferritin monomeric subunit protein (gi 13675 gb AAA49524.1) |
| 70 | Rana catesbeiana | Amino acid sequence encoded by SEQ ID NO: 69 SEQ ID NO: 8 from 6137NIAID-34-PCT |
| 71 | Rana catesbeiana | Complement of SEQ ID NO: 69 |
| | | Hybrid Ferritin Proteins |
| 72 | Artificial Sequence | Coding sequence for *H. pylori*-ferritin/bullfrog-ferritin fusion protein |
| 73 | Artificial Sequence | Amino acid sequence encoded by SEQ ID NO: 72 |
| 74 | Artificial Sequence | Complement of SEQ ID NO: 72 |
| 75 | Artificial Sequence | Coding sequence for *E. coli*-ferritin/bullfrog-ferritin fusion protein |
| 76 | Artificial Sequence | Amino acid sequence encoded by SEQ ID NO: 75 |
| 77 | Artificial Sequence | Complement of SEQ ID NO: 75 |
| | | Other Self-Assembling Monomeric Subunits |
| 78 | *Thermotoga maritima* | Coding sequence for encapsulin protein |
| 79 | *Thermotoga maritime* | Amino acid sequence encoded by SEQ ID NO: 78 |
| 80 | *Thermotoga maritime* | Complement of SEQ ID NO: 78 |
| 81 | Artificial Sequence | Coding sequence for Salmonella enteritis 03-33 protein (gi 390136278 pdb 3VCD) |
| 82 | Artificial Sequence | Amino acid sequence encoded by SEQ ID NO: 81 |
| 83 | Artificial Sequence | Complement of SEQ ID NO: 81 |
| 84 | *Acidianus ambivalens* | Coding sequence for sulfur oxygenase reductase protein from *Acidianus ambivalens* (gi 93279016 pdb 2CB2) |
| 85 | *Acidianus ambivalens* | Amino acid sequence encoded by SEQ ID NO: 84 |
| 86 | *Acidianus ambivalens* | Complement of SEQ ID NO: 84 |
| 87 | Aquifex aeolicus | Coding sequence for lumazine synthase protein from Aquifex aeolicus (gi 18159011 pdb1HQK) |
| 88 | Aquifex aeolicus | Amino acid sequence encoded by SEQ ID NO: 87 |
| 89 | Aquifex aeolicus | Complement of SEQ ID NO: 87 |
| 90 | *Bacillus stearothermophilus* | Coding sequence for dihydrolipoamide acetyltransferase (E2p) protein from *Bacillus stearothermophilus* (gi 4558102 pdb1B5S |
| 91 | *Bacillus stearothermophilus* | Amino acid sequence encoded by SEQ ID NO: 90 |
| 92 | *Bacillus stearothermophilus* | Complement of SEQ ID NO: 90 |
| 93 | Chikungunya virus | Coding sequence for Chikungunya virus capsid, envelope E3, E2, 6K, and E1 polyprotein |
| 94 | Chikungunya virus | Amino acid sequence encoded by SEQ ID NO: 93 |
| 95 | Chikungunya virus | Complement of SEQ ID NO: 93 |
| | | Ferritin Fusion Proteins |
| 96 | Artificial Sequence | Nucleic acid sequence of H1 NC99 RBD-Ferritin (56-264, F264A) |
| 97 | Artificial Sequence | Amino acid sequence of H1 NC99 RBD-Ferritin (56-264, F264A) |
| 98 | Artificial Sequence | Complement of SEQ ID NO: 96 |
| 99 | Artificial Sequence | Nucleic acid sequence of H1 NC99 RBD-Ferritin (56-264, Y98F, F264A) |
| 100 | Artificial Sequence | Amino acid sequence of H1 NC99 RBD-Ferritin (56-264, F264A) |
| 101 | Artificial Sequence | Complement of SEQ ID NO: 99 |
| 102 | Artificial Sequence | Nucleic acid sequence of H1 CA09 RBD-Ferritin (56-264) |
| 103 | Artificial Sequence | Amino acid sequence of H1 CA09 RBD-Ferritin (56-264) |
| 104 | Artificial Sequence | Complement of SEQ ID NO: 102 |
| 105 | Artificial Sequence | Nucleic acid sequence of H1 CA09 RBD-Ferritin (56-264, Y98F) |
| 106 | Artificial Sequence | Amino acid sequence of H1 CA09 RBD-Ferritin (56-264, Y98F) |
| 107 | Artificial Sequence | Complement of SEQ ID NO: 105 |
| 108 | Artificial Sequence | Nucleic acid sequence of H1 WS33 RBD-Ferritin (56-264, Y98F, F264A) |
| 109 | Artificial Sequence | Amino acid sequence of H1 WS33 RBD-Ferritin (56-264, Y98F, F264A) |

TABLE 1-continued

| SEQ ID NOs. | ORGANISM | DESCRIPTION |
|---|---|---|
| 110 | Artificial Sequence | Complement of SEQ ID NO: 108 |
| 111 | Artificial Sequence | Nucleic acid sequence of H1 Tien 77 RBD-Ferritin (56-264, Y98F, F264A) |
| 112 | Artificial Sequence | Amino acid sequence of H1 Tien 77 RBD-Ferritin (56-264, Y98F, F264A) |
| 113 | Artificial Sequence | Complement of SEQ ID NO: 111 |
| 114 | Artificial Sequence | Nucleic acid sequence of H1 TX91 RBD-Ferritin (56-264, Y98F, F264A) |
| 115 | Artificial Sequence | Amino acid sequence of H1 TX91 RBD-Ferritin (56-264, Y98F, F264A) |
| 116 | Artificial Sequence | Complement of SEQ ID NO: 114 |
| 117 | Artificial Sequence | Nucleic acid sequence of H1 SG86 RBD-Ferritin (56-264, Y98F, F264A) |
| 118 | Artificial Sequence | Amino acid sequence of H1 SG86 RBD-Ferritin (56-264, Y98F, F264A) |
| 119 | Artificial Sequence | Complement of SEQ ID NO: 117 |
| 120 | Artificial Sequence | Nucleic acid sequence of H1 Mem83 RBD-Ferritin (56-264, Y98F, F264A) |
| 121 | Artificial Sequence | Amino acid sequence of H1 Mem83 RBD-Ferritin (56-264, Y98F, F264A) |
| 122 | Artificial Sequence | Complement of SEQ ID NO: 120 |
| 123 | Artificial Sequence | Nucleic acid sequence of H1 Mal54 RBD-Ferritin (56-264, Y98F) |
| 124 | Artificial Sequence | Amino acid sequence of H1 Mal54 RBD-Ferritin (56-264, Y98F) |
| 125 | Artificial Sequence | Complement of SEQ ID NO: 123 |
| 126 | Artificial Sequence | Nucleic acid sequence of H1 IA43 RBD-Ferritin (56-264, Y98F, F264A) |
| 127 | Artificial Sequence | Amino acid sequence of H1 IA43 RBD-Ferritin (56-264, Y98F, F264A) |
| 128 | Artificial Sequence | Complement of SEQ ID NO: 126 |
| 129 | Artificial Sequence | Nucleic acid sequence of H1 HK77 RBD-Ferritin (56-264, Y98F, F264A) |
| 130 | Artificial Sequence | Amino acid sequence of H1 HK77 RBD-Ferritin (56-264, Y98F, F264A) |
| 131 | Artificial Sequence | Complement of SEQ ID NO: 129 |
| 132 | Artificial Sequence | Nucleic acid sequence of H1 FM47 RBD-Ferritin (56-264, Y98F, F264A) |
| 133 | Artificial Sequence | Amino acid sequence of H1 FM47 RBD-Ferritin (56-264, Y98F, F264A) |
| 134 | Artificial Sequence | Complement of SEQ ID NO: 132 |
| 135 | Artificial Sequence | Nucleic acid sequence of H1 BRO7 RBD-Ferritin (56-264, Y98F, F264A) |
| 136 | Artificial Sequence | Amino acid sequence of H1 BRO7 RBD-Ferritin (56-264, Y98F, F264A) |
| 137 | Artificial Sequence | Complement of SEQ ID NO: 135 |
| 138 | Artificial Sequence | Nucleic acid sequence of H1 Bay81 RBD-Ferritin (56-264, Y98F, F264A) |
| 139 | Artificial Sequence | Amino acid sequence of H1 Bay81 RBD-Ferritin (56-264, Y98F, F264A) |
| 140 | Artificial Sequence | Complement of SEQ ID NO: 138 |
| 141 | Artificial Sequence | Nucleic acid sequence of H1 Alb48 RBD-Ferritin (56-264, Y98F, F264A) |
| 142 | Artificial Sequence | Amino acid sequence of H1 Alb48 RBD-Ferritin (56-264, Y98F, F264A) |
| 143 | Artificial Sequence | Complement of SEQ ID NO: 141 |
| 144 | Artificial Sequence | Nucleic acid sequence of H5 IN05 RBD-Ferritin (56-264, Y98F) |
| 145 | Artificial Sequence | Amino acid sequence of H5 IN05 RBD-Ferritin (56-264, Y98F) |
| 146 | Artificial Sequence | Complement of SEQ ID NO: 144 |
| 147 | Artificial Sequence | Nucleic acid sequence of H5 HK97(c0) RBD-Ferritin (56-264, Y98F) |
| 148 | Artificial Sequence | Amino acid sequence of H5 HK97(c0) RBD-Ferritin (56-264, Y98F) |
| 149 | Artificial Sequence | Complement of SEQ ID NO: 147 |
| 150 | Artificial Sequence | Nucleic acid sequence of H5 HK07(c2.3.2.1) RBD-Ferritin (56-264, Y98F) |
| 151 | Artificial Sequence | Amino acid sequence of H5 HK07(c2.3.2.1) RBD-Ferritin (56-264, Y98F) |
| 152 | Artificial Sequence | Complement of SEQ ID NO: 150 |
| 153 | Artificial Sequence | Nucleic acid sequence of H5 SX06(c7.2) RBD-Ferritin (56-264, Y98F) |
| 154 | Artificial Sequence | Amino acid sequence of H5 SX06(c7.2) RBD-Ferritin (56-264, Y98F) |
| 155 | Artificial Sequence | Complement of SEQ ID NO: 153 |
| 156 | Artificial Sequence | Nucleic acid sequence of H5 HK01(c3) RBD-Ferritin (56-264, Y98F) |
| 157 | Artificial Sequence | Amino acid sequence of H5 HK01(c3) RBD-Ferritin (56-264, Y98F) |

TABLE 1-continued

| SEQ ID NOs. | ORGANISM | DESCRIPTION |
|---|---|---|
| 158 | Artificial Sequence | Complement of SEQ ID NO: 156 |
| 159 | Artificial Sequence | Nucleic acid sequence of H5 HN04(c8) RBD-Ferritin (56-264, Y98F) |
| 160 | Artificial Sequence | Amino acid sequence of H5 HN04(c8) RBD-Ferritin (56-264, Y98F) |
| 161 | Artificial Sequence | Complement of SEQ ID NO: 159 |
| 162 | Artificial Sequence | Nucleic acid sequence of H3 Vic11 RBD-Ferritin (56-264, Y98F, K264A) |
| 163 | Artificial Sequence | Amino acid sequence of H3 Vic11 RBD-Ferritin (56-264, Y98F, K264A) |
| 164 | Artificial Sequence | Complement of SEQ ID NO: 162 |
| 165 | Artificial Sequence | Nucleic acid sequence of B MA12 RBD-Ferritin (63-294) |
| 166 | Artificial Sequence | Amino acid sequence of B MA12 RBD-Ferritin (63-294) |
| 167 | Artificial Sequence | Complement of SEQ ID NO: 165 |
| 168 | Artificial Sequence | Nucleic acid sequence of B BRO8 RBD-Ferritin (63-295) |
| 169 | Artificial Sequence | Amino acid sequence of B BRO8 RBD-Ferritin (63-295) |
| 170 | Artificial Sequence | Complement of SEQ ID NO: 168 |
| | | Ferritin Single Polypeptide Design Fusion Proteins |
| 171 | Artificial Sequence | Nucleic acid sequence H1/H3 CA09 TX12 F2A RBD-Ferritin |
| 172 | Artificial Sequence | Amino acid sequence of H1/H3 CA09 TX12 F2A RBD-Ferritin |
| 173 | Artificial Sequence | Complement of SEQ ID NO: 171 |
| 174 | Artificial Sequence | Nucleic acid sequence of B/B BRO8 MA12 F2A RBD-Ferritin |
| 175 | Artificial Sequence | Amino acid sequence of B/B BRO8 MA12 F2A RBD-Ferritin |
| 176 | Artificial Sequence | Complement of SEQ ID NO: 174 |
| 177 | Artificial Sequence | Nucleic acid sequence H1/H3/B CA09 TX12 MA12 F2A RBD-Ferritin |
| 178 | Artificial Sequence | Amino acid sequence of H1/H3 CA09 TX12 MA12 F2A RBD-Ferritin |
| 179 | Artificial Sequence | Complement of SEQ ID NO: 177 |
| | | Encapsulin Fusion Proteins |
| 180 | Artificial Sequence | Nucleic acid sequence of H1 NC99 RBD-Encapsulin (56-264, F264A) |
| 181 | Artificial Sequence | Amino acid sequence of H1 NC99 RBD-Encapsulin (56-264, F264A) |
| 182 | Artificial Sequence | Complement of SEQ ID NO: 180 |
| 183 | Artificial Sequence | Nucleic acid sequence of H1 CA09 RBD-Encapsulin (56-264) |
| 184 | Artificial Sequence | Amino acid sequence of H1 CA09 RBD-Encapsulin (56-264) |
| 185 | Artificial Sequence | Complement of SEQ ID NO: 183 |
| | | CHIK VLP Fusion Proteins |
| 186 | Artificial Sequence | Nucleic acid sequence of H1 NC99 RBD-CHIKVLP (59-264, Y98F, F264A) |
| 187 | Artificial Sequence | Amino acid sequence of NC99 RBD-CHIKVLP (59-264, Y98F, F264A) |
| 188 | Artificial Sequence | Complement of SEQ ID NO: 186 |
| 189 | Artificial Sequence | Nucleic acid sequence of H1 CA09 RBD-CHIKVLP (59-264, Y98F) |
| 190 | Artificial Sequence | Amino acid sequence of H1 CA09 RBD-CHIKVLP (59-264, Y98F) |
| 191 | Artificial Sequence | Complement of SEQ ID NO: 189 |

It is understood by those skilled in the art that HA proteins from different influenza viruses may have different lengths, due to insertions and/or deletions of amino acid residue in one or both of the HA proteins. Thus, reference to a corresponding region refers to a region of another proteins that is identical, or nearly so (e.g., at least 95%, identical, at least 98% identical or at least 99% identical), in sequence, structure and/or function to the region being compared. For example, with regard to the globular head region or RBD of a hemagglutinin protein, the corresponding region in another hemagglutinin protein may not have the same residue numbers, but will have a very similar sequence and will perform the same function. To improve sequence comparisons between viruses, numbering systems are used by those in the field, which relate amino acid positions to a reference sequence. Thus, corresponding amino acid residues in hemagglutinin proteins from different strains of influenza may not have the same residue number with respect to their distance from the N-terminal amino acid of the mature protein. For example, using the H3 numbering system, reference to residue 100 in A/New Caledonia/20/1999 (1999 NC, H1) does not mean it is the 100th residue from the N-terminal amino acid of the mature protein. Instead, residue 100 of A/New Caledonia/20/1999 (1999 NC, H1) HA protein aligns with residue 100 of the HA protein from influenza H3N2 strain. The use of such numbering systems is understood by those skilled in the art. Unless otherwise noted, reference to amino acid positions in hemagglutinin proteins herein is made using the H3 numbering system.

As used herein, the term immunogenic refers to the ability of a specific protein, or a specific region thereof (i.e., a specific amino acid sequence), to elicit an immune response to the specific protein, or to proteins comprising an amino acid sequence having a high degree of identity with the specific protein. According to the present invention, two proteins having a high degree of identity have amino acid sequences at least 80% identical, at least 85% identical, at least 87% identical, at least 90% identical, at least 92% identical, at least 94% identical, at least 96% identical, at least 98% identical or at least 99% identical. Preferred immunogenic proteins, or portions thereof, are those that elicit neutralizing antibodies to influenza virus.

As used herein, a heterogeneous population refers to a population of molecules in which at least one molecule in the population differs in sequence from at least one other molecule in the population. For example, with particular regard to the present invention, in a heterogeneous population of immunogenic portions from influenza HA proteins, the population is heterologous due to the fact that the amino acid sequence of at least one immunogenic portion in the population differs from the amino acid sequence of at least one other immunogenic portion in the population. With regard to the present invention, each unique sequence is referred to as a species of molecule (e.g., a species of immunogenic portion, a species of fusion protein, etc.). The difference in sequence between two species of molecule can involve a single amino acid difference or it can involve more than one amino acid difference. Moreover, such differences may, or may not, result in different species having different epitopes.

As used herein, epitopes are clusters of amino acid residues that are recognized by (e.g., bound by) components of the immune system, such as B-cell receptors, T-cell receptors, antibodies, and the like, thus forming an immune complex and eliciting an immune response. Such epitopes may consist of contiguous amino acids residues (i.e., amino acid residues that are adjacent to one another in the protein), or they may consist of non-contiguous amino acid residues (i.e., amino acid residues that are not adjacent one another in the linear protein) but which are in close spatial proximity in three-dimensional space in the finally folded protein. Thus, in one embodiment the immunogenic portion comprises at least one epitope from an influenza virus HA protein.

As used herein, a monovalent nanoparticle refers to a nanoparticle that displays a single species of immunogenic portion from an HA protein on its surface. That is, all of the immunogenic portions have the same sequence. As used herein, Admixed nanoparticles refers to a population of nanoparticles that contains a mixture of monovalent nanoparticle species. In such a population, each monovalent nanoparticle is produced separately from other monovalent nanoparticles, and the monovalent nanoparticles are then mixed together to produce Admixed nanoparticles. It will be understood by those skilled in the art that while a population of Admixed nanoparticles comprises more than one species of immunogenic portion, each monovalent nanoparticle in the Admixed population comprises a single species of immunogenic portion. As used herein, a multivalent co-assembled nanoparticle, co-assembled nanoparticle, and the like, refers to a nanoparticle made by combining more than one species of fusion protein, wherein at least two fusion proteins differ in the sequence of their immunogenic portions. The result is a nanoparticle comprising a heterogeneous population of self-assembling fusion proteins, wherein the nanoparticle displays on its surface a heterogeneous population of immunogenic portions from HA proteins. Such multivalent nanoparticles can also be referred to as mosaic nanoparticles.

One embodiment of the present invention is a nanoparticle comprising a heterologous population of fusion proteins, wherein each fusion protein comprises at least one immunogenic portion from an influenza HA protein joined to at least 25 contiguous amino acids from a monomeric subunit protein capable of assembling into a nanoparticle (i.e., a self-assembly (SA) protein), wherein the heterologous population of fusion proteins comprises at least two different species of fusion proteins. Nanoparticles of the present invention can be made from fusion proteins comprising immunogenic portions of HA proteins from any Type, sub-type, strain, or combinations thereof, of influenza virus. In certain embodiments, the immunogenic portions are from HA proteins from one or more influenza viruses selected from the group consisting of Type A influenza viruses, Type B influenza viruses and Type C influenza viruses. In one embodiment, the immunogenic portions are from HA proteins from one or more virus selected from the group consisting of Group I influenza viruses and Group II influenza virus. In one embodiment, the immunogenic portions are from HA proteins from one or more virus selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus, an H16 influenza virus, an H17 influenza virus, an H18 influenza virus and an influenza B lineage virus. In certain embodiments, the immunogenic portions are from HA proteins from one or more influenza viruses selected from the group consisting of A/New Caledonia/20/1999 (H1N1), A/California/04/2009 (H1N1), A/Singapore/1/1957 (H2N2), A/Hong Kong/1/1968 (H3N2), A/Brisbane/10/2007 (H3N2), A/Indonesia/05/2005 (H5N1), B/Florida/4/2006 (influenza B), A/Perth/16/2009 (H3N2), A/Brisbane/59/2007 (H1N1), B/Brisbane/60/2008 (influenza B), A/Wilson-Smith/33 (H1N1), A/Tientsin/78/77 (H1N1), A/Texas/36/91 (H1N1), A/Singapore/6/86 (H1N1), A/Memphis/39/83 (H1N1), A/Malaysia/54 (H1N1), A/Iowa/43 (H1N1), A/Hong Kong/117/77 (H1N1), A/Fort Monmouth/1/47 (H1N1), A/Brisbane/59/07 (H1N1), A/Baylor/4052/81 (H1N1), A/Albany/4835/48 (H1N1), A/Hong Kong/156/97 (H5N1), A/common magpie/Hong Kong/5052/07 (H5N1), A/chicken/Shanxi/2/06 (H5N1), A/silky chicken/Hong Kong/SF189/01 (H5N1), A/chicken/Henan/16/04 (H5N1), A/Victoria/361/11 (H3N2), B/Massachusetts/2/12 (influenza B), B/Brisbane/60/08 (influenza B) and A/Texas/50/12 (H3N2). In certain embodiments, the immunogenic portions are from one or more HA proteins Listed in Table 1. In certain embodiments, the immunogenic portions are from one or more HA proteins selected from the group consisting of HA proteins comprising SEQ ID NO:1-SEQ ID NO:62. In certain embodiments, the immunogenic portions are from one or more HA proteins selected from the group consisting of HA proteins consisting of SEQ ID NO:1-SEQ ID NO:62.

Immunogenic portions useful for constructing nanoparticles of the present invention can also be obtained from variants of influenza virus HA proteins disclosed herein. As used herein, a variant refers to a protein, or nucleic acid molecule, the sequence of which is similar, but not identical to, a reference sequence, wherein the activity of the variant protein (or the protein encoded by the variant nucleic acid molecule) is not significantly altered. These variations in sequence can be naturally occurring variations or they can be engineered through the use of genetic engineering technique known to those skilled in the art. Examples of such techniques are found in Sambrook J, Fritsch E F, Maniatis T et al., in Molecular Cloning—A Laboratory Manual, 2nd Edition, Cold Spring Harbor Laboratory Press, 1989, pp.

9.31-9.57), or in Current Protocols in Molecular Biology, John Wiley & Sons, N.Y. (1989), 6.3.1-6.3.6, both of which are incorporated herein by reference in their entirety.

With regard to variants, any type of alteration in the amino acid, or nucleic acid, sequence is permissible so long as such alterations do not significantly affect the activity of the variant protein and the variant protein retains the desired activity. Examples of such variations include, but are not limited to, deletions, insertions, substitutions and combinations thereof. For example, with regard to proteins, it is well understood by those skilled in the art that one or more (e.g., 2, 3, 4, 5, 6, 7, 8, 9 or 10), amino acids can often be removed from the amino and/or carboxy terminal ends of a protein without significantly affecting the activity of that protein. Similarly, one or more (e.g., 2, 3, 4, 5, 6, 7, 8, 9 or 10) amino acids can often be inserted into a protein without significantly affecting the activity of the protein.

As noted, variant proteins of the present invention can contain amino acid substitutions relative to the influenza HA proteins disclosed herein. Any amino acid substitution is permissible so long as the activity of the protein is not significantly affected. In this regard, it is appreciated in the art that amino acids can be classified into groups based on their physical properties. Examples of such groups include, but are not limited to, charged amino acids, uncharged amino acids, polar uncharged amino acids, and hydrophobic amino acids. Preferred variants that contain substitutions are those in which an amino acid is substituted with an amino acid from the same group. Such substitutions are referred to as conservative substitutions.

Naturally occurring residues may be divided into classes based on common side chain properties:

1) hydrophobic: Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

For example, non-conservative substitutions may involve the exchange of a member of one of these classes for a member from another class.

In making amino acid changes, the hydropathic index of amino acids may be considered. Each amino acid has been assigned a hydropathic index on the basis of its hydrophobicity and charge characteristics. The hydropathic indices are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). The importance of the hydropathic amino acid index in conferring interactive biological function on a protein is generally understood in the art (Kyte et al., 1982, J. Mol. Biol. 157:105-31). It is known that certain amino acids may be substituted for other amino acids having a similar hydropathic index or score and still retain a similar biological activity. In making changes based upon the hydropathic index, the substitution of amino acids whose hydropathic indices are within +2 is preferred, those within +1 are particularly preferred, and those within +0.5 are even more particularly preferred.

It is also understood in the art that the substitution of like amino acids can be made effectively on the basis of hydrophilicity, particularly where the biologically functionally equivalent protein or peptide thereby created is intended for use in immunological invention, as in the present case. The greatest local average hydrophilicity of a protein, as governed by the hydrophilicity of its adjacent amino acids, correlates with its immunogenicity and antigenicity, i.e., with a biological property of the protein. The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); and tryptophan (−3.4). In making changes based upon similar hydrophilicity values, the substitution of amino acids whose hydrophilicity values are within +2 is preferred, those within +1 are particularly preferred, and those within +0.5 are even more particularly preferred. One may also identify epitopes from primary amino acid sequences on the basis of hydrophilicity.

Desired amino acid substitutions (whether conservative or non-conservative) can be determined by those skilled in the art at the time such substitutions are desired. For example, amino acid substitutions can be used to identify important residues of the HA protein, or to increase or decrease the immunogenicity, solubility or stability of the HA proteins described herein. Exemplary amino acid substitutions are shown below in Table 2.

TABLE 2

| Amino Acid Substitutions | |
| --- | --- |
| Original Amino Acid | Exemplary Substitutions |
| Ala | Val, Leu, Ile |
| Arg | Lys, Gln, Asn |
| Asn | Gln |
| Asp | Glu |
| Cys | Ser, Ala |
| Gln | Asn |
| Glu | Asp |
| Gly | Pro, Ala |
| His | Asn, Gln, Lys, Arg |
| Ile | Leu, Val, Met, Ala |
| Leu | Ile, Val, Met, Ala |
| Lys | Arg, Gln, Asn |
| Met | Leu, Phe, Ile |
| Phe | Leu, Val, Ile, Ala, Tyr |
| Pro | Ala |
| Ser | Thr, Ala, Cys |
| Thr | Ser |
| Trp | Tyr, Phe |
| Tyr | Trp, Phe, Thr, Ser |
| Val | Ile, Met, Leu, Phe, Ala |

As used herein, the phrase significantly affect a proteins activity refers to a decrease in the activity of a protein by at least 10%, at least 20%, at least 30%, at least 40% or at least 50%. With regard to the present invention, such activity may be ability to elicit antibodies, including neutralizing antibodies, against an influenza virus. The determination of antibody production may be measured by measuring the titer of such antibodies against influenza virus, or by measuring the number of types, subtypes or strains bound by the elicited antibodies. Methods of determining antibody titers and methods of performing virus neutralization assays are known to those skilled in the art. In addition to the activities described above, examples of other activities that may be measured include the ability to agglutinate red blood cells, the ability to bind sialic acid or the binding affinity of the protein for a cell. Methods of measuring such activities are known to those skilled in the art.

Thus, in one embodiment, nanoparticles of the present invention comprise fusion proteins comprising immunogenic portions from HA proteins comprising amino acid sequences at least 80%, at least 85%, at least 90%, at least 92%, at least 94%, at least 96%, at least 98% or at least 99% identical to amino acid sequences from one or more HA proteins from any Type, sub-type, strain, or combinations thereof, of influenza virus. In certain embodiments, the immunogenic portions are from HA proteins from one or more influenza viruses selected from the group consisting of Type A influenza virus, Type B influenza virus and Type C influenza viruses. In certain embodiments, the immunogenic portions are from HA proteins from one or more influenza viruses selected from the group consisting of Group 1 influenza virus and Group 2 influenza viruses. In one embodiment, the immunogenic portions are from one or more HA proteins comprising amino acid sequences at least 80%, at least 85%, at least 90%, at least 92%, at least 94%, at least 96%, at least 98% or at least 99% identical to amino acid sequences of HA proteins from one or more viruses selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus, an H16 influenza virus, an H17 influenza virus, an H18 influenza virus and an influenza lineage B virus. In certain embodiments, the immunogenic portions are from HA proteins comprising amino acid sequence at least 80%, at least 85%, at least 90%, at least 92%, at least 94%, at least 96%, at least 98% or at least 99% identical to amino acid sequences of HA proteins from one or more influenza viruses selected from the group consisting of A/New Caledonia/20/1999 (H1N1), A/California/04/2009 (H1N1), A/Singapore/1/1957 (H2N2), A/Hong Kong/1/1968 (H3N2), A/Brisbane/10/2007 (H3N2), A/Indonesia/05/2005 (H5N1), B/Florida/4/2006 (influenza B), A/Perth/16/2009 (H3N2), A/Brisbane/59/2007 (H1N1), B/Brisbane/60/2008 (influenza B), A/Wilson-Smith/33 (H1N1), A/Tientsin/78/77 (H1N1), A/Texas/36/91 (H1N1), A/Singapore/6/86 (H1N1), A/Memphis/39/83 Monmouth/1/47 (H1N1), A/Brisbane/59/07 (H1N1), A/Baylor/4052/81 (H1N1), A/Albany/4835/48 (H1N1), A/Hong Kong/156/97 (H5N1), A/common magpie/Hong Kong/5052/07 (H5N1), A/chicken/Shanxi/2/06 (H5N1), A/silky chicken/Hong Kong/SF189/01 (H5N1), A/chicken/Henan/16/04 (H5N1), A/Victoria/361/11 (H3N2), B/Massachusetts/2/12 (influenza B), B/Brisbane/60/08 (influenza B) and A/Texas/50/12 (H3N2). In certain embodiments, the immunogenic portions are from HA proteins comprising amino acid sequences at least 80%, at least 85%, at least 90%, at least 92%, at least 94%, at least 96%, at least 98% or at least 99% identical to amino acid sequences of one or more HA proteins Listed in Table 1. In certain embodiments, the immunogenic portions are from HA proteins comprising amino acid sequences at least 80%, at least 85%, at least 90%, at least 92%, at least 94%, at least 96%, at least 98% or at least 99% identical to amino acid sequences of one or more HA proteins selected from the group consisting of HA proteins comprising SEQ ID NO:1-SEQ ID NO:62. In certain embodiments, the immunogenic portions are from HA proteins comprising amino acid sequences at least 80%, at least 85%, at least 90%, at least 92%, at least 94%, at least 96%, at least 98% or at least 99% identical to amino acid sequences of one or more HA proteins selected from the group consisting of HA proteins consisting of SEQ ID NO:1-SEQ ID NO:62.

It is understood by those skilled in the art that the influenza HA protein contains different regions or domains. Examples of such regions include the stem region and the globular head region. Thus, while nanoparticle-based influenza vaccines can be made using immunogenic portions from any influenza HA proteins, in preferred embodiments the immunogenic portions are from a specific region or domain of the selected HA proteins. One embodiment of the present invention is a nanoparticle comprising a heterologous population of fusion proteins, wherein each fusion protein comprises at least one immunogenic portion from the globular head region of an influenza HA protein joined to at least 25 contiguous amino acids from a monomeric subunit protein capable of assembling into a nanoparticle (i.e., a self-assembly (SA) protein), wherein the heterologous population of fusion proteins comprises at least two different species of fusion proteins. The globular head region, which comprises (approximately) amino acid residues 52-277 of influenza A HA protein (H3 numbering system), consists exclusively of the major portion of the HA1 polypeptide and includes two domains: the receptor binding domain (RBD and the vestigial esterase sub-domain. One example of a globular head region is represented by amino acids 52-277 from an HA protein comprising a region corresponding to an amino acid sequence selected from the group consisting of SEQ ID NO:1-62. In one embodiment, the immunogenic portions are from the globular head regions of HA proteins comprising amino acid sequences at least 80%, at least 85%, at least 90%, at least 92%, at least 94%, at least 96%, at least 98% at least 99%, or which are, identical to the amino acid sequences of HA proteins from one or more influenza viruses selected from the group consisting of Type A influenza viruses, Type B influenza viruses and Type C influenza viruses. In one embodiment, the immunogenic portions are from the globular head regions of HA proteins comprising amino acid sequences at least 80%, at least 85%, at least 90%, at least 92%, at least 94%, at least 96%, at least 98% at least 99%, or which are, identical to the amino acid sequences of HA proteins from one or more influenza viruses selected from the group consisting of Group I influenza viruses and Group II influenza viruses. In one embodiment, the immunogenic portions are from globular head regions of HA proteins comprising amino acid sequences at least 80%, at least 85%, at least 90%, at least 92%, at least 94%, at least 96%, at least 98%, at least 99%, or which are, identical to the amino acid sequences of HA proteins from one or more viruses selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus, an H16 influenza virus, a H17 influenza virus, an H18 influenza virus and an influenza linage B virus. In one embodiment, the immunogenic portions are from the globular head regions of HA proteins comprising amino acid sequences at least 80%, at least 85%, at least 90%, at least 92%, at least 94%, at least 96%, at least 98% at least 99%, or which are, identical to the amino acid sequences of HA proteins from one or more influenza viruses selected from the group consisting of A/New Caledonia/20/1999 (H1N1), A/California/04/2009 (H1N1), A/Singapore/1/1957 (H2N2), A/Hong Kong/1/1968 (H3N2), A/Brisbane/10/2007 (H3N2), A/Indonesia/05/2005 (H5N1), B/Florida/4/2006 (influenza B), A/Perth/16/2009 (H3N2), A/Brisbane/59/2007 (H1N1), B/Brisbane/60/2008 (influenza B), A/Wilson- Smith/33 (H1N1), A/Tientsin/78/77 (H1N1), A/Texas/36/91 (H1N1), A/Singapore/6/86 (H1N1), A/Memphis/39/83 (H1N1), A/Malaysia/54 (H1N1), A/Iowa/43 (H1N1), A/Hong Kong/117/77 (H1N1), A/Fort Monmouth/1/47 (H1N1), A/Brisbane/59/07 (H1N1), A/Baylor/4052/81 (H1N1), A/Albany/4835/48 (H1N1), A/Hong Kong/156/97 (H5N1), A/common magpie/Hong Kong/5052/07 (H5N1), A/chicken/Shanxi/2/06 (H5N1), A/silky chicken/Hong Kong/SF189/01 (H5N1), A/chicken/Henan/16/04 (H5N1), A/Victoria/361/11 (H3N2), B/Massachusetts/2/12 (influenza B), B/Brisbane/60/08 (influenza B) and A/Texas/50/12 (H3N2). In one embodiment, the immunogenic portions are from the globular head regions of HA proteins comprising amino acid sequences at least 80%, at least 85%, at least 90%, at least 92%, at least 94%, at least 96%, at least 98% at least 99%, or which are, identical to the amino acid sequences of one or more HA proteins Listed in Table 1.

As has been discussed, the globular head region comprises several other regions or domains. Thus, it will be appreciated by those skilled in the art that the immunogenic portions of the self-assembling fusion proteins can be fragments from the globular head regions from one or more influenza virus HA proteins. In one embodiment, the immunogenic portions comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from globular head regions of influenza virus HA proteins. In one embodiment, the immunogenic portions comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from the globular head regions of HA proteins, or variant, thereof, from one or more influenza viruses selected form the group consisting of Type A influenza viruses, Type B influenza viruses and Type C influenza viruses. In one embodiment, the immunogenic portions comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from the globular head regions of HA proteins, or variants, thereof, from one or more influenza viruses selected from the group consisting of Group I influenza viruses and Group II influenza viruses. In one embodiment, the immunogenic portions comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from the globular head regions of HA proteins, or variant thereof, from one or more viruses selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus, an H16 influenza virus, an H17 influenza virus, an H18 influenza virus and an influenza lineage B virus. In one embodiment, the immunogenic portions comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from the region corresponding to the globular head regions of HA proteins, or variant thereof, from one or more influenza viruses selected from the group consisting of A/New Caledonia/20/1999 (H1N1), A/California/04/2009 (H1N1), A/Singapore/1/1957 (H2N2), A/Hong Kong/1/1968 (H3N2), A/Brisbane/10/2007 (H3N2), A/Indonesia/05/2005 (H5N1), B/Florida/4/2006 (influenza B), A/Perth/16/2009 (H3N2), A/Brisbane/59/2007 (H1N1), B/Brisbane/60/2008 (influenza B), A/Wilson-Smith/33 (H1N1), A/Tientsin/78/77 (H1N1), A/Texas/36/91 (H1N1), A/Singapore/6/86 (H1N1), A/Memphis/39/83 (H1N1), A/Malaysia/54 (H1N1), A/Iowa/43 (H1N1), A/Hong Kong/117/77 (H1N1), A/Fort Monmouth/1/47 (H1N1), A/Brisbane/59/07 (H1N1), A/Baylor/4052/81 (H1N1), A/Albany/4835/48 (H1N1), A/Hong Kong/156/97 (H5N1), A/common magpie/Hong Kong/5052/07 (H5N1), A/chicken/Shanxi/2/06 (H5N1), A/silky chicken/Hong Kong/SF189/01 (H5N1), A/chicken/Henan/16/04 (H5N1), A/Victoria/361/11 (H3N2), B/Massachusetts/2/12 (influenza B), B/Brisbane/60/08 (influenza B) and A/Texas/50/12 (H3N2). In one embodiment, the immunogenic portions comprises at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from the regions corresponding to the globular head regions of one or more HA proteins, or variant thereof, listed in Table 1. In one embodiment, the immunogenic portions comprises at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from regions corresponding to the globular head regions of one or more HA proteins, or variant thereof, comprising sequences selected from the group consisting of SEQ ID NO:1-SEQ ID NO:31.

A particularly useful portion of the globular head region is the receptor-binding domain (RBD). The receptor-binding domain comprises (approximately) amino acid residues 56-264 of influenza A HA protein (H3 numbering system). One embodiment of the present invention is a nanoparticle comprising a heterologous population of fusion proteins, wherein each fusion protein comprises at least one immunogenic portion from the RBD of an influenza HA protein joined to at least 25 contiguous amino acids from a monomeric subunit protein capable of assembling into a nanoparticle (i.e., a self-assembly (SA) protein), wherein the heterologous population of fusion proteins comprises at least two different species of fusion proteins. In one embodiment, the immunogenic portions comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from the receptor-binding domains (RBDs) of one or more influenza virus HA proteins. In one embodiment, the immunogenic portions comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from the RBDs of HA proteins, or variants thereof, from one or more influenza viruses selected from the group consisting of Type A influenza viruses, Type B influenza viruses and Type C influenza viruses. In one embodiment, the immunogenic portions comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from the RBDs of HA proteins, or variants thereof, from one or more influenza viruses selected from the group consisting of Group 1 influenza viruses and Group 2 influenza viruses. In one embodiment, the immunogenic portions comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from the RBDs of HA proteins, or variants thereof, from one or more viruses selected from the group consisting of an H1 influenza virus, an H2 influenza virus, an influenza H3 virus, an influenza H4 virus, an influenza H5 virus, an influenza H6 virus, an H7 influenza virus, an H8 influenza virus, an H9 influenza virus, an H10 influenza virus, an H11 influenza virus, an H12 influenza virus, an H13 influenza virus, an H14 influenza virus, an H15 influenza virus, an H16 influenza virus, an H17 influenza virus, an H18 influenza virus and an influenza lineage B virus. In one embodiment, the immunogenic portions comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from the RBDs of HA proteins, or variants thereof, from one or more influenza viruses selected from the group consisting of A/New Caledonia/20/1999 (H1N1), A/California/04/2009 (H1N1), A/Singapore/1/1957 (H2N2), A/Hong Kong/1/1968 (H3N2), A/Brisbane/10/2007 (H3N2), A/Indonesia/05/2005 (H5N1), B/Florida/4/2006 (influenza B), A/Perth/16/2009 (H3N2), A/Brisbane/59/2007 (H1N1), B/Brisbane/60/2008 (influenza B), A/Wilson-Smith/33 (H1N1), A/Tientsin/78/77 (H1N1), A/Texas/36/91 (H1N1), A/Singapore/6/86 (H1N1), A/Memphis/39/83 Monmouth/1/47 (H1N1), A/Brisbane/59/07 (H1N1), A/Baylor/4052/81 (H1N1), A/Albany/4835/48 (H1N1), A/Hong Kong/156/97 (H5N1), A/common magpie/Hong Kong/5052/07 (H5N1), A/chicken/Shanxi/2/06 (H5N1), A/silky chicken/Hong Kong/SF189/01 (H5N1), A/chicken/Henan/16/04 (H5N1), A/Victoria/361/11 (H3N2), B/Massachusetts/2/12 (influenza B), B/Brisbane/60/08 (influenza B) and A/Texas/50/12 (H3N2). In one embodiment, the immunogenic portions comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from the RBDs of one or more HA proteins, or variants thereof, Listed in Table 1. In one embodiment, the immunogenic portions comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from an amino acid sequence at least 80%, at least 85%, at least 90%, at least 92%, at least 94%, at least 96%, at least 98% or at least 99% identical to a sequence selected from the group consisting of SEQ ID NO:32-SEQ ID NO:62. In one embodiment, the immunogenic portions comprise at least 10, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190 or at least 200 contiguous amino acid residues from one or more amino acid sequences selected from the group consisting of SEQ ID NO:32-SEQ ID NO:62. In one embodiment, the immunogenic portions comprise one or more amino acid sequence selected from the group consisting of SEQ ID NO:32-SEQ ID NO:62.

As described herein, in order to form nanoparticles expressing immunogenic portions of influenza HA proteins on theirs surfaces, each immunogenic portion is joined to a self-assembly (SA) subunit protein, or a functional portion or variant thereof, thereby forming a hemagglutinin-self-assembly (HA-SA) fusion protein. Upon expression, the HA-SA fusion proteins assemble into a nanoparticle that displays the immunogenic portion of the HA protein on its surface. Any self-assembly subunit protein, or variant thereof, can be used to produce a fusion protein of the present invention, as long as the resulting fusion protein is capable of self-assembling into a nanoparticle. Examples of self-assembly subunit proteins useful for constructing fusion proteins of the present invention include, but are not limited to, ferritin, encapsulin, sulfur oxygenase reductase, lumazine synthase, dihydrolipoamide acetyltransferase (E2), Chikungunya virus envelope proteins, and fragments and/or variants thereof.

In one embodiment, the self-assembly protein is ferritin. Ferritin, which is found in all animals, bacteria and plants, forms a spherical protein complex that acts primarily to control the rate and location of polynuclear $Fe(III)_2O_3$ formation through the transportation of hydrated iron ions and protons to and from a mineralized core. The spherical form of ferritin is made up of monomeric subunit proteins (also referred to as monomeric ferritin subunits), which are polypeptides having a molecule weight of approximately 17-20 kDa. Examples of the sequences of monomeric ferritin subunits are represented by SEQ ID NO:64, SEQ ID NO:67 and SEQ ID NO:69. Each monomeric ferritin subunit has the topology of a helix bundle which includes a four antiparallel helix motif, with a fifth shorter helix (the c-terminal helix) lying roughly perpendicular to the long axis of the 4 helix bundle. According to convention, the helices are labeled 'A, B, C, and D & E' from the N-terminus respectively. The N-terminal sequence lies adjacent to the capsid three-fold axis and extends to the surface, while the E helices pack together at the four-fold axis with the C-terminus extending into the particle core. The consequence of this packing creates two pores on the capsid surface. While not intended to be bound by theory, it is expected that one or both of these pores represent the point by which the hydrated iron diffuses into and out of the capsid. Following production, these monomeric ferritin subunit proteins self-assemble into the spherical ferritin protein. Thus, the spherical form of ferritin comprises 24 monomeric, ferritin subunit proteins, and has a capsid-like structure having 432 symmetry.

According to the present invention, a monomeric ferritin subunit of the present invention is a full length, single polypeptide of a ferritin protein, or any portion thereof, which is capable of directing self-assembly of monomeric ferritin subunits into the spherical form of the protein. Amino acid sequences from monomeric ferritin subunits of any known ferritin protein can be used to produce fusion proteins of the present invention, so long as the monomeric ferritin subunit is capable of directing self-assembly of the fusion protein into a nanoparticle displaying immunogenic portions from influenza virus HA proteins on its surface. In one embodiment, the monomeric ferritin subunit is selected from the group consisting of a bacterial ferritin protein, a plant ferritin protein, an algal ferritin protein, an insect ferritin protein, a fungal ferritin protein and a mammalian ferritin protein. In one embodiment, the monomeric ferritin subunit is from *Helicobacter pylori*. In one embodiment, the monomeric ferritin subunit is from *E. coli*. In one embodiment, the monomeric ferritin subunit is bullfrog ferritin. In one embodiment, the monomeric ferritin subunit is a hybrid ferritin protein made by joining amino acid sequences from more than one ferritin proteins selected from the group consisting of *H. pylori* ferritin, *E. coli* ferritin and bullfrog ferritin. Amino acid sequences from representative ferritin proteins of the present invention are disclosed herein as SEQ ID NO:64 (*H. pylori* ferritin), SEQ ID NO:66 (*E. coli* ferritin), SEQ ID NO:70 (bullfrog ferritin). Examples of representative hybrid ferritin proteins of the present invention include SEQ ID NO:73 (*H. pylori* ferritin-bullfrog ferritin fusion) and SEQ ID NO:76 (*E. coli* ferritin-bullfrog ferritin fusion. In one embodiment, nanoparticles of the present invention contain fusion proteins comprising an amino acid sequence selected from the group consisting of SEQ ID NO:64, SEQ ID NO:67, SEQ ID NO:70, SEQ ID NO:73 and SEQ ID NO:76.

In one embodiment, the self-assembly protein is encapsulin. According to the present invention, a monomeric encapsulin subunit of the present invention is a full length, single polypeptide of an encapsulin protein, or any portion thereof, which is capable of directing self-assembly of monomeric encapsulin subunits into a nanoparticle. Amino acid sequences from monomeric encapsulin subunits of any known encapsulin protein can be used to produce fusion proteins of the present invention, so long as the monomeric encapsulin subunit is capable of directing self-assembly of the fusion protein into a nanoparticle displaying immunogenic portions from influenza virus HA proteins on its surface. The amino acid sequence of a representative encapsulin protein is disclosed herein as SEQ ID NO:79. The spherical form of encapsulin comprises 60 monomeric encapsulin subunit proteins.

In one embodiment, the self-assembly protein is artificially designed *Salmonella* enteritis 03-33 subunit protein. According to the present invention, a monomeric 03-33 subunit of the present invention is a full length, single polypeptide of an 03-33 protein, or any portion thereof, which is capable of directing self-assembly of monomeric 03-33 subunits into a nanoparticle. Amino acid sequences from monomeric 03-33 subunits of any known 03-33 protein can be used to produce fusion proteins of the present invention, so long as the monomeric 03-33 subunit is capable of directing self-assembly of the fusion protein into a nanoparticle displaying immunogenic portions from influenza virus HA proteins on its surface. The amino acid sequence of a representative 03-33 protein is disclosed herein as SEQ ID NO:82.

In one embodiment, the self-assembly protein is sulfur oxygenase reductase (SOR). According to the present invention, a monomeric SOR subunit of the present invention is a full length, single polypeptide of an SOR protein, or any portion thereof, which is capable of directing self-assembly of monomeric SOR subunits into a nanoparticle. Amino acid sequences from monomeric SOR subunits of any known SOR protein can be used to produce fusion proteins of the present invention, so long as the monomeric SOR subunit is capable of directing self-assembly of the fusion protein into a nanoparticle displaying immunogenic portions from influenza virus HA proteins on its surface. The amino acid sequence of a representative SOR protein is disclosed herein as SEQ ID NO:85. The spherical form of SOR comprises 24 monomeric SOR subunit proteins.

In one embodiment, the self-assembly protein is lumazine synthase (LS). According to the present invention, a monomeric LS subunit of the present invention is a full length, single polypeptide of an LS protein, or any portion thereof, which is capable of directing self-assembly of monomeric LS subunits into a nanoparticle. Amino acid sequences from monomeric LS subunits of any known LS protein can be used to produce fusion proteins of the present invention, so long as the monomeric LS subunit is capable of directing self-assembly of the fusion protein into a nanoparticle displaying immunogenic portions from influenza virus HA proteins on its surface. The amino acid sequence of a representative LS protein is disclosed herein as SEQ ID NO:88. The spherical form of LS comprises a 60 monomeric subunit capsid comprising 12 pentameric units.

In one embodiment, the self-assembly protein is pyruvate dehydrogenase complex (PDC) dihydrolipoamide acetyltransferase (E2p). According to the present invention, a monomeric E2p subunit of the present invention is a full length, single polypeptide of an E2p protein, or any portion thereof, which is capable of directing self-assembly of monomeric E2p subunits into a nanoparticle. Amino acid sequences from monomeric E2p subunits of any known E2p protein can be used to produce fusion proteins of the present invention, so long as the monomeric E2p subunit is capable of directing self-assembly of the fusion protein into a nanoparticle displaying immunogenic portions from influenza virus HA proteins on its surface. The amino acid sequence of a representative E2p protein is disclosed herein as SEQ ID NO:91. In one embodiment, the nanoparticles comprise self-assembly proteins from Chikungunya virus. In particular, the nanoparticles comprises one or more structural proteins (e.g., capsid, E1, E2 an E3) from Chikungunya virus (CHKV). Methods of forming nanoparticles from CHKV are disclosed herein and are also taught in U.S. patent application Ser. No. 13/131,287, which is incorporated herein in its entirety by reference. According to the present invention, CHKV structural proteins are full length, single polypeptides of CHKV envelope proteins, or any portion thereof, which are capable of directing self-assembly of monomeric structural proteins into a nanoparticle. Amino acid sequences of structural proteins from any known CHKV virus can be used to produce fusion proteins of the present invention, so long as the amino acid sequences are capable of directing self-assembly of the fusion protein into a nanoparticle displaying immunogenic portions from an influenza virus HA protein on its surface. It is understood by those skilled in the art that CHKV proteins are expressed as a polyprotein, which is subsequently cleaved into individual proteins. The amino acid sequence of a representative CHKV polyprotein is disclosed herein as SEQ ID NO:94. It should be further understood that the amino acid sequences of immunogenic portions can be inserted into the polyprotein such upon cleavage of the polyprotein and formation of the virus-like particle, the immunogenic portions are properly folded and displayed on the surface of the nanoparticle.

HA-SA fusion proteins of the present invention need not comprise the full-length sequence of a monomeric subunit polypeptide of a self-assembly protein. Portions, or regions, of the monomeric SA subunit protein can be utilized so long as the portion comprises an amino acid sequence that directs self-assembly of the HA-SA fusion protein into a nanoparticle. One example of such a portion is located between amino acids 5 and 167 of the *Helicobacter pylori* ferritin protein (SEQ ID NO:64). More specific regions of the ferritin protein are described in Zhang, Y. Self-Assembly in the Ferritin Nano-Cage Protein Super Family. 2011, Int. J. Mol. Sci., 12, 5406-5421, which is incorporated herein by reference in its entirety.

One embodiment of the present invention is a nanoparticle comprising a heterogeneous population of HA-SA fusion proteins, wherein each HA-SA fusion protein comprises at least one immunogenic portion an influenza virus HA protein, joined to at least 25 contiguous amino acids, at least 50 contiguous amino acids, at least 75 contiguous amino acids, at least 100 contiguous amino acids, or at least 150 contiguous amino acids from a protein selected from the group consisting of ferritin, encapsulin, sulfur oxygenase reductase, lumazine synthase and pyruvate dehydrogenase complex (PDC) dihydrolipoamide acetyltransferase (E2), wherein the HA-SA fusion protein is capable of being assembled into a nanoparticle. One embodiment of the present invention is a nanoparticle comprising a heterogeneous population of HA-SA fusion proteins, wherein each HA-SA fusion protein comprises at least one immunogenic portion of an influenza virus HA protein joined to at least 25 contiguous amino acids, at least 50 contiguous amino acids, at least 75 contiguous amino acids, at least 100 contiguous amino acids, or at least 150 contiguous amino acids from an amino acid sequence selected from the group consisting of SEQ ID NO:64, SEQ ID NO:67, SEQ ID NO:70, SEQ ID NO:73, SEQ ID NO:76, SEQ ID NO:79, SEQ ID NO:82, SEQ ID NO:85, SEQ ID NO:88, SEQ ID NO:91 and SEQ ID NO:94, wherein the HA-SA fusion protein is capable of being assembled into a nanoparticle. One embodiment of the present invention is nanoparticle comprising a heterogeneous population of HA-SA fusion proteins, wherein each fusion protein comprises at least one immunogenic portion of an influenza virus HA protein joined to at least 25 contiguous amino acids, at least 50 contiguous amino acids, at least 75 contiguous amino acids, at least 100 contiguous amino acids, or at least 150 contiguous amino acids from a region of a ferritin protein comprising amino acid residues 5-167 of SEQ ID NO:64, wherein the HA-SA fusion protein is capable of being assembled into a nanoparticle.

As has been previously discussed, it is well-known in the art that some variations can be made in the amino acid sequence of a protein without affecting the activity of that protein. Such variations include insertion of amino acid residues, deletions of amino acid residues, and substitutions of amino acid residues. Thus, in one embodiment, the sequence of a SA protein subunit is divergent enough from the sequence of a SA protein subunit found in nature, such that when the variant SA protein subunit is introduced into an animal, such as a mouse, it does not result in the production of antibodies that react with the natural SA protein. According to the present invention, such a monomeric subunit is referred to as immunogenically neutral. One embodiment of the present invention is a nanoparticle comprising a heterogeneous population of HA-SA fusion proteins, wherein each fusion protein comprises at least one immunogenic portion from an influenza virus HA protein joined to an amino acid sequence at least 80%, at least 85%, at least 90%, at least 95%, or at least 97% identical to the amino acid sequence of a monomeric SA protein subunit protein capable of self-assembling into a nanoparticle, wherein the HA-SA fusion protein is capable of self-assembling into nanoparticles. In one embodiment, the HA-SA fusion protein comprises a polypeptide sequence identical in sequence to a monomeric SA protein subunit selected from the group consisting of ferritin, encapsulin, sulfur oxygenase reductase, lumazine synthase, pyruvate dehydrogenase complex (PDC) dihydrolipoamide acetyltransferase (E2) and the structural proteins of CHKV. One embodiment of the present invention is a nanoparticle comprising a heterogeneous population of HA-SA fusion proteins, wherein each fusion protein comprises at least one influenza virus HA protein immunogenic portion of the present invention joined to an amino acid sequence at least 80%, at least 85%, at least 90%, at least 95%, or at least 97% identical to the amino acid sequence of a monomeric SA protein subunit selected from the group consisting of ferritin, encapsulin, sulfur oxygenase reductase, lumazine synthase, pyruvate dehydrogenase complex (PDC) dihydrolipoamide acetyltransferase (E2) and the envelope proteins of CHKV, wherein the HA-SA fusion protein is capable of self-assembling into nanoparticles. One embodiment of the present invention is a nanoparticle comprising a heterogeneous population of HA-SA fusion proteins, wherein each fusion protein comprises at least one immunogenic portion of an influenza HA protein of the present invention joined to an amino acid sequence at least 80%, at least 85%, at least 90%, at least 95%, and at least 97% identical to a sequence selected from the group consisting of SEQ ID NO:64, SEQ ID NO:67, SEQ ID NO:70, SEQ ID NO:73, SEQ ID NO:76, SEQ ID NO: 79, SEQ ID NO:82, SEQ ID NO:85, SEQ ID NO:88, SEQ ID NO:91 and SEQ ID NO:94, wherein the HA-SA fusion protein is capable of self-assembling into nanoparticles.

In some embodiments of the present invention, the immunogenic portion of an influenza virus HA protein and the amino acid sequence of the SA protein may be joined directly to one another. In other embodiments, it may be necessary to employ linkers (also referred to as a spacer sequences) so that the various domains are in the proper special orientation. The linker sequence is designed to position the immunogenic portion of the influenza virus HA protein in such a way to that it maintains the ability to elicit an immune response to the influenza virus. Linker sequences of the present invention comprise amino acids. Preferable amino acids to use are those having small side chains and/or those which are not charged. Such amino acids are less likely to interfere with proper folding and activity of the fusion protein. Accordingly, preferred amino acids to use in linker sequences, either alone or in combination are serine, glycine and alanine. Examples of such linker sequences include, but are not limited to, SG, SGG, GSG, GG and GGSGG (SEQ ID NO: 192). Amino acids can be added, subtracted or rearranged as needed. Those skilled in the art are capable of determining appropriate linker sequences for proteins of the present invention.

In addition to linker sequences, fusion proteins of the present invention can also comprise other heterologous amino acid sequences. For example, fusion proteins may comprise signal sequences that direct the fusion protein into the proper cellular pathway. For example, a signal sequence may direct the protein into the ER-golgi complex so that it is properly glycosylated and secreted. Any signal sequence can be used as long as it directs the fusion protein in the desired manner. Examples of signal sequences useful for preparing fusion proteins of the present invention include, but are not limited to, the signal sequence from bovine prolactin, the human CD5 signal sequence and the CHIKV signal sequence.

Figure 2:
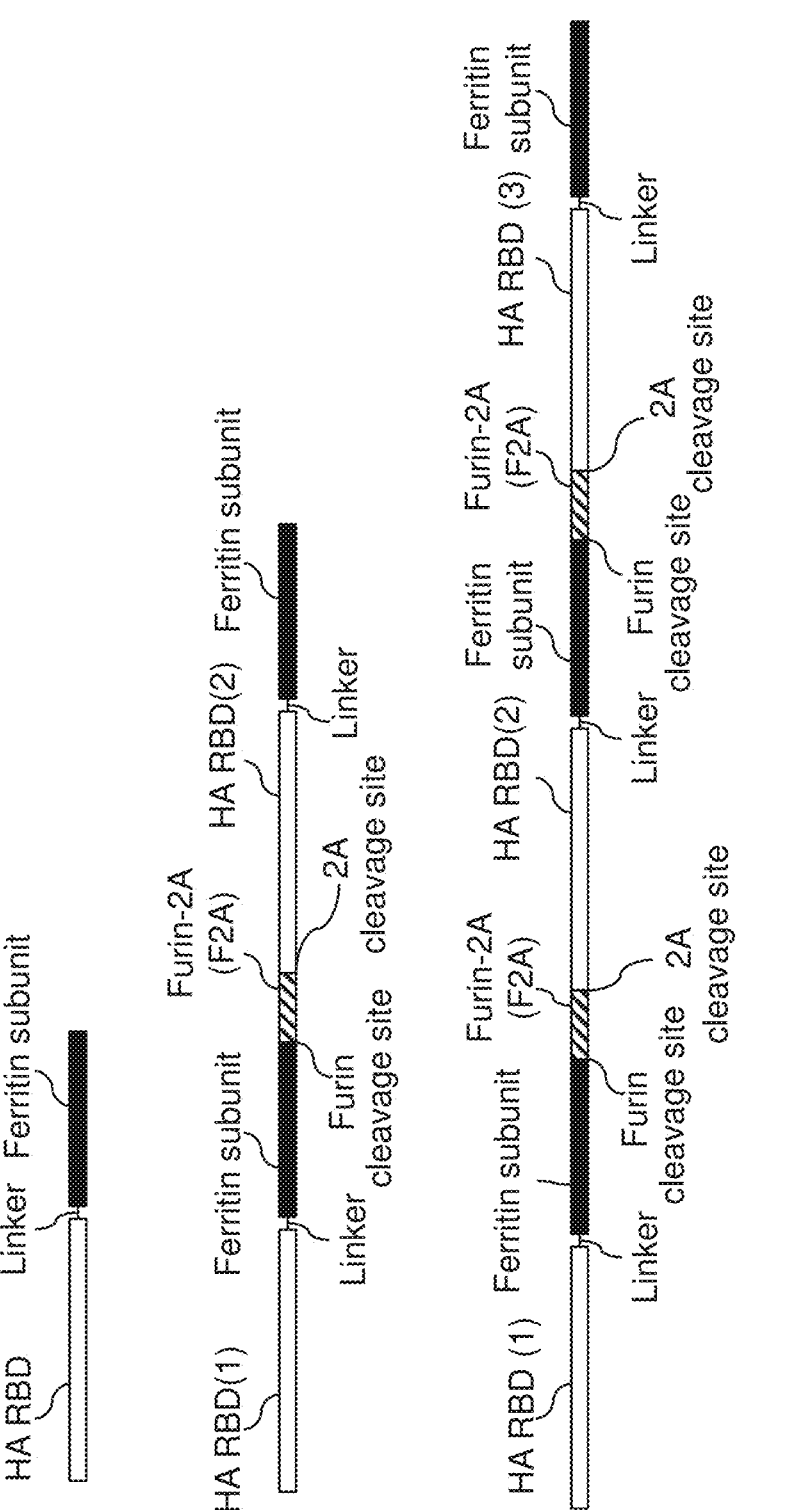
FIG. 2. Schematic representation of HA RBD-ferritin single polypeptide design. HA RBD-ferritin construct without Furin-2A (F2A) self cleavage module (top). Two or three HA RBD-ferritin constructs are connected with F2A self cleavage module (middle or bottom, respectively). As the fusion proteins are produced in producer cells, the cellular protease furin cleaves its cleavage site at the N-terminus of F2A module, and 2A protease cleaves the second (and third) HA RBD-ferritin from the F2A module. As the result, equimolar amount of each HA-RBD-ferritin is produced.

Fusion proteins of the present invention can also contain cleavage sequences. For example, in embodiments in which more than one immunogenic portion from influenza HA proteins are linked together in the fusion protein, enzyme cleavage sites can be included between segments of the fusion protein (e.g., immunogenic portions, SA proteins, linker sequences, etc.) such that upon expression of the protein, the various domains are cleaved from one another. Any cleavage sequence can be used to prepare fusion proteins of the present invention. Examples of such cleavage sequences are furin and 2A cleavage sequences. An exemplary embodiment is illustrated in FIG. 2.

In some embodiments, it may be useful to engineer mutations into the amino acid sequences of fusion proteins of the present invention. For example, it may be useful to alter sites such as enzyme recognition sites or glycosylation sites in the monomeric SA protein, the linker sequence or the immunogenic portions of the influenza HA proteins, in order to give the fusion protein beneficial properties (e.g., stability, solubility, half-life, mask portions of the protein from immune surveillance, avoid steric hinderance, etc). For example, it is known that the monomeric subunit of ferritin is not glycosylated naturally. However, it can be glycosylated if it is expressed as a secreted protein in mammalian or yeast cells. Thus, in one embodiment, potential N-linked glycosylation sites in the amino acid sequences from the monomeric ferritin subunit are mutated so that the mutated ferritin subunit sequences are no longer glycosylated at the mutated site. Examples of useful sites at which to introduce mutations include, but are not limited to, amino acid residues 98 and 264 of influenza virus HA proteins.

One embodiment of the present invention is a fusion protein encoded by a nucleic acid molecule of the present invention. One embodiment of the present invention is a fusion protein encoded by a nucleic acid molecule comprising a nucleic acid sequence at least 80%, at least 85%, at least 90%, at least 95% at least 97%, or which is, identical to a sequence selected from the group consisting of SEQ ID NO:96, SEQ ID NO:99, SEQ ID NO: 102, SEQ ID NO:105, SEQ ID NO: 108, SEQ ID NO: 111, SEQ ID NO: 114, SEQ ID NO: 117, SEQ ID NO:120, SEQ ID NO: 123, SEQ ID NO: 126, SEQ ID NO: 129, SEQ ID NO: 132, SEQ ID NO:135, SEQ ID NO: 138, SEQ ID NO: 141, SEQ ID NO: 144, SEQ ID NO: 147, SEQ ID NO:150, SEQ ID NO: 153, SEQ ID NO: 156, SEQ ID NO: 159, SEQ ID NO: 162, SEQ ID NO:165, SEQ ID NO: 168, SEQ ID NO: 171, SEQ ID NO: 174, SEQ ID NO: 177, SEQ ID NO:180, SEQ ID NO: 183, SEQ ID NO: 186 and SEQ ID NO:189. One embodiment of the present invention is a fusion protein encoded by a nucleic acid molecule comprising a nucleic acid sequence selected from the group consisting of SEQ ID NO:96, SEQ ID NO:99, SEQ ID NO:102, SEQ ID NO: 105, SEQ ID NO: 108, SEQ ID NO: 111, SEQ ID NO: 114, SEQ ID NO:117, SEQ ID NO: 120, SEQ ID NO: 123, SEQ ID NO: 126, SEQ ID NO: 129, SEQ ID NO:132, SEQ ID NO:135, SEQ ID NO: 138, SEQ ID NO: 141, SEQ ID NO: 144, SEQ ID NO:147, SEQ ID NO:150, SEQ ID NO: 153, SEQ ID NO: 156, SEQ ID NO: 159, SEQ ID NO:162, SEQ ID NO: 165, SEQ ID NO: 168, SEQ ID NO:171, SEQ ID NO:174, SEQ ID NO:177, SEQ ID NO: 180, SEQ ID NO: 183, SEQ ID NO: 186 and SEQ ID NO: 189. One embodiment of the present invention is a fusion protein encoded by a nucleic acid molecule consisting of a nucleic acid sequence selected from the group consisting of SEQ ID NO:96, SEQ ID NO:99, SEQ ID NO: 102, SEQ ID NO: 105, SEQ ID NO: 108, SEQ ID NO: 111, SEQ ID NO:114, SEQ ID NO:117, SEQ ID NO: 120, SEQ ID NO: 123, SEQ ID NO: 126, SEQ ID NO:129, SEQ ID NO: 132, SEQ ID NO: 135, SEQ ID NO: 138, SEQ ID NO: 141, SEQ ID NO:144, SEQ ID NO: 147, SEQ ID NO: 150, SEQ ID NO: 153, SEQ ID NO: 156, SEQ ID NO:159, SEQ ID NO: 162, SEQ ID NO: 165, SEQ ID NO: 168, SEQ ID NO: 171, SEQ ID NO:174, SEQ ID NO: 177, SEQ ID NO: 180, SEQ ID NO: 183, SEQ ID NO: 186 and SEQ ID NO:189.

One embodiment of the present invention is a fusion protein comprising an amino acid sequence at least 80%, at least 85%, at least 90%, at least 95% at least 97%, or which is, identical to an amino acid sequence selected form the group consisting of SEQ ID NO:97, SEQ ID NO:100, SEQ ID NO: 103, SEQ ID NO: 106, SEQ ID NO: 109, SEQ ID NO:112, SEQ ID NO:115, SEQ ID NO:118, SEQ ID NO: 121, SEQ ID NO: 124, SEQ ID NO: 127, SEQ ID NO:130, SEQ ID NO: 133, SEQ ID NO: 136, SEQ ID NO: 139, SEQ ID NO: 142, SEQ ID NO:145, SEQ ID NO:148, SEQ ID NO:151, SEQ ID NO: 154, SEQ ID NO: 157, SEQ ID NO: 160, SEQ ID NO: 163, SEQ ID NO: 166, SEQ ID NO: 169, SEQ ID NO: 172, SEQ ID NO:175, SEQ ID NO: 178, SEQ ID NO: 181, SEQ ID NO: 184, SEQ ID NO: 187 and SEQ ID NO:190. One embodiment of the present invention is a fusion protein consisting of an amino acid sequence selected form the group consisting of SEQ ID NO:97, SEQ ID NO: 100, SEQ ID NO:103, SEQ ID NO: 106, SEQ ID NO: 109, SEQ ID NO: 112, SEQ ID NO:115, SEQ ID NO:118, SEQ ID NO:121, SEQ ID NO: 124, SEQ ID NO: 127, SEQ ID NO: 130, SEQ ID NO: 133, SEQ ID NO: 136, SEQ ID NO: 139, SEQ ID NO: 142, SEQ ID NO: 145, SEQ ID NO:148, SEQ ID NO: 151, SEQ ID NO: 154, SEQ ID NO: 157, SEQ ID NO: 160, SEQ ID NO:163, SEQ ID NO: 166, SEQ ID NO: 169, SEQ ID NO: 172, SEQ ID NO: 175, SEQ ID NO:178, SEQ ID NO: 181, SEQ ID NO: 184, SEQ ID NO: 187 and SEQ ID NO: 190.

Fusion proteins of the present invention are encoded by nucleic acid molecules of the present invention. In addition, they are expressed by nucleic acid constructs of the present invention. As used herein a nucleic acid construct is a recombinant expression vector, i.e., a vector linked to a nucleic acid molecule encoding a protein such that the nucleic acid molecule can effect expression of the protein when the nucleic acid construct is administered to, for example, a subject or an organ, tissue or cell. The vector also enables transport of the nucleic acid molecule to a cell within an environment, such as, but not limited to, an organism, tissue, or cell culture. A nucleic acid construct of the present disclosure is produced by human intervention. The nucleic acid construct can be DNA, RNA or variants thereof. The vector can be a DNA plasmid, an mRNA, a viral vector, or other vector. In one embodiment, a vector can be a cytomegalovirus (CMV), retrovirus, adenovirus, adeno-associated virus, herpes virus, vaccinia virus, poliovirus, sindbis virus, or any other DNA or RNA virus vector. In one embodiment, a vector can be a pseudotyped lentiviral or retroviral vector. In one embodiment, a vector can be a DNA plasmid. In one embodiment, a vector can be a DNA plasmid comprising viral components and plasmid components to enable nucleic acid molecule delivery and expression. Methods for the construction of nucleic acid constructs of the present disclosure are well known. See, for example, *Molecular Cloning: a Laboratory Manual,* 3$^{rd}$ edition, Sambrook et al. 2001 Cold Spring Harbor Laboratory Press, and *Current Protocols in Molecular Biology,* Ausubel et al. eds., John Wiley & Sons, 1994. In one embodiment, the vector is a DNA plasmid, such as a CMV/R plasmid such as CMV/R or CMV/R 8 KB (also referred to herein as CMV/R 8κb). Examples of CMV/R and CMV/R 8 κb are provided herein. CMV/R is also described in U.S. Pat. No. 7,094,598 B2, issued Aug. 22, 2006.

As used herein, a nucleic acid molecule comprises a nucleic acid sequence that encodes an HA-SA fusion protein of the present invention. A nucleic acid molecule can be produced recombinantly, synthetically, or by a combination of recombinant and synthetic procedures. A nucleic acid molecule of the disclosure can have a wild-type nucleic acid sequence or a codon-modified nucleic acid sequence to, for example, incorporate codons better recognized by the human translation system. In one embodiment, a nucleic acid molecule can be genetically-engineered to introduce, or eliminate, codons encoding different amino acids, such as to introduce codons that encode an N-linked glycosylation site. Methods to produce nucleic acid molecules of the disclosure are known in the art, particularly once the nucleic acid sequence is know. It is to be appreciated that a nucleic acid construct can comprise one nucleic acid molecule or more than one nucleic acid molecule. It is also to be appreciated that a nucleic acid molecule can encode one protein or more than one protein.

One embodiment of the present invention is a nucleic acid molecule comprising a nucleic acid sequence encoding a fusion protein of the present invention. One embodiment of the present invention is a nucleic acid molecule comprising a nucleic acid sequence encoding a fusion protein that comprises a monomeric self-assembly subunit protein joined to one or more immunogenic portions of one or more influenza hemagglutinin proteins. One embodiment of the present invention is a nucleic acid molecule comprising a nucleic acid sequence encoding a fusion protein comprising one or more amino acid sequence at least 80%, at least 85%, at least 90%, at least 95% at least 97%, or which are, identical to one or more immunogenic portions from one or more influenza hemagglutinin proteins of the present invention, wherein the fusion protein is capable of forming a nanoparticle displaying the immunogenic portions on its surface. In a further embodiment, a nucleic acid molecule of the present invention comprises a nucleic acid sequence encoding a fusion protein comprising an amino acid sequence at least 80%, at least 85%, at least 90%, at least 95% at least 97%, or which is, identical to the amino acid sequence of a monomeric self-assembly subunit protein of the present invention, wherein the fusion protein is capable of forming a nanoparticle displaying the immunogenic portions on its surface. In one embodiment, a nucleic acid molecule of the present invention comprises a nucleic acid sequence encoding a fusion protein comprising i) one or more amino acid sequence at least 80%, at least 85%, at least 90%, at least 95% at least 97%, or which are, identical to one or more immunogenic portions from one or more influenza hemagglutinin proteins of the present invention; and, ii) an amino acid sequence at least 80%, at least 85%, at least 90%, at least 95% at least 97%, or which is, identical to the amino acid sequence of a monomeric self-assembly subunit protein of the present invention, wherein the fusion protein is capable of forming a nanoparticle displaying the immunogenic portions on its surface. One embodiment of the present invention is a nucleic acid molecule comprising a nucleic acid sequence encoding a fusion protein comprising an amino acid sequence at least 80%, at least 85%, at least 90%, at least 95% at least 97%, or which is, identical to an amino acid sequence selected form the group consisting of SEQ ID NO:97, SEQ ID NO: 100, SEQ ID NO: 103, SEQ ID NO: 106, SEQ ID NO:109, SEQ ID NO:112, SEQ ID NO:115, SEQ ID NO: 118, SEQ ID NO: 121, SEQ ID NO:124, SEQ ID NO: 127, SEQ ID NO: 130, SEQ ID NO: 133, SEQ ID NO: 136, SEQ ID NO:139, SEQ ID NO: 142, SEQ ID NO: 145, SEQ ID NO: 148, SEQ ID NO: 151, SEQ ID NO:154, SEQ ID NO: 157, SEQ ID NO: 160, SEQ ID NO: 163, SEQ ID NO: 166, SEQ ID NO:169, SEQ ID NO: 172, SEQ ID NO: 175, SEQ ID NO: 178, SEQ ID NO: 181, SEQ ID NO:184, SEQ ID NO:187 and SEQ ID NO:190. One embodiment of the present invention is a nucleic acid molecule comprising a nucleic acid sequence encoding a fusion protein comprising an amino acid sequence selected form the group consisting of SEQ ID NO:97, SEQ ID NO:100, SEQ ID NO: 103, SEQ ID NO: 106, SEQ ID NO: 109, SEQ ID NO: 112, SEQ ID NO: 115, SEQ ID NO:118, SEQ ID NO: 121, SEQ ID NO:124, SEQ ID NO:127, SEQ ID NO:130, SEQ ID NO:133, SEQ ID NO: 136, SEQ ID NO: 139, SEQ ID NO: 142, SEQ ID NO: 145, SEQ ID NO:148, SEQ ID NO: 151, SEQ ID NO: 154, SEQ ID NO: 157, SEQ ID NO: 160, SEQ ID NO:163, SEQ ID NO: 166, SEQ ID NO: 169, SEQ ID NO: 172, SEQ ID NO: 175, SEQ ID NO:178, SEQ ID NO: 181, SEQ ID NO: 184, SEQ ID NO: 187 and SEQ ID NO:190. One embodiment of the present invention is a nucleic acid molecule comprising a nucleic acid sequence at least 80%, at least 85%, at least 90%, at least 95% at least 97%, or which is, identical to a sequence selected form the group consisting of SEQ ID NO:96, SEQ ID NO:98, SEQ ID NO:99, SEQ ID NO: 101, SEQ ID NO: 102, SEQ ID NO: 104, SEQ ID NO: 105, SEQ ID NO:107, SEQ ID NO: 108, SEQ ID NO: 110, SEQ ID NO: 111, SEQ ID NO: 113, SEQ ID NO:114, SEQ ID NO: 116, SEQ ID NO:117, SEQ ID NO: 119, SEQ ID NO: 120, SEQ ID NO: 122, SEQ ID NO: 123, SEQ ID NO: 125, SEQ ID NO: 126, SEQ ID NO: 128, SEQ ID NO: 129, SEQ ID NO: 131, SEQ ID NO: 132, SEQ ID NO: 134, SEQ ID NO:135, SEQ ID NO:137, SEQ ID NO: 138, SEQ ID NO: 140, SEQ ID NO:141, SEQ ID NO: 143, SEQ ID NO:144, SEQ ID NO: 146, SEQ ID NO: 147, SEQ ID NO: 149, SEQ ID NO: 150, SEQ ID NO:152, SEQ ID NO: 153, SEQ ID NO: 155, SEQ ID NO: 156, SEQ ID NO: 158, SEQ ID NO:159, SEQ ID NO: 161, SEQ ID NO: 162, SEQ ID NO: 164, SEQ ID NO: 165, SEQ ID NO: 167, SEQ ID NO: 168, SEQ ID NO: 170, SEQ ID NO: 171, SEQ ID NO: 173, SEQ ID NO:174, SEQ ID NO: 176, SEQ ID NO: 177, SEQ ID NO: 179, SEQ ID NO: 180, SEQ ID NO:182, SEQ ID NO:183, SEQ ID NO: 185, SEQ ID NO: 186, SEQ ID NO: 188, SEQ ID NO:189 and SEQ ID NO: 191. One embodiment of the present invention is a nucleic acid molecule comprising a nucleic acid sequence selected from the group consisting of SEQ ID NO:96, SEQ ID NO:98, SEQ ID NO:99, SEQ ID NO: 101, SEQ ID NO: 102, SEQ ID NO: 104, SEQ ID NO: 105, SEQ ID NO: 107, SEQ ID NO: 108, SEQ ID NO: 110, SEQ ID NO: 111, SEQ ID NO:113, SEQ ID NO: 114, SEQ ID NO: 116, SEQ ID NO: 117, SEQ ID NO:119, SEQ ID NO:120, SEQ ID NO: 122, SEQ ID NO:123, SEQ ID NO: 125, SEQ ID NO: 126, SEQ ID NO: 128, SEQ ID NO: 129, SEQ ID NO: 131, SEQ ID NO: 132, SEQ ID NO: 134, SEQ ID NO:135, SEQ ID NO:137, SEQ ID NO: 138, SEQ ID NO: 140, SEQ ID NO: 141, SEQ ID NO: 143, SEQ ID NO: 144, SEQ ID NO: 146, SEQ ID NO: 147, SEQ ID NO: 149, SEQ ID NO: 150, SEQ ID NO: 152, SEQ ID NO: 153, SEQ ID NO: 155, SEQ ID NO: 156, SEQ ID NO: 158, SEQ ID NO: 159, SEQ ID NO: 161, SEQ ID NO: 162, SEQ ID NO: 164, SEQ ID NO:165, SEQ ID NO: 167, SEQ ID NO: 168, SEQ ID NO: 170, SEQ ID NO: 171, SEQ ID NO:173, SEQ ID NO:174, SEQ ID NO: 176, SEQ ID NO: 177, SEQ ID NO: 179, SEQ ID NO:180, SEQ ID NO: 182, SEQ ID NO: 183, SEQ ID NO: 185, SEQ ID NO: 186, SEQ ID NO:188, SEQ ID NO: 189 and SEQ ID NO:191. One embodiment of the present invention is a nucleic acid molecule consisting of a nucleic acid sequence selected from the group consisting of SEQ ID NO:96, SEQ ID NO:98, SEQ ID NO:99, SEQ ID NO: 101, SEQ ID NO: 102, SEQ ID NO:104, SEQ ID NO: 105, SEQ ID NO: 107, SEQ ID NO: 108, SEQ ID NO:110, SEQ ID NO: 111, SEQ ID NO: 113, SEQ ID NO: 114, SEQ ID NO: 116, SEQ ID NO:117, SEQ ID NO:119, SEQ ID NO: 120, SEQ ID NO: 122, SEQ ID NO: 123, SEQ ID NO: 125, SEQ ID NO:126, SEQ ID NO: 128, SEQ ID NO: 129, SEQ ID NO: 131, SEQ ID NO: 132, SEQ ID NO: 134, SEQ ID NO: 135, SEQ ID NO: 137, SEQ ID NO: 138, SEQ ID NO: 140, SEQ ID NO:141, SEQ ID NO: 143, SEQ ID NO: 144, SEQ ID NO: 146, SEQ ID NO: 147, SEQ ID NO:149, SEQ ID NO: 150, SEQ ID NO: 152, SEQ ID NO: 153, SEQ ID NO: 155, SEQ ID NO: 156, SEQ ID NO: 158, SEQ ID NO: 159, SEQ ID NO: 161, SEQ ID NO: 162, SEQ ID NO:164, SEQ ID NO:165, SEQ ID NO: 167, SEQ ID NO: 168, SEQ ID NO: 170, SEQ ID NO:171, SEQ ID NO: 173, SEQ ID NO: 174, SEQ ID NO: 176, SEQ ID NO: 177, SEQ ID NO:179, SEQ ID NO: 180, SEQ ID NO: 182, SEQ ID NO: 183, SEQ ID NO: 185, SEQ ID NO:186, SEQ ID NO: 188, SEQ ID NO: 189 and SEQ ID NO:191.

As has been discussed, nanoparticles of the present invention comprise populations of fusion proteins which are heterogeneous due to at least two fusion proteins in the population differing in their amino acid sequences by at least one amino acid. It will be appreciated by those skilled in the art that, as described hereto, a heterogeneous population of fusion proteins can be due to the aforementioned amino acid difference being at any location in the fusion protein, including in the SA portion of the protein. However, preferred nanoparticles of the present invention are those in which a single nanoparticle is capable of eliciting an immune response to more than one Type, sub-type or strain of influenza virus. Consequently, preferred nanoparticles are those comprising a heterogeneous population of fusion proteins, wherein at least two fusion proteins in the heterogeneous population differ in the sequences of their immunogenic portions by at least one amino acid. It should be understood that fusion proteins of preferred nanoparticles are not excluded from having sequences differences in regions other than the immunogenic portion. However, in order to elicit an immune response against more than one Type, Group, sub-type or strain of influenza virus, preferred nanoparticles comprise at least two fusion proteins that differ by at least one amino acid residue in the their immunogenic portions. It will be understood by those skilled in the art that differences in the amino acid sequences of the immunogenic portion of two fusion proteins may or may not cause the two different immunogenic portions (i.e., the two species of immunogenic portions) to be recognized by two different receptors (e.g., B-cell, T-cell, etc). Such differences, or lack thereof, in recognition depend on such things as, for example, the differences in properties between the corresponding amino acid residues in the immunogenic portions and whether or not the locations at which the sequences differ (i.e., the amino acid residue) are part of the recognized epitope. In preferred embodiments, the heterogeneous population comprises at least two species of fusion proteins, wherein the immunogenic portions of each of the species is recognized by the same B-cell receptor, T-cell receptor and/or antibody. Thus, in one embodiment, a nanoparticle of the present invention elicits a cross-reactive immune response (an immune response against more than one Type, subtype or strain of influenza virus).

It should be understood that the number of immunogenic regions displayed by nanoparticles of the present invention is only limited by the number of fusion proteins that make up the nanoparticle, which itself is determined by the SA protein used to construct the fusion proteins. For example, ferritin forms a nanoparticle consisting of 24 monomeric, ferritin subunit proteins. Thus, ferritin-based nanoparticle of the present invention can comprise a maximum of 24 fusion proteins and thus, can display a maximum of 24 different immunogenic portions. Similarly, encapsulin proteins from *Thermotoga maritima* form nanoparticles having 60 subunits. Thus, encapsulin-based nanoparticle of the present invention can display a maximum of 60 different immunogenic portions. Likewise, structural proteins from CHIKV form virus-like particles having 240 envelope E2 subunits. Thus CHIKV-based virus-like particle of the present invention can display a maximum of 240 different immunogenic portions. Those skilled in the art will understand that such calculations assume each fusion protein comprises a single immunogenic portion. Nanoparticles displaying higher numbers of immunogenic portions could of course be constructed using fusion proteins comprising two or more immunogenic portions. An example of a fusion protein comprising multiple epitopes is illustrated in FIG. 2. In one embodiment, the nanoparticles comprises a heterogeneous population of fusion proteins, wherein each fusion protein comprises a single immunogenic portion of an influenza HA protein. In one embodiment, the nanoparticles comprises a heterogeneous population of fusion proteins, wherein each fusion protein comprises multiple immunogenic portions from one or more influenza HA proteins. In one embodiment, the nanoparticles comprises a heterogeneous population of fusion proteins, wherein each fusion protein comprises at least 2, at least 3, at least 4 or at least 5 immunogenic portions from one or more influenza HA proteins.

In one embodiment, a nanoparticle of the present invention comprises between 2 and 240 species of fusion proteins, wherein each species differs from every other species, at least in part, by at least one amino acid in change in the sequence of its immunogenic portion. In certain embodiments, a nanoparticle of the present invention comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 3, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230 or at least 240 species of fusion proteins, wherein the species differ from one another, at least in part, by at least one amino acid in their immunogenic portions. In certain embodiments, a nanoparticle of the present invention display at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 3, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59 or at least 60 unique immunogenic portions.

One embodiment of the present invention is a method of producing nanoparticles of the present invention, the method comprising introducing one or more nucleic acid molecules encoding fusion proteins of the present invention into a cell, and incubating the cell under conditions suitable for expressing the encoded proteins and forming nanoparticles. In a further embodiment, the nanoparticles are isolated from the cell into which the nucleic acid molecule was introduced. Methods of isolating nanoparticles are known to those skilled in the art and are also described in U.S. patent application Ser. No. 13/131,287 and International Application No. PCT/US14/60142, both of which are incorporated herein by reference in their entirety. It should be realized by those skilled in the art nanoparticles displaying a heterogeneous population of immunogenic portions on its surface can be produced by either i) introducing more than one nucleic acid molecule into the cell, wherein each nucleic acid molecule encodes a different species of fusion protein; and/or ii) introducing one or more nucleic acid molecule into a cell, wherein at least one nucleic acid molecule encode at least one of the one or more nucleic acid molecules encode a species of fusion protein that differs from a fusion protein encoded by a nucleic acid molecule introduced into the cell. Thus, for example, a nanoparticle comprising a heterogeneous population of fusion proteins can be produced by introducing into a cell a nucleic acid molecule encoding two different species of fusion proteins.

Nanoparticles of the present invention can also be produced by combining expressed and isolated recombinant proteins. Thus, one embodiment of the present invention is a method of producing nanoparticles of the present invention, the method comprising introducing into a cell a nucleic acid molecule encoding a fusion protein of the present invention, incubating the cell under conditions suitable for expressing the protein encoded by the nucleic acid molecule, and isolating the expressed protein. The isolated proteins are then disassembled and combined with one or more heterogeneous species of isolated, disassembled fusion protein (i.e., fusion proteins having a different sequence, especially in their immunogenic portion) such that the mixture of heterogeneous species of fusion proteins reassembles in a nanoparticle comprising a heterogeneous population of fusion proteins, wherein each nanoparticle comprises at least two different species of fusion proteins.

Because nanoparticles of the present invention elicit an immune response to an infectious agent, such as influenza virus, they can be used as vaccines to protect individuals against infection by one or more Types, sub-types, strains and/or species of infectious agent (e.g., influenza virus). Thus, one embodiment of the present invention is a vaccine comprising a nanoparticle of the present invention. Vaccines of the present invention can also contain other components such as adjuvants, buffers and the like. Although any adjuvant can be used, preferred embodiments can contain: chemical adjuvants such as aluminum phosphate, benzy- alkonium chloride, ubenimex, and QS21; genetic adjuvants such as the IL-2 gene or fragments thereof, the granulocyte macrophage colony-stimulating factor (GM-CSF) gene or fragments thereof, the IL-18 gene or fragments thereof, the chemokine (C—C motif) ligand 21 (CCL21) gene or fragments thereof, the IL-6 gene or fragments thereof, CpG, LPS, TLR agonists, and other immune stimulatory genes; protein adjuvants such IL-2 or fragments thereof, the granulocyte macrophage colony-stimulating factor (GM-CSF) or fragments thereof, IL-18 or fragments thereof, the chemokine (C—C motif) ligand 21 (CCL21) or fragments thereof, IL-6 or fragments thereof, CpG, LPS, TLR agonists and other immune stimulatory cytokines or fragments thereof; lipid adjuvants such as cationic liposomes, N3 (cationic lipid), monophosphoryl lipid A (MPL1); other adjuvants including cholera toxin, enterotoxin, Fms-like tyrosine kinase-3 ligand (Flt-3L), bupivacaine, marcaine, and levamisole.

One embodiment of the present invention is a method to vaccinate an individual against an infectious agent, the method comprising administering to the individual a nanoparticle of the present invention. One embodiment of the present invention is a method to vaccinate an individual against influenza virus, the method comprising administering to the individual a nanoparticle vaccine of the present invention. In one embodiment, the nanoparticle comprises self-assembling fusion proteins of the present invention, and the nanoparticle displays on its surface a heterogeneous population of immunogenic portions from HA proteins from one or more types, subtypes or strains of influenza virus.

One embodiment of the present invention is a method to vaccinate an individual against infection with influenza virus, the method comprising:

a) obtaining a nanoparticle of the present invention; and,
  b) administering the nanoparticle to an individual such that an immune response against an influenza virus is produced. As used herein, an immune response to a vaccine, or nanoparticle, of the present invention is the development in a subject of a humoral and/or a cellular immune response to a hemagglutinin protein present in the vaccine. For purposes of the present invention, a "humoral immune response" refers to an immune response mediated by antibody molecules, including secretory IgA or IgG molecules, while a "cellular immune response" is one mediated by T-lymphocytes and/or other white blood cells. One important aspect of cellular immunity involves an antigen-specific response by cytolytic T-cells ("CTL"s). CTLs have specificity for peptide antigens that are presented in association with proteins encoded by the major histocompatibility complex (MHC) and expressed on the surfaces of cells. CTLs help induce and promote the destruction of intracellular microbes, or the lysis of cells infected with such microbes. Another aspect of cellular immunity involves an antigen-specific response by helper T-cells. Helper T-cells act to help stimulate the function, and focus the activity of, non-specific effector cells against cells displaying peptide antigens in association with MHC molecules on their surface. A cellular immune response also refers to the production of cytokines, chemokines and other such molecules produced by activated T-cells and/or other white blood cells, including those derived from CD4+ and CD8+T-cells.

Thus, an immunological response may be one that stimulates CTLs, and/or the production or activation of helper T-cells. The production of chemokines and/or cytokines may also be stimulated. The vaccine may also elicit an antibody-mediated immune response. Hence, an immunological response may include one or more of the following effects: the production of antibodies (e.g., IgA or IgG) by B-cells; and/or the activation of suppressor, cytotoxic, or helper T-cells and/or T-cells directed specifically to a protein (e.g., hemagglutinin) present in the vaccine. These responses may serve to neutralize infectivity, and/or mediate antibody-complement, or antibody dependent cell cytotoxicity (ADCC) to provide protection to an immunized individual. Such responses can be determined using standard immunoassays and neutralization assays, well known in the art.

As used herein, neutralizing antibodies are antibodies that prevent in infectious agent from replicating and spreading within a host. With regard to influenza virus, neutralizing antibodies prevent influenza virus from completing one round of replication. As defined herein, one round of replication refers the life cycle of the virus, starting with attachment of the virus to a host cell and ending with budding of newly formed virus from the host cell. This life cycle includes, but is not limited to, the steps of attaching to a cell, entering a cell, cleavage and rearrangement of the HA protein, fusion of the viral membrane with the endosomal membrane, release of viral ribonucleoproteins into the cytoplasm, formation of new viral particles and budding of viral particles from the host cell membrane.

In one embodiment, a vaccine or nanoparticle of the present invention elicits broadly neutralizing antibodies. As used herein, broadly neutralizing antibodies are antibodies that neutralize more than one genera, type, subtype, species and/or strain of infectious agent within a taxonomic family. With specific regard to influenza viruses used herein, broadly neutralizing antibodies are antibodies that neutralize more than one type, subtype and/or strain of influenza virus. For example, broadly neutralizing antibodies elicited against an HA protein from a Type A influenza virus may neutralize a Type B or Type C virus. As a further example, broadly neutralizing antibodies elicited against an HA protein from Group 1 influenza virus may neutralize a Group 2 virus. As an additional example, broadly neutralizing antibodies elicited against an HA protein from one sub-type or strain of virus, may neutralize another sub-type or strain of virus. For example, broadly neutralizing antibodies elicited against an HA protein from an H1 influenza virus may neutralize viruses from one or more sub-types selected from the group consisting of H2, H3, H4, H5, H6, H7, H8, H8, H10, H11, H12, H13, H14, H15, H16, H17 or H18.

The terms individual, subject, and patient are well-recognized in the art, and are herein used interchangeably to refer to any human or other animal susceptible to influenza infection. Examples include, but are not limited to, humans and other primates, including non-human primates such as chimpanzees and other apes and monkey species; farm animals such as cattle, sheep, pigs, seals, goats and horses; domestic mammals such as seals, dogs and cats; laboratory animals including rodents such as mice, rats and guinea pigs; birds, including domestic, wild and game birds such as chickens, turkeys and other gallinaceous birds, ducks, geese, and the like. The terms individual, subject, and patient by themselves, do not denote a particular age, sex, race, and the like. Thus, individuals of any age, whether male or female, are intended to be covered by the present disclosure and include, but are not limited to the elderly, adults, children, babies, infants, and toddlers. Likewise, the methods of the present invention can be applied to any race, including, for example, Caucasian (white), African-American (black), Native American, Native Hawaiian, Hispanic, Latino, Asian, and European. An infected subject is a subject that is known to have influenza virus in their body.

Methods of the present invention can be used to vaccinate any individual. Such individual can, but need not, be suspected of having been exposed to an infectious agent, such as influenza virus. Similarly, methods of the present invention can be used to vaccinate an individual known to have been exposed to and infectious agent, such as influenza virus, or a person suspected of, or known to have, having been exposed to an infectious agent, such as influenza virus. As such, methods of the present invention can be used to contain a known, or potential, out break of an infectious agent, such as influenza (e.g., epidemic, pandemic).

One embodiment of the present invention is a method to vaccinate an individual against influenza virus, the method comprising administering a vaccine of the embodiments to an individual in need of such a vaccine, such that an immune response against influenza virus is produced in the individual, wherein the vaccine comprises a nanoparticle comprising self-assembling fusion proteins, wherein the nanoparticle displays on its surface a heterogeneous population of immunogenic portions from HA proteins from one or more Type, Group, sub-type or strain of influenza virus. In one embodiment, the immunogenic portions are from the globular head regions of HA proteins from one or more Type, Group, sub-type or strain of influenza virus. In one embodiment, the immunogenic portions are from the RBDs of HA proteins from one or more Type, group, sub-type or strain of influenza virus.

Another embodiment of the present invention is a method to vaccinate an individual against infection with influenza virus, the method comprising:

a) obtaining a vaccine comprising at least one nanoparticle comprising HA-SA fusion proteins, wherein the fusion proteins comprise an SA protein joined to an immunogenic portion of an influenza HA protein, and wherein the nanoparticle displays on its surface a heterogeneous population of immunogenic portions from HA proteins from one or more Type, Group, sub-type or strain of influenza virus; and, b) administering the vaccine to an individual such that an immune response against an influenza virus is produced. In one embodiment, the immunogenic portions are from the globular head regions of HA proteins from one or more Types, sub-types or strains of influenza virus. In one embodiment, the immunogenic portions are from the RBDs of HA proteins from one or more Types, sub-types or strains of influenza virus.

Vaccines of the present invention can be used to vaccinate individuals using a prime/boost protocol. Such a protocol is described in U.S. Patent Publication No. 20110177122, which is incorporated herein by reference in its entirety. In such a protocol, a first vaccine composition may be administered to the individual (prime) and then after a period of time, a second vaccine composition may be administered to the individual (boost). Administration of the boosting composition is generally weeks or months after administration of the priming composition, preferably about 2-3 weeks or 4 weeks, or 8 weeks, or 16 weeks, or 20 weeks, or 24 weeks, or 28 weeks, or 32 weeks. In one embodiment, the boosting composition is formulated for administration about 1 week, or 2 weeks, or 3 weeks, or 4 weeks, or 5 weeks, or 6 weeks, or 7 weeks, or 8 weeks, or 9 weeks, or 16 weeks, or 20 weeks, or 24 weeks, or 28 weeks, or 32 weeks after administration of the priming composition. As used herein, a vaccinated subject is a subject that has been administered a vaccine that is intended to provide a protective effect against an influenza virus.

The first and second vaccine compositions can be, but need not be, the same composition. Thus, in one embodiment of the present invention, the step of administering the vaccine comprises administering a first vaccine composition, and then at a later time, administering a second vaccine composition. In one embodiment, the first vaccine composition comprises a nanoparticle of the present invention.

In one embodiment, the individual has been exposed to influenza virus. As used herein, the terms exposed, exposure, and the like, indicate the subject has come in contact with a person of animal that is known to be infected with an influenza virus. Vaccines of the present invention may be administered using techniques well known to those in the art. Techniques for formulation and administration may be found, for example, in "Remington's Pharmaceutical Sciences", 18th ed., 1990, Mack Publishing Co., Easton, PA. Vaccines may be administered by means including, but not limited to, traditional syringes, needleless injection devices, or microprojectile bombardment gene guns. Suitable routes of administration include, but are not limited to, parenteral delivery, such as intramuscular, intradermal, subcutaneous, intramedullary injections, as well as, intrathecal, direct intraventricular, intravenous, intraperitoneal, intranasal, or intraocular injections, just to name a few. For injection, the compounds of one embodiment of the invention may be formulated in aqueous solutions, preferably in physiologically compatible buffers such as Hanks' solution, Ringer's solution, or physiological saline buffer.

In one embodiment, vaccines, or nanoparticles, of the present invention can be used to protect an individual against infection by heterologous influenza virus. That is, a vaccine made using hemagglutinin protein from one strain of influenza virus is capable of protecting an individual against infection by different strains of influenza. For example, a vaccine made using hemagglutinin protein from influenza A/New Caledonia/20/1999 (H1N1), A/California/04/2009 (H1N1), A/Singapore/1/1957 (H2N2), A/Hong Kong/1/1968 (H3N2), A/Brisbane/10/2007 (H3N2), A/Indonesia/05/2005 (H5N1), B/Florida/4/2006 (influenza B), A/Perth/16/2009 (H3N2), A/Brisbane/59/2007 (H1N1), B/Brisbane/60/2008 (influenza B), A/Wilson-Smith/33 (H1N1), A/Tientsin/78/77 (H1N1), A/Texas/36/91 (H1N1), A/Singapore/6/86 (H1N1), A/Memphis/39/83 (H1N1), A/Malaysia/54 (H1N1), A/Iowa/43 (H1N1), A/Hong Kong/117/77 (H1N1), A/Fort Monmouth/1/47 (H1N1), A/Brisbane/59/07 (H1N1), A/Baylor/4052/81 (H1N1), A/Albany/4835/48 (H1N1), A/Hong Kong/156/97 (H5N1), A/common magpie/Hong Kong/5052/07 (H5N1), A/chicken/Shanxi/2/06 (H5N1), A/silky chicken/Hong Kong/SF189/01 (H5N1), A/chicken/Henan/16/04 (H5N1), A/Victoria/361/11 (H3N2), B/Massachusetts/2/12 (influenza B), B/Brisbane/60/08 (influenza B) and A/Texas/50/12 (H3N2).

In one embodiment, vaccines, or nanoparticles, of the present invention can be used to protect an individual against infection by an antigenically divergent influenza virus. In this regard, the term antigenically divergent refers to the tendency of a strain of influenza virus to mutate over time, thereby changing the amino acids that are displayed to the immune system. Such mutation over time is also referred to as antigenic drift. Thus, for example, a vaccine made using hemagglutinin protein from an A/New Caledonia/20/1999 (H1N1) strain of influenza virus is capable of protecting an individual against infection by earlier, antigenically divergent New Caledonia strains of influenza, and by evolving (or diverging) influenza strains of the future.

One embodiment of the present invention is a kit for practicing methods of the present invention. Kits can include nanoparticles or vaccines of the present invention as well components for making such nanoparticles and vaccines. As such, kits can include, for example, primers, nucleic acid molecules, expression vectors, DNA constructs encoding proteins of the present invention, cells, buffers, reagents, syringes, and directions for using any of said components. It should be appreciated that a kit may comprise more than one container comprising any of the aforementioned, or related, components. For example, certain parts of the kit may require refrigeration, whereas other parts can be stored at room temperature. Thus, as used herein, a kit comprises components sold in separate containers by one or more entity, with the intention that the components contained therein be used together.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

The inventors have discovered that specific fusion proteins comprising portions of hemagglutinin protein are useful for eliciting a broad immune response against influenza viruses. Each of these embodiments will now be disclosed in detail below.

EXAMPLES

Example 1. Production of Heterogeneous
Nanoparticles

A. Gene Synthesis and Vector Construction

All genes used in the study were human codon optimized. The gene encoding *Helicobacter pylori*-bullfrog hybrid ferritin was constructed by fusing residues 2-9 of bullfrog (*Rana catesbeiana*) ferritin lower subunit (UniProt: P07797 with a point mutation at residue 8 (N8Q) to abolish a potential N-glycosylation site) to *H. pylori* nonheme ferritin (UniProt: Q9ZLI1, residues 3-167) with mutations at residue 7 (17E) and residue 19 (N19Q) to make a salt bridge with 6R of bullfrog ferritin and abolish a potential N-glycosylation site, respectively. In some cases, there were extra GS residues at the carboxyl terminus of *H. pylori* ferritin. The secreted encapsulin gene was constructed by fusing a human CD5 signal to *Termotoga maritima* encapsulin (UniProt: Q9WZP2, residues 1-264). The genes encoding HA RBD (residues 56-264, H3 numbering system) were synthesized or amplified from appropriate plasmids. In some cases, the Y98F mutation was introduced to abolish sialic acid binding property of HA, and the F/K264A mutation to avoid potential steric crash at the junction between HA RBD and nanoparticle scaffolds. These fragments were fused to downstream of a modified bovine prolactin signal sequence (bPRL: MDSKGSSQKG SRLLLLLVVS NLLLPQGVLA (SEQ ID NO: 192, which is also residues 1-30 of SEQ ID NO: 97) and upstream of the hybrid ferritin with a SG linker to give rise to the HA RBD-ferritin genes. To construct the HA RBD-encapsulin genes, gp350 fragments were fused to downstream of encapsulin with a SG linker. To construct HA RBD-Chikungunya virus-like particle (CHIKVLP), the HA RBD gene fragments (residues 59-264, H3 numbering system) were amplified and inserted in the furin cleavage loop between envelope E3 and E2. To accommodate HA RBD insertion and furin cleavage, there were 3 amino acid deletions in E3 (E3 residues 58-60, SPH) and 4 amino acid deletions in E2 (E2 residues 1-4, STKD). All genes were then cloned into the CMV/R or CMV/R 8кb mammalian expression vector for protein production.

B. Biosynthesis of Recombinant Proteins and Purification

The expression vectors were transiently transfected into FreeStyle 293F or Expi293F cells (Life Technologies) using 293fectin or ExpiFectamine 293 transfection reagents, respectively (Life Technologies). For co-transfection, equimolar amount of 2-8 different plasmids were mixed (a total DNA amount was constant for all transfections). Four days after transfection, culture supernatants were harvested and cleared. The HA RBD-ferritin and HA RBD-encapsulin nanoparticles were purified by ion exchange chromatography using Q Sepharose HP (GE Healthcare) followed by size exclusion chromatography with a Superose 6 10/300 GL column (GE Healthcare) in PBS. The HA RBD-CHIKVLP were purified by ultracentrifugation using Opriprep (Sigma-Aldrich). Briefly, the cleared culture supernatants were overlaid on 1 ml of Optiprep and spun at 50,000 ref in an SW 32 Ti rotor for 90 min. After the spin, bottom 2 ml was collected, mixed thoroughly to make 1:1 Optiprep/concentrated supernatant mixture, and spun again at 360,000 rcf in an NVT 100 rotor for 3 hours. The band corresponding HA RBD-CHIKVLP was collected and further purified by a Sephacryl S-500 16/60 HR column (GE Healthcare) in PBS.

C. Electron Microscopy (EM) of Purified Nanoparticles

Figures 3A, 3B, 3C:
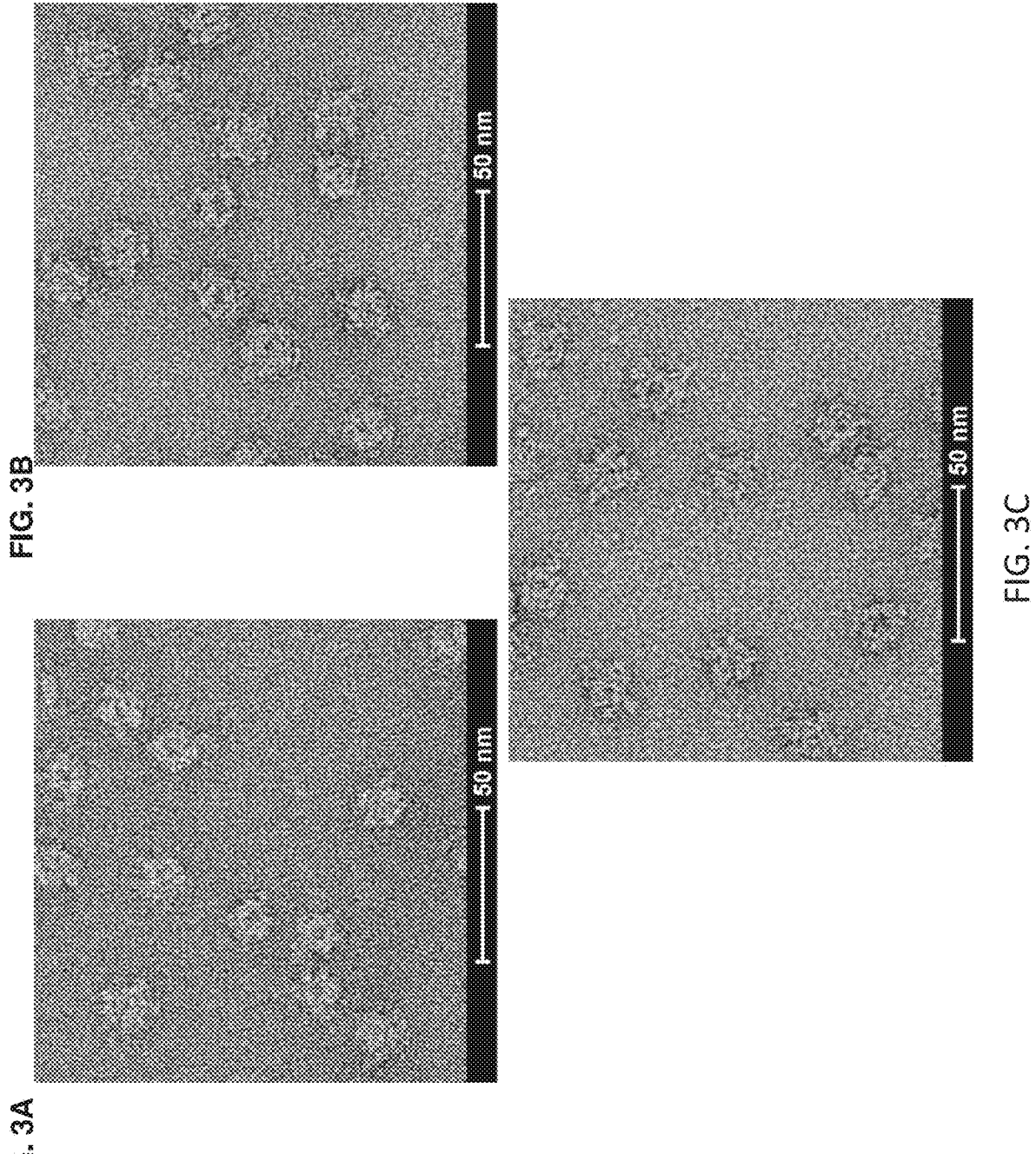
FIGS. 3A-3C. Electron microscopic analysis of HA RBD-nanoparticles. (A) Negative stain electron micrographs of NC99 RBD-nanoparticles; (B) Negative stain electron micrographs of CA09 RBD-nanoparticles; (C) Negative stain electron micrographs of co-assembled (CoAsmbl 2) RBD-nanoparticles. Purified particles were adsorbed to freshly glow-discharged carbon-coated grids and stained with uranyl formate.
Figure 4:
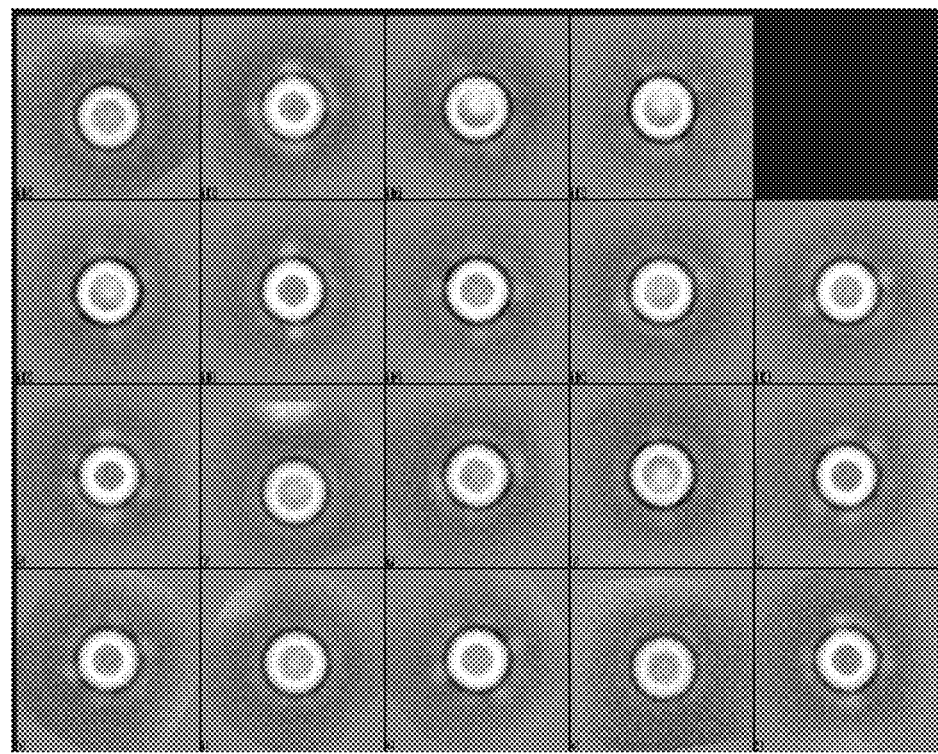
FIG. 4. Two-dimension classifications of NC99 RBD-nanoparticles were calculated using images stained with ammonium molybdate instead of uranyl formate.

The nanoparticles purified in part (B) were analyzed by negative stain EM. Briefly, samples of about 50 μg ml$^{-1}$ were adsorbed to freshly glow-discharged carbon-coated grids, rinsed with PBS, and stained with 0.75% uranyl formate solution. Images were recorded on an FEI T20 microscope with an Eagle CCD camera. The results of these analyses are shown in FIGS. 3 and 4.

Figure 5:
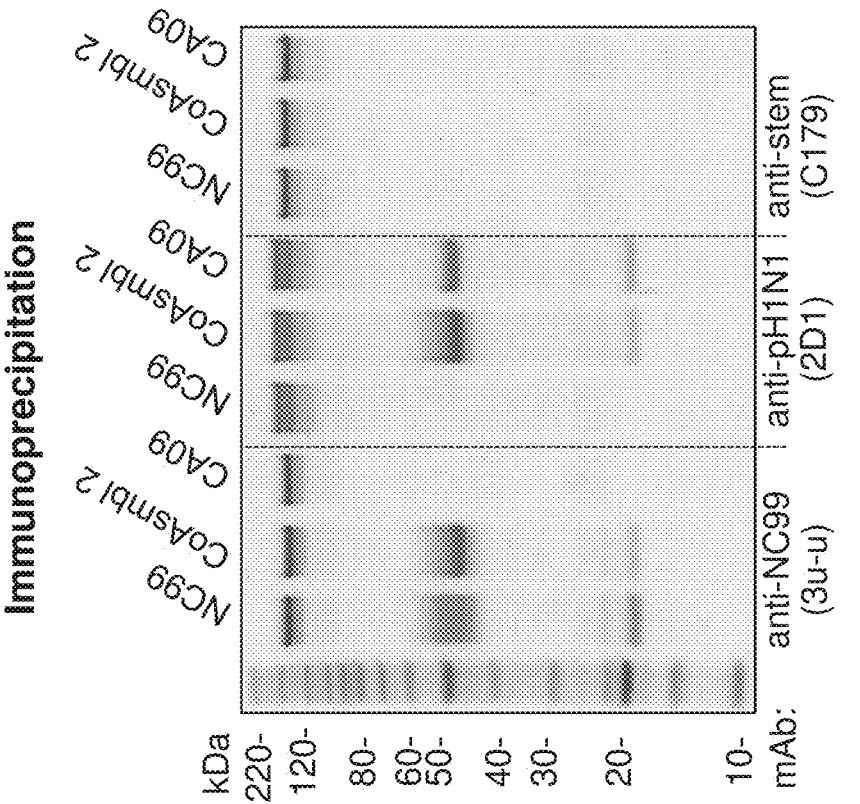
FIG. 5. Characterization of HA RBD-nanoparticles. Monovalent (NC99=A/New Caledonia/20/1999 and CA09 A/California/04/2009) and co-assembled (CoAsmbl2=A/New Caledonia/20/99 (NC99)+A/California/04/09 (CA09)) nanoparticles were immunoprecipitated using either anti-NC99 (3u-u)(left), anti-pandemic H1N1 HA (2D1)(center) or anti-HA stem (C179) (right) monoclonal antibodies. The precipitated material was then analyzed by SDS-PAGE Protein bands at ~150 and ~50 kDa correspond to IgG, RBD-nanoparticle subunits, respectively.
Figure 6:
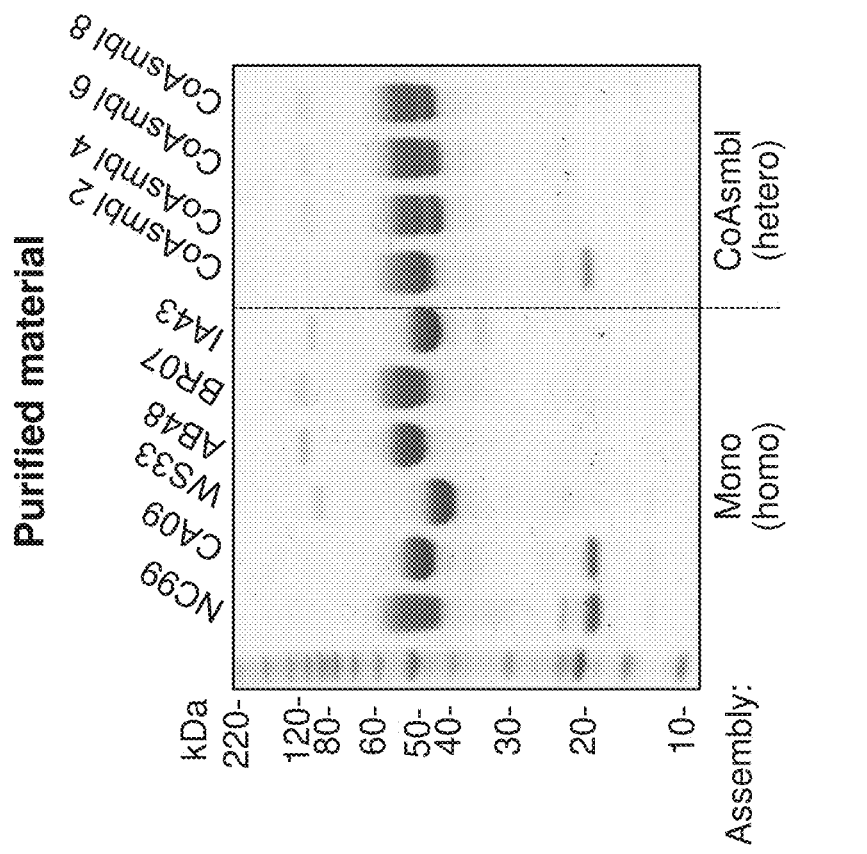
FIG. 6. SDS-PAGE analysis of purified HA RBD-nanoparticles from different H1N1 strains and co-assembled RBD-nanoparticles with different combinations of HA. NC99=A/New Caledonia/20/1999; CA09=A/California/04/2009; WS33=A/Wilson-Smith/1933; AB48=A/Albany/4835/1948; BR07=A/Brisbane/59/2007; IA43=A/Iowa/1943; HK77=A/Hong Kong/117/1977; FM47=A/Fort Monmouth/1/1947. CoAsmbl 2=A/New Caledonia/20/99 (NC99)+A/California/04/09 (CA09); CoAsmbl 4=CoAsmbl 2+A/Wilson-Smith/33 (WS33)+A/Albany/4835/48 (AB48); CoAsmbl 6=CoAsmbl 4+A/Brisbane/59/07 (BR07)+A/Iowa/43 (IA43); CoAsmbl 8=CoASmbl 6+A/Hong Kong/117/77 (HK77)+A/Fort Monmouth/1/47 (FM47)

Example 2. Immunoprecipitation Analysis of Purified Nanoparticles Expressing Influenza HA Protein RBDs HA RBD-nanoparticles expressing RBDs from NC99, CA09 or both (CoAsmbl 2) were prepared and purified as described in Example 1. Four micrograms of purified RBD-nanoparticles were incubated with 4 μg of either anti-NC99 (3u-u), anti-pandemic H1N1 HA (2D1) or anti-HA stem (C179) monoclonal antibodies for 30 min at room temperature. Immune complexes were then captured using protein G-conjugated magnetic beads, and the complexes washed thoroughly with PBS containing 0.01% Tween 20. The washed pellets were resuspended in 20 μl of Laemmli buffer without reducing agent and analyzed on SDS-PAGE. Five micrograms of each protein were loaded. NC99, A/New Caledonia/20/1999; CA09, A/California/04/2009; WS33, A/Wilson-Smith/1933; AB48, A/Albany/4835/1948; BR07, A/Brisbane/59/2007; IA43, A/Iowa/1943; HK77, A/Hong Kong/117/1977; FM47, A/Fort Monmouth/1/1947. The results of these analyses are shown in FIGS. 5 and 6

Example 3. Immunization of Mice Using Purified Nanoparticles

The ability of compositions comprising purified monovalent, admixed, or heterogeneous nanoparticles to elicit a neutralizing immune response was tested in mice. Six to eight week old BALB/c mice were divided into 9 groups (N=5). To each group was administered a composition comprising 2 μg of either a) a monovalent (i.e., expresses single HA RBD) nanoparticle, b) a mixture of various monovalent nanoparticle, or c) the indicated, co-assembled nanoparticles, in the presence of Sigma Adjuvant System (SAS) at weeks 0 and 3. The immunogens administered and the dosing schedule is shown below in Table 3.

TABLE 3

| Group[1] | HA RBD[2] | Dose[3] | Adjuvant[4] | Immunization |
|---|---|---|---|---|
| Mono (NC99) | NC99 | 2 μg | SAS | Week 0, 3 (20) |
| Mono (CA09) | CA09 | 2 μg | SAS | Week 0, 3 (20) |
| Admixed 2 | NC99/CA09 | 2 μg total | SAS | Week 0, 3 (20) |
| Admixed 4 | 2 + WS33/AB48 | 2 μg total | SAS | Week 0, 3 (20) |
| Admixed 6 | 4 + BR07/IA43 | 2 μg total | SAS | Week 0, 3 (20) |
| CoAsmbl 2 | NC99/CA09 | 2 μg | SAS | Week 0, 3 (20) |
| CoAsmbl 4 | 2 + WS33/AB48 | 2 μg | SAS | Week 0, 3 (20) |
| CoAsmbl 6 | 4 + BR07/IA43 | 2 μg | SAS | Week 0, 3 (20) |
| CoAsmbl 8 | 6 + HK77/FM47 | 2 μg | SAS | Week 0, 3 (20) |

[1]Balb/c mice (N = 5)
[2]A/New Caledonia/20/99 (NC99); A/California/04/09 (CA09); A/Wilson-Smith/33 (WS33); A/Albany/4835/48 (AB48); A/Brisbane/59/07 (BR07); A/Iowa/43 (IA43); A/Hong Kong/117/77 (HK77); A/Fort Monmouth/1/47 (FM47)
[3]Total protein amount per dose
[4]Sigma Adjuvant System (SAS)

Figure 7:
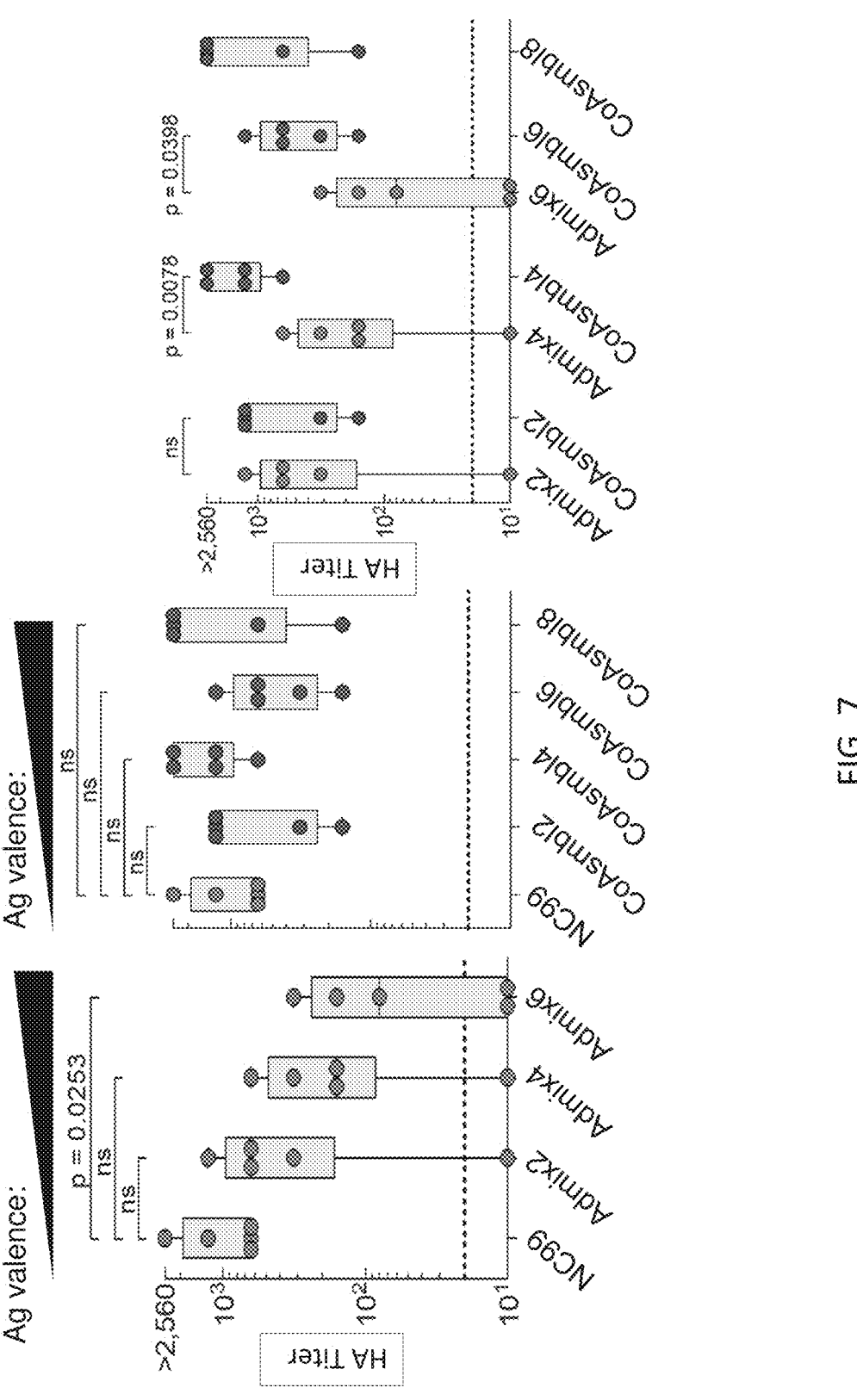
FIG. 7. Hemagglutination inhibitory (HAI) titers against influenza A/New Caledonia/20/1999 virus. (Left panel) Hemagluttination inhibition titers of sera from mice immunized with monovalent nanoparticles (NC99) or mixtures of monovalent nanoparticles (Admix 2, 4 or 6). (Middle panel) Hemagluttination inhibition titers of sera from mice immunized with monovalent nanoparticles (NC99) or multivalent nanoparticles (CoAsmbl2, 4, 6 or 8). (Right panel) Side by side comparison, using the data from the left and middle panels, comparing the HAI titers generated by immunizing mice with either admixed monovalent nanoparticles or multivalent nanoparticles displaying corresponding influenza HA proteins. All sera was collected at 2 weeks following the second immunization and tested for hemagluttination inhibition activity. Each dot indicates individual serum sample and is plotted as box-and-whiskers graph. P values were calculated by Student's t-test.
Figure 8:
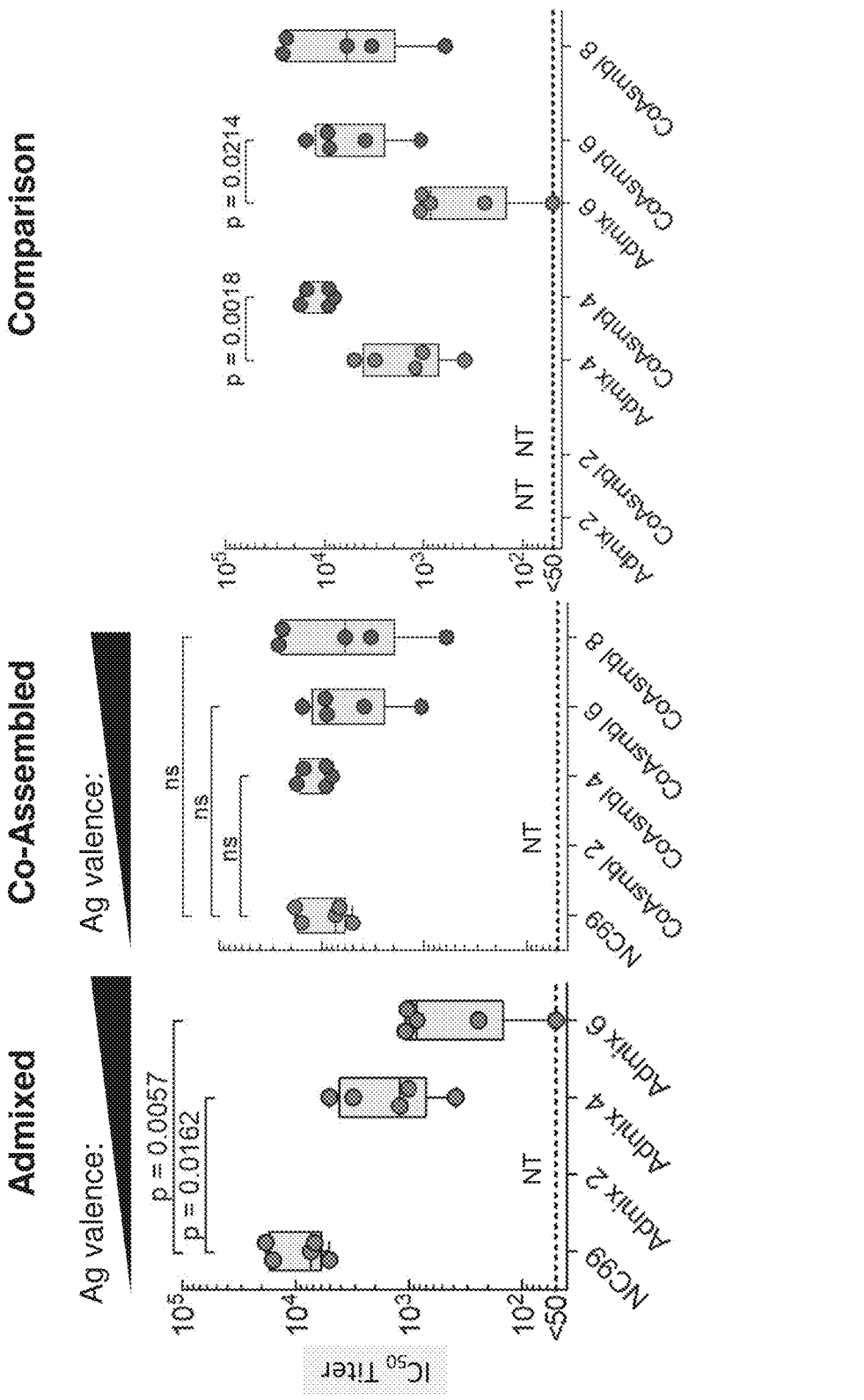
FIG. 8. Neutralization titers against NC99 pseudotyped lentivirus.

Serum samples were collected prior to the first immunization and at two and three weeks after the second immunization for serological analyses. More specifically the immune sera were tested for their ability to inhibit hemagglutination mediated by NC99 virus and neutralize NC99 pseudotyped lentivirus The results of these analyses are shown in FIGS. 7 and 8.

Example 4. Analysis of Breadth of Immune Response Using Monovalent Nanoparticles, Admixed Monovalent Nanoparticles or Multivalent, Co-Assembled Nanoparticles Mice (N=5) were immunized with either monovalent nanoparticles against NC99 or CA09, admixed nanoparticles (Admix 4), or multivalent nanoparticles (CoAsmbl 4 or CoAsmbl 8) (N=5) at week 0 and again at week 3. At 2-3 weeks following the second immunization, sera was collected from each mouse and the sera analyzed by HAI assays using a panel of 18 H1N1 viruses. The resulting titers are shown as a heatmap in FIG. 9.

The results of this analysis demonstrate that immunization with multivalent co-assembled particles produces a broader immune response (i.e., an immune response against a wider range of influenza viruses) than does immunization with either monovalent nanoparticles or admixed monovalent nanoparticles.

Example 5. Detection of HA-Specific, Cross-Reactive B-Cells in Peripheral Cells in HA RBD-Nanoparticle Immunized Mice Mice (N=5) were immunized with either monovalent nanoparticles against NC99 or CA09, admixed nanoparticles (Admix 2, Admix 4, or Admix 6), or multivalent nanoparticles (CoAsmbl 2, CoAsmbl 4, CoAsmbl 6 or CoAsmbl 8) at week 0, 3 and 20. At 10 days following the third immunization, peripheral blood was collected from each mouse and the white blood cells were isolated and analyzed by flow cytometer using NC99 and CA09 HA probes. Live, non-T, non-mactophage, IgD negative, singlet memory B cells were gated and the cell population (percentage of memory B cells) positive to both NC99 and CA09 HA was quantitated. The gating strategy and the resulting frequency of HA double positive cells across different immunization groups are shown in FIGS. 10 and 11.

The results of this analysis demonstrate that immunization with multivalent co-assembled particles induces an increased frequency of cross-reactive HA-specific memory B cells in immunized animals (i.e., B cells specific for both NC99 and CA09 HA) than does immunization with either monovalent nanoparticles or admixed monovalent nanoparticles.

Example 6. Correlation of NC99/CA09 Cross-Reactive B-Cell Frequency and Antigenic Heterogeneity of Co-Assembled RDP-Nanoparticle Relationship between frequency of HA double positive cells in immunized animals and antigen valence of co-assembled immunogens was examined by Pearson product moment correlation analysis. This relationship is illustrated by the graph in FIG. 12.

The result of this analysis show that the degree of heterogeneity on the co-assembled immunogens positively correlates with frequency of cross-reactive HA-specific memory B cells in immunized animal.

Example 7. Neutralization Breadth Elicited by Vaccination with Co-Assembled HA RBD-Nanoparticles Mice were vaccinated with co-assembled nanoparticles, according to the schedule shown above in Table 3. Ten days after the final immunization, sera were collected and tested for its ability to neutralize pseudotyped lentiviruses expressing HA and NA from various H1N1 virus strains. The serum neutralization titers obtained from these assays are shown below in Table 4.

TABLE 4

| Serum neutralization titers from mice immunized with co-assembled nanoparticles | | | | | |
|---|---|---|---|---|---|
| | $IC_{50}$ (serum dilution) | | | | |
| H1N1 pseudovirus | #8441 | #8442 | #8443 | #8444 | #8445 |
| A/California/4/09 | NT | NT | NT | NT | NT |
| A/New Jersey/76 | 2528 | 947 | 27580 | 11222 | 7463 |
| A/South Carolina/1/18 | 1146 | 242 | 1354 | 11129 | 217 |

TABLE 4-continued

| Serum neutralization titers from mice immunized with co-assembled nanoparticles | | | | | |
|---|---|---|---|---|---|
| | $IC_{50}$ (serum dilution) | | | | |
| H1N1 pseudovirus | #8441 | #8442 | #8443 | #8444 | #8445 |
| A/Wilson-Smith/33 | NT | NT | NT | NT | NT |
| A/Puerto Rico/8/34 | 5439 | <40 | 3440 | 9822 | 2817 |
| A/Iowa/43 | 3062 | 1709 | 12821 | 12095 | 2466 |
| A/Fort Monmouth/1/47 | 31302 | 85350 | 77846 | 126781 | 719 |
| A/Malaysia/54 | NT | NT | NT | NT | NT |
| A/Albany/4835/48 | NT | NT | NT | NT | NT |
| A/Hong Kong/117/77 | 2636 | 7525 | 16876 | 37845 | 1724 |
| A/Singapore/6/86 | 8888 | 4064 | 9822 | 3469 | 24751 |
| A/New York/146/00 | 13366 | 7780 | 6866 | 3113 | 15399 |
| A/New York/653/96 | 17302 | 158 | 9190 | 5349 | 22212 |
| A/Beijing/262/95 | 5960 | <40 | 1905 | 9422 | 96 |
| A/New Caledonia/20/99 | 5217 | 15788 | 18649 | 42171 | 46992 |
| A/New York/8/06 | 1695 | 423 | 947 | 620 | 2317 |
| A/Solomon Islands/3/06 | 1072 | 604 | 226 | 1072 | 1858 |
| A/Brisbane/59/07 | NT | NT | NT | NT | NT |

NT, not tested.

Example 8. Neutralization Breadth of an Isolated, Anti-HA Monoclonal Antibody B cells obtained from mouse #8441 in Example 7 were sorted using fluorescently labeled HA probe as bait. Genes encoding variable regions of the antibody heavy and light chains were then amplified from single B cells, sequenced, and cloned into appropriate backbone vectors (mouse IgG2a heavy and kappa light chain backbone) to express the encoded proteins as an antibody. Reconstructed antibody vectors were used for transient transfection in 293-Freestyle expression system (Life technologies) and the IgG was purified by affinity column purification using protein A resin. The resulting antibody was referred to as 441D6. Neutralization $IC_{50}$ titers of 441D6 were determined by lentivirus pseudotype neutralization assays in which pseudoviruses express HA and NA from various H1N1 viral strains. Monoclonal antibodies CH65 (anti-receptor binding site of HA) and FI6v3 (anti-HA stem region) were used as controls. NT=not tested. The neutralization titers obtained from these assays are shown below in Table 5.

TABLE 5

| Neutralization titers of monoclonal antibody 441D6 | | | |
|---|---|---|---|
| | $IC_{50}$ (µg/ml) | | |
| H1N1 pseudovirus | CH65 | 441D6 | FI6v3 |
| A/California/4/09 | 6.25 | 0.16 | 0.13 |
| A/New Jersey/76 | >25 | 0.03 | 0.36 |
| A/South Carolina/1/18 | 0.57 | 0.04 | 4.40 |
| A/Wilson-Smith/33 | NT | NT | NT |
| A/Puerto Rico/8/34 | 0.44 | 0.08 | 0.97 |
| A/Iowa/43 | >50 | 11.08 | 3.40 |
| A/Fort Monmouth/1/47 | 5.86 | 0.02 | 22.17 |
| A/Malaysia/54 | NT | NT | NT |
| A/Albany/4835/48 | NT | NT | NT |
| A/Hong Kong/117/77 | 0.97 | 0.04 | 0.09 |
| A/Singapore/6/86 | <0.005 | 0.01 | 0.01 |
| A/New York/146/00 | 0.03 | 0.01 | 0.08 |
| A/New York/653/96 | <0.005 | 0.02 | 0.15 |
| A/Beijing/262/95 | 0.01 | 0.07 | 1.01 |
| A/New Caledonia/20/99 | 0.01 | 0.04 | 0.09 |

TABLE 5-continued

Neutralization titers of monoclonal antibody 441D6

| | IC$_{50}$ (μg/ml) | | |
|---|---|---|---|
| H1N1 pseudovirus | CH65 | 441D6 | FI6v3 |
| A/New York/8/06 | 0.02 | 0.14 | >25 |
| A/Solomon Islands/3/06 | 1.30 | 0.29 | 0.94 |
| A/Brisbane/59/07 | NT | NT | NT |

NT, not tested.

The results demonstrate the ability of the monoclonal antibody 441D6 to neutralize broader range of H1N1 viruses than CH65 and more potently neutralize viruses than FI6v3, documenting a novel broad and potent neutralizing monoclonal antibody 441D6 against H1N1 viruses.

To better understand the interaction of monoclonal antibody 441D6 with influenza HA protein, a three-dimensional reconstruction model of an HA trimer complexed with Fab 441D6 was produced. Briefly, HA trimer (A/New York/653/1996 (H1N1)) was incubated with 1.5 times excess amount of Fab 441D6 and the complex purified by size exclusion column chromatography. The purified HA-Fab complex was then used in negative stain electron microscopy experiments. Approximately 9,000 particles were used for three dimensional reconstruction and the calculated resolution of the final model was ~18.5 Å. HA and Fab models were docked in the EM density (bottom). The resulting three-dimensional model is shown in FIG. 13.

What is claimed:

1. A method of producing a nanoparticle, comprising: culturing a cell comprising at least two nucleic acid molecules, wherein:

each nucleic acid molecule encodes a unique species of self-assembling fusion protein, each fusion protein comprises a self-assembling, monomeric subunit protein joined to an immunogenic portion of an influenza virus hemagglutinin (HA) protein, wherein the immunogenic portion of the influenza virus HA protein is a receptor binding domain (RBD);

the immunogenic portion in each species of self-assembling fusion protein differs from the immunogenic portion in the other species of self-assembling fusion proteins by at least one amino acid;

the fusion proteins self-assemble to form a nanoparticle that displays on its surface, the immunogenic portions of the at least two species of self-assembling fusion proteins;

at least one of the species of self-assembling fusion proteins comprises an amino acid sequence at least 90% identical to SEQ ID NO: 97; and the cell is cultured under conditions suitable for expressing the encoded self-assembling fusion proteins to form the nanoparticle.

2. The method of claim 1, wherein at least one of the species of self-assembling fusion proteins comprises an amino acid sequence at least 95% identical to SEQ ID NO: 97.

3. The method of claim 1, wherein at least one of the species of self-assembling fusion proteins comprises an amino acid sequence at least 99% identical to SEQ ID NO: 97.

4. The method of claim 1, wherein the at least one species of self-assembling fusion protein comprises an amino acid sequence set forth as SEQ ID NO:97, SEQ ID NO: 100, SEQ ID NO:112, SEQ ID NO: 115, SEQ ID NO:118, SEQ ID NO:121, SEQ ID NO: 124, SEQ ID NO: 127, SEQ ID NO: 130, SEQ ID NO:133, SEQ ID NO:136, SEQ ID NO: 139, or SEQ ID NO:142.

5. The method of claim 1, wherein the at least one species of self-assembling fusion protein comprises an amino acid sequence set forth as SEQ ID NO: 97.

6. A method of producing a nanoparticle, comprising:

culturing a cell comprising at least four nucleic acid molecules, wherein:

each nucleic acid molecule encodes a unique species of self-assembling fusion protein, each fusion protein comprises a self-assembling, monomeric subunit protein joined to an immunogenic portion of an influenza virus hemagglutinin (HA) protein, wherein the immunogenic portion of the influenza virus HA protein is a receptor binding domain (RBD);

the immunogenic portion in each species of self-assembling fusion protein differs from the immunogenic portion in the other species of self-assembling fusion proteins by at least one amino acid;

the fusion proteins self-assemble to form a nanoparticle that displays on its surface, the immunogenic portions of the at least four species of self-assembling fusion proteins;

at least one of the species of self-assembling fusion proteins comprises an amino acid sequence at least 90% identical to SEQ ID NO: 97; and the cell is cultured under conditions suitable for expressing the encoded self-assembling fusion proteins to form the nanoparticle.

7. The method of claim 6, wherein at least one of the species of self-assembling fusion proteins comprises an amino acid sequence at least 95% identical to SEQ ID NO: 97.

8. The method of claim 6, wherein at least one of the species of self-assembling fusion proteins comprises an amino acid sequence at least 99% identical to SEQ ID NO: 97.

9. The method of claim 6, wherein the at least one species of self-assembling fusion protein comprises an amino acid sequence set forth as SEQ ID NO:97, SEQ ID NO:100, SEQ ID NO:112, SEQ ID NO: 115, SEQ ID NO:118, SEQ ID NO:121, SEQ ID NO: 124, SEQ ID NO:127, SEQ ID NO: 130, SEQ ID NO: 133, SEQ ID NO:136, SEQ ID NO:139, or SEQ ID NO:142.

10. The method of claim 6, wherein the at least one species of self-assembling fusion protein comprises an amino acid sequence set forth as SEQ ID NO: 97.

* * * * *